US012678547B2

(12) United States Patent
Treu et al.

(10) Patent No.: US 12,678,547 B2
(45) Date of Patent: Jul. 14, 2026

(54) FLOW BALANCING DEVICES, METHODS, AND SYSTEMS

(71) Applicant: NxStage Medical, Inc., Lawrence, MA (US)

(72) Inventors: Dennis M. Treu, Castle Rock, CO (US); Jerome James, Vestavia, AL (US); Jeffrey H. Burbank, Manchester, MA (US); Daniel Joseph Rubery, Jr., Nashua, NH (US)

(73) Assignee: NxStage Medical, Inc., Lawrence, MA (US)

( * ) Notice: Subject to any disclaimer, the term of this patent is extended or adjusted under 35 U.S.C. 154(b) by 506 days.

(21) Appl. No.: 17/920,331

(22) PCT Filed: Apr. 21, 2021

(86) PCT No.: PCT/US2021/028428
§ 371 (c)(1),
(2) Date: Oct. 20, 2022

(87) PCT Pub. No.: WO2021/216730
PCT Pub. Date: Oct. 28, 2021

(65) Prior Publication Data
US 2023/0211059 A1 Jul. 6, 2023

Related U.S. Application Data

(60) Provisional application No. 63/013,802, filed on Apr. 22, 2020.

(51) Int. Cl.
*A61M 1/16* (2006.01)
*A61M 1/34* (2006.01)
*A61M 1/36* (2006.01)

(52) U.S. Cl.
CPC ........ *A61M 1/1647* (2014.02); *A61M 1/3401* (2022.05); *A61M 1/36224* (2022.05);
(Continued)

(58) Field of Classification Search
CPC ........ A61M 2205/70; A61M 2205/702; A61M 2205/705; A61M 2205/707; A61M 1/16;
(Continued)

(56) References Cited

U.S. PATENT DOCUMENTS 4,769,001 A * 9/1988 Prince ................. A61M 1/3644
604/6.11
5,000,664 A * 3/1991 Lawless ............ A61M 5/16831
417/63
(Continued)

FOREIGN PATENT DOCUMENTS

EP          3753588 A1    12/2020

OTHER PUBLICATIONS

International Search Report and Written Opinion dated Oct. 14, 2021, issued in International Application No. PCT/US2021/028428.
(Continued)

*Primary Examiner* — Adam Marcetich
(74) *Attorney, Agent, or Firm* — Potomac Law Group, PLLC

(57) ABSTRACT

The disclosed subject matter relates to extracorporeal blood processing or other processing of fluids. Volumetric fluid balance, a required element of many such processes, may be achieved with multiple pumps or other proportioning or balancing devices which are to some extent independent of each other. This need may arise in treatments that involve multiple fluids. Safe and secure mechanisms to ensure fluid balance in such systems are described.

20 Claims, 81 Drawing Sheets

(52) U.S. Cl.
CPC ...... *A61M 1/36225* (2022.05); *A61M 1/3643*
(2013.01); *A61M 2205/3331* (2013.01)

(58) Field of Classification Search
CPC .............. A61M 1/1601; A61M 1/1603; A61M
1/3401; A61M 1/3643; A61M 2205/3331;
A61M 2205/15; A61M 1/3656; A61M
2205/14
See application file for complete search history.

(56) References Cited

U.S. PATENT DOCUMENTS

| | | | | |
|---|---|---|---|---|
| 5,711,883 | A * | 1/1998 | Folden | A61M 1/16 |
| | | | | 73/40 |
| 2005/0000868 | A1 | 1/2005 | Weigel et al. | |
| 2012/0078181 | A1* | 3/2012 | Smith | H02J 7/0044 |
| | | | | 604/404 |
| 2013/0020237 | A1 | 1/2013 | Wilt et al. | |
| 2013/0026098 | A1* | 1/2013 | Haecker | A61M 1/16 |
| | | | | 210/97 |
| 2013/0028788 | A1* | 1/2013 | Gronau | A61M 1/14 |
| | | | | 73/1.69 |
| 2013/0213890 | A1 | 8/2013 | Kelly et al. | |
| 2014/0299544 | A1* | 10/2014 | Wilt | A61M 1/154 |
| | | | | 417/474 |
| 2016/0015872 | A1* | 1/2016 | Luckemeyer | A61M 3/022 |
| | | | | 604/315 |
| 2016/0151554 | A1* | 6/2016 | Jansson | G05B 15/02 |
| | | | | 700/282 |
| 2016/0175510 | A1* | 6/2016 | Patel | A61M 5/16854 |
| | | | | 137/12 |
| 2017/0089746 | A1* | 3/2017 | Rossi | A61M 1/3666 |
| 2017/0258975 | A1* | 9/2017 | Fulkerson | A61M 1/14 |
| 2017/0296727 | A1* | 10/2017 | Burbank | A61M 1/165 |
| 2018/0001009 | A1* | 1/2018 | Crawford | A61M 1/159 |
| 2018/0078690 | A1 | 3/2018 | Rohde | |
| 2019/0125950 | A1* | 5/2019 | Noack | A61M 1/14 |
| 2019/0209766 | A1* | 7/2019 | Thiebaud | A61M 1/1561 |
| 2019/0240387 | A1 | 8/2019 | Burbank et al. | |
| 2020/0061281 | A1 | 2/2020 | Desouza et al. | |
| 2022/0387681 | A1* | 12/2022 | Chamney | A61M 1/28 |

OTHER PUBLICATIONS

Extended European Search Report dated Apr. 24, 2024 for European
Patent Application No. 21793760.6.

* cited by examiner

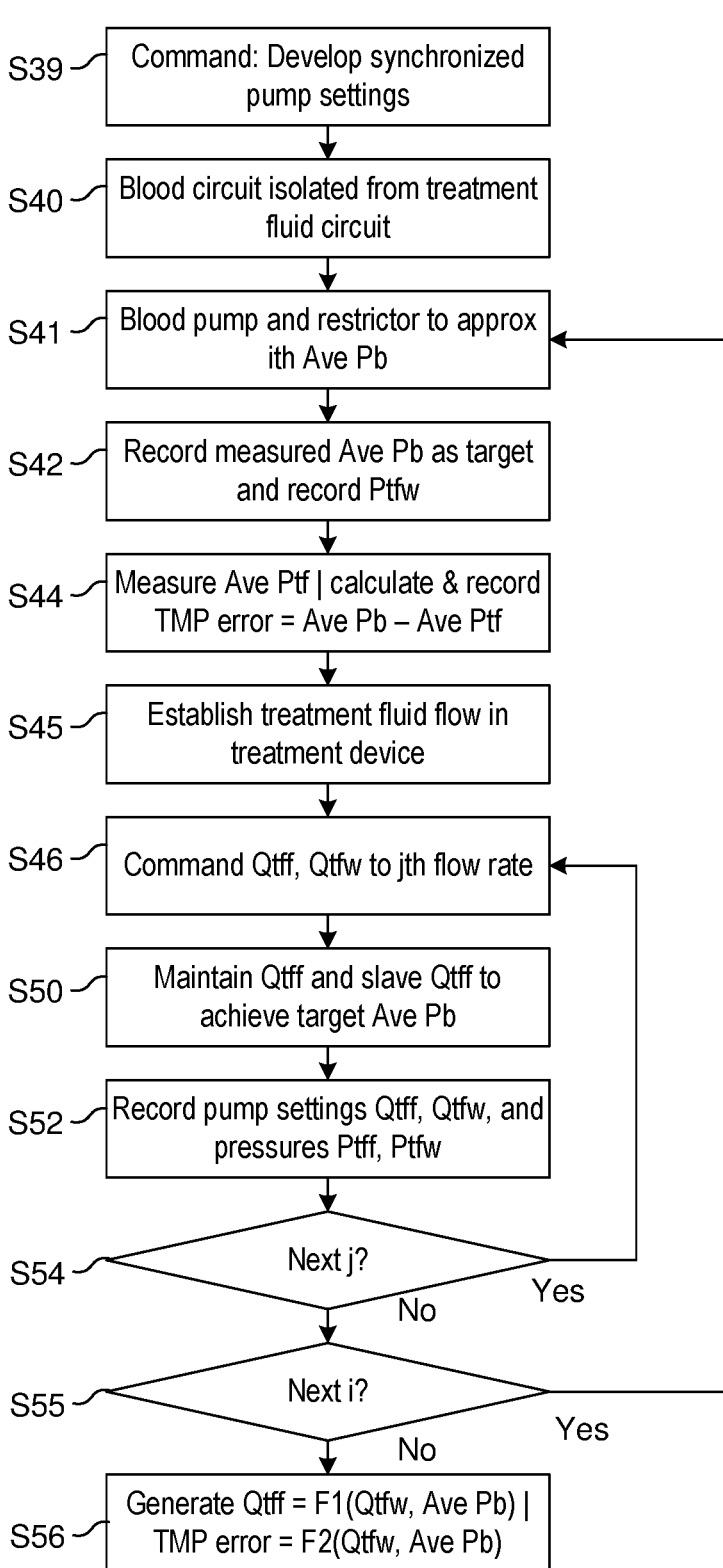

S39 — Command: Develop synchronized pump settings

S40 — Blood circuit isolated from treatment fluid circuit

S41 — Blood pump and restrictor to approx ith Ave Pb

S42 — Record measured Ave Pb as target and record Ptfw

S44 — Measure Ave Ptf | calculate & record TMP error = Ave Pb – Ave Ptf

S45 — Establish treatment fluid flow in treatment device

S46 — Command Qtff, Qtfw to jth flow rate

S50 — Maintain Qtff and slave Qtff to achieve target Ave Pb

S52 — Record pump settings Qtff, Qtfw, and pressures Ptff, Ptfw

S54 — Next j?      Yes / No

S55 — Next i?      Yes / No

S56 — Generate Qtff = F1(Qtfw, Ave Pb) | TMP error = F2(Qtfw, Ave Pb)

Fig. 4B

S100 — Recalibrate synch of tf pump

S102 — Halt tf pumps

S104 — Run blood pump and record target blood compartment pressure Ave Pb

S106 — Run tfw pump at prescribed rate

S108 — Bring tff pump to rate at which blood side pressure returns to target

S109 — Establish ultrafiltration pumping rate

S110 — Continue treatment

S112 — Δ Ave Pb exceed threshold ?    No    Yes

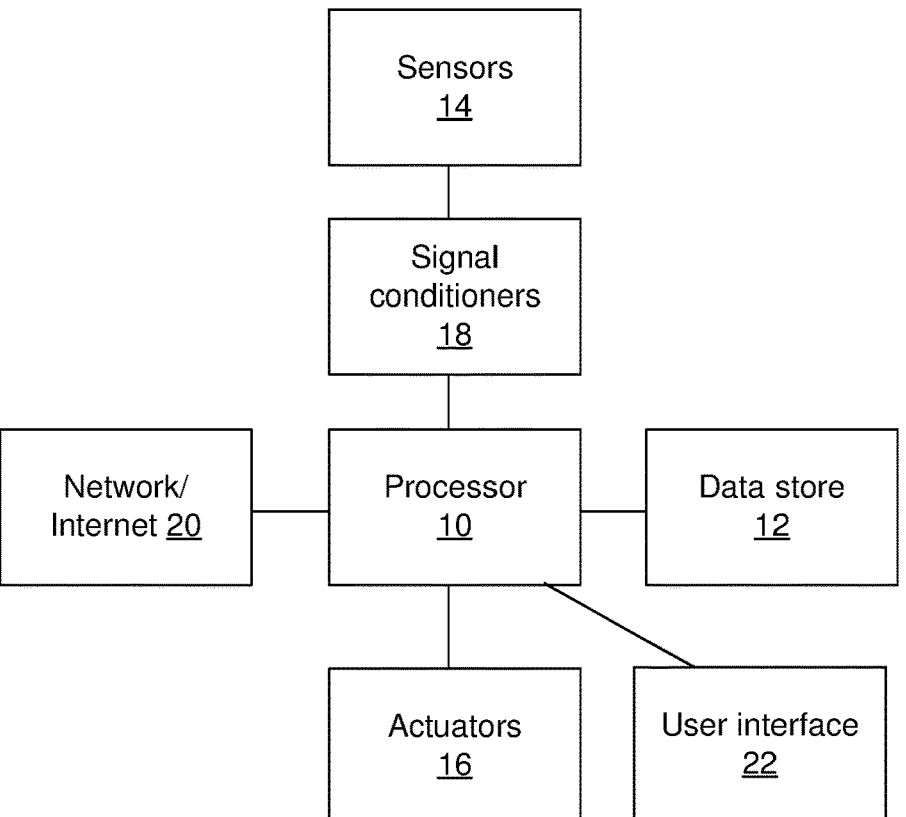
Fig. 9
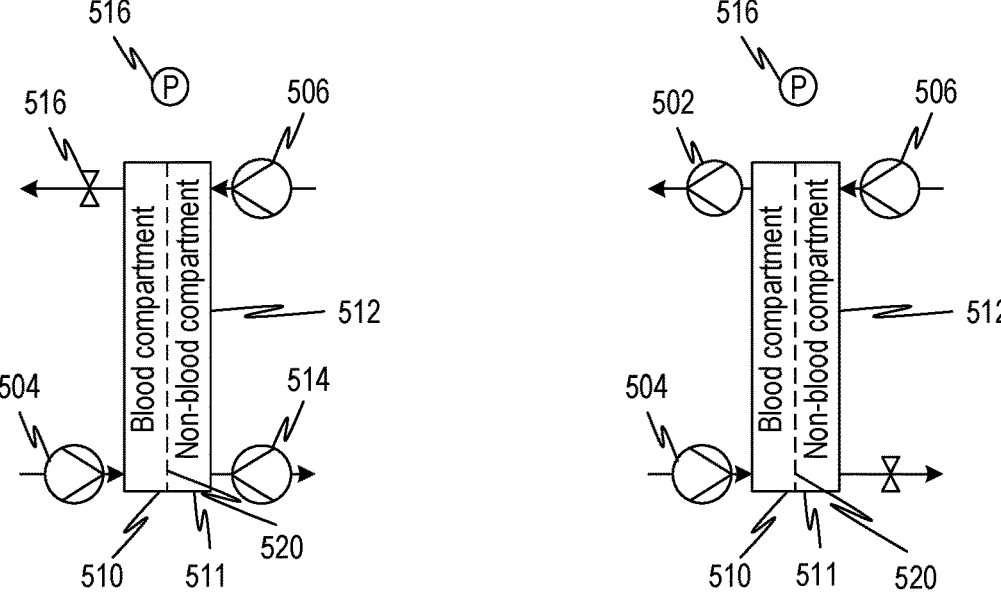
Fig. 10A                    Fig. 10B

Set EP

Set FP3, acquire FP2-sync

Set FP2 = FP2-sync, turn on PC

Set target HD avg = avg(Pout1, EP)
Set target EP = EP

Set FP3, sync FP1 to
target, target = HD avg

Set FP3, sync FP2 to
target

Set FP3 = FP1-sync+FP2-
sync, turn on PC

Command predefined
flow rates

Run sync

Adjust and turn on
pressure compensation

Commanded rates

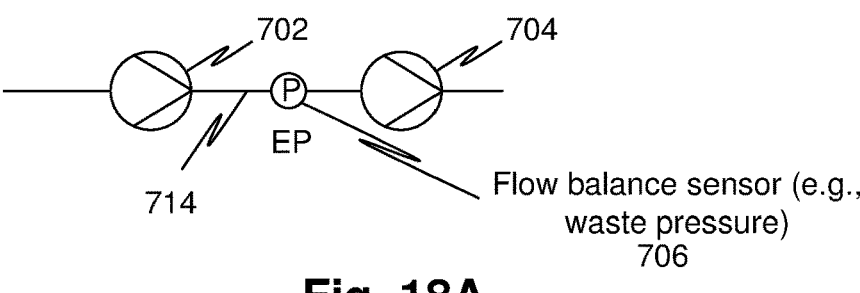

714     EP     Flow balance sensor (e.g., waste pressure) 706

Fig. 18A

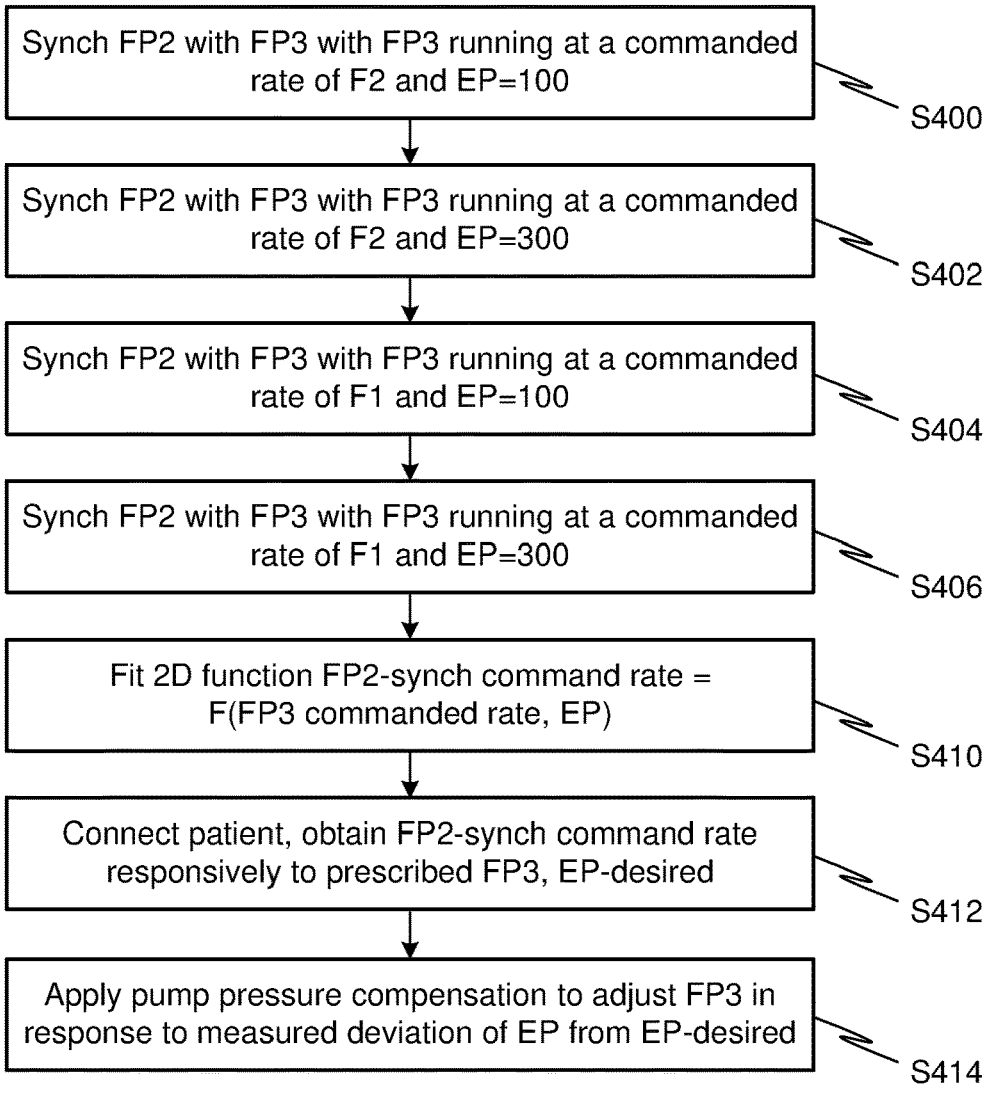

| Synch FP2 with FP3 with FP3 running at a commanded rate of F2 and EP=100 | S400 |

↓

| Synch FP2 with FP3 with FP3 running at a commanded rate of F2 and EP=300 | S402 |

↓

| Synch FP2 with FP3 with FP3 running at a commanded rate of F1 and EP=100 | S404 |

↓

| Synch FP2 with FP3 with FP3 running at a commanded rate of F1 and EP=300 | S406 |

↓

| Fit 2D function FP2-synch command rate = F(FP3 commanded rate, EP) | S410 |

↓

| Connect patient, obtain FP2-synch command rate responsively to prescribed FP3, EP-desired | S412 |

↓

| Apply pump pressure compensation to adjust FP3 in response to measured deviation of EP from EP-desired | S414 |

Fig. 18B

| Abbreviation | identifier and reference numeral |
|---|---|
| AC | Supplemental fluid 132 |
| ADAc | Arterial control air sensor 567A |
| ADAs | Arterial secondary air sensor 567B |
| ADVc | Venous control primary air sensor 566A |
| ADVs | Venous secondary air sensor 566B |
| Air1 | fresh treatment fluid air sensor 579 |
| Air2 | Air sensor 587 |
| Air4 | Air sensor 589 |
| Air5 | Air sensor 521 |
| AP | Pump inlet pressure sensor 568 |
| APF | Blood pump outlet pressure sensor 564 |
| BDA | Arterial blood detector 565 |
| BDV | Venous blood detector 597 |
| BLD | Blood detector 580 |
| BP | Blood pump 563 |
| BPC | Bypass line clamp 572 |
| CAR | Cartridge 599 |
| D | Treatment fluid 124 |
| DC | Pinch clamp 581 |
| EP | Inlet waste pressure sensor 575 |
| FHB | Free hemoglobin sensor 577 |
| FP1, DP | Fresh treatment fluid pump 573 |
| FP2 | Replacement fluid pump 542 |
| FP3 | Waste treatment fluid pump 574 |
| FP4 | Second replacement fluid pump 540 |
| FP5 | Supplemental fluid pump 541 |
| PC1 | Pinch clamp 571 |
| PC2 | Pinch clamp 554 |
| PC4 | Pinch clamp 556 |
| PC5 | Pinch clamp 558 |
| PCB | Pinch clamp 539 |
| PDP | Pressure sensor 534 |
| Pin1 | Fresh treatment fluid inlet pressure sensor 569A |
| Pin2 | Pressure sensor 560 |
| Pin4 | Pressure sensor 552 |
| Pout1 | Fresh treatment outlet pressure sensor 570A |
| Pout2 | Pressure sensor 555A |
| Pout4 | Pressure sensor 557A |
| Pout5 | Pressure sensor 559A |
| RF1 | First replacement fluid 120 |
| RF2 | Second replacement fluid 133 |
| Tin1 | Fresh treatment fluid inlet temperature sensor 569B |
| Tout1 | Fresh treatment fluid outlet temperature sensor 570B |
| Tout2 | Temperature sensor 555B |
| VC | Venous line clamp 562 |
| VPc | Venous primary control pressure sensor 532A |
| VPs | Venous secondary pressure sensor 532B |
| W | Drain 126 |
| WBP | Outlet waste pressure sensor 576 |
| WC | Waste clamp 578 |

Fig. 19D

Pressure test/valve and pump occlusion S2074

Close valve to be tested S2086

Pressurize pump upstream of closed valve until pressure reaches predetermined range S2087

Halt pump at roller and record pressure decay and plateau S2088

NO          Pressure plateaus in-range? S2089          YES

Fail test S2090

Open clamp, pressurize, halt at next roller, increment roller counter S2091

NO          All rollers tested? S2092

YES

YES          Next valve, next pump S2098          DONE

Pass test S2093

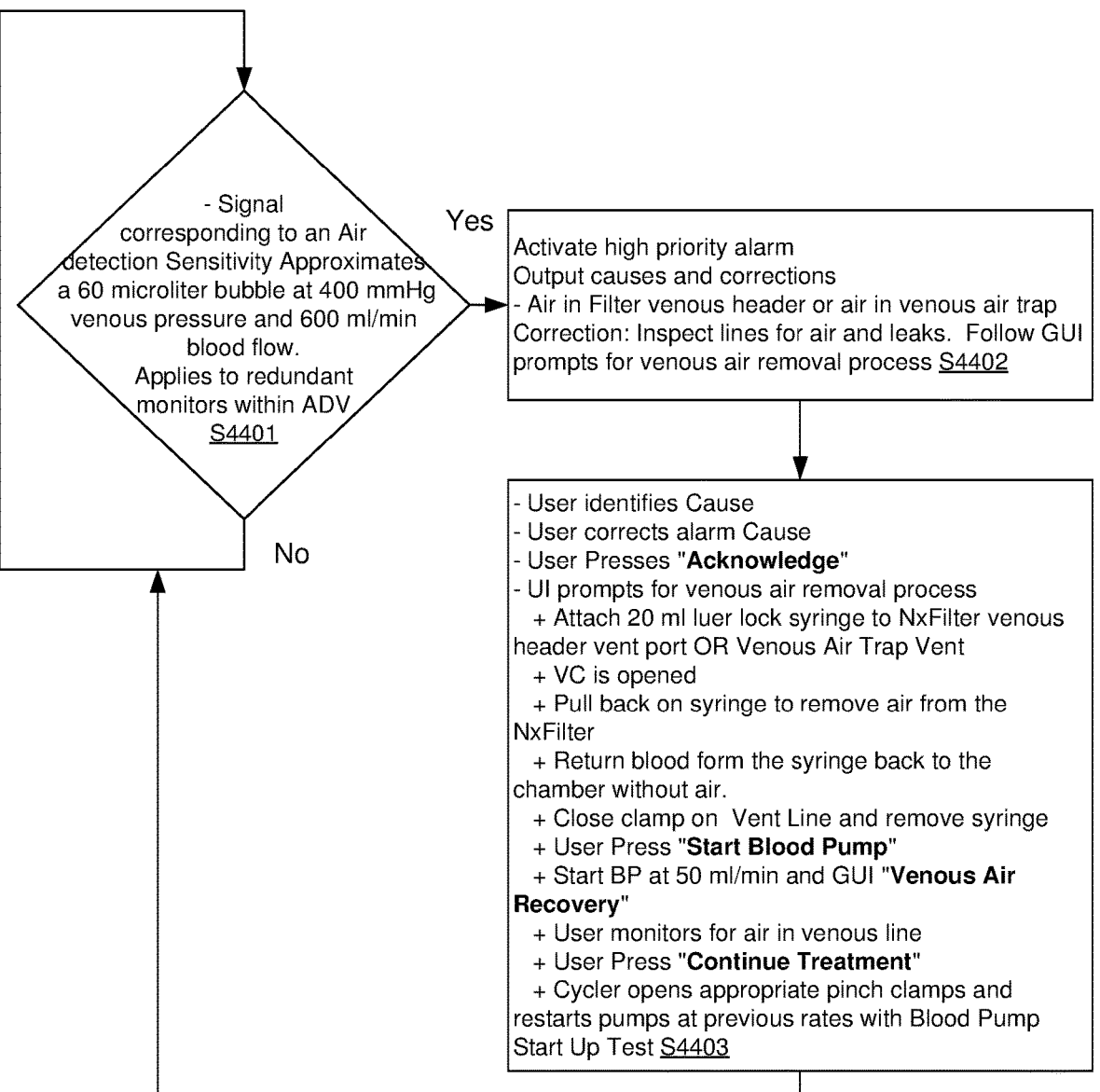

- Signal corresponding to an Air detection Sensitivity Approximates a 60 microliter bubble at 400 mmHg venous pressure and 600 ml/min blood flow. Applies to redundant monitors within ADV S4401

Yes

No

Activate high priority alarm
Output causes and corrections
- Air in Filter venous header or air in venous air trap
Correction: Inspect lines for air and leaks. Follow GUI prompts for venous air removal process S4402

- User identifies Cause
- User corrects alarm Cause
- User Presses "Acknowledge"
- UI prompts for venous air removal process
    + Attach 20 ml luer lock syringe to NxFilter venous header vent port OR Venous Air Trap Vent
    + VC is opened
    + Pull back on syringe to remove air from the NxFilter
    + Return blood form the syringe back to the chamber without air.
    + Close clamp on  Vent Line and remove syringe
    + User Press "Start Blood Pump"
    + Start BP at 50 ml/min and GUI "Venous Air Recovery"
    + User monitors for air in venous line
    + User Press "Continue Treatment"
    + Cycler opens appropriate pinch clamps and restarts pumps at previous rates with Blood Pump Start Up Test S4403

Fig. 44

Pressure test/valve and pump occlusion S4774

Close valve to be tested S4786

Pressurize pump upstream of closed valve until pressure reaches predetermined range S4787

Halt pump at roller and record pressure decay and plateau S4788

NO          YES

Pressure plateaus in-range? S4789

Fail test S4790

Open clamp, pressurize, halt at next roller, increment roller counter S4791

NO

All rollers tested? S4792

YES

YES          DONE

Next valve, next pump S4798

Pass test S4793

Fig. 47C

Monitor Pout5 pump 559 output pressure S5701

Pump 559 output pressure exceeds1st  limit? S5702

No

Yes

Pump 559 output pressure exceeds limit for predefined time interval S5703

No

Yes

Output line restriction error message; halt pump 559 S5705

System inputs acknowledge after problem corrected S5706

System restarts pumps at previous rates with BP start test S5707

FLOW BALANCING DEVICES, METHODS, AND SYSTEMS

CROSS-REFERENCE TO RELATED APPLICATIONS

This application is a U.S. national stage filing under 35 U.S.C. § 371 of International Application No. PCT/US2021/028428 filed Apr. 21, 2021, which claims priority to and the benefit of U.S. Provisional Patent Application No. 63/013,802 filed Apr. 22, 2020, all of which are hereby incorporated by reference in their entireties.

STATEMENT OF GOVERNMENT SUPPORT

This invention was made with government support under HR0011-13-C-0023 awarded by Department of Defense/Defense Advanced Research Projects Agency (DOD/DARPA). The government has certain rights in the invention.

BACKGROUND

A basic function of many extracorporeal blood treatment systems (ECBT systems), including hemodialysis, hemofiltration, hemodiafiltration, apheresis systems, etc., is the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total mass or volume of fluid pumped into, and removed from, the non-blood side of a filter, for example a dialyzer, are equal. To provide for a desired differential between the net quantity removed/added, the inflow and outflow rates can be controlled to produce a net difference. This may be provided by regulating the relative flow rates provided by ingoing and outgoing pumps or by using a separate bypass, driven by a separate pump. In an example, such a bypass pump pumps at an ultrafiltration ("UF") line rate which is added to the balanced withdrawal rate.

Gravimetric systems that balance flow by weighing mass from a source and collected fluid from the treatment device and comparing the two are known. Another approach is to measure incremental volume transfer. Hard plumbed or disposable lined balance chambers alternately fill and empty in a manner that assures equal and opposite volume exchange. Systems using this approach are balancing a single inlet fluid flow with an effluent stream. A second stream of fluid is frequently added to the extracorporeal circuit using an additional pump, or external IV pump. The volume of this second stream may be balanced by the isolated ultrafiltration (UF) pump in an attempt to maintain patient fluid balance. This approach is limited by the calibration inaccuracies of the additional or external pump and the isolated UF pump. These inaccuracies are acceptable at low flow rates. However, at higher flow rates the cumulative volumetric inaccuracies may not achieve the desired patient volumetric balance. Additionally, this approach requires an operator to independently set the pump rates to achieve the desired balance.

SUMMARY

The subject matter described in this disclosure is based on a system that uses and approach to volumetric fluid balance based on multiple volumetric or fixed-displacement pumps to control inflows and outflows from an extracorporeal circuit that have corresponding pump rates synchronized relative to each other to assure balanced flow rates. The system described also accommodates multiple configurations including one that employs optional multiple filters such as sepsis filters and a dialyzer (See FIG. 19A). A less complex system is shown in FIG. 11. These systems are not the only types to which the disclosed embodiments apply as will be evident from the description but are provided as examples.

In certain systems, volumetric fluid balancing may be performed for a single therapy fluid stream using a system configuration including balance chambers, peristaltic pumps, and mechanically controlled pinch valves. The therapy fluid entering the blood path of the extracorporeal circuit may be balanced with effluent removed from the blood path through the dialyzer of the circuit so that the patient volume is not affected by this exchange of fluids. The limitation to a single therapy fluid inlet flow is a common limitation of various dialysis machines that use balance chambers. Some extracorporeal therapies can use more than one therapy fluid inlet flows that may be volumetrically controlled to achieve an overall patient fluid balance. For example, the difference between the total fluid that moves into the patient (for example, by flowing into the patient's blood stream) and that withdrawn from the patient must be precisely controlled. For example, in dialysis treatment, the amount of fluid entering the patient, for example through predilution, post-dilution, citrate infusion, and reverse ultrafiltration streams may be balanced against the net ultrafiltration stream to achieve a target net ultrafiltration rate. The subject matter described in this disclosure provides alternate machine configurations that support one or more therapy fluid flows synchronized with the effluent fluid flow from the extracorporeal circuit to achieve accurate fluid balance.

The disclosed subject matter includes several different system configurations that support one or more therapy fluid inlet flows balanced with the effluent flow by diverting each therapy flow pump individually using a valving/flow diversion mechanisms that flow fluids, including blood and/or treatment fluid treatment configuration into a series configuration in which fluid is pumped from one pump to another and the pumping rates synchronized using an imbalance detection device. One imbalance detection is the change in weight of fluid accumulating due to back-up of the serial flow. Another imbalance detection is the pressure buildup due to fluid volume accumulation caused by back-up of the serial flow. In other embodiments, pumps are individually calibrated at relevant times (one or more times per treatment for example) against a common or gold standard flow rate measurement device. In still other embodiments, imbalance is detected during treatment without establishing a special configuration by directly measuring the flow rates of fluid, directly by flow measurement or indirectly by measuring pressure changes to infer balanced or imbalanced flow conditions from a temporal trend which can be predict the magnitude of imbalance. For example, one of the pumps can be incrementally stepped, the pressure change or fluid weight trend sampled for a period of time for each step, to establish a trend, and perfect balance fitted to the trend in order to back out the synchronized flow rates arithmetically. Any type of fitting function may be used such as a straight line or polynomial. When pumps are synchronized, the operating condition are maintained to ensure the synchronization conditions, for example suction pressure, are comparable to those during synchronization.

In embodiments, reliable flow balance is obtained by synchronizing the pump flows and using the pressure sensor to synchronize the rates rather than enforcing a fixed-volume flow channel. A controller connected to the pressure sensor and pumps adjusts the effluent flow pump to the desired flow rate and the selected therapy fluid flow pump to achieve a desired pressure between the pumps and holds the pressure stable for a period of time to achieve a synchronization flow value for the therapy fluid pump. This can be repeated for one or multiple inlet pump pressure values and stabilization times to achieve a synchronization curve for the therapy fluid flow pump versus pressure. Alternatively, it can be done for a single condition that is to be maintained during treatment. If the system needs to change operation state due to an uncontrolled change such as a change of flow resistance of a patient access or a controlled change such as a shift to a lower or higher flow rate, new synchronization at the new condition may be performed. Once synchronized, small excursions from the synchronized condition that occur thereafter, for example during treatment, will be adjusted-for, such as when the rates of the pumps that were synchronized during synchronization are varied from their absolute or relative operating speeds, for example to provide a selected ultrafiltration rate. The accommodation is provided by continuously performing pump pressure compensation, which refers to recalculating the relationship between the commanded flow rate (or equivalent such as shaft speed or cycle rate depending on the type of pump) and estimated actual flow rate based on known or measured pump curves. The pump curves may flow versus outlet minus inlet pressure or flow versus inlet pressure only. Other variations are possible depending on the type of pump. In variations, the synchronization process may be triggered by change in arterial pressure, blood treatment device blood side pressure, blood treatment device treatment fluid side pressure, or after a time interval. Such triggered synchronizations may be done for prescribed (i.e., predefined) blood and treatment fluid flow rates only so that a synchronization process over multiple conditions is not required. This "spot synchronization" process is particularly relevant in combination synchronization processes where no bypass flow is established so that treatment does not have to be significantly disrupted as described below with reference to FIG. 8, for example. Synchronization may be done during a priming operation, during treatment, or both. Spot synchronization may be done after a period of time over a treatment as well. The reason for triggering a synchronization after a period of time in the absence of any other change may be, for example, changes in material properties over time or due to extended use, for example a plastic pumping tube segment may exhibit changes in characteristics over continued use during a treatment. Thus to maintain accuracy of balancing, a synchronization may be performed after a time estimated to ensure that the amount of change is limited.

In embodiments, rather than continuously or repeatedly readjusting the flow rates of pumps to compensate for inlet pressure variation, the cumulative error caused by variations in pumping rates over a treatment interval are calculated and stored over time. Then the pumping rates are adjusted at a single time (at several times) for a calculated period of time to compensate for the impact of the error on total ultrafiltration that occurred over the treatment interval. The stepwise correction may be done in a single operation at one time toward the end of a single treatment interval or multiple times over multiple treatment intervals into which a single treatment session is divided. These operations may be done automatically without operator intervention. The treatment intervals may be defined according to events such as shutdowns due to automatic alarms or operator commands. For example, the pumping rates may be adjusted according to cumulative effect of error prior to a shutdown by adjusting the pumping rates immediately after restart. Also, compensation by adjusting the pumping rates can be done multiple times at regular intervals or at other predefined times during a treatment.

Once synchronized, the pumps rates may be changed to implement a predefined difference in commanded pump speeds according to a stored pump curve. The pump curve is not limited to a stored formula or algorithm but may also be implemented as a look up table or equivalent. The difference in commanded pump speeds is adapted to provide for a prescribed or otherwise provided ultrafiltration rate. The different speeds may provide for a desired fluid balance outcome in the extracorporeal circuit (neutral, positive, or negative balance). In embodiments, the difference in speed may be limited to a minor fractional difference (i.e., less than 50% speed difference) and may be limited to fractional differences of less than 20% or 10% to ensure and improve accuracy during treatment. In any of the embodiments, the synchronization may include multiple flow, for example, a predilution flow of replacement fluid which would flow into a patient's blood during treatment, plus a fresh dialysate flow and synchronized with a flow of waste. As indicated, the pump rates may be further compensated to account for transient effects such as changes in inlet/outlet pressures, changes due to pump life, and other factors. A compliant accumulator or additional tubing lengths can be used to reduce pressure spikes and aid in achieving stable pressure control during the synchronization process.

The embodiments are applicable to synchronization of series (serially interconnected through a treatment device) blood pumps or series treatment fluid pumps. In embodiments, directly flow between the series pumps is provided by halting flow through lines that exchange fluid with the flow path connecting the series pumps to be synchronized. For example, two series blood pumps connected to a filter have a fixed volume path between then when flow through lines connected to the non-blood side is prevented, such as by halting one or more treatment fluid pumps, clamping one or more treatment fluid lines, or both. For another example, two series treatment fluid pumps connected to a filter have a fixed volume path between then when flow through lines connected to the blood side is prevented, such as by halting one or more pumps, clamping one or more blood lines, or both. The fixed volume can be implemented by any suitable means for halting flow on the other side (other side of the pumps used for balancing) of the treatment fluid device including halting inflow and outflow pumps on said other side or halting a single pump such as an inflow pump and clamping the other line, such as an outflow line. These may depend on the configuration.

All pumps may be equipped with an inlet pressure sensor and may also be fitted with an outlet pressure sensor to support pressure compensation of the pump rate. In a pressure compensation method, the flow rate of the pump may be derived from the pump rotation or reciprocation rate and adjusted responsively to the inlet and/or outlet pressure. This derivation and compensation may be done using a single function of both pressure (inlet, outlet, or pressure change) and rotation speed. For example, the function may be embodied in a look up table stored in a data store of a controller. Additionally, the control valves may be closed so that pump occlusion may be confirmed by the reading of the various pressure sensors.

In embodiments, flow is halted in the non-blood compartment of a treatment device and an average blood compartment pressure is established by flowing fluid through the blood compartment of the treatment device by pumping fluid into the blood compartment and with a predefined resistance at the outlet of the blood compartment. This average pressure is stored as a target. The dialysate compartment pressure is affected by the oncotic pressure caused by the presence of protein in the blood. Fresh and waste treatment fluid pumps connected to the non-blood compartment are then synchronized by commanding the waste treatment fluid pump to a predefined treatment fluid flow rate and adjusting the fresh treatment fluid pump rate until the target average blood compartment pressure is restored in the blood compartment. In alternative embodiments, the target may be established from the treatment fluid pressure (e.g., taking an average of the inlet and outlet treatment fluid pressure at the inlet and outlet ports of the treatment fluid device). By measuring the difference between treatment fluid device treatment fluid compartment pressure and blood compartment pressure during zero (or near-zero) transmembrane flow conditions, oncotic pressure may be directly determined. The technique may be used to determine the oncotic pressure which may be used as well for other purposes, such as determining the magnitude of ultrafiltration required (i.e., how much excess fluid is in the patient's blood—hypervolemia). The synchronized fresh treatment fluid pump rate is recorded. This procedure may be repeated for multiple predefined pumping rates and blood compartment pressures to record a table of blood compartment average pressures and predefined treatment fluid flow rates as the independent variables (e.g., rows and columns although any data storage element may be used) and a corresponding synchronized fresh treatment fluid flow rate for each combination (e.g., recorded in the cells of the table). The data may be fitted to a function to estimate a synchronized fresh treatment fluid pumping rate for any prescribed combination of treatment fluid flow rate and blood flow rate through the blood compartment, which will correspond, during treatment, to an average pressure of the blood compartment. When treatment is performed, the average blood compartment pressure is measured and applied to the fitted function, with a prescribed treatment fluid flow rate, to obtain an estimated fresh treatment fluid flow rate. A modified waste treatment fluid flow rate is then calculated to provide for a prescribed ultrafiltration rate. The pumping rate of the waste treatment fluid flow rate may be generated from a function of inlet pressure and target flow rate that provides a command flow rate to be applied to the pump. Such functions are commonly used for controlling peristaltic pumps. The step in commanded flow required by the waste treatment fluid pump to achieve the required ultrafiltration may be calculated from such a function and the current waste treatment fluid inlet pressure, then the waste treatment fluid pump commanded correspondingly. The new inlet pressure may be fed back iteratively to obtain a refined command flow for the waste treatment fluid pump until the inlet pressure stops changing within a predefined interval. Whenever, during treatment, the average blood compartment pressure changes beyond a predefined threshold, the fresh treatment fluid pump rate may be adjusted to return the average blood compartment pressure to the target and the waste treatment fluid pump rate reestablished iteratively as above. If the average blood compartment pressure changes beyond a greater threshold, the fresh treatment fluid pumping rate may be recalculated based on the prescribed treatment fluid flow rate as above and the waste treatment fluid pumping rate adjusted iteratively as above based upon a prescribed ultrafiltration rate.

The above summary and present disclosure describes an example system to which the claimed subject matter relates. It should be clear that aspects of the subject matter described below may be applied to other systems, for example, ones that do not perform flow balancing. The following portion of the summary describes the subject matter to which the present claims relate but is in no way to be interpreted as comprehending the entire disclosure and claims. Generally the claimed subject matter relates, according to embodiments, systems, devices, and methods for detecting error conditions, potential error conditions, or warnings to operators. It further relates to aspects that identify and respond by halting an on-going process and/or outputting relevant information and alarms. The relevant information may include alternative causes for the alarm and instructions for resolving the particular alternative causes. In embodiments, the user interaction permits the user to acknowledge fixing the condition associated with the alarm or caution, restart treatment, priming, or a system self-testing after taking the steps indicated by the relevant information. Among the embodiments are mechanisms for detecting user error in setup. Among the embodiments are mechanisms for detecting a discrepancy between a commanded configuration and a detected configuration of an installed fluid circuit. Among embodiments are mechanisms for automatically halting an on-going priming, treatment, or rinseback operation in response to the detecting. Among the embodiments are mechanism for detecting out-of-range values for critical systems for performing correct flow balancing in a cycler. Among the embodiments valves and pumps are tested for their ability to control flow. Among other embodiments are mechanisms for testing components responsible for detecting alarm conditions. Among the embodiments are mechanisms for shutting off malfunctioning systems.

Embodiments indicate problematic conditions related to misuse of the treatment system, faulty equipment/components, incorrect connection of fluid lines, erroneous installations/fittings, etc., and provide various corresponding alarms and cautions. In one embodiment, each indication is categorized as one of a caution, a medium priority alarm, a high priority alarm, and a high priority shutdown alarm, indicating successively more severe conditions. In response to determining to provide a caution, embodiments respond by providing corresponding textual instructions to caution a user and/or instructions for recovery. In embodiments, the caution may produce a visual message, images including text and graphics, video, or a combination thereof on a human-readable display device. Cautions may also include sounds output through an audio output device and/or providing a signal to a connection jack that may be connected to an audio output device such as a loudspeaker, headphone, or other types of transducers. In response to determining to provide a medium priority alarm, embodiments respond by activating an audible and visual alarm, leaving blood pumps running, leaving anti-coagulation pump(s) running, stopping all other pumps, and closing all non-blood pathway pinch clamps. In response to determining to provide a high priority alarm, embodiments respond by activating an audible and visual alarm, stopping all pumps, and closing all pinch clamps. In response to determining to provide a high priority shutdown alarm, embodiments respond by activating an audible and visual alarm, stopping all pumps, closing all pinch clamps, and waiting for the user to power cycle the system.

The principles of the subject matter disclosed herein are applicable to both peristaltic pumps with disposable fluid pathways as well as hard plumbed systems and combinations of the two. In a hard plumbed configuration, the flow path components may require disinfection similar to standard dialysis machines and would require special techniques to meet the requirements for direct infusion of therapy fluids.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 4A through 4D are flow charts for discussion of synchronization operations discussed with reference to FIGS. 3B through 3E according to various embodiments of the disclosed subject matter.

FIG. 9 shows a programmable control system with details that may be inherent in any of the controller embodiments disclosed herein and according to various embodiments of the disclosed subject matter.

FIGS. 10A and 10B illustrate the generalization of the flow balancing scheme in which blood side or non-blood side inflow and outflow pumps may be used to regulate the fluid balance according to embodiments of the disclosed subject matter.

FIGS. 18A-18B illustrate the generation and use of a map of commanded flow and pressure conditions for determining the synchronized command speed of a slave pump according to various embodiments of the disclosed subject matter.

FIG. 19D shows abbreviations used in flow charts in the present disclosure and the non-abbreviated identifiers and corresponding reference numerals.

FIGS. 20A-20D illustrate a method for performing tests of components required for accurate pump synchronization according to embodiments of the disclosed subject matter.

FIGS. 40A through 40C illustrate a system method of detecting the lack of a bag of fluid by means of a warmer with a pressure sensor according to embodiments of the disclosed subject matter.

FIG. 44 illustrates a process flow of an embodiment of a test process that continuously monitors the venous blood line for possible air in the line, according to embodiments of the disclosed subject matter.

FIGS. 47A-47D illustrate a method for performing tests of components required for accurate pump synchronization according to embodiments of the disclosed subject matter.

DETAILED DESCRIPTION

Figure 1A:
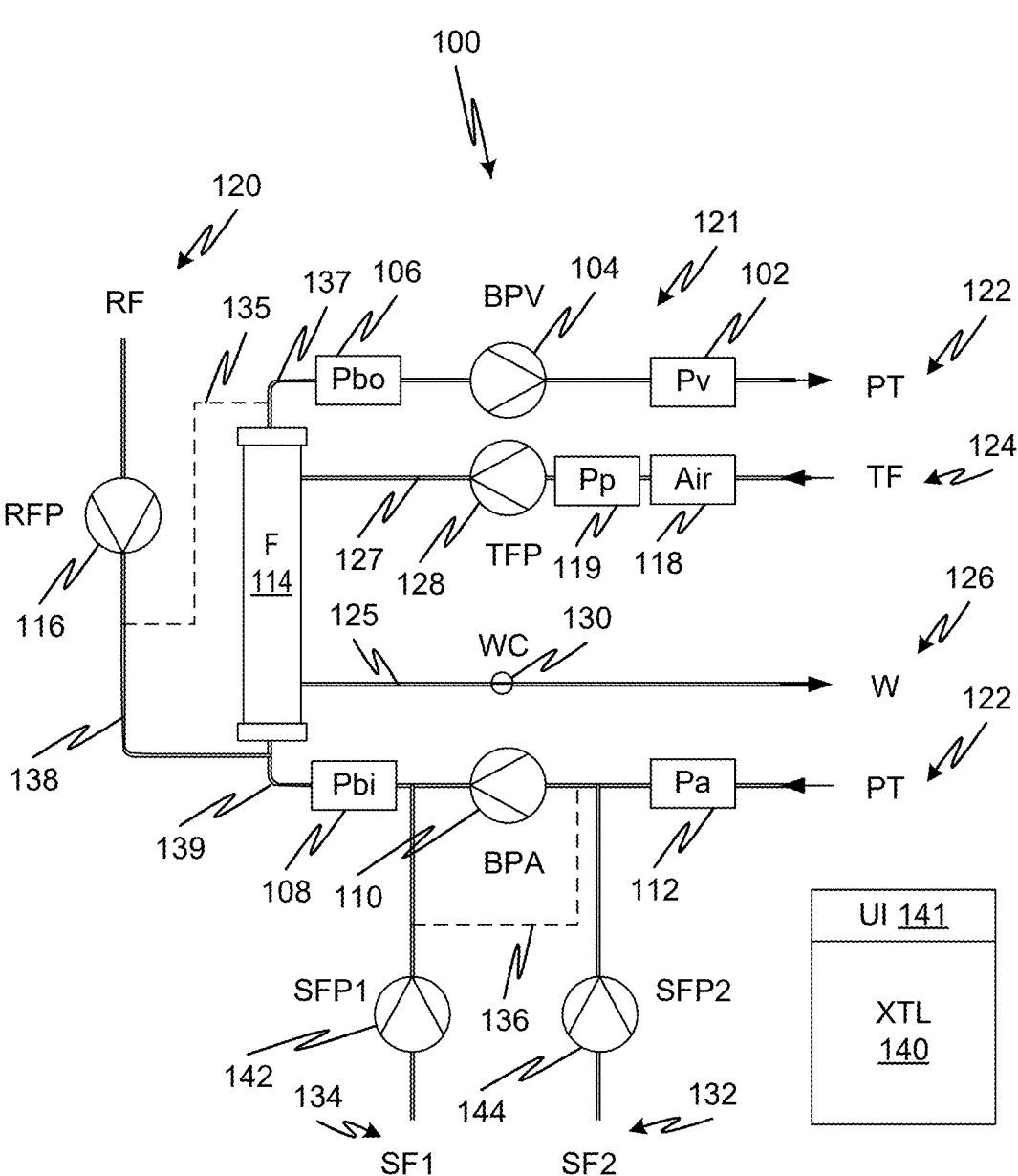
FIG. 1A shows a blood treatment system that regulates the flow of blood into and out of a treatment device to generate a cumulative target ratio of fluid drawn or infused into a patient over the course of a treatment according to various embodiments of the disclosed subject matter.

FIG. 1A shows a blood treatment system 100 that regulates the flow of fluid in a fluid circuit 121 that includes an arterial blood line 139, a venous blood line 137, a fresh treatment fluid line 127 and a waste treatment fluid line 125. In particular, the blood treatment system 100 regulates the flow of fluid across a membrane of a treatment device 114 to generate a cumulative target ratio of fluid drawn from, or infused into, a patient over the course of a treatment. During set-up procedures, instead of a patient being hooked up to a patient access 122B and at those times, a priming fluid container 123 may be connected to flow priming fluid through the fluid circuit 500 blood circuit portion. The control of the pumps provides a net flow of fluid across a membrane (and concomitantly to/from a patient or priming fluid source/sink). Hereafter it should be understood that in any of the embodiments, any reference to "patient" and/or "blood" with reference to a fluid balancing or pump synchronization may be replaced by priming fluid and/or a combination source and sink thereof, because the fluid balancing and synchronization mode/operation modes discussed herein can be done during priming as well as using blood during a treatment. It should also be understood that the priming fluid source/sink may be a single recirculating channel or chamber as well as a single-pass arrangement with a separate source and sink. At any given time, the net rate of flow across the membrane (identified in renal treatment as the ultrafiltration rate) is determined by a then-instant difference between the volume of blood pumped out of the treatment device 114 (for example a dialyzer) to the volume of blood pumped into the treatment device 114 plus the fluid pumped into the blood lines. The ultrafiltration rate may also be understood as the total amount of fluid transferred from the patient taking into account any replacement fluid 120 and/or other fluid (supplemental fluids SF1 and SF2 such as anticoagulant or drug) that are conveyed directly to the patient's blood.

Returning to FIG. 1A, blood is pumped into the treatment device 114 by an arterial blood pump 110 and pumped from the treatment device 114 by a venous blood pump 104. The illustrated configuration is common for dialysis systems, and may include all the typical incidents thereof, but differs specifically in that there are two blood pumps: the arterial blood pump 110 and the venous blood pump 104.

During a treatment mode and also in embodiments of a synchronization mode, blood is pumped to and from a patient access 122A. In other embodiments synchronization may be performed, instead, with a priming fluid. During priming operations, the patient access or priming connector(s) may be connected to priming fluid source, sink, or recirculating container instead.

Control and sensing are provided by a controller 140 which may be of any form but typically some type of programmable digital controller, for example, an embedded computer. A treatment fluid is pumped from a treatment fluid source 124 through an air detector 118 (also referred to as an air sensor) through the treatment device 114, past a waste line clamp 130, to a drain 126 (which could be a container or any other vehicle for disposal in any embodiment). The pumps, clamp, and all sensors may be connected for control and input by the controller 140. Drain 126 may be a drain of a plumbing system or a collection container or any other device for disposal of waste treatment fluid. Treatment fluid 124 may be dialysate, replacement fluid, or any other medicament.

A replacement fluid 120 may be pumped into the arterial blood line 139 or the venous blood line 137 through a replacement fluid line 135 or 138, respectively (or both) for predilution, post-dilution or a combination of both. In alternative embodiments, the dilution may occur at a midpoint of the treatment device 114, for example in a case where the treatment device 114 were composed of two smaller units that provided a fluid connection junction between them to admit fluid at that point to the blood compartment. A mid-dilution treatment device may have a special construction to provide for mid-dilution. The treatment device 114 may be adapted for a variety of types of blood treatment that require balancing flows into and out of a patient blood compartment, including, but not limited to, dialysis, hemo-filtration, hemodiafiltration, apheresis, adsorption, or hemoperfusion. These treatment modalities may apply as alternatives to any of the disclosed embodiments including those originally disclosed in the claims. Further supplemental fluids indicated by supplemental fluid 134 and supplemental fluid 132 may be pumped into the arterial blood line 139 by respective pumps, namely, a supplemental fluid pump 142 and a supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the arterial blood line 139 upstream of the arterial blood pump 110. In embodiments, each pump contributing to flow balance may have a pressure sensor up stream of it to ensure that pressure compensated control of its speed can be provided. For example, an additional treatment fluid pump pressure sensor 119 may be provided. In embodiments, pressure sensors used for pressure compensated speed control are positioned such that they provide a reliable and consistent indication of pressure upstream of the respective pump or pumps. Thus, they may be positioned close or at least such that there are no intervening possible interferences such as tube lengths that could become kinked. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 104 and downstream of the treatment device 114. A venous blood pressure sensor 102 may detect pressure in the venous blood line 137 downstream of the venous blood pump 104 and upstream of the patient access 122A. The controller 140 receives signals from each of the arterial pressure sensor 112, blood inlet pressure sensor 108, blood outlet pressure sensor 106, and venous blood pressure sensor 102 as well as an air detector 118 that is positioned to detect air in the fresh treatment fluid line 127. The controller 140 is also connected to control each of the arterial blood pump 110, venous blood pump 104, replacement fluid pump 116, supplemental fluid pump 142, and supplemental fluid pump 144, as well the waste line clamp 130.

Note that the waste line clamp 130 could be replaced by any type of valve that selectively halts or permits flow or another pump. Note that the pressure sensors may be of any of a variety of types of pressure sensors used for indicating pressure in a fluid circuit, for example bubble chambers, pressure pods (e.g. U.S. Pat. No. 8,092,414), and the like.

In alternative configurations, instead of treatment fluid pump 128 and waste line clamp 130 being used to halt flow as described below, a waste fluid pump may be provided in the position of waste line clamp 130, which can halt flow by halting rotation. In any of the embodiments, including the present and further embodiments to be described below or described above, any element identified as a line or fluid line (or fluid circuit) could be any type of flow channel including interconnected tubes including pumping tube segments, channels formed in a cartridge (as a pattern of troughs sealed by an overlying welded film), a pattern-welded pair of weldable sheets, a laminated stack of elements that defines flow channels, or any other device that guides the flow of fluid. Any element identified as a pump may be any type of pump or actuator that is volumetric aka, positive displacement type. Such embodiments of lines and fluid lines or fluid circuits may be disposable or otherwise replaceable components that engage pumps, sensors, and actuators of a treatment machine that includes such pumps, sensors, and actuators as identified in the embodiments. Such a machine may be illustrated schematically in the drawings, but not necessarily as a separate component, for example a pump indicated by a single element may include a pump actuator, e.g., a rotor, that works together with a pump tubing segment of a fluid circuit, while both are indicated by a pump symbol schematically in the drawing. Similarly, sensors and clamps are not illustrated separately in all the drawings. Such a machine may be embodied in multiple separate components and may be generally described as having a receiving adapter to allow the connection of a disposable fluid circuit.

The term, receiving adapter, or similar term is an abstraction that may cover all the various mechanisms that permit the operative association between a permanent device and a disposable or replaceable component which together form one of the apparatuses disclosed or claimed. This applies to all the disclosed and claimed embodiments. For example, the drawings described above and below illustrate a system which, when considering that portions are replaceable, indicate the presence of a blood circuit receiving adapter and a medicament (treatment fluid, dialysate, or similar fluid) receiving adapter. The fluid circuits (including blood circuits) may include treatment components as well as portions that engage with sensors and actuators. Again, these comments apply to all embodiments.

Any element identified as a pressure sensor may be a combination of a fluid circuit portion such as a pressure pod or drip chamber and an electronic transducer such as a strain gauge or displacement encoder connected to an element such as a diaphragm that registers pressure. The foregoing elements are well known classes of devices and further elaboration is not needed to permit the skilled reader to develop the details of working embodiments of the described subject matter. Fluids may be supplied from containers such as bags or inline fluid generators such as used in dialysis clinics.

In a treatment operation of blood treatment system 100, arterial blood pump 110 and venous blood pump 104 pump blood or priming fluid in the directions indicated by the respective arrowhead of each pump symbol. They pump at rates controlled by the controller 140 to approximately balance (equivalently, "equalize") the flow of blood in the arterial blood line 139 against the flow of blood in the venous blood line 137 such that a net take-off of fluid (ultrafiltrate) or a net infusion of fluid takes place (which may be called negative ultrafiltrate). The instantaneous rate of ultrafiltrate referring to net loss of fluid by the patient and negative referring to net gain of fluid by the patient) is achieved through control of the total displaced volume by the arterial blood pump 110 relative to the venous blood pump 104. The ultrafiltrate may be established by a predetermined ratio of the flow rates of the arterial 110 and venous 104 blood pumps if the transfer is spread uniformly over the treatment interval or the net ultrafiltrate may be established in a discontinuous manner by varying the ratio of the flow rates of the arterial 110 and venous 104 blood pumps to achieve a cumulative ultrafiltrate. Thus, ultrafiltrate volume is established by the total volume transported by the venous blood pump 104 minus the total volume transported by the arterial blood pump 110 over the course of a treatment. Ultrafiltrate rate may identify the instantaneous difference between the rates of the venous 104 and arterial 110 blood pumps.

The controller 140 may be configured to ensure that the net volume of ultrafiltrate or infused fluid meets a prescribed target which may be stored by the controller 140. The pumping speeds required to achieve commanded flow rates may be determined by the controller 140 using data stored by the controller such as look up tables or formulas. A commanded flow rate refers to the operational property (e.g., shaft speed of a peristaltic pump) that is under directly control of the controller which corresponds more or less accurately to a flow rate, conditions that may vary from those used to establish a transfer function defining the relationship between the operational property and an actual flow rate produced by it. The conditions may include manufacturing variability such as pumping tube segment and fluid line diameter, material properties of the pumping tube segment, pump lubrication, as well as factors that change due to operation history and storage such as distortions, material creep, etc. The ratio of flow rate to pump speed may be presented by stored look-up table data to indicate target pump speeds by a relationship between pressure difference and flow rate.

Treatment fluid 124 is pumped by fresh treatment fluid pump 128 at a predefined rate stored in the controller 140, which rate may be selected to correspond to the blood flow rate. The replacement fluid 120 may be pumped at a rate controlled by the controller 140 by controlling the commanded rate of replacement fluid pump 116. The supplemental fluid 134 may be pumped at a rate controlled by the controller 140 by controlling the commanded rate of supplemental fluid pump 142. The supplemental fluid 132 may be pumped at a rate controlled by the controller 140 by controlling the commanded rate of supplemental fluid pump 144. Any of the replacement fluid 120, supplemental fluid 134, or supplemental fluid 132 are optional and may or may not be included, along with the respective lines and pumps, in alternative embodiments.

Valves or pinch clamps identified anywhere in the current patent application may be of any type. For example, flexible membranes closed over cartridge-embedded ports, electrically actuated pinch clamps employing linear actuators such as solenoid plungers or stepper motor actuators may be used. The particular type of valve mechanism does not limit the disclosed subject matter. Line 136 is present to indicate that in alternative embodiments, the supplemental fluids may enter the arterial blood line 139 upstream or downstream of the arterial blood pump 110.

As indicated above, in any of the embodiments, the fluid balance (net ultrafiltrate volume) resulting from the flows to and from a patient is understood to accrue over a period of time. Thus, although in the embodiments, the controller is described as controlling pumping rates to achieve a fluid balance, optionally offset by a net transfer of fluid to or from the patient (net ultrafiltrate volume), it is understood that the pumping rates need not be constant, define a constant ratio over time, or even define a smoothly varying ratio over time. Since the ultimate goal is to control the total loss or gain of fluid from a patient (net ultrafiltrate volume), pumping rates can establish a variety of rates over time such that the cumulative effect is the target ultrafiltrate volume at the end of the treatment. Rates may be constant or vary step-wise, smoothly, and may result in a temporary gain of fluid by the patient during a portion of a treatment interval and net loss during another portion to achieve a total gain or loss for the entire treatment. For another example, the entire fluid gain or loss can be confined to a single part of the treatment interval. The controller may also limit estimated ultrafiltrate so that overall balance does not exceed a certain volume at a given time. A rate of ultrafiltration may also, or alternatively, be limited by the controller.

Figure 1B:
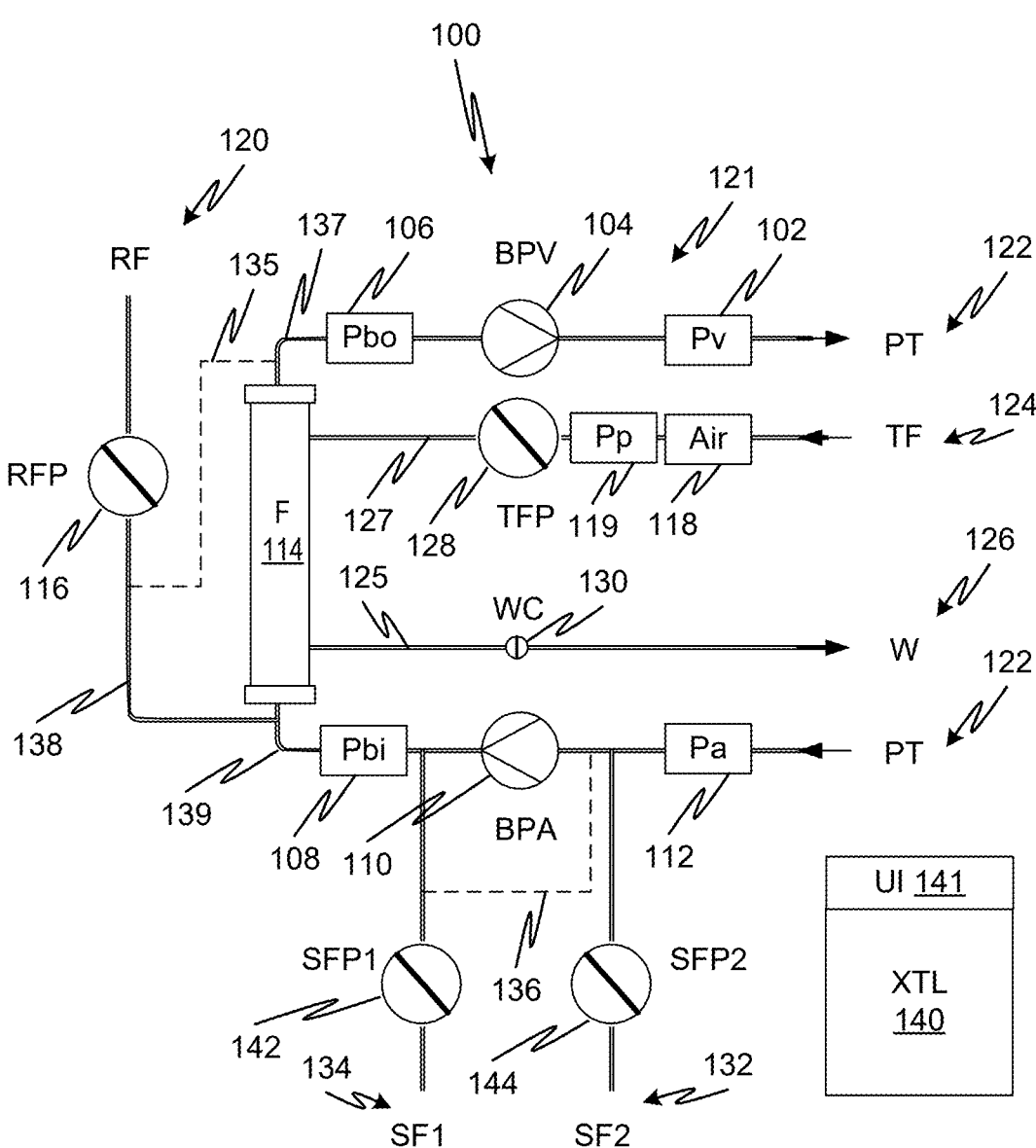
FIG. 1B shows the system of FIG. 1A in a configuration, implemented by the controller, for synchronizing pumps with only one fluid source according to various embodiments of the disclosed subject matter.

FIG. 1B shows the system of FIG. 1A in a configuration implemented by the controller 140 to synchronize the pumps for equal flow while pumping a single fluid, blood or priming fluid 123. At the beginning of a treatment or at times during a treatment (as further discussed later with reference to FIGS. 2A and 2B), a synchronization procedure is performed. The treatment fluid pump 128, the replacement fluid pump 116, supplemental fluid pump 142, and supplemental fluid pump 144 are all held in a halted configuration to block flow (i.e., prevent flow) through a respective line into or out of the treatment device 114. Where non-positive displacement pumps are used, an auxiliary valve, such as a pinch clamp, may be included to prevent flow and in such cases, the combination of the non-positive displacement pump and valve may by identified compactly in the current specification and claims as a pump. The halted flow configuration is indicated by the universal prohibition safety sign (/) over-lying the pump symbols. The waste line clamp 130 is shown closed (again the waste line clamp 130 may be any type of valve). In this configuration, the arterial blood pump 110 and the venous blood pump 104 are directly connected in series such that there exists a fixed volume between the arterial blood pump 110 and the venous blood pump 104.

To perform a synchronization, during a synchronization mode, the arterial and venous blood pumps 110, 104 may be initially commanded to flow at a predefined pump speed corresponding to a commanded flow rate of the blood stored by the controller 140. During preparation for a treatment, this may be done, as indicated elsewhere, using priming fluid rather than blood. It may be done during treatment using blood. The commanded flow rate may be one indicated for a prescription for treatment. The latter may also be directly entered through a user interface 141 of the controller 140. Any differences in the volume flow rates pumped by the arterial blood pump 110 and venous blood pump 104 may be detected from the blood outlet pressure sensor 106, the blood inlet pressure sensor 108, or an average of the two. That is, a rising pressure trend indicates the arterial blood pump 110 is pumping at a higher flow rate than the venous blood pump 104 providing a feedback. Using the pressure signal, the controller may compensate by slaving one of the venous blood pump 104 and arterial blood pump 110 to the other of the venous blood pump 104 and arterial blood pump 110 until the volume rates of the two pumps are equal, i.e., the pumps are synchronized. By "slaving" it is meant that one pump is PID or PD feedback-controlled until the flow is synchronized with that of the other pump. The synchronization may be performed for one, or more than one flow rate. This may be done in this embodiment and others during an initial priming stage. For each flow rate, the relative speeds of the arterial blood pump 110 and venous blood pump 104 that correspond to identical flow rates may be recorded by the controller, for example as a ratio. The ratio corresponding to equal flows may then be compared to a predicted ratio stored by the controller and a control parameter used for future predicted ratios of commanded flow to actual flow may be derived and stored by the controller 140 for using during treatment. Other data structures to allow the controller 140 to determine and command one of the arterial blood pump 110 and venous blood pump 104 speed to be selected for a speed of the other calculated to provide a commanded flow rate of blood.

Note that in the foregoing embodiment, instead of blocking flow in the treatment fluid lines and synchronizing blood pumps, a system may balance flow using the treatment fluid pumps. In such a system, the flow of blood may be blocked forming a fixed volume channel between the treatment fluid pumps for synchronization. The procedure for this embodiments would be analogous.

Note that in all embodiments, a synchronization operation performed during a synchronization mode as described according to one embodiment above may provide a control parameter for treatment without fully synchronizing the pumps. That is, the controller 140 can determine from the dynamic response of the pressure and commanded flow rates, sufficient information to extrapolate the control parameter. This may save considerable time during a synchronization mode that is implemented during treatment. Thus, a dynamic hydraulic model of the flow system may provide a number of equations whose unknown parameters can be fitted using the pressure and flow rate signals over a period of time which is insufficient to establish equal flows of the pump but sufficient to estimate the control parameter for improving the equal flow estimate during a treatment. There are many choices for a dynamic model depending on the conditions and level of accuracy required. An unsteady hydrostatic model may be sufficient if pumping rates are so low as to produce low flow resistance. Factors such as flow resistance can be incorporated using steady state equations and time-varying flow for rheological fluid and non-rheological fluids may be used)

The synchronization mode operation of FIG. 1B may be triggered by various indications that may be automatically detected by the controller 140. For example, one trigger may be a command received from the user interface 141 to provide an ultrafiltrate volume that corresponds to an average or instantaneous ultrafiltration rate that exceeds a predefined magnitude. For example, the ultrafiltration rate may be recalculated to achieve an ultrafiltrate volume based on a remaining treatment time. The rate may correspond to rates of pumping of the arterial blood pump 110 and the venous blood pump 104 of a certain magnitude. The trigger point for implementing the synchronization mode may be stored as a predefined difference between the commanded pumping rates or a ratio thereof. Alternatively, numerical bounds on absolute or relative ultrafiltration (infusion) rate may be stored and applied by the controller 140. When the blood treatment system 100 is commanded to operate beyond those bounds, the synchronization mode may be implemented. The synchronization mode may be implemented with the additional flows of replacement fluid 120, supplemental fluid 134, and/or supplemental fluid 132 as discussed below.

In a preferred embodiment, the synchronization process covers multiple operating conditions and is done during priming. In this embodiment, the control parameters for multiple operating conditions are used to control the system during treatment. The need to perform a synchronization during a treatment can be avoided. However, various trigger conditions may cause the system to perform a synchronization during a treatment.

Figure 1C:
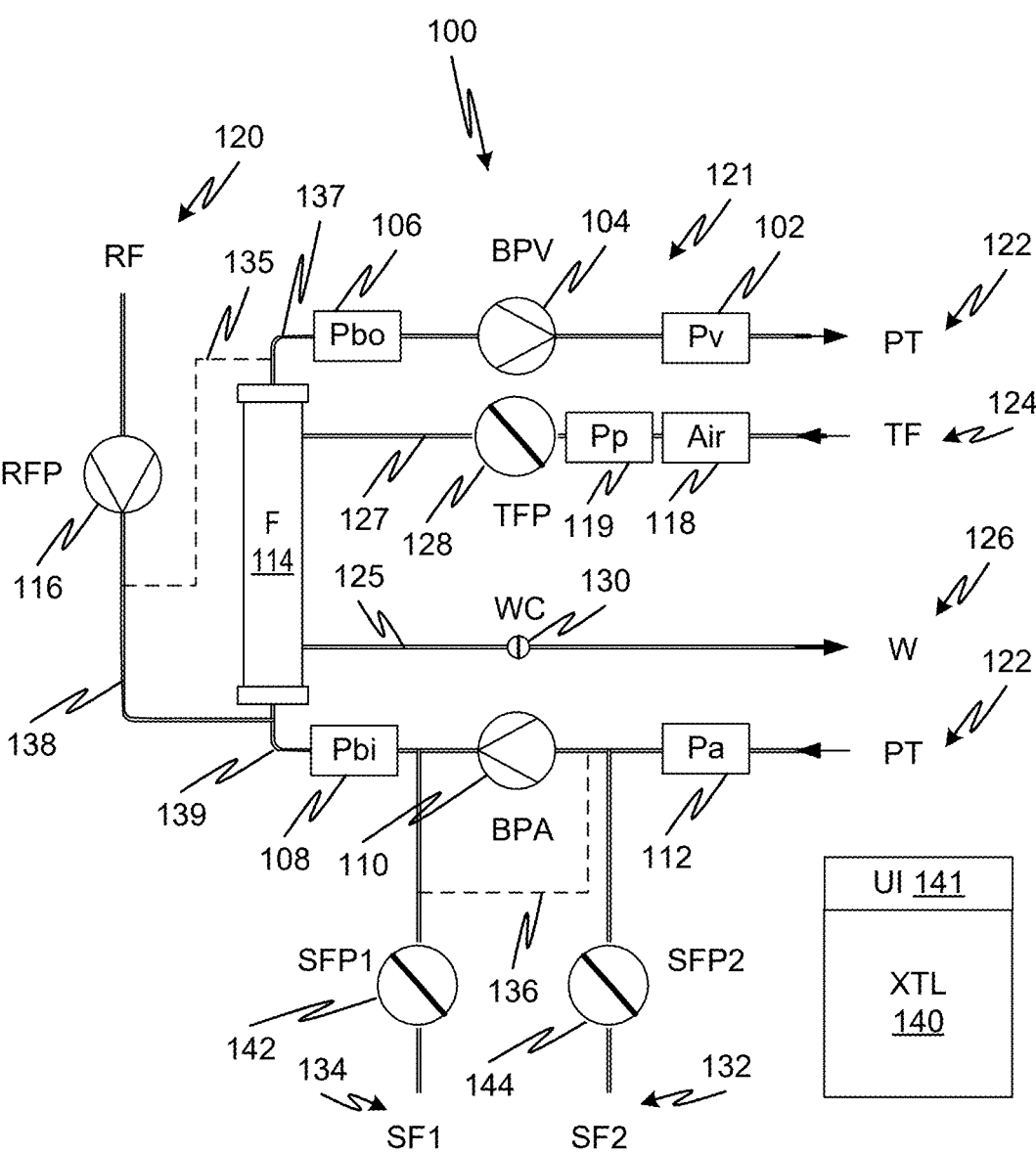
FIG. 1C shows the system of FIG. 1A in a configuration, implemented by the controller, for synchronizing pumps with more than one fluid source according to various embodiments of the disclosed subject matter.

FIG. 1C shows the system of FIG. 1A in a configuration, implemented by the controller, for synchronizing pumps with more than one fluid source. At the beginning of a treatment or at times (determined by trigger events) during a treatment, a further synchronization procedure is performed. The treatment fluid pump 128, supplemental fluid pump 142, and supplemental fluid pump 144 are all held in a halted configuration to prevent flow through a respective line into or out of the treatment device 114. The controller 140 calculates a speed for the venous blood pump 104 and then the controller 140 calculates a flow rate and a pump speed for the operation of each of the replacement fluid pump 116 and the arterial blood pump 110 based on a commanded ultrafiltration rate or infusion rate. The waste line clamp 130 is shown closed (again the waste line clamp 130 may be any type of valve). In this configuration, the arterial blood pump 110 and the replacement fluid pump 116 are connected in series with the venous blood pump 104 such that there exists a fixed volume between the parallel-arranged arterial blood pump 110 and replacement fluid pump 116 and the venous blood pump 104. Thus, the flow through the venous blood pump 104 must match the sum of the flows through the arterial blood pump 110 and replacement fluid pump 116 in order for the pumps to be synchronized.

To perform a synchronization, the pumps may be initially commanded to flow at a predefined pump speed corresponding to a commanded flow rate of the blood stored by the controller 140 and representing a prescription for treatment. The latter may also be directly entered through a user interface 141 of the controller 140. Any differences in the volume flow rates pumped by the arterial blood pump 110 and venous blood pump 104 may be detected from the blood outlet pressure sensor 106, the blood inlet pressure sensor 108, or an average of the two. Using the pressure signal, the controller may compensate by slaving one of the venous blood pump 104 and arterial blood pump 110 toward a matched flow with the other of the venous blood pump 104 and arterial blood pump 110 until the two pump flow rates equalized as indicated by the pressure of the fixed-volume channel. During a synchronization cycle, the replacement fluid pump 116 may be kept at a fixed ratio or a fixed rate of pumping and a slaved one of the arterial blood pump 110 and venous blood pump 104 may be varied until synchronization is achieved or (equivalently) sufficient information is obtained to fit a hydraulic model that can provide the required control parameter. Alternatively, other combinations of the pumps may be halted and/or operated to achieve a relevant target. A PID or PD algorithm, with the pressure signal as a feedback control variable, may be applied by the controller to achieve synchronized pumps. The synchronization may be performed for one, or more than one flow rate. For each, the relative speeds of the replacement fluid pump 116, arterial blood pump 110 and venous blood pump 104 that correspond to identical flow rates may be recorded by the controller, for example as a ratio. Various data structures may be used to store the relevant one or more control parameters to ensure the ratio of speeds of the pumps provides a balance or ultrafiltration rate that is required.

During any synchronization procedures, a target range for venous pressure, as indicated by venous blood pressure sensor 102, may be established. This pressure may be stored by the controller 140 and have a predefined magnitude that is selected based on safety or other operational requirements.

Pumping rates may be commanded and regulated to achieve the target venous pressure. During any of the synchronizations and/or during treatment, a predefined flow rate of the supplemental fluid pump 142 and supplemental fluid pump 144 may be established according to prescription. The rates of the supplemental fluid pump 142 and supplemental fluid pump 144 may be imposed by controlling the corresponding pump speeds based on a predefined commanded rate. Generally, the supplemental fluid pump 142 and supplemental fluid pump 144 will not contribute sufficient volume to be relevant to include in fluid balance and thus synchronization may not take their contributions into account. However, this may or may not be the case.

Synchronization may be performed to provide accurate reproduction of balanced flow any time the operational configuration changes or will change, including when new fluid circuits are installed, a new treatment is begun, the flow rates are changed, a flow characteristic of a fluid circuit component (such as flow restriction of a flow element, the patient access, or treatment device) changes, or the commanded characteristics of a treatment are changed. In particular, the synchronization of pumps that contribute significantly to the balance of fluid of the patient is performed under conditions that are as close as possible to those that exist during treatment so that the synchronization data are valid during treatment. In embodiments, a new synchronization may be indicated by the controller based on variables that are estimated or predicted rather than directly measured. For example, the compliance of materials may change with time and/or temperature, for example pumping tube segments of peristaltic pumps. So the lapse of time may be used as a proxy for an indication of material changes. A pause in the operation of a machine, for example an alarm stoppage, may be a trigger for a synchronization mode immediately after restart.

Figure 2A:
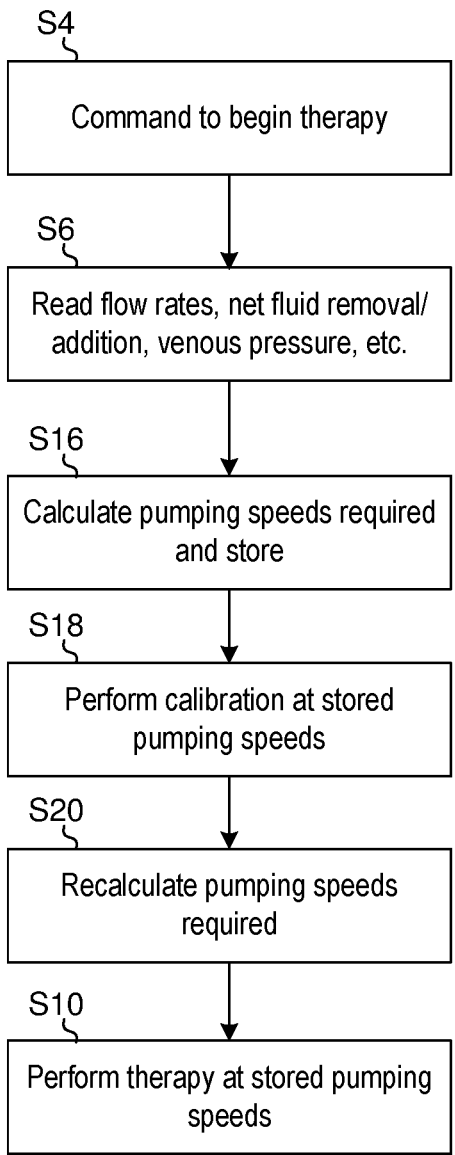
FIG. 2A shows a flow chart of a control method for delivering a treatment while providing balanced flows of independently-controlled pumps where two pumps, an inlet and outlet, are balanced according to various embodiments of the disclosed subject matter.

FIG. 2A illustrates an operating scenario. A command is received by the controller 140 at S4 to begin a treatment. The command may be entered through a user interface operated by the patient, caregiver, or clinician, or it may be received from a remote or local operator directly or indirectly through the user interface 141. At S6, the controller 140 reads prescription data from a data store, which may include user profile information, data about prior treatments and other information. At S16, the pumping speeds required to achieve the commanded flow rate are calculated for each pump based on stored data. Then at S18, the pumps are run and synchronized as described. When the synchronization is achieved, the data that permits the calculation of pump speeds from commanded flow rates are stored and then used at S20 to calculate the pump speeds for the treatment which is performed at S10.

Figure 2B:
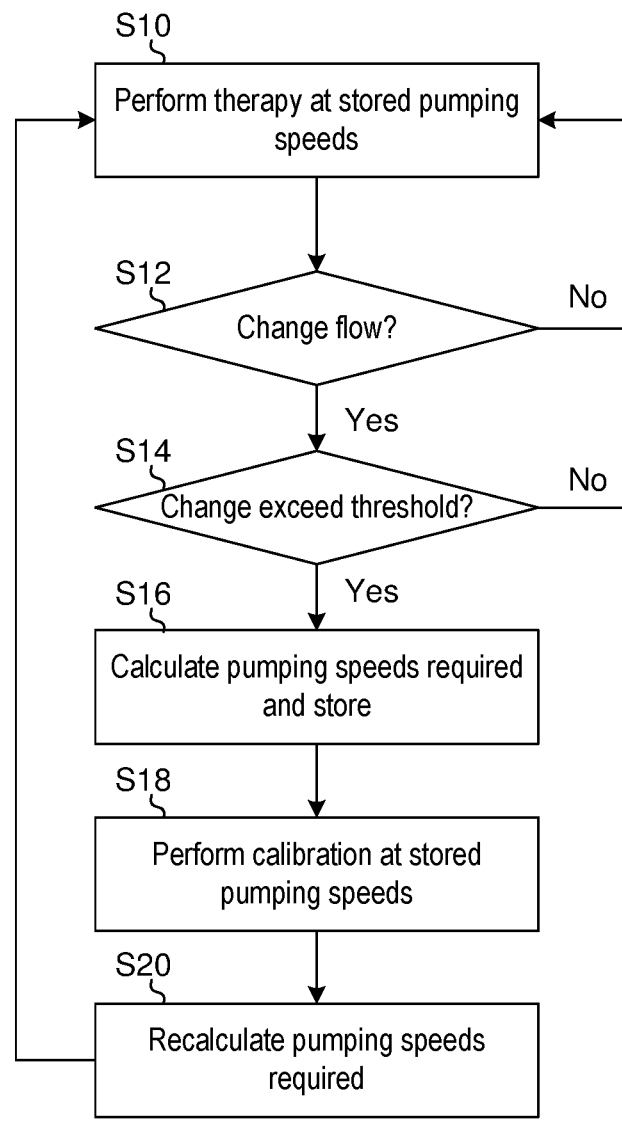
FIG. 2B shows a flow chart of a control method for delivering a treatment while providing balanced flows of independently-controlled pumps where multiple inlet pumps are balanced against one outlet pump according to various embodiments of the disclosed subject matter.

Referring now to FIG. 2B, at S10 (continued from FIG. 2A), before treatment or at any time during a treatment if conditions change such as a commanded change in flow rate as indicated at S12, the controller 140 may determine if a threshold of the flow change exceeds a predefined range at S14. If such an event is determined by the controller and the controller may perform a new synchronization procedure to generate updated control parameter for calculating pump speeds from commanded flow rates as described above. At S16, the pumping speeds required to achieve the commanded flow rate are calculated for each pump based on stored data. Then at S18, the pumps are run and synchronized as described. When the synchronization is achieved, the data that permits the calculation of pump speeds from commanded flow rates are stored and then used at S20 to calculate the pump speeds for the treatment which is performed at S10.

As indicated above, any change in conditions or a programmed lapse of time or other condition at S12 may indicate a candidate for resynchronization. For example, at S12, venous pressure rise to a predefined level may cause the controller to self-command a flow rate reduction. An operator command may indicate a change in flow rate or a change in hemofiltration rate. An operator command to reduce treatment time may require the controller to calculate new flow rates and attending new synchronization. The controller may store product-specific parameters such as the fluid circuit materials or product identifier which may in turn indicate schedule of resynchronization. This may allow the system to compensate for materials with known material property drift which can cause inaccuracy in net fluid balance over the course of a treatment. Such compensation may take the form of more frequent pre-schedule resynchronizations of the flow rate-to-pump speed data using pump synchronization as described.

Note that the system of FIGS. 1A-1C can be modified to place a line clamp like waste line clamp 130 in place of the venous blood pump 104 and using a pump on the waste treatment fluid line 125. In that case, fluid balancing can be done on the medicament side rather that the blood side. The fixed volume channel can be implemented for synchronization by clamping the blood line and stopping the blood pump. In other respects, the system may operate as described above.

Figure 3A:
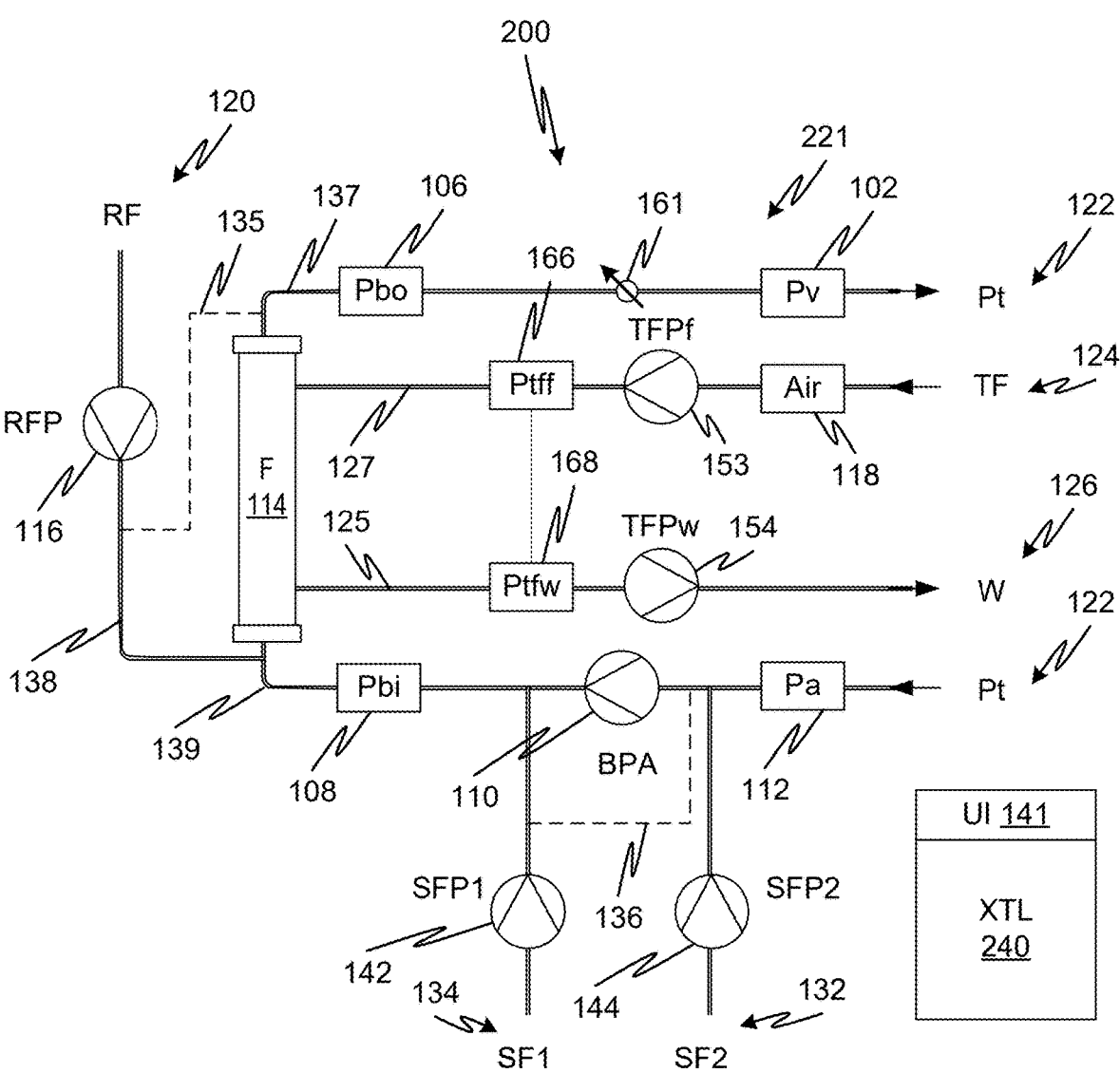
FIG. 3A shows a flow of a blood treatment system that regulates the flow of treatment fluid into and out of a treatment device to generate a cumulative target ratio of fluid drawn or infused into a patient over the course of a treatment, according to various embodiments of the disclosed subject matter.

FIG. 3A shows a flow a blood treatment system 200 that regulates the flow of treatment fluid relative to generate a cumulative target ratio of fluid drawn or infused into a patient 122B over the course of a treatment. The blood treatment system 200 regulates the flow of fluid in a fluid circuit 221 that includes an arterial blood line 139, a venous blood line 137, a fresh treatment fluid line 127 and a waste treatment fluid line 125. The net flow of fluid into or out of a patient or priming source/sink, at any given time, is determined by a current difference between the volume of treatment fluid pumped from treatment device 114 (labeled F for filter) to the volume pumped into the treatment device 114 plus the volume pumped into the blood lines. Fluid (blood or priming fluid) is pumped from a source (e.g., patient 122B or priming fluid 123—see later embodiments 3B et seq) into the treatment device 114 by an arterial blood pump 110 and flows from the treatment device 114 back to the patient 122B or priming fluid sink, drain, collection container, or recirculating container. As discussed elsewhere, for synchronization, the patient may be a priming fluid source/sink. For example, it may be a container of priming fluid to which priming fluid is returned thereby allowing endless recirculation and functioning as both source and sink of fluid. The illustrated configuration is common for dialysis systems, and may include all the typical incidents thereof, but differs specifically in that there are two treatment fluid pumps: a fresh treatment fluid pump 153, which pumps fresh treatment fluid 124 into the treatment device 114, and a waste treatment fluid pump 154, which pumps waste (spent) treatment fluid from the treatment device 114 to a drain 126. As above, control and sensing are provided by a controller 240 which may be of any form and again, typically, a programmable digital controller; an embedded computer. Treatment fluid 124 is pumped from a source through an air detector 118 through the treatment device 114, to the drain 126.

A replacement fluid 120 may be pumped into the arterial blood line 139 or the venous blood line 137 through a replacement fluid line 135 or 138, respectively (or both) for predilution, post-dilution. In alternative embodiments, the dilution may occur at a midpoint of the treatment device 114 as discussed above. The treatment device 114 may be adapted for any type of blood treatment including, but not limited to, dialysis, hemofiltration, hemodiafiltration, apheresis, adsorption, and hemoperfusion. Further supplemental fluids indicated by supplemental fluid 134 and supplemental fluid 132 may be pumped into the arterial blood line 139 by respective pumps, namely, supplemental fluid pump 142 and supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the arterial blood line 139 upstream of the arterial blood pump 110. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 110 and downstream of the treatment device 114. A venous blood pressure sensor 102 may detect pressure in the venous blood line 137 downstream of the venous blood pump 104 and upstream of the patient access 122A. A fresh treatment fluid pressure sensor 166 indicates the pressure of treatment fluid downstream of the fresh treatment fluid pump 153 and a waste treatment fluid pressure sensor 168 indicates the pressure of waste treatment fluid upstream of the waste treatment fluid pump 154. The controller 240 receives signals from each of the arterial pressure sensor 112, blood inlet pressure sensor 108, blood outlet pressure sensor 106, and venous blood pressure sensor 102, the fresh treatment fluid pump 153, the waste treatment fluid pump 154, as well as an air detector 118 that is positioned to detect air in the fresh treatment fluid line 127. The controller 240 is also connected to control each of the arterial blood pump 110, replacement fluid pump 116, the supplemental fluid pump 142, the supplemental fluid pump 144, the fresh treatment fluid pump 153, and the waste treatment fluid pump 154. In embodiments, each pump contributing to flow balance may have a pressure sensor upstream of it to ensure that pressure compensated control of its speed can be provided. For example, an additional treatment fluid pump pressure sensor 119 shown in FIGS. 1A-1C may be provided here and in any embodiments as well. In embodiments, pressure sensors used for pressure compensated speed control are positioned such that they provide a reliable and consistent indication of pressure upstream of the respective pump or pumps. Thus, they may be positioned close or at least such that there are no intervening possible interferences such as tube lengths that could become kinked.

The blood treatment system 200 may also differ from a conventional system in having a controllable flow restrictor 161 that is controlled by the controller to regulate flow resistance in the venous blood line 137. The controllable flow restrictor 161 may be of any description. For example, it may be a progressive valve controlled by a servo or stepper motor. It may be a variable pinch clamp operatively engaged with a tubing length. It may be multiple fixed flow restrictors interconnected by a manifold that has valves to select a particular of the multiple flow restrictors.

In a treatment operation of blood treatment system 200, fresh treatment fluid pump 153 and waste treatment fluid pump 154 pump in the directions indicated by the respective arrowhead of each pump symbol, pump at rates controlled to balance the flow of blood in the arterial against the flow in the venous such that a net take-off of fluid (ultrafiltration) or a net infusion or ultrafiltration of fluid takes place as calculated by the controller 240 or per a command received by the controller 240. The instantaneous rate of ultrafiltration or infusion may vary during the course of a treatment. The controller 240 may be configured to ensure that the net level of ultrafiltrate or infused fluid meets a prescribed target which may be stored by the controller 240. The pumping speeds required to achieve commanded flow rates may be determined by the controller 240 using data stored by the controller such as look up tables or formulas. The ratio of flow rate to pump speed (equivalently, the commanded flow rate) may be presented by this stored data to indicate target pump speeds in a relationship between pressure difference across the pump as well as flow rate; the pump curves. For example, in any of the embodiments, a look up table may have cells with pump speeds where columns and rows correspond to the independent variables of pressure at the pump inlet (or pressure differential across the pump for non-peristaltic pumps) and flow rate. Operating points may be interpolated or extrapolated for operating conditions that lie between or outside those corresponding to the cells or the formula or look-up table may provide interpolated or extrapolated values.

Note that in this or any of the embodiments, including those defined by the claims, the ratio of commanded pump speed to estimated flow may be given by a pump curve that is based on inlet pressure rather than outlet-inlet pressure difference depending on suitability for the type of pump used.

Treatment fluid 124 is pumped by fresh treatment fluid pump 128 at a predefined rate stored in the controller, which rate may be selected responsively to the blood flow rate or according to prescription. The replacement fluid 120 may be pumped at a rate controlled by the controller 240 by controlling the rate of replacement fluid pump 116. The supplemental fluid 134 may be pumped at a rate controlled by the controller 240 by controlling the pumping rate of supplemental fluid pump 142. The supplemental fluid 132 may be pumped at a rate controlled by the controller 240 by controlling the rate of supplemental fluid pump 144. Any combination of the replacement fluid 120, supplemental fluid 134, or supplemental fluid 132 may be included, or none of these. Each may be included or not along with the respective lines and pumps, in alternative embodiments. Flow control valves may be of any type as indicated above. As before, line 136 is present to indicate that in alternative embodiments, the supplemental fluids may enter the arterial blood line 139 upstream or downstream of the arterial blood pump 110.

Figure 4A:
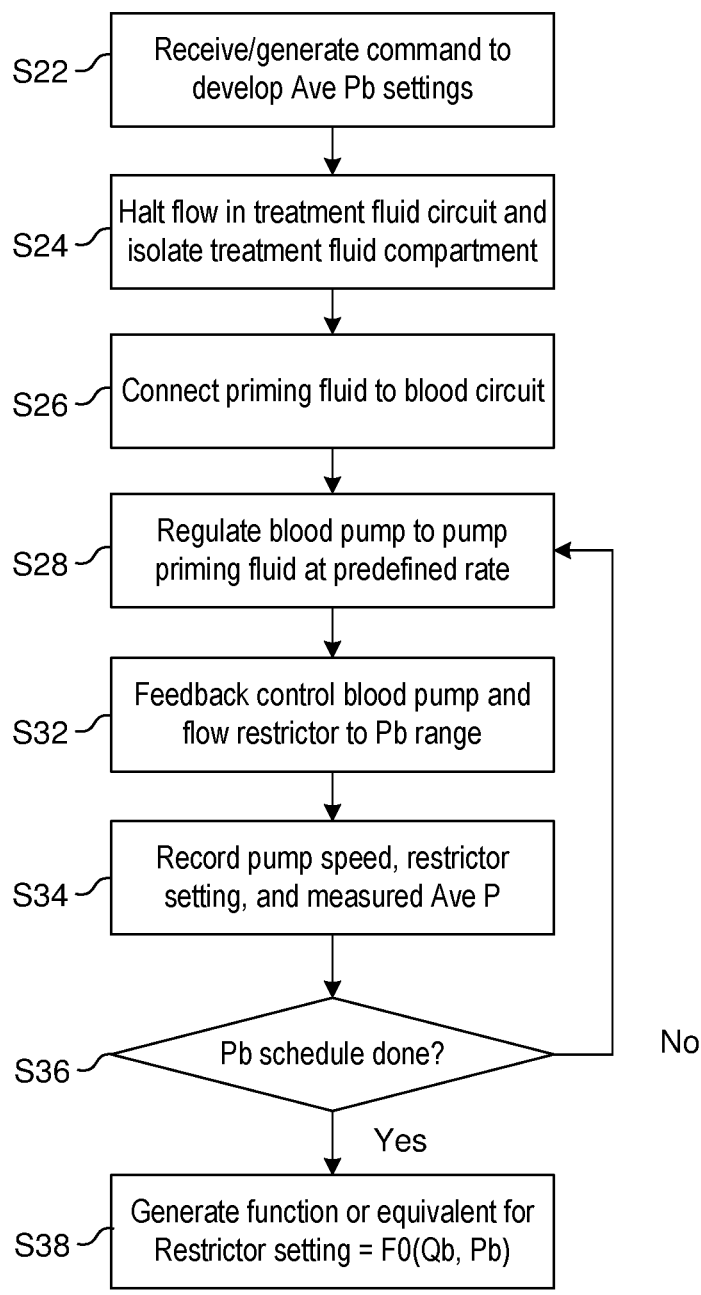
Figure 4C:
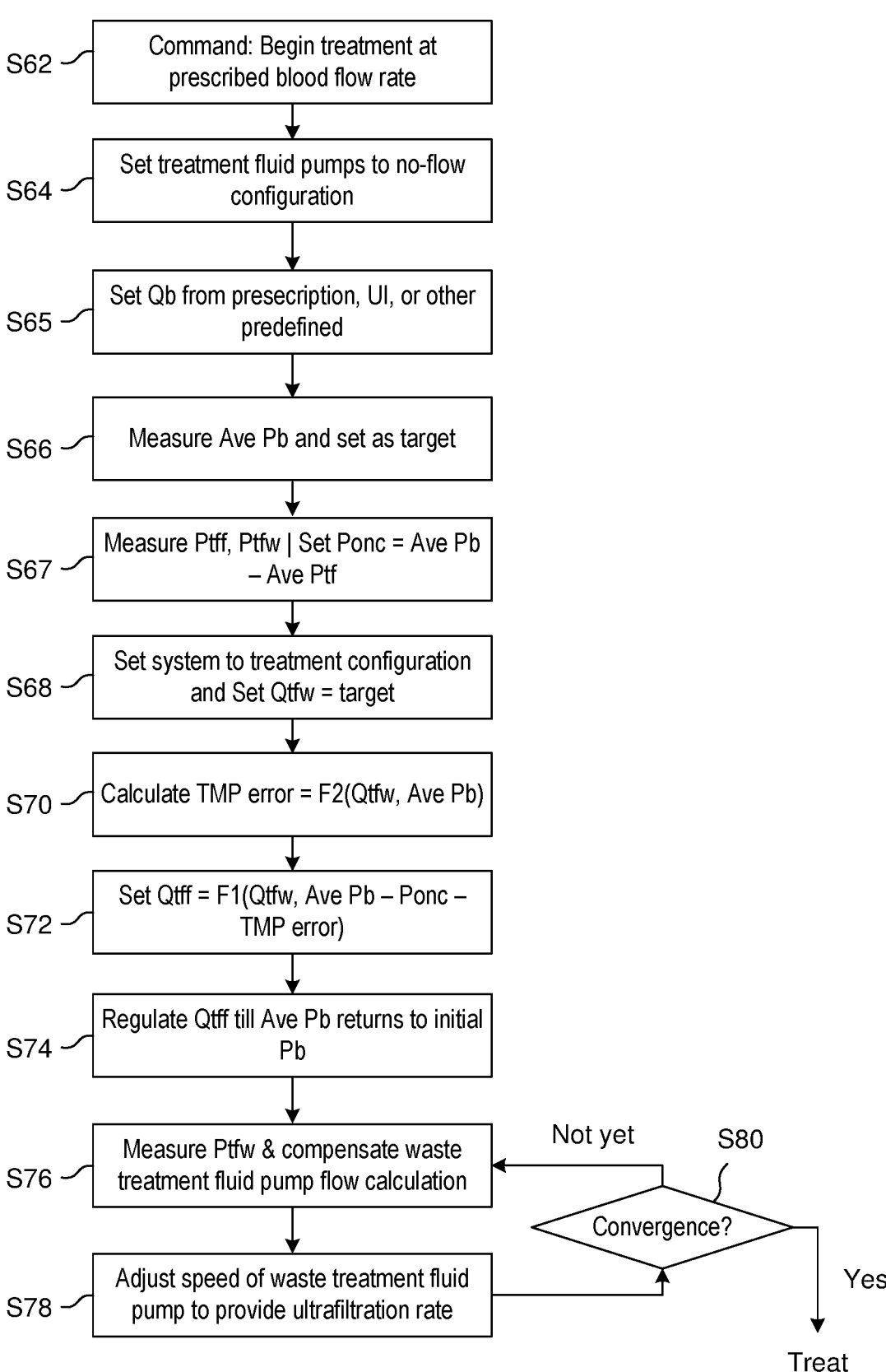
Figure 4D:
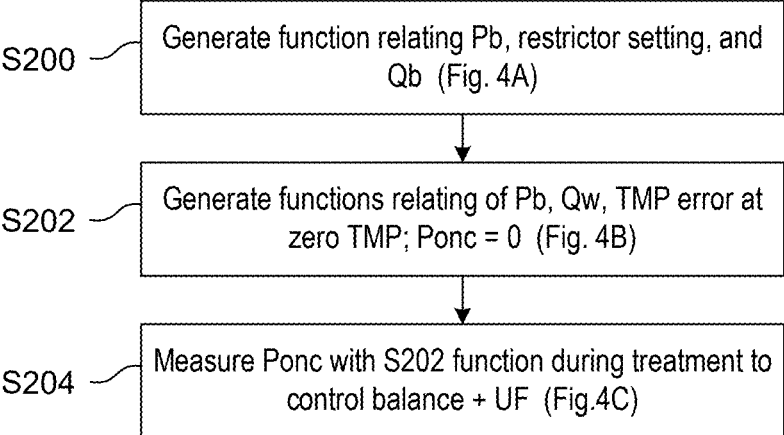

Referring now to FIG. 4D, which shows an overview of a method to be described below with reference to FIGS. 4A through 4C, for establishing and maintaining a condition of fluid balance by fresh treatment fluid pump 153 and waste treatment fluid pump 154 during a treatment based on the measurement of pressures on the treatment device 114 during a treatment. In a first stage S2, the controller determines flow rates and settings of controllable flow restrictor 161 and arterial blood pump 110 that establish a given average blood side pressure in treatment device 114. The process loops through a schedule of predefined blood side pressures each indicated by an average of readings from blood outlet pressure sensor 106 and blood inlet pressure sensor 108 Ave Pb and flow rates of waste treatment fluid pump 154 Qb commanded by the controller 240. For each combination and flow Qb and pressure Ave Pb, the controller 240 determines, through error control, a position of controllable flow restrictor 161 (restrictor setting) that establishes the given blood side pressure. A function or equivalent is finally generated to provide the restrictor setting as a function of Qb and Ave Pb. This function is then used in a following step S202 to generate functions that indicate a command flow rate for fresh treatment fluid pump 153 given a command flow rate of waste treatment fluid pump 154 and a blood side pressure Ave Pb.

At S202, the controller 240 loops through combinations of command flow rates of waste treatment fluid pump 154 and blood side pressures Ave Pb and determines a command flow rate of fresh treatment fluid pump 153 at which the treatment device 114 blood compartment pressure Ave Pb is maintained. This condition corresponds to zero convection between the blood and treatment fluid compartments. Any difference between average blood compartment pressure and average treatment fluid compartment pressure may be taken as a systematic error in pressure difference. A function or equivalent may be fitted to estimate the fresh treatment fluid pump 153 and error from a given commanded (prescribed, during treatment) flow rate of the waste treatment fluid pump 154 (taken as a desired or prescribed treatment fluid flow rate) and measured blood compartment pressure Ave Pb for a prescribed blood flow rate during a treatment. This fresh treatment fluid pump 153 rate will then correspond to zero flow in the absence of any oncotic pressure as existed during the procedure of S202 using fluids having the same osmotic potential such as the treatment fluid and priming fluid, for example. Note that both fluids can be the same fluid for the procedures of S200 and S202.

At S204, a treatment is performed in which the treatment device 114 blood compartment is filled with blood. In this case, the pressure difference between the blood and treatment fluid compartments Ave Pb and Ave Ptf are measured and stored to represent a difference caused by oncotic pressure due to the composition of blood. The oncotic pressure and error calculated from the function generated at S202 are used to determine a balanced flow rate Qtff of the fresh treatment fluid pump 153 given prescribed blood and treatment fluid flow rates during treatment. The process of flow chart of FIG. 4D summarizes the processes of flow charts 4A through 4C as indicated in each operation S200-S204 of FIG. 4D.

As shown further below, the of FIG. 4D is used for determining the fresh treatment fluid pump 153 and waste treatment fluid pump 154 flow rates for achieving a desired target fluid balance of the patient (net removal or infusion of a volume of fluid) through the maintenance of a target ratio and total displacement of these pumps. The method may be extended to account for the contribution of other sources of fluid, such as replacement fluid pump 116.

Figure 3B:
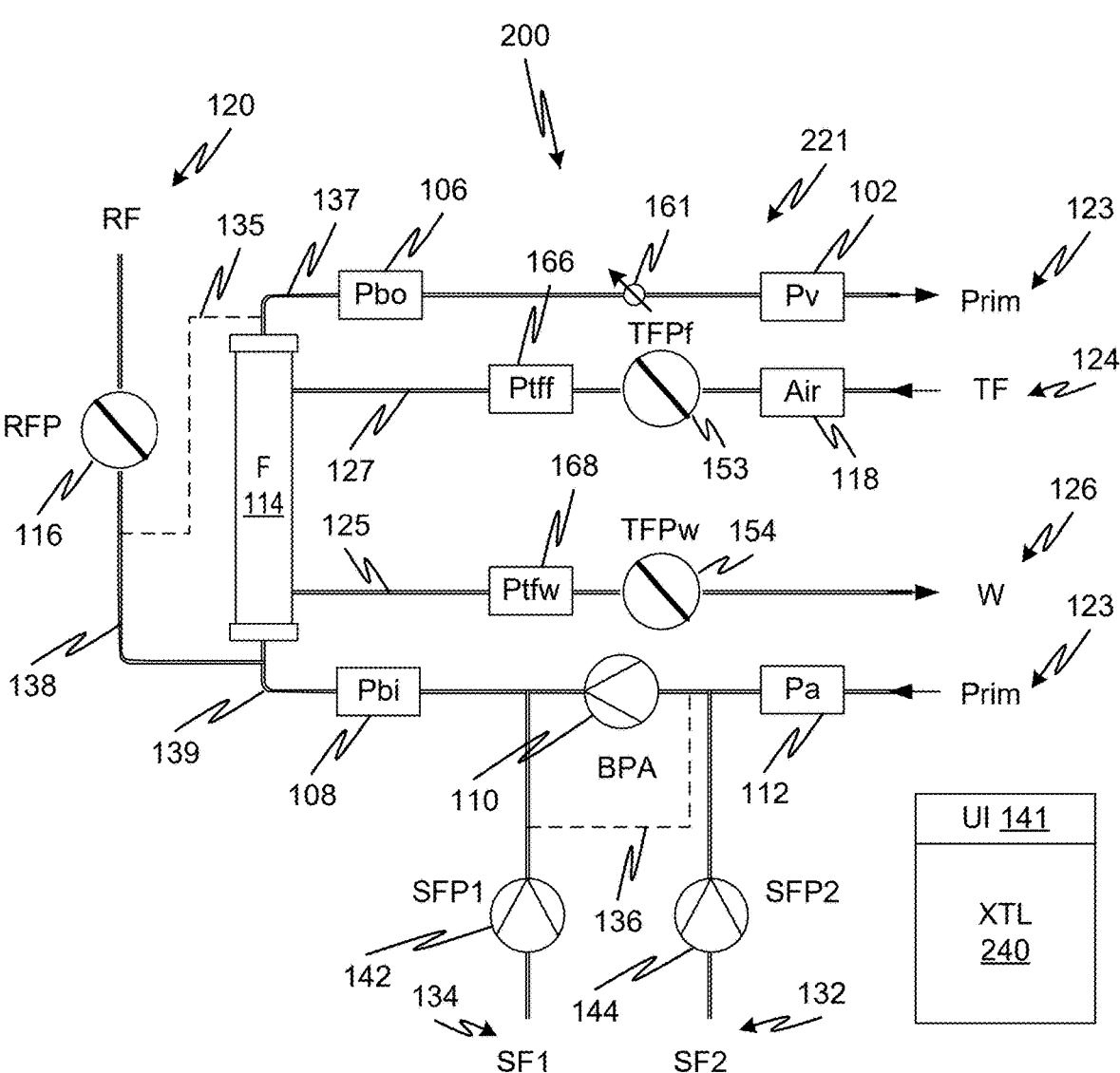
FIGS. 3B through 3E illustrate configurations of the blood treatment system of FIG. 3A at various phases of a synchronization sequence according to embodiments of the disclosed subject matter.

FIGS. 3B and 4A illustrate a configuration and operation of the blood treatment system 200 for determining conditions for the establishment of target fluid pressure Pb, typically priming fluid, on the blood side of the treatment device 114. Initially, before the establishment of the treatment fluid no-flow condition illustrated in FIG. 3B, the treatment fluid compartment of treatment device 114 would be filled in a priming operation. This may be done in a variety of ways including initially pumping treatment fluid or priming fluid through the waste treatment fluid line 125 and fresh treatment fluid line 127 and thereby through the treatment device 114. Then the configuration of FIG. 3B is established and the procedure of FIG. 4A is performed.

At S22 a command is received, or generated, by the controller 240 to begin a process for determining combinations of blood pump speed settings and/or flow restrictor settings selected to produce a predefined schedule of average blood pressure in the treatment device 114 during treatment operations which setting permit the establishment of a desired ultrafiltration rate.

See Table 1 infra. At S24, fresh treatment fluid pump 153 and waste treatment fluid pump 154 are halted. In further embodiments, the treatment fluid compartment of the treatment device 114 may be isolated, or further isolated, by closing control valves (not shown) such as pinch clamps, rather than shutting off pumps. In embodiments, the pumps are peristaltic pumps that occlude the line such that they prevent flow when halted. The halting of the fresh treatment fluid pump 153 and waste treatment fluid pump 154 is effective to block flow through, or from, the treatment fluid compartment of the treatment device 114 thereby isolating it except for a membrane of the treatment device. A source of priming fluid is connected S26 and the blood pump operated to establish a priming fluid flow in the blood compartment (blood side) of the treatment fluid device. Preferably priming fluid is provided in a container so that a recirculating flow can be established. During the priming operation, normally incident to the set-up of a blood treatment, a table of treatment fluid flow rates vs pressures is filled out as described below. An example is shown in Table 1. During the priming, the venous blood line 137 and arterial blood line 139 may be connected to priming fluid 123 recirculating through a container (not shown separately). The priming fluid 123 can come from an inline source or a container for single-pass to a drain. Other arrangements for achieving flowing or recirculating priming fluid in the blood circuit of a blood treatment device are known and any of these may be implemented in any of the disclosed embodiments.

TABLE 1

| Schedule of flow rates and pressures for estimating restrictor setting | | | |
| --- | --- | --- | --- |
| Command Qb (ml/min) | Command Ave Pb (mmHg) | Measured Ave Pb (mmHg) | Measured Restrictor setting |
| 50 | 100 | 100.14 | AU |
| 50 | 250 | 250.59 | AU |
| 50 | 400 | 400.08 | AU |
| 200 | 100 | 100.89 | AU |
| 200 | 250 | 251.54 | AU |
| 200 | 400 | 398.71 | AU |
| 400 | 100 | 98.72 | AU |
| 400 | 250 | 248.46 | AU |
| 400 | 400 | 398.15 | AU |

At S28, after the controller 240 has implemented the above conditions it controls the arterial blood pump 110 to a predefined speed (working through each row in the table) and then at S32, modulates the speed of the blood pump and the adjustment of controllable flow restrictor 161 to achieve predefined pressure (second column of Table 1) of the priming fluid in the treatment device 114 as indicated by an average of the pressures in the venous blood line 137 and arterial blood line 139: Pba and Pbv, the average being denoted as Ave Pb. This is done in accord with a first pressure value in a schedule as illustrated by example in Table 1 (column 2). The regulation proceeds in a feedback control operation until the target Ave Pb is at least approximately established. The arterial blood pump 110 rate and setting of the controllable flow restrictor 161 that provides approximates the target predefined pressure on the treatment device 114 blood side (Ave Pb) may be recorded at S34. Also recorded is the actual measured value of the blood side pressure Ave Pb and the pumping rate Qb required to achieve that blood side pressure Ave Pb. The combination of blood pump rate and controllable flow restrictor setting are later used to establish an Ave Pb for the treatment filter represented in Table 1. The restrictor settings depend on the type of flow restrictor and may be, for example, steps or resistance of an encoder, force, or other unit. After The third through fifth column is generated, the data may be fit to a function or function-equivalent that relates the Ave Pb to the restrictor setting and blood pump flow rate. This process may be done at the beginning of a treatment or it may be performed for each configuration of the treatment apparatus and provided to the controller for use over multiple treatments.

The targeted set of Ave Pb may be selected to cover a realistic range of variability during a treatment when blood is flowing simultaneously with the treatment fluid. Table 1 shows as an example of such targets (100, 250, and 400 mmHg) that is suitable for a dialysis system but not generally limiting of the disclosed subject matter. The treatment device 114 blood side pressure may be taken by the controller 240 as an average of the pressures indicated by blood outlet pressure sensor 106 and blood inlet pressure sensor 108 which the controller 240 may calculate. The blood side pressure may also be taken as one or the other or some weighted average of the indications of the blood outlet pressure sensor 106 and blood inlet pressure sensor 108 which corresponds to a type of filter being used. The controller 240 may predict the arterial blood pump 110 speed corresponding to fixed target flow rate, vary the resistance or fix the resistance and vary the arterial blood pump 110, or vary both. The procedure repeats at S36 until all the target Pb values are established and the pump and restrictor settings determined and recorded. In the table, three Ave Pb values are generated and the settings required to achieve them recorded. At S38, a look-up table or formula is generated from the Ave Pb and the pump speed and flow restrictor settings so that they can be reestablished from the settings during a further synchronization operation and during treatment.

Figure 3C:
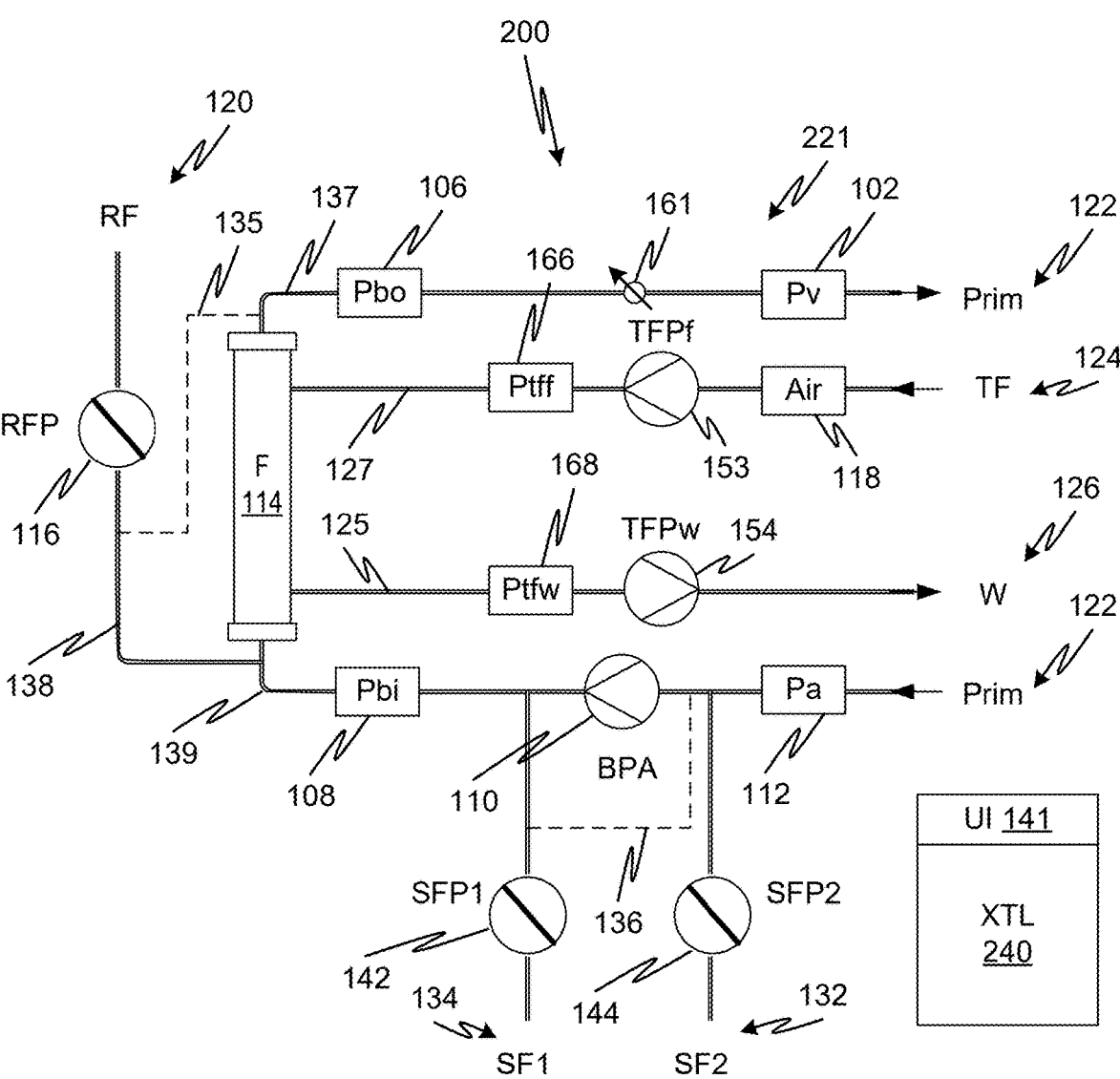

Referring now to FIGS. 3C and 4B, at S39 a command is received by the controller 240, or generated by it, to develop data that provides functions allowing blood treatment system 200 controller 240 to estimate pump settings for treatment. The command initiates the present procedure. See Table 2. The blood flow rate Qb and Ave Pb are the same as the schedule from the first two columns of Table 1. These represent target blood side flow rate Qb and pressure Ave Pb. The restrictor setting for each target blood side flow rate Qb and pressure Ave Pb is calculated from the function calculated at S38. However, the input for the Ave Pb is the measured input rather than the target. Since the function provides a restrictor setting that will provide a given flow rate and blood side pressure, there is no need at this point to feedback-regulate the restrictor setting to obtain the predefined Ave Pb. However, in other embodiments, this may be done and the derivation of the function for restrictor setting can be skipped.

Note that although the pressures of the dialysate and blood compartment are taken to be a combination (such as an average) of the values indicated by the pressures at the inlet and outlet pressure sensors for the respective compartment, it is possible to provide a pressure sensor on the blood treatment device, at least in some embodiments thereof, to measure a midpoint pressure directly. In a microtubular fiber-type dialyzer, for example, this could be done for the dialysate side by fitting a pressure measurement pod or tap on the dialyzer housing to measure dialyzer compartment pressure, but would be difficult for the blood compartment which is divided among multiple small channels. It is also possible to employ models of the pressure drop over the length of the blood treatment device to obtain a curve of pressure vs. displacement so that the average is a weighted average. Blood pressure may be taken from the treatment fluid compartment if the oncotic pressure is known. As disclosed herein, at any time, the oncotic pressure may be determined directly so that the controller can store the oncotic pressure and calculate the blood compartment pressure from the treatment fluid compartment pressure based on the oncotic pressure. A model can similarly be used if the convective flow exists between the blood and treatment fluid compartments (e.g., transmembrane flow) to allow the controller to numerically compensate for pressure difference caused by flow between the blood and treatment fluid compartments. Additionally, in embodiments, the pressure of the blood or treatment fluid compartment may be taken as one of the respective inlet and outlet pressures. This estimate can be refined based on a predefined hydraulic model that accounts for the pressure drop within the blood treatment device.

The parameters generated in the method of FIG. 4A and fitting of the function at S38 can be done once for multiple treatment cycles as when the configurations are the same and therefore the parameters are applicable to a current treatment cycle. This saves time during the priming operation at each treatment for the operation of FIG. 4B. At a point in the priming operation, a treatment apparatus, in priming mode, with the blood circuit filled with priming fluid and connected to recirculate (or otherwise permit the passage of priming fluid through it), a command is generated at S39 to perform a synchronization operation as now described. In S40, the blood circuit is isolated from the treatment fluid circuit.

thereby (See S56 infra) is still valid for use during a treatment. For example, fluid circuit itself may be the same. However, it is advantageous that it be done immediately prior to treatment because wetting the fluid circuits and letting them stand, especially if portions are compressed by control valves and pumping actuators, may make the conditions during treatment different from those during the synchronization process and thereby reduce the applicability of the function fit at step S56 during treatment.

The regulating to achieve an actual ith value in the schedule of Ave Pb values does not require high precision and an approximation sufficient to ensure that a variety of conditions are obtained and used to fit an estimation function at S56 may be used. A value that is close may be determined by comparison of a current measured Ave Pb (indicated by the average of blood outlet pressure sensor 106 and blood inlet pressure sensor 108) with a stored range of errors may be used by the controller 240 to indicate that the current actual measured Ave Pb is close enough to the ith value of Ave Pb stored in the schedule. At that point, at S42, the actual Ave Pb determined from the average of (Pbv) blood outlet pressure sensor 106 and (Pba) blood inlet pressure sensor 108 may be stored in the data table subsequently to be used for the fitting of a predictive function or function-equivalent. Note that in further embodiments, values of the blood inlet and outlet pressures themselves may be stored. Also, the average may represent a weighted average rather than a simple average that is indicated for the particular type of treatment device. The sparse data may be fitted to a smooth function to allow estimation of commanded flow rates for conditions during treatment. The table of conditions may be stored after reduction to a function or function-equivalent such as a dense lookup table. They may also be stored in unreduced form as) as raw sparse data and extrapolation and/or interpolation for instant conditions interpolation computed according to treatment conditions. The table may be sparse matrix, that is, not every cell necessarily has a value.

TABLE 2

Schedule of flow rates and pressures for estimating Qtff and TMP error

| Cmd Qb (ml/min) | Target Ave Pb (mmHg) | Calc Restrictor setting | Measured Ave Pb (mmHg) | Measured Ave Ptf (mmHg) | Calc TMP error (mmHg) | Pump setting Qtff (ml/min) | Pump setting Qtfw (ml/min) |
|---|---|---|---|---|---|---|---|
| 50 | 100 | AU | 100.00 | 100.00 | 1.48 | 101.48 | 100 |
| 50 | 250 | AU | 249.00 | 249.00 | 0.06 | 249.06 | 250 |
| 50 | 400 | AU | 401.00 | 401.00 | 0.16 | 401.16 | 400 |
| 200 | 100 | AU | 101.00 | 101.00 | 1.97 | 102.97 | 100 |
| 200 | 250 | AU | 249.00 | 249.00 | −2.39 | 246.61 | 250 |
| 200 | 400 | AU | 401.00 | 401.00 | 1.52 | 402.52 | 400 |
| 400 | 100 | AU | 100.00 | 100.00 | 2.26 | 102.26 | 100 |
| 400 | 250 | AU | 251.00 | 251.00 | −2.36 | 248.64 | 250 |
| 400 | 400 | AU | 399.00 | 399.00 | −0.74 | 398.26 | 400 |

At S41, the blood pump and restrictor are controlled to establish an ith Ave Pb in the schedule of multiple Ave Pb values. The restrictor 161 setting can be established quickly using the function calculated at S38 or it can be determined for the current Qb and target (ith) Ave Pb by feedback control. The latter may take longer which is the advantage of fitting the function at S38 at a time prior to treatment and only once for multiple treatments. Note also that although the present procedure of FIG. 4B may be done immediately prior to treatment, during a priming stage thereof, it can also be done at other times such that the function generated At S44, an average Ptf (Ave Ptf) is calculated and the difference between Ave Pb and Ave Ptf recorded. This difference provides an estimate of systematic error in the TMP that can be used for determining TMP at other conditions including those during treatment. Now for each of the original target Ave Pb values the controller has stored a measured Ave Pb and a measured Ave Ptf as well as an error indicating the difference. In embodiments, the error is stored but not the Ave Ptf and in other embodiments, all raw data may be stored including Pba, Pbv, Ptff, Ptfw.

At S45, the fresh treatment fluid pump 153 and waste treatment fluid pump 154 and control valves (again, if present) are set to pump fluid through the treatment device 114 as in a treatment. At S46, a jth target flow rate is established for the waste treatment fluid pump 154 and fresh treatment fluid pump 153 by operating at speeds calculated from a standard conversion (i.e. a predefined ratio of pump speed to expected flow rate, rather than measured, pressure condition for applying a pump curve) to for the jth target flow rate as indicated by example in Table 1 (Qtfw flow). At S50, the controller 240 regulates the speed of the fresh treatment fluid pump 153 to bring the current measured Ave Pb toward the target Ave Pb, recorded at S41, by adjusting the speed of the fresh treatment fluid pump 153. This brings about the synchronization of the fresh treatment fluid pump 153 and waste treatment fluid pump 154. In embodiments, a flow through fresh treatment fluid pump 153 is adjusted until synchronization is established, but either pump could be controlled as the master and the other as the slave. Another alternative is a combination approach, where both pumps take turns being adjusted to achieve synchronization. The pressure and pump settings identified in Table 1 are recorded at S52. This is repeated by looping through j and i at S54 and S55 until all conditions have been generated and the corresponding values in Table 1 recorded. Thus, a matrix of combinations of Ave Pb and Qtfw plus attending data for each combination including the Qtff speed, and pressures indicated by fresh treatment fluid pressure sensor 166 (Ptff) and waste treatment fluid pressure sensor 168 (Ptfw) are recorded in a data store of the controller 240.

At S56, the data recorded at S44 and S52 may be fitted to a look up table or fitted to a function to be used for control which maps a given combination of Ave Pb and Qtfw to an output Qtff and TMP error. By fitting to a look up table it is meant that values may be interpolated between cells of the table by a fitted curve or surface and a table many more cells generated to allow rapid use of the fitted data for looking combinations of Ave Pb and Qtfw that were not used for the procedure of FIG. 4B. Calculated values of Ptff and Ptfw may also be yielded by a function or look up table to provide a validity check on the estimate. That is, the controller 240 may also, or alternatively, generate an error signal if one or both of the Ptff and Ptfw is beyond a predefined range from the output Qtff.

The values of Ptff and Ptfw may provide a mechanism for compensating the input value of Qtfw and the commanded speed for fresh treatment fluid pump 153, Qtff. The flow rates commanded during treatment based on the function derived from Table 2 may adjust for differences between the pressure at the respective inlets of the waste and fresh treatment fluid pumps corresponding to the function and those existing at the time of treatment when balanced flow is implemented.

During a treatment, given an average blood pressure Ave Pb indicated by the average of blood outlet pressure sensor 106 and blood inlet pressure sensor 108, for a commanded blood flow rate Qb, and a commanded treatment fluid flow rate of waste treatment fluid pump 154 Qtfw, a speed of the fresh treatment fluid pump 153 Qtff is automatically generated which is assured to provide the precise 1:1 flow synchronization of the fresh treatment fluid pump 153 and waste treatment fluid pump 154 at those operating conditions. The controller 240 then operates the fresh treatment fluid pump 153 at the output speed. This speed may be further refined to compensate for differences between the pump inlet pressure conditions when the map of conditions was created versus the conditions when the function is called upon to estimate the speed of the fresh treatment fluid pump 153. FIG. 4C provides the implementation details that further refine this process in order to provide precise balancing of the Qtff and Qtfw and further permit the implantation of a prescribed ultrafiltration rate.

Figure 3D:
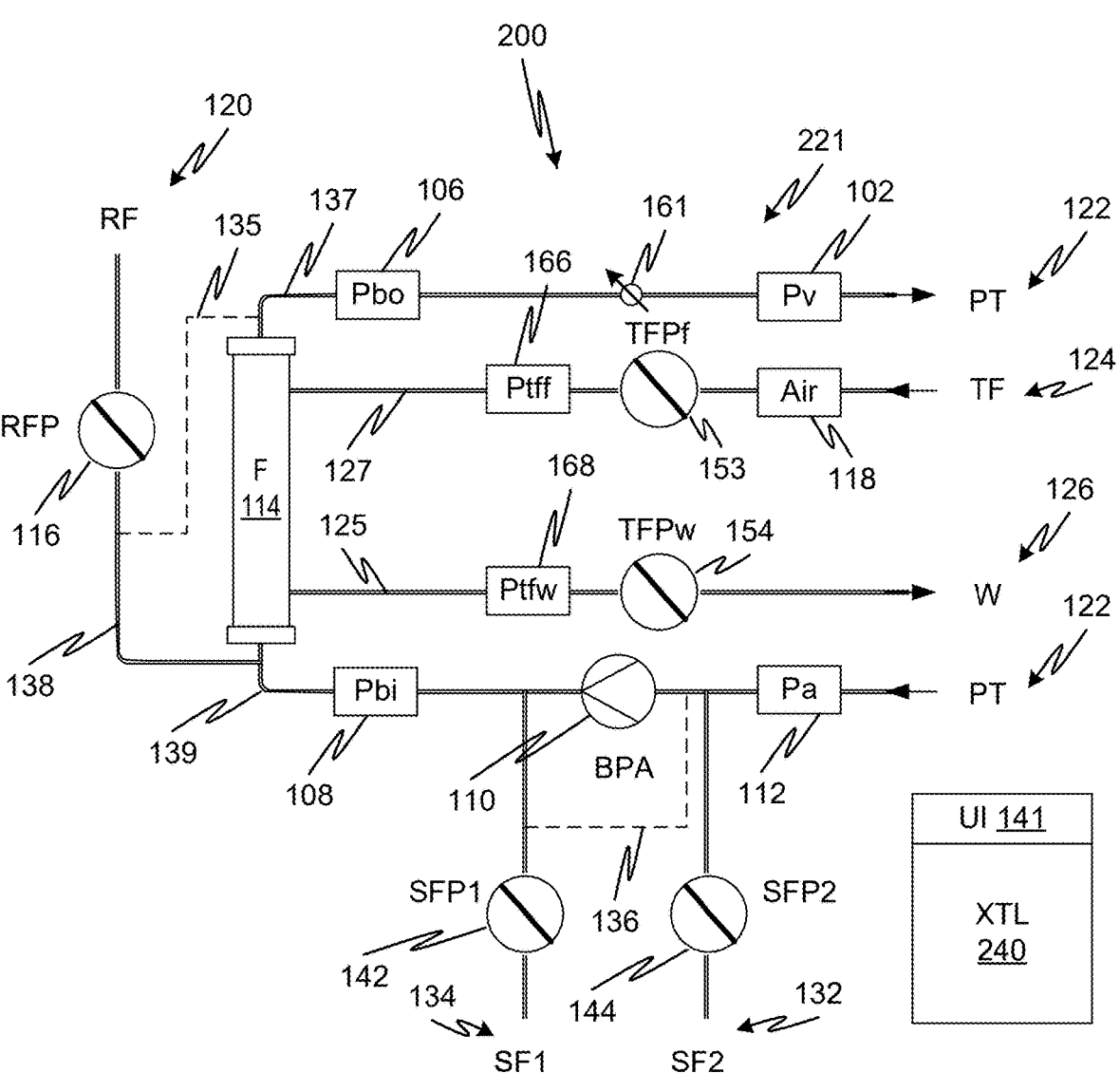

Referring now to FIGS. 3D and 4C, at S62, a command is received by, or generated by, the controller 240 to perform a treatment. During a treatment, blood is pumped by arterial blood pump 110 with fresh treatment fluid pump 153 and waste treatment fluid pump 154 turned off. The treatment fluid circuit may be filled with priming fluid or treatment fluid at this point which is presumed to be at the beginning of a treatment, however it can be repeated at other times during a treatment in order to reestablish balanced operating conditions for the treatment fluid pumps.

Figure 3E:
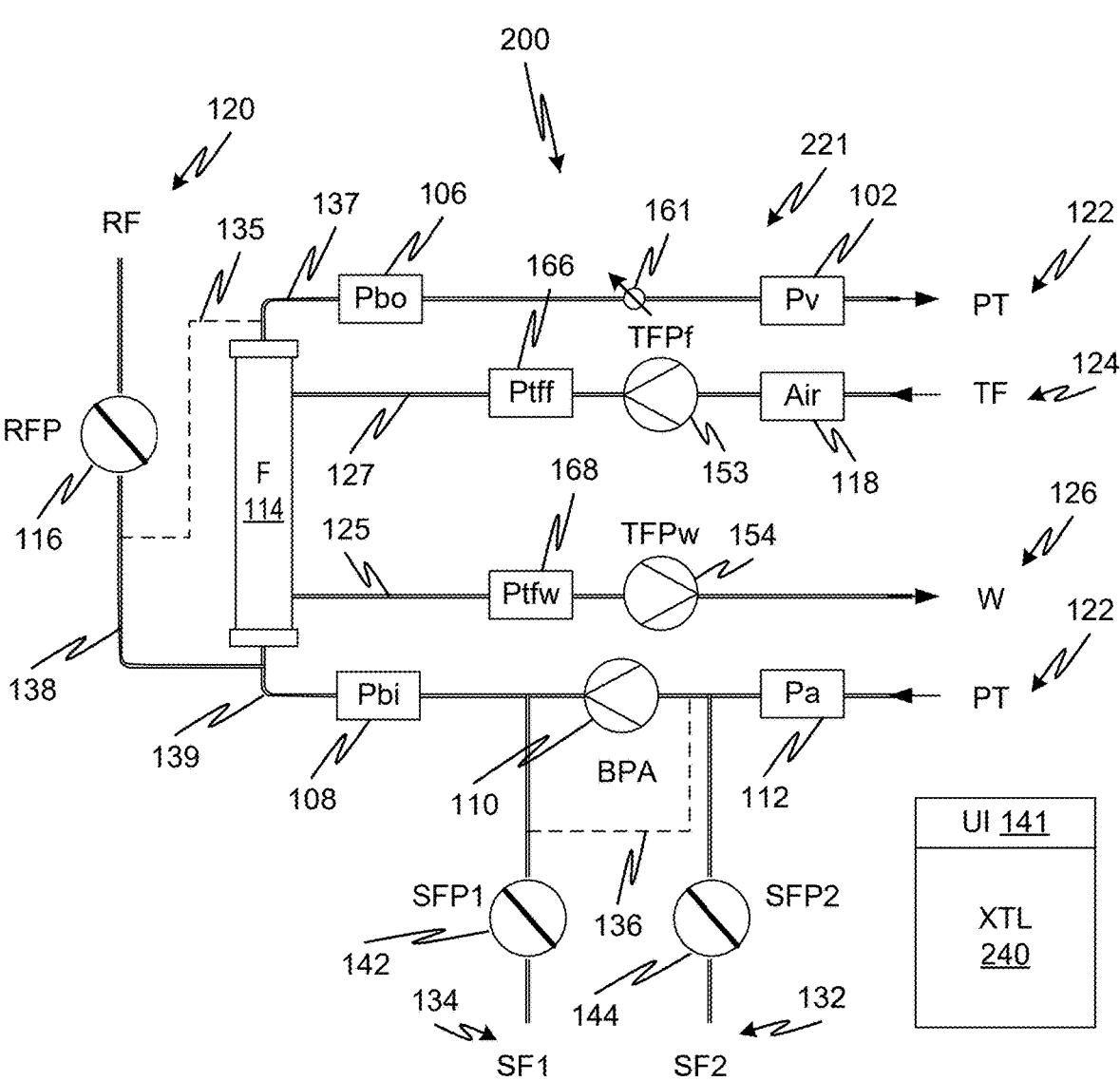

The treatment fluid no-flow configuration is established at S64. The prescribed blood flow rate Qb is established by controlling the arterial blood pump 110 at S65. At S66, the Ave Pb is calculated from blood outlet pressure sensor 106 and blood inlet pressure sensor 108 and stored. This measured Ave Pb is stored as a target Ave Pb. Next, at S67, the difference between the target Ave Pb and Ave Ptf may be calculated from the blood outlet pressure sensor 106, blood inlet pressure sensor 108, fresh treatment fluid pressure sensor 166, and waste treatment fluid pressure sensor 168 readings. This may be recorded as a measure of the oncotic pressure Ponc which biases the transmembrane pressure TMP relative to the condition where blood and treatment fluid compartments contain fluids with the same osmotic potential. As indicated elsewhere herein, the oncotic pressure may be used for a number of functions. Referring now also to FIG. 3E, at S68 the controller 240 selects a speed of the waste treatment fluid pump 154, for example based on a stored prescription entered by an operator or retrieved from an external source, such as a patient treatment profile database. At S70, the TMP error is calculated from the function fitted at S56 of FIG. 4B based on Qtfw and target Ave Pb. At S72, the fresh treatment fluid pump 153 speed Qtff is calculated based on the function fitted at S56 based on Qtfw and target Ave Pb reduced by the TMP error calculated at S70 and the oncotic pressure Ponc calculated at S67. This corrects the estimate of Qtff for the TMP error and the oncotic pressure caused by the blood. The fresh treatment fluid pump 153 is commanded to the calculated speed Qtff and the controller 240 at S74 adjusts the speed of fresh treatment fluid pump 153 Qtff such that current measured Ave Pb is restored to the initial target Ave Pb. Once the fresh treatment fluid pump 153 and of treatment fluid pump 154 are thus synchronized, the pressure indicated by waste treatment fluid pressure sensor 168 may then be used at S76 to determine the flow rate, with compensation based on inlet pressure, and the speed of the of treatment fluid pump 154 adjusted to provide a desired ultrafiltration rate or infusion rate at S78, as prescribed. Since the speed adjustment may affect the inlet pressure of the of waste treatment fluid pump 154, the pump compensation may be recalculated, the pump speed adjusted again until it stops changing by looping through S80. The fresh treatment fluid pump, at any time, may be adjusted in response to a measured inlet pressure, for example using a pressure sensor such as 119.

The synchronization process of FIGS. 4B and 4C can run again based on any of a variety of different criteria, automatically, under control of the controller. For example, if the blood or treatment fluid flow rates is/are changed, the ultrafiltration or infusion rate is changed, a period of time has elapsed, a component is changed such as a treatment device swap, a change in pressure at any point, access patency change, patient position change, and others.

The measured oncotic pressure may be stored by the controller and used to provide multiple functions. In embodiments, the oncotic pressure can be used to estimate a patient's fluid level in order to permit a more accurate determination of the required ultrafiltration. The oncotic pressure may be combined with other data to improve the estimate of the patient's fluid level, for example hematocrit can be measured directly. In embodiments, the controller may be configured to calculate oncotic pressure at multiple times during a treatment and to combine the oncotic pressure with other data such as hematocrit to generate adjustments to a prescribed ultrafiltration rate that was previously stored in the controller. In addition, a predicted and currently estimated—estimated from measured data such as oncotic pressure and hematocrit—fluid level may be generated as well. The predicted level may be calculated from the implemented ultrafiltration rate over time which yields a predicted total fluid removed. The controller may alternatively or further be configured to generate a signal indicating a mismatch between a prescribed ultrafiltration rate and a current fluid level of the patient with accounting for the remaining time left in a treatment. Here, we use the term oncotic pressure to refer to the pressure difference due to all the differences in the compositions of the blood and treatment fluid including proteins, middle molecules, electrolytes, and any other components that may contribute to diffusion potential.

In any of the embodiments where blood side pressure of the blood treatment device is used as a target to bring the fresh treatment fluid pump to represent a state of zero ultrafiltration (equivalently, zero transmembrane flow or zero transmembrane pressure), in further embodiments, the non-blood side pressure of the treatment device may instead be stored and used in the same manner. That is Ave Pb may be replaced with Ave Ptf may for purposes of characterizing the zero ultrafiltration condition. This does not include the measurement of oncotic pressure or TMP error. It has been determined that feedback controlling to achieve a target Ave Ptf to achieve synchronization converges more rapidly, under certain conditions and in certain types of systems, than feedback controlling on Ave Pb.

Figure 5:
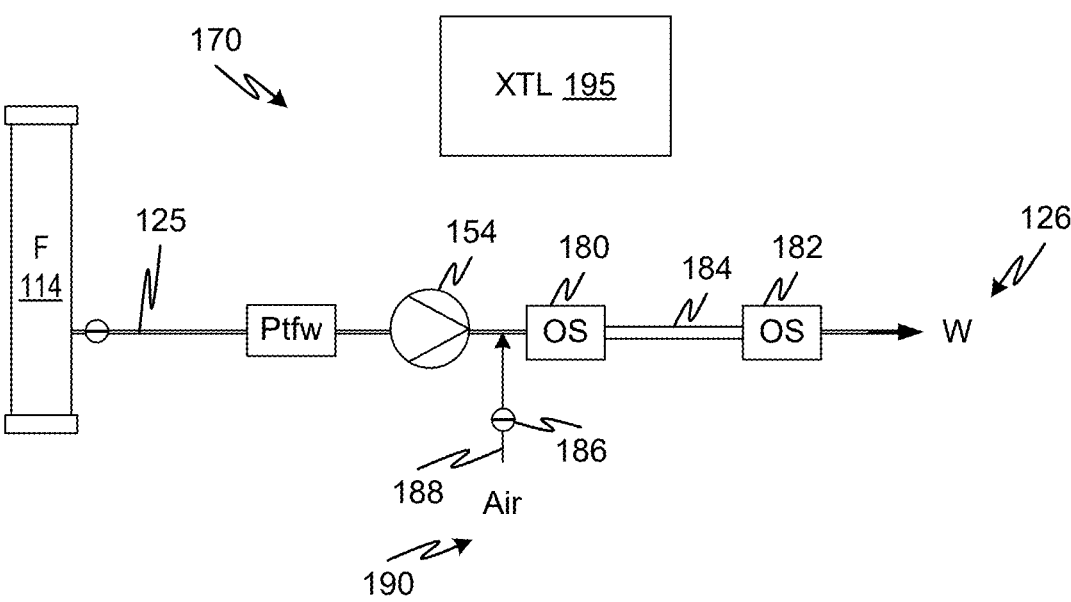
FIG. 5 shows a flow meter adapted for use in blood treatment systems according to embodiments of the disclosed subject matter.

FIG. 5 shows a flow meter 170 that can be used as a reference for synchronizing pumps to a common flow rate standard. A tube segment 184 that is manufactured to precise tolerances and has a known volume and length is positioned in the waste treatment fluid line 125. An air line 188 is connected to a source of pressurized air 190 and further connected to the waste treatment fluid line 125 through a control valve 186 connected to be controlled by a controller 195. The controller 195 injects a predefined bolus or air into the waste treatment fluid line 125 which is carried past two optical sensors 180 and 182 arranged in series. The optical sensors detect the bolus of air and convey the signals to the controller 195 which calculates a time difference—a time-of-flight. With the predefined length and diameter of the tube segment 184, plus the known characteristics of fully developed flow for the fluid therein, the controller 195 can calculate a volume flow rate. Since the fluid carried by waste treatment fluid line 125 is disposed of to the drain 126, there is no detriment injecting air into the waste treatment fluid line 125. Such a flow measurement device, or some other, may be employed advantageously to provide a further estimate of the flow rates on which the pump pressure compensations are based. In addition, an indication of absolute flow rate of a pump may be used by the controller to detect an anomalous state of the system and therefore a potential source of error in the flow synchronization mechanisms employed to achieve balance. The flow rate of a single pump, for instance the waste treatment fluid pump, may be sufficient since the synchronization process accurately.

Figure 6A:
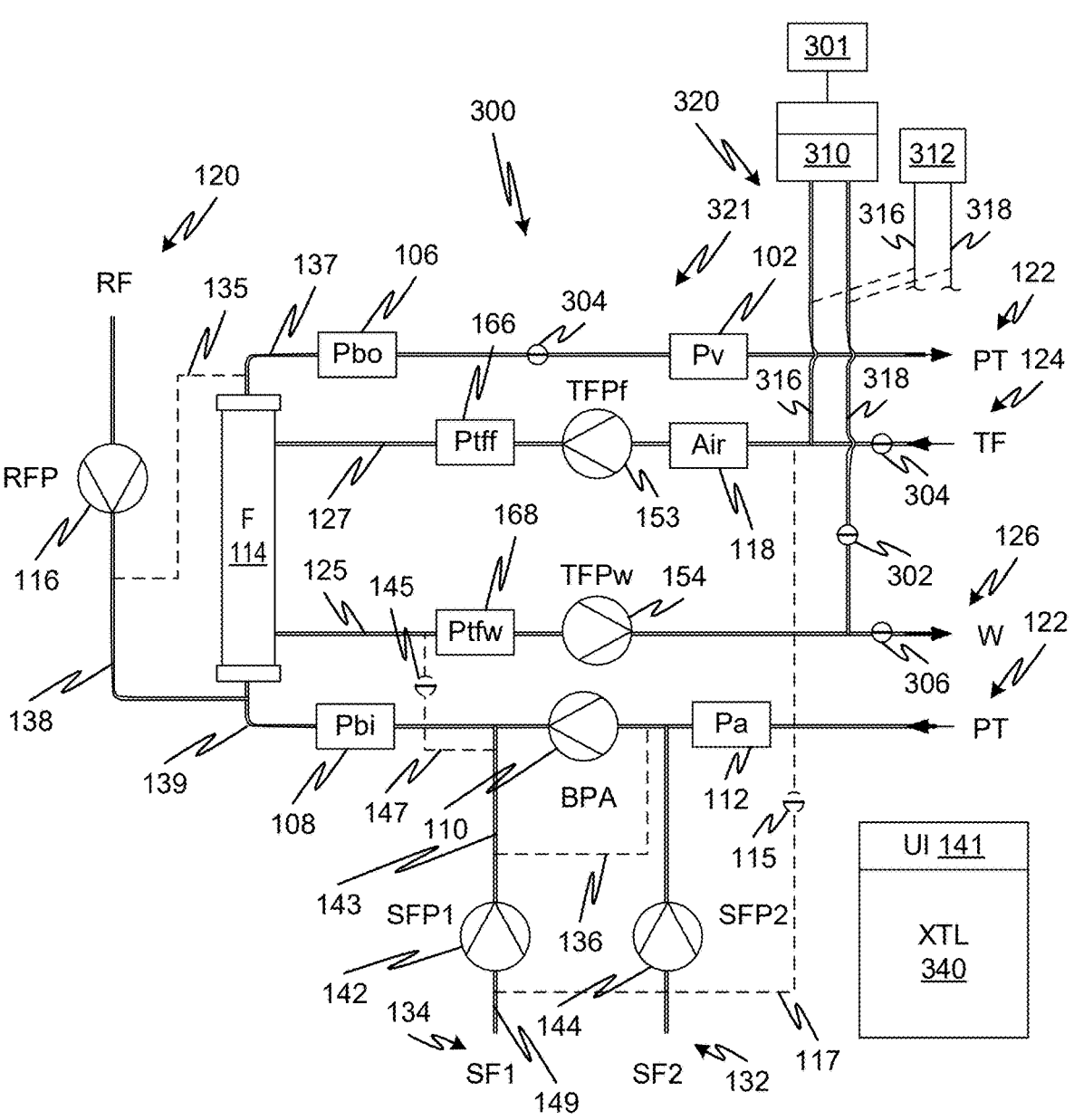
FIGS. 6A and 6B show a blood treatment system that regulates the flow of treatment fluid to generate a cumulative target ratio of fluid drawn or infused into a patient over the course of a treatment in a treatment mode and a synchronization mode, respectively, according to further embodiments of the disclosed subject matter.
Figure 6B:
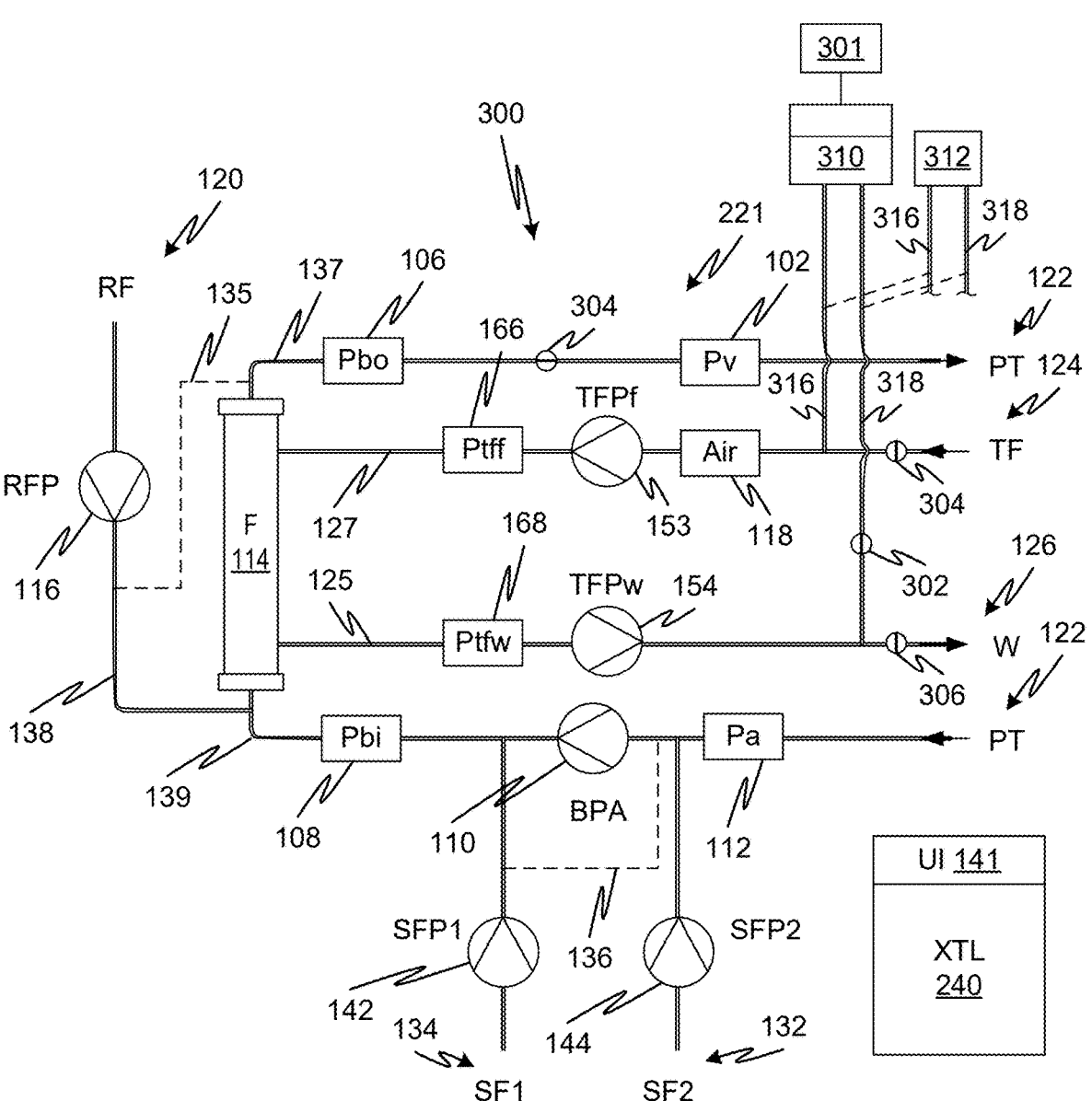

FIGS. 6A and 6B show a blood treatment system 300 in which fresh treatment fluid pump 153 and treatment fluid pump 154 are synchronized, to provide a control parameter that can be used as a basis for fluid flow balance. To do so, a synchronization operation is performed as in other embodiments, but in this case, it is done without establishing a fixed volume flow through the treatment device 114 as in the embodiments discussed above, for example as described with reference to FIGS. 1A-1E. As will be observed, a series flow of treatment fluid is established in the treatment fluid circuit without a need to block flow in the blood circuit. In the blood treatment system 100, the flow of treatment fluid was blocked to form a fixed volume channel between the blood pumps through the blood treatment device 114. Here, instead, a direct connection between the treatment fluid pumps is established by closing the circuit on the source/sink side of the treatment fluid circuit. In first embodiments, the volume of the direction connection channel is fixed and pressure is measured to indicate a mismatch in the pumping rates. In second embodiments, a level of treatment fluid volume in an accumulator provides in indication of flow mismatch. The approach of closing the fluid circuit on the source/sink side of the treatment fluid circuit may be advantageous for a variety of reasons not least of which is that it avoids halting flow in the blood circuit which reduce the risk of blood clotting. During priming or during treatment, to implement a synchronization operation, a closed loop is temporarily formed to circulate treatment fluid and the net uptake or loss of fluid into the closed loop, which represents fluid passing through the treatment device 114 into the closed loop, is detected and the pumps regulated to bring the net rate of uptake or loss to zero, thereby synchronizing the fresh treatment fluid pump 153 and of treatment fluid pump 154. The detection of net uptake or loss may be accomplished by measuring pressure in the closed loop with a pressure measurement device or pressure sensor (such as a pressure transducer) 312 or by measuring the weight gain of a fluid accumulator 310 (also referred to as an accumulator) in the loop using a scale 301. Instead of a scale, a level indicator in a fixed volume chamber may be used as will be evident from the further description below.

FIG. 6A shows a flow a blood treatment system 300 that regulates the flow of treatment fluid to generate a cumulative target ratio of fluid drawn or infused into a patient over the course of a treatment. A blood treatment system 300 regulates the flow of fluid in a fluid circuit 321 that includes an arterial blood line 139, a venous blood line 137, a fresh treatment fluid line 127 and a waste treatment fluid line 125. The net flow of fluid into or out of a patient, at any given time, is determined by a then-instant difference between the volume of treatment fluid pumped from a treatment device 114 to the combined volume pumped into the both the treatment device 114 and the blood lines. Blood is pumped from a patient 122B (conventionally, via a patient access 122A) into the treatment device 114 by an arterial blood pump 110 and flows from the treatment device 114 back to the patient 122B. The illustrated configuration is common for dialysis systems, and may include all the typical incidents thereof, but differs specifically in that there are two treatment fluid pumps: a fresh treatment fluid pump 153, which pumps fresh treatment fluid 124 into the treatment device 114, and a waste treatment fluid pump 154, which pumps waste (spent) treatment fluid from the treatment device 114 to the drain 126. Control and sensing are provided by a controller 340 which may be of any form but typically a programmable digital controller; an embedded computer. Treatment fluid 124 is pumped from a source through an air detector 118 through the treatment device 114, to the drain 126.

A replacement fluid 120 may be pumped into the arterial blood line 139 or the venous blood line 137 through a replacement fluid line 135 or 138, respectively (or both) for predilution, post-dilution. In alternative embodiments, the dilution may occur at a midpoint of the treatment device 114, for example by splitting the treatment device 114 into two parts and providing a junction between them. The treatment device 114 may be adapted for any type of blood treatment including, but not limited to, dialysis, hemofiltration, hemodiafiltration, apheresis, adsorption, hemoperfusion, and blood oxygenation. Further supplemental fluids indicated by supplemental fluid 134 and supplemental fluid 132 may be pumped into the arterial blood line 139 by respective pumps, namely, supplemental fluid pump 142 and supplemental fluid pump 144, either or both of which may be present. Examples of supplemental fluids are drugs and anticoagulant (e.g., citrate, heparin).

Pressure sensors may be provided at various points throughout the fluid circuit 121. In particular, an arterial pressure sensor 112 may detect pressure of the blood in the arterial blood line 139 upstream of the arterial blood pump 110. A blood inlet pressure sensor 108 may detect pressure of the blood in the arterial blood line 139 downstream of the arterial blood pump 110 and upstream of the treatment device 114. A blood outlet pressure sensor 106 may detect pressure of the blood in the venous blood line 137 upstream of the venous blood pump 104 and downstream of the treatment device 114. A venous blood pressure sensor 102 may detect pressure in the venous blood line 137 downstream of the venous blood pump 104 and upstream of the patient access 122A. An inlet treatment fluid pressure sensor 166 indicates the pressure of treatment fluid downstream of the fresh treatment fluid pump 153 and a waste treatment fluid pressure sensor 168. The controller 340 receives signals from each of the arterial pressure sensor 112, blood inlet pressure sensor 108, blood outlet pressure sensor 106, and venous blood pressure sensor 102, the fresh treatment fluid pump 153, the waste treatment fluid pump 154, as well as an air detector 118 that is positioned to detect air in the fresh treatment fluid line 127. The controller 340 is also connected to control each of the arterial blood pump 110, replacement fluid pump 116, the supplemental fluid pump 142, the supplemental fluid pump 144, the fresh treatment fluid pump 153, and the waste treatment fluid pump 154.

The blood treatment system 200 also differs from a conventional system in having a treatment fluid branch loop closer 320 that includes an outgoing loop line 316 and an incoming loop line 318, either an accumulator 310 weighed by the scale 301, or a pressure measurement device 312, as well as a loop control valve 302, a fresh treatment fluid control valve 304 and a waste treatment fluid control valve 306. In FIG. 6A, the loop control valve 302, the fresh treatment fluid control valve 304 and the waste treatment fluid control valve 306 are set in a treatment mode to allow fresh treatment fluid to circulate through the treatment device 114 and to permit waste treatment fluid to pass to the drain 126. The treatment fluid branch loop closer 320 is not in the loop as determined by the closed position of the waste treatment fluid control valve 306. Thus, fluid passes directly from the treatment fluid 124 to the drain 126 by way of the treatment device 114 and the fresh treatment fluid pump 153 and waste treatment fluid pump 154. Instead of a scale 301 a fluid level detector may be used to indicate changes in fluid volume of the accumulator 310.

In a synchronization mode shown in FIG. 6A, the treatment fluid source 124 and the drain 126 are cut off by the closed positions of fresh treatment fluid control valve 304 and waste treatment fluid control valve 306. The open position of 6A, the loop control valve 302 causes a closed loop to be formed by the venous blood line 137, arterial blood line 139, outgoing loop line 316, accumulator 310, and the incoming loop line 318. In the alternative embodiment, the loop includes the pressure measurement device 312 instead of the accumulator 310. When the fresh treatment fluid pump 153 and waste treatment fluid pump 154 are out of synch, the scale 301 or the pressure sensor 312 will indicate a rise or fall in weight or pressure over time and the controller 340 changes one of the fresh treatment fluid pump 153 and waste treatment fluid pump 154 into synch. The data converting pump flow to pump speed can thereby be adjusted so that fluid balance is better maintained during treatment.

In a treatment operation of blood treatment system 300, fresh treatment fluid pump 153 and waste treatment fluid pump 154 pump in the directions indicated by the respective arrowhead of each pump symbol, pump at rates controlled to balance the flow of treatment fluid in the fresh treatment fluid line 127 against the flow of blood in the venous blood line waste treatment fluid line 125 such that a net take-off of fluid (ultrafiltration) or a net infusion of fluid takes place as calculated by the controller 340 or per a command received by the controller 240. The instantaneous rate of ultrafiltration or infusion may vary during the course of a treatment.

The controller 340 may be configured to ensure that the net level of ultrafiltrate or infused fluid meets a prescribed target which may be stored by the controller 340. The pumping speeds required to achieve balanced flow rates may be determined by the controller 340 using data stored by the controller such as look up tables or formulas. These data are generated using the synchronization procedures of the various embodiments and optionally by using pump curve data as well. The ratio of flow rate to pump speed may be presented by this stored data to indicate target pump speeds (or, equivalently, commanded flow rates) in a relationship between pressure difference as well as flow rate. For example, in any of the embodiments, a look up table may have cells with pump speeds where columns and rows correspond to the independent variables of pressure at the pump inlet (or pressure differential across the pump for non-peristaltic pumps) and flow rate.

At the same time treatment fluid 124 is pumped by fresh treatment fluid pump 128 at a predefined rate stored in the controller, which rate may be selected to correspond to the blood flow rate. The replacement fluid 120 may be controlled by the controller 340 which determines the rate of replacement fluid pump 116. The supplemental fluid 134 may be pumped at a rate regulated by the controller 340 by controlling the pumping rate of supplemental fluid pump 142. The supplemental fluid 132 may be pumped at a rate controlled by the controller 340 by controlling the rate of supplemental fluid pump 144. Any of the replacement fluid 120, supplemental fluid 134, or supplemental fluid 132 may or may not be included, along with the respective lines and pumps, in alternative embodiments. Flow control valves may be of any type as indicated above. As before, line 136 is present to indicate that in alternative embodiments, the supplemental fluids may enter the arterial blood line 139 upstream or downstream of the arterial blood pump 110.

Referring to FIG. 6B, in additional embodiments, a bridge line 147 that can be opened or closed selectively by the controller 340, connects the replacement fluid line 143 and the waste treatment fluid line 125. This may be controlled by means of a control valve 145. Another bridge line 117 that can be opened or closed selectively by the controller 340, connects the replacement fluid inlet line 149 and the waste treatment fluid line 125. This may be controlled by means of a control valve 115. Thus waste treatment fluid pump 154 and supplemental fluid pump 142 may be connected in series through treatment fluid branch loop closer 320. This allows the supplemental fluid pump 142 to be synchronized against the waste treatment fluid pump 154 by selected actuation of the control valves, e.g., 115, 145, 304, as will be evident from inspection. In alternative embodiments, any of the non-blood pumps may be synchronized with any other non-blood pump in the same manner using the same or similar devices.

Figure 7:
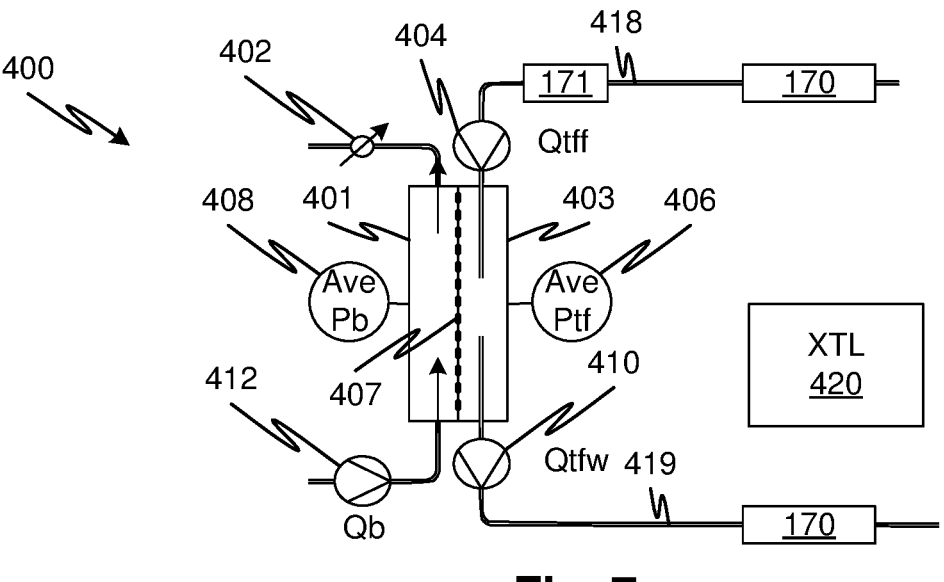
FIG. 7 is for describing certain principles of operation of the controller and blood treatment apparatus, according to embodiments of the disclosed subject matter.

Referring to FIG. 7, a blood treatment system 400 is illustrated schematically with some key elements of certain embodiments of the disclosed subject matter. A treatment device has a membrane 407 that divides blood 401 and non-blood 403 compartments. The blood compartment 401 may include the composite volume of the internal lumens of a microfiber bundle and the non-blood compartment 403 may be net space outside of such a microfiber bundle confined by a housing. A blood pump 412 pumps priming fluid or blood into the blood compartment 401 and a variable restrictor 402 restricts the flow of priming fluid to permit the pressure in the blood compartment 401 to be adjusted selectively by a controller 420. In treatment mode, the variable restrictor is not used. The controller 420 controls the speeds of pumps and detects the pressures of the blood 401 and non-blood 403 compartments by means of pressure sensors 406 and 408, which are shown schematically but may represent inlet and outlet pressure sensors for each compartment as in the foregoing embodiments. Net fluid transfer to/from the non-blood compartment is controlled by regulating the relative speeds of fresh 404 and waste 410 treatment fluid pumps. Flow meters 170 as described with reference to FIG. 5 may be provided on one or both of the fresh 418 and waste 419 treatment fluid lines. Since in the embodiment of FIG. 5, air is injected in the fluid traversing the flow meter 170, an air removal filter 171 may be provided in the fresh treatment fluid line 418 downstream of the flow meter 170. The flow meter 170 may be used as a confirmation of the synchronization procedure of the embodiments. If a controller 420 detects a disagreement between the flow rates when synchronization is established (e.g., S74, S108), then the controller 420 may generate a signal indicating the disagreement. The signal may be used to generate an alert or alarm condition.

Figure 8:
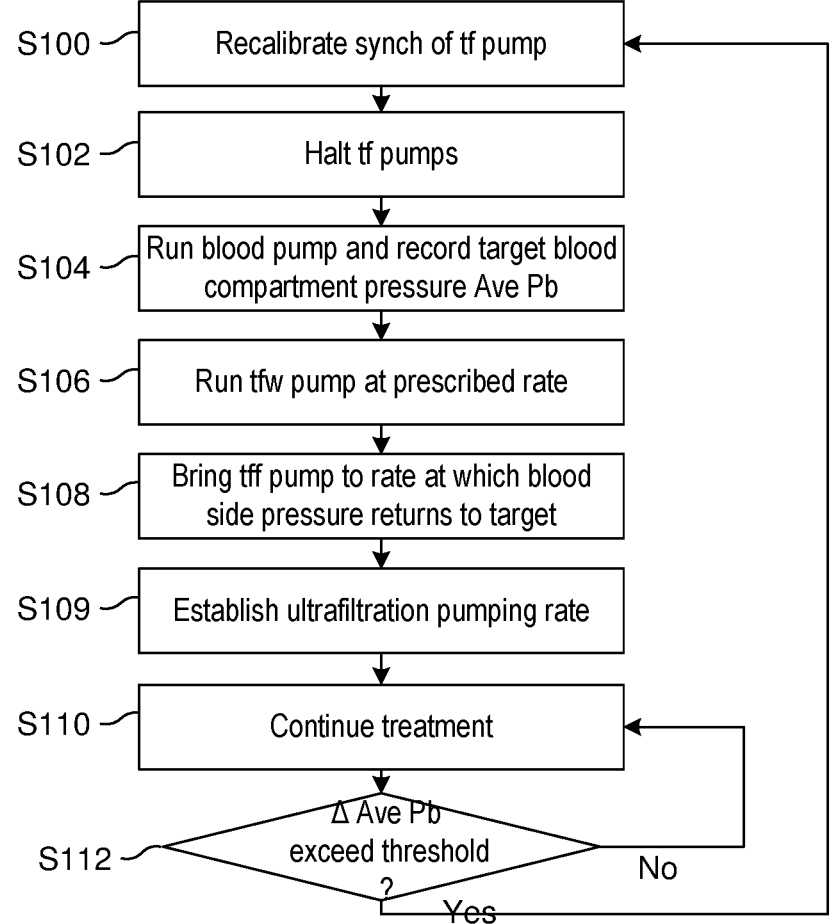
FIG. 8 shows a method for synchronizing fresh and waste treatment fluid pumps during a treatment, according to embodiments of the disclosed subject matter.

FIG. 8 shows a spot method for synchronizing fresh and waste treatment fluid pumps during a treatment, according to embodiments of the disclosed subject matter. In this method the treatment fluid pumps are synchronized for the then-current set of conditions in a treatment phase. This is similar to the procedures of FIGS. 4B and 4C except that instead of mapping a number of conditions of Ave Pb and Qtfw to estimate Qtff, a single Ave Pb (or as discussed above, a single Ave Ptf may apply) is measured, with no treatment fluid flow, from the current operating conditions and stored as a target and used with the current—prescribed—Qtf to determine a synchronous speed for the fresh treatment fluid pump. This is then offset to achieve ultrafiltration and refined by regulating the waste treatment fluid pump to achieve inlet pressure compensation. This has the benefit of determining the synchronous speed of the fresh treatment fluid pump for the precise conditions for treatment.

In the procedure of FIG. 8, a procedure for spot synchronization is now disclosed in further detail. instead of deriving a function to estimate fresh treatment fluid pumping rate from waste treatment fluid pumping rate and average blood compartment pressure, the fresh treatment fluid pumping rate is determined for a current, or predefined combination of waste treatment fluid flow rate and blood compartment average pressure. This can also be done as a complement to the derivation of an estimation function. For example, an operator may command the system to perform a single operating-point synchronization. At S100, during or before a treatment, a command is received or generated by the controller to resynchronize the treatment fluid pumps. At S102, the treatment fluid pumps are halted establishing a zero transmembrane pressure while the blood pump keeps running (or is started). At S104, with the blood pump running at a prescribed rate, the blood compartment average pressure Ave Pb (or Ave Ptf) is measured and stored as a target. Then the prescribed treatment fluid flow rate is established by commanding the waste treatment fluid pump at S106. The fresh treatment fluid pump is then controlled until the target blood compartment average pressure is restored at S108. At S109, the ultrafiltration is established by stepping the waste treatment fluid pumping rate up and iteratively compensating based on the measured inlet pressure to the waste treatment fluid pump. At S110, the treatment fluid pumping rates having been precisely established for the current blood flow rate, the treatment resumes at S110. At S112, if, during treatment, there is a change in average blood compartment pressure, the controller may command that the foregoing operation be repeated otherwise treatment continues at S110.

It will be observed that FIG. 8 illustrates a method for controlling flow in a fluid circuit. In the method, a controller regulates the flow of fluid across a blood treatment device membrane contacting a blood flow path responsively to a pressure signal indicating pressure in the blood treatment device. The regulating includes controlling speeds of inflow and outflow pumps, the inflow pump pumping treatment fluid into the blood treatment device and the outflow pump pumping treatment fluid out of the blood treatment device responsively to a target pressure indicating a blood and/or treatment fluid side of the membrane. At a synchronization time prior to the regulating, the target pressure is obtained and stored in a data store of the controller. The target pressure is calculated from a detected pressure on the blood and/or treatment fluid side of the membrane at a time when the inflow and outflow pumps are halted. The controller, at the synchronization time, halts the inflow and outflow pumps.

The regulating operation may be followed by, or include, advancing the downstream synchronized pump speed to provide a prescribed or calculated ultrafiltration rate such that a target net ultrafiltered volume is removed from a patient by the end of the treatment. The advancing may be accomplished simply by increasing the flow rate of the downstream pump by an amount equal to the targeted ultrafiltration rate. So if the commanded flow rate of the effluent pump is 100 ml/min and the ultrafiltration rate is 5 ml/min, then the advanced effluent pump rate will be changed from the value 100 ml/min, at which the synchronization was performed, to 105 ml/min.

The target pressure may be obtained from the blood side of the treatment device or from the treatment fluid side of the treatment device, respectively, by averaging inlet and outlet pressures on the respective side. Alternatively, the pressure may be obtained from the treatment fluid (non-blood) side outlet only. The foregoing method embodiment may be performed during priming and repeated during treatment.

In any embodiments, the pressure sensor may be located on the downstream non-blood side of the treatment device and the pressure sensor may be used alone for synchronization. Alternatively, pressure sensors on non-blood inlet and outlet may be averaged for purposes of synchronization. In yet additional embodiments, a pressure sensor may form part of the blood treatment device and indicate a temperature at a middle point, the inlet, or the outlet of the non-blood compartment of the blood treatment device. In any embodiments, the pressure sensor may be located on the downstream blood side of the treatment device and the pressure sensor may be used alone for synchronization. Alternatively, pressure sensors on blood inlet and outlet may be averaged for purposes of synchronization. In yet additional embodiments, a pressure sensor may form part of the blood treatment device and indicate a temperature at a middle point, the inlet, or the outlet of the blood compartment of the blood treatment device.

FIG. 9 shows a programmable control system with details that may be inherent in any of the controller embodiments disclosed herein. A processor 10 receives signals from sensors 14, optionally by way of one or more signal conditioners represented collectively at 18. Examples of signal conditioners will be evident from the embodiments, but may include analog filters to more complex devices such as machine learning processors that classify diffuse signal combinations. The processor may store and receive data to and from a data store 12 or a network/Internet 20. Actuators 16 represent the various actuators described herein. The processor may connected for interaction with users via one or more user interface 22 elements such as buttons, screens, keyboard, pointing devices, alarm annunciators, speakers, lights, etc.

FIGS. 10A and 10B show a figurative representation of a blood treatment device 512 with blood compartment 510 and non-blood compartment 511 separated by a membrane 520. In FIG. 10A, the fluid balance of a patient is controlled by a controller (not shown) by regulating the relative speeds of treatment fluid pumps 506 and 514. In FIG. 10B, the fluid balance of a patient is controlled by a controller (not shown) by regulating the relative speeds of blood pumps 502 and 504. The synchronization procedure of FIG. 8 may be used to obtain a speed of the treatment fluid pump 506 that is synchronized to the speed of the pump 514 by determining a target pressure of the non-blood compartment 511 at which there is no flow through the membrane and synchronizing finding the speed of the pump 506 that achieves that target pressure for the desired pumping rate of the pump 514. However, a similar procedure can also be used when blood flow is balanced instead of treatment fluid as in the embodiment of FIG. 10B by determining the speed of the blood pump 504 that is synchronized with the blood pump 502 based on a target pressure obtained by establishing the no-transmembrane flow condition during priming. The target pressure may be obtained by halting flow of priming fluid or blood by halting both blood pumps 502 and 504. Then, the pressure while there is treatment fluid flowing through the non-blood compartment may be measured. The pressure may be any of the disclosed embodiments including the average of the blood inlet and outlet pressures. Then the blood pump 502 can set to a predetermined flow rate and the pump 504 operated to determine a synchronized speed of the blood pump 504 for a selected speed of the blood pump 502.

Note that 516 indicates one or more pressures sensors which may be any of those listed as alternatives including average of inlet and outlet pressure.

Figure 11:
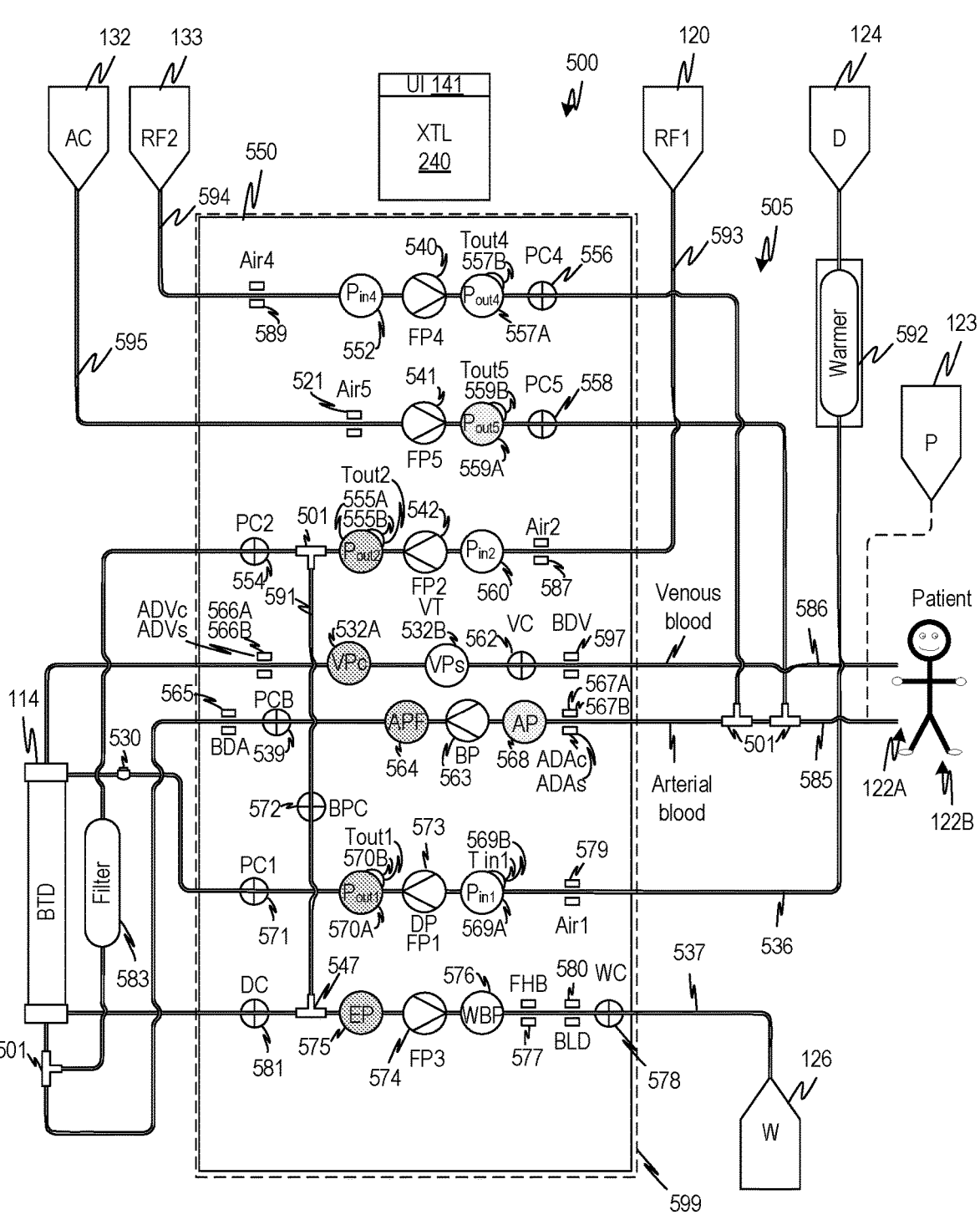
FIG. 11 shows a blood treatment machine figuratively with various actuators and sensors and an attached fluid circuit according to embodiments of the disclosed subject matter.

Referring to FIG. 11, a multiple fluid blood treatment system 500 (also referred to as a device 500) includes a fluid circuit 505, which may be supported by a cartridge 599, and a blood treatment machine 550. The system 500 is capable of hemofiltration, hemodialysis, and hemodiafiltration. The blood treatment machine 550 regulates the flow of treatment fluid to generate a cumulative target ratio of fluid drawn or infused into a patient 122B over the course of a treatment. The blood treatment system 500 regulates the flow of fluid in a fluid circuit 505 that includes an arterial blood line 585, a venous blood line 586, a fresh treatment fluid line 536 and a waste treatment fluid line 537. The net flow of fluid into or out of a patient or priming source/sink, at any given time, is determined by a current difference between the volume of treatment fluid pumped from a treatment device 114 to the combined volume pumped into the treatment device 114 and pumped into the arterial blood line 585, a venous blood line 586. Fluid (blood or priming fluid) is pumped from a source (e.g., patient 122B or priming fluid 123) into the treatment device 114 by a blood pump 563 and flows from the treatment device 114 back to the patient 122B or priming fluid 123, which may be a drain, collection container, or recirculating container. The illustrated configuration may include typical incidents of dialysis machines such as detachable fluid circuits, peristaltic pumps, sensors, etc. In this case, flow balance to achieve the desired ultrafiltration is provided by regulating the rates of fluid pumps including two treatment fluid pumps: fresh treatment fluid pump 573, which pumps fresh treatment fluid 124 into the treatment device 114, and a waste treatment fluid pump 574, which pumps waste (spent) treatment fluid from the treatment device 114 to the drain 126. The treatment fluid may be a hemodialysis fluid, a replacement fluid or other therapeutic medicament. Other fluid pumps include a supplemental fluid pump 541, which pumps a supplement, such as an anti-coagulant, from a supplemental fluid source 132 into the arterial blood line 585, and a second replacement fluid pump 540 and replacement fluid pump 542, which pump a first replacement fluid 120 and a second replacement fluid 133, respectively, into the arterial blood line 585 at the locations therealong indicated in the drawing. Note that other fluids can be added or substituted according to the requirements of different treatment modalities and the illustrated examples are not intended to be limiting.

As above, control and sensing are provided by a controller 240 which may be of any form and again, typically, a programmable digital controller such as an embedded computer. Treatment fluid is pumped from a treatment fluid source 124, such as a bag or fluid proportioning system, by a fresh treatment fluid pump 573. The treatment fluid passes through a warmer 592, a fresh treatment fluid air sensor 579, a treatment fluid inlet pressure sensor 569A, a treatment fluid inlet temperature sensor 569B, a fresh treatment fluid outlet pressure 570A, a fresh treatment fluid outlet temperature sensor 570B and into the treatment device 114. Before entering the treatment device 114 the fresh treatment fluid line 536 passes a pinch clamp 571 (though a fluid control valve may also be used) that is controlled by the controller 240. The treatment fluid flows through the treatment device 114 pumped by the waste treatment fluid pump 574. The treatment fluid flowing from the treatment device 114 passes to the drain 126. The waste treatment fluid line 537 from the treatment device 114 engages with a pinch clamp 581 that is controlled by the controller 240. The waste treatment fluid line 537 also passes an inlet waste pressure sensor 575 upstream of the waste treatment fluid pump 574. The waste treatment fluid line 537 also passes an outlet waste pressure sensor 576 downstream of the waste treatment fluid pump 574. The waste treatment fluid line 537 also passes a blood detector 580 and a free hemoglobin sensor 577. Flow in the waste treatment fluid line 537 is controlled by a pinch clamp 581. The pinch clamp 581 is located between a junction 547 and the treatment device 114. A waste clamp 578 is located between the drain 126 and the waste treatment fluid pump 574.

A replacement fluid a first replacement fluid pump may be pumped into the arterial blood line 585 (or alternatively or in addition into the venous blood line 586) via a first replacement fluid line 593. In alternative embodiments, the dilution by a replacement fluid may occur at a midpoint of the treatment device 114 as discussed above. The first replacement fluid 120 is pumped by replacement fluid pump 542 through the first replacement fluid line 593 which passes through an air sensor 587, a pressure sensor 560, a pressure sensor 555A, a temperature sensor 555B, and a pinch clamp 554. The replacement fluid passes through a sterilizing filter 583 before it flows into the arterial blood line 585.

A second replacement fluid 133 may be pumped into the arterial blood line 585 (or alternatively or in addition into the venous blood line 586) through a second replacement fluid line 594. In alternative embodiments, the dilution by second replacement fluid 133 may occur at a midpoint of the treatment device 114 as discussed above. The second replacement fluid 133 is pumped by the second replacement fluid pump 540 through the second replacement fluid line 594 which passes through an air sensor 589, a pressure sensor 552, a pressure sensor 557A, temperature sensor 557B, and a pinch clamp 556.

A supplemental fluid 132 (such as an anti-coagulant) may be pumped into the arterial blood line 585 (or alternatively or in addition into the venous blood line 586) through a supplemental fluid line 595. The supplemental fluid 132 is pumped by supplemental fluid pump 541 through the supplemental fluid line 595 which passes through an air sensor 521, a pressure sensor 559A and a pinch clamp 558.

Blood is pumped by the blood pump 563 through an arterial control air sensor 567A and an arterial secondary air sensor 567B which are sensitive air bubble detectors connected to independent alarm systems for safety. Note that two arterial air detectors may be used one as a control and one as a secondary to provide redundant signals as an assurance against the use of incorrect signals. The arterial blood also passes a pump inlet pressure sensor 568 and blood pump outlet pressure sensor 564. The arterial blood also passes an arterial blood detector 565. Venous blood returns from the treatment device 114 via venous blood line 586. Venous control primary air sensor 566A and venous secondary air sensor 566B are positioned to detect air in the venous blood line 586. Note that two venous air detectors may also be used one as a control and one as a supplemental to provide redundant signals as an assurance against the use of incorrect signals. A venous blood detector 597 is also in the venous line. A venous line clamp 562 blocks returning blood if a safety hazard is detected, such as air in the blood lines. Venous control primary air sensor 566A and venous secondary air sensor 566B are sensitive air detectors for indicating the presence of bubbles in the venous line.

A bypass line 591 is used for synchronizing the flow of replacement fluid pump 542 with the waste treatment fluid pump 574. The bypass line 591 is opened and closed by means of a bypass line clamp 572 (though a fluid control valve may also be used). The bypass line 591 connects the first replacement fluid line 593 with the waste treatment fluid line 537.

The treatment device 114 may be adapted for any type of blood treatment including, but not limited to, dialysis, hemofiltration, hemodiafiltration, apheresis, adsorption, and hemoperfusion. Further the fluids supplemental fluid 132, second replacement fluid 133, first replacement fluid 120, and treatment fluid 124 may be any type of fluid and the types described are examples not intended to limit the disclosed subject matter. Examples of fluids are medicaments, drugs, and anticoagulant (e.g., citrate, heparin).

Various additional features may be included in the fluid circuit and the cycler including junctions 501, sampling ports 530, connectors 528, and a leak detector 526 (detects leaks from the fluid circuit). These elements may be located as needed depending on the configuration and needs of the system.

The controller 240 is also connected to control each of the blood pump 563, replacement fluid pump 542, the second replacement fluid pump 540, the supplemental fluid pump 541, the fresh treatment fluid pump 573, and the waste treatment fluid pump 574. In embodiments, each pump contributing to flow balance may have a pressure sensor upstream of it to ensure that pressure compensated control of its speed can be provided. This is the case in the illustrated example. In embodiments, pressure sensors are used for pressure-compensated speed control. They may be positioned such that they provide a reliable and consistent indication of pressure upstream of the respective pump or pumps.

In a treatment operation of blood treatment system 500, the pumps pump fluids in the directions indicated by the arrowheads of each pump symbol. The controller 240 regulates the speeds of the pumps to effect a flow balance of fluid to and from the patient to meet a target net ultrafiltration over the course of a treatment. The system can also control the rate of ultrafiltration within a target rate range as well. The flow of treatment fluid in the fresh treatment fluid line 536 against the flow of waste in the waste treatment fluid line 537 is controlled such that a net take-off of fluid (ultrafiltration) or a net infusion of fluid takes place as calculated by the controller 240 per a prescription or operator command entered through the user interface 141 or by other means. The instantaneous rate of ultrafiltration or infusion may vary during the course of a treatment. The controller 240 may be configured to ensure that the net level of ultrafiltrate or infused fluid meets a prescribed target which may be stored by the controller 240. The pumping speeds required to achieve commanded flow rates may be determined by the controller 240 using data stored by the controller such as look up tables or formulas. The ratio of flow rate to pump speed (equivalently, the commanded flow rate) may be presented by this stored data to indicate target pump speeds in a relationship between pressure difference across the pump as well as flow rate; the pump curves. For example, in any of the embodiments, a look up table may have cells with pump speeds where columns and rows correspond to the independent variables of pressure at the pump inlet (or pressure differential across the pump for non-peristaltic pumps) and flow rate. Operating points may be interpolated or extrapolated for operating conditions that lie between or outside those corresponding to the cells or the formula or look-up table may provide interpolated or extrapolated values.

A procedure in which the embodiment of FIG. 11 is used for performing hemofiltration is now described. In FIGS.

Figure 12A:
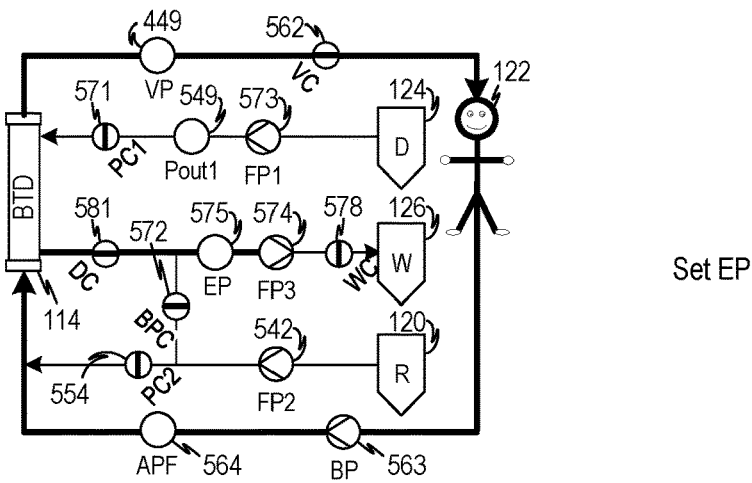
FIG. 12A-12C show elements of a hemofiltration system or a hemodiafiltration system, the elements being common to, but not limited to, the multiple stream system of FIG. 11, for purposes of describing a synchronization procedure for balancing flow for a hemofiltration treatment according to various embodiments of the disclosed subject matter.

12A-12G, the thicker lines indicate lines where a flow is established and the thin lines indicate no-flow. Also, closed clamps are indicated by circles with a line perpendicular the controlled line when closed parallel to it when opened. Referring now to FIG. 12A, a simplified version of the drawing of FIG. 11 is shown in an operating mode in which blood is pumped, at a desired blood flow rate, through the treatment device 114 by the blood pump 563. The other pumps are halted. The pinch clamp 581 is open and other clamps including pinch clamp 571, bypass line clamp 572, and pinch clamp 554. Waste clamp 578 may have no effect because the waste treatment fluid pump 574 is halted preventing any flow through the waste line. Since there is a flow passage between the non-blood compartment of the treatment device 114 and the inlet waste pressure sensor 575, and since there is no flow in the non-blood compartment of the treatment device 114 and no flow through the membrane to the blood compartment owing to the fact that the pinch clamp 571, bypass line clamp 572, and pinch clamp 554 are closed and the waste treatment fluid pump 574 is halted, the inlet waste pressure sensor 575 indicates the pressure of the non-blood compartment of the treatment device 114 which also reflects the average pressure in the blood compartment. The effluent pressure is recorded as a target pressure indicated by the inlet waste pressure sensor 575 by the controller in the operating mode shown in FIG. 12A and then the controller implements the configuration of FIG. 12B.

Figure 12B:
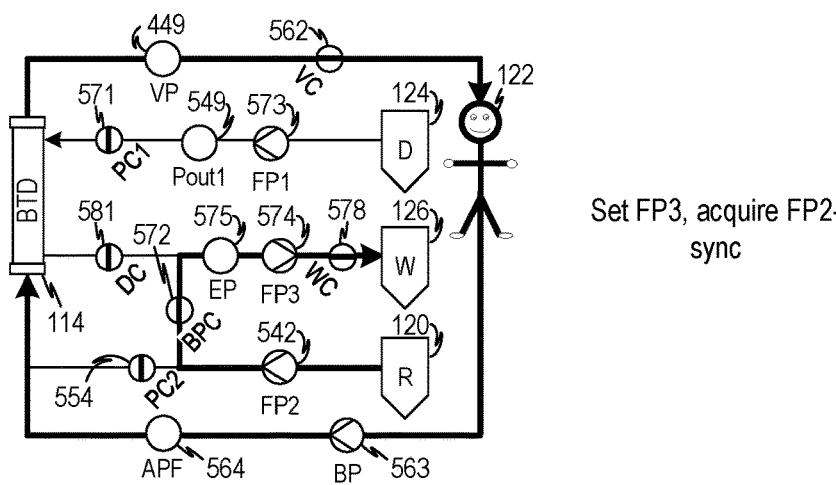

In FIG. 12B, the bypass line clamp 572 and the waste clamp 578 are opened and the pinch clamp 581 is closed. This connects the replacement fluid pump 542 and the and the waste treatment fluid pump 574 in series. The waste treatment fluid pump 574 and the replacement fluid pump 542 are commanded to run at a predefined replacement fluid pump rate according to a hemofiltration prescription. That is, the rate of both pumps is set to the rate at which replacement fluid is planned to be infused into the patient blood line. The replacement fluid pump 542 is then adjusted while monitoring the effluent pressure from inlet waste pressure sensor 575 so that the pressure indicated by the inlet waste pressure sensor 575 is equal to the target pressure indicated by the inlet waste pressure sensor 575. The commanded rate of the replacement fluid pump 542 that provides this target pressure is recorded as a target (Q-sync) commanded flow rate of the replacement fluid pump 542. Next the controller configures the system as shown in FIG. 12C.

Figure 12C:
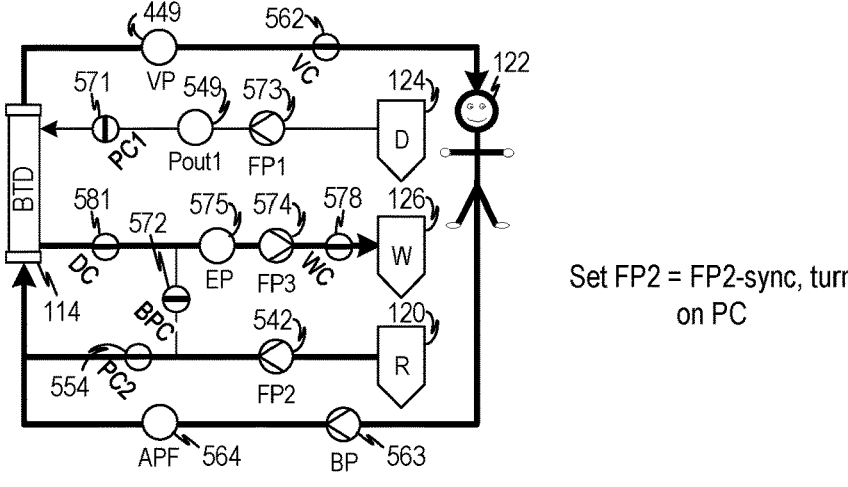

Referring to FIG. 12C, in a hemofiltration treatment, the replacement fluid pump 542 is set to the target q-sync. The effluent pump is operated at the predefined replacement pump speed used for synchronizing in the procedures discussed with regard to FIG. 12B. Immediately thereafter, the pressure compensation is used to maintain the speed of the effluent pump. As a result, if the pressure indicated by the inlet waste pressure sensor 575 falls, the speed of the waste treatment fluid pump 574 is increased and vice versa.

Note that the configuration of FIGS. 12A-12C was identified as a simplified view of the system of FIG. 11. However, it should be clear that the configuration of FIGS. 12A-12C is consistent with other embodiments that include other elements or a bare minimum or equivalent of those shown in alternative embodiments.

Figure 12D:
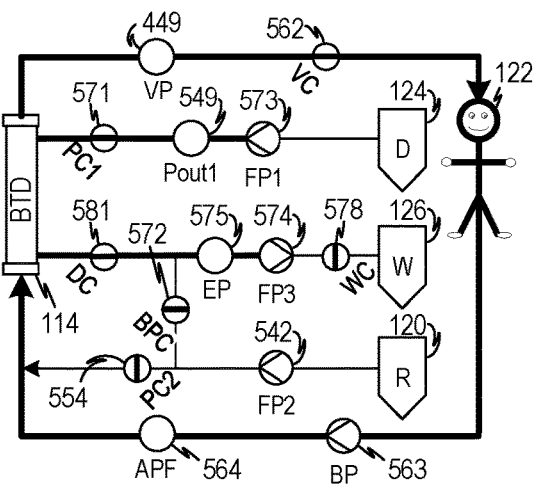
FIG. 12D-12G show elements of a hemodiafiltration system, the elements being common to, but not limited to, the multiple stream system of FIG. 11, for purposes of describing a synchronization procedure for balancing flow for a hemodiafiltration treatment according to various embodiments of the disclosed subject matter.

A procedure in which the embodiment of FIG. 11 is used for performing hemodiafiltration is now described. Referring to FIG. 12D, the same procedure as discussed above for obtaining the effluent pressure as a target pressure indicated by the inlet waste pressure sensor 575 is performed except that both the pressure indicated by the inlet waste pressure sensor 575 and an average of the pressure indicated by the fresh treatment fluid outlet pressure 570A and the pressure indicated by the inlet waste pressure sensor 575 (the latter average equal to an average pressure of the non-blood compartment, HD avg) are recorded as respective target pressures. The same configuration is established by the controller as in FIG. 12A except that the pinch clamp 571 is opened to permit a pressure sensor 549 to detect the non-blood compartment pressure. Next, after the target pressure is recorded, the controller implements the configuration of FIG. 12E.

Figure 12E:
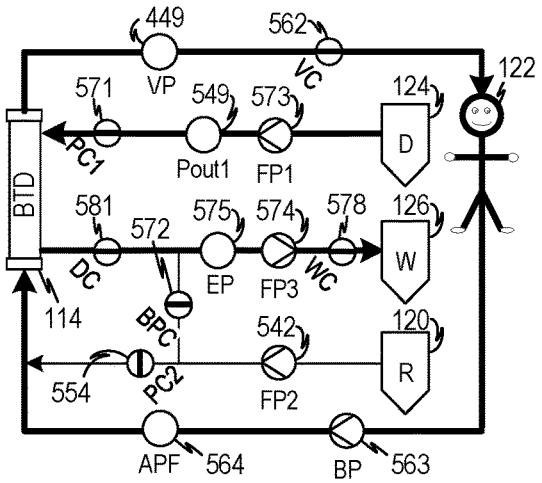

In FIG. 12E, the pinch clamp 571 is opened and the fresh treatment fluid pump 573 and the waste treatment fluid pump 574 are commanded to a speed equal to a prescribed dialysate flow rate for the treatment to be performed. The fresh treatment fluid pump 573 is commanded by the controller to vary its speed while sampling the inlet waste pressure sensor 575 to determine the commanded flow rate of the fresh treatment fluid pump 573 that coincides with a measured HD-avg equal to the HD-avg-target as indicated by the inlet waste pressure sensor 575 and the pressure sensor 549 pressure sensor. As should be clear from the present disclosure, the commanded flow rate may be generated from a dynamic model such as a curve fit of the pressure data or it may be obtained from the pump rate after the synchronization feedback (PID) control has reached equilibrium or synchronous flow lock of the fresh treatment fluid pump 573 and the waste treatment fluid pump 574. In embodiments, the fresh treatment fluid pump 573 is feedback-controlled based on the error, (effluent pressure HD-Avg)–(HD-Avg-target) so that the fresh treatment fluid pump 573 runs at a speed that maintains the effluent pressure indicated by the measured HD-avg. This establishes a command speed of fresh treatment fluid pump 573 Q-Dialysate-sync that is flow-synchronized with the command speed of the waste treatment fluid pump 574. The command speed of the dialysate pump is recorded.

Figure 12F:
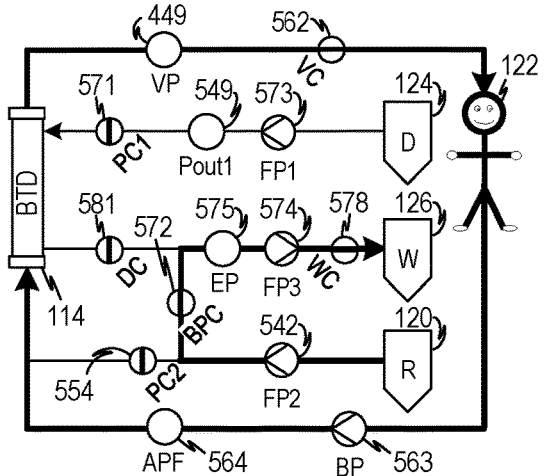

In FIG. 12F, the bypass line clamp 572 is opened and the pinch clamp 581 is closed. The fresh treatment fluid pump 573 is halted and pinch clamp 571 closed. The illustrated configuration connects the replacement fluid pump 542 and the waste treatment fluid pump 574 in series as in FIG. 12B. The same procedure is performed as described with reference to FIG. 12B to obtain the commanded rate of the replacement fluid pump 542 that provides the target pressure. This commanded rate at synchronization is recorded as a target (RF-Q-sync). This is a commanded flow rate of the replacement fluid pump 542 that will be used during treatment. Next the controller configures the system as shown in FIG. 12G.

Figure 12G:
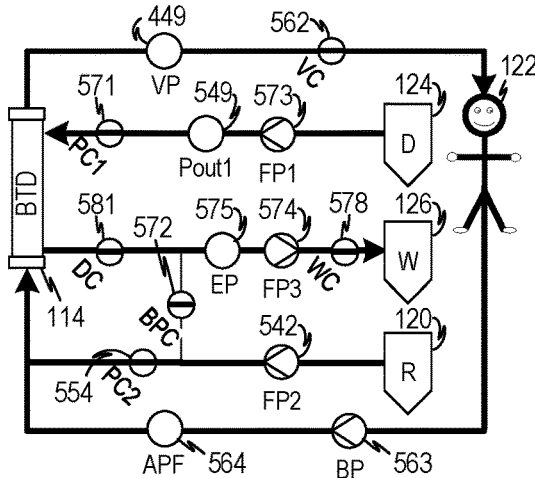

Referring to FIG. 12G, the pinch clamp 571 is next opened and the dialysate pump operated at the speed Q-dialysate-sync. The waste treatment fluid pump 574 is commanded to a rate equal to the commanded dialysate flow rate used during synchronization procedure of FIG. 12F plus the hemofiltration rate. Then the replacement fluid pump 542 is commanded to run at RF-Q-sync. The controller then implements pressure compensation of the waste treatment fluid pump 574. The controller may also implement pressure compensation control of all the pumps as inlet pressure conditions (and/or other conditions) depart from the conditions at the time of synchronization. In this mode, hemodiafiltration treatment is performed.

Note that in a variation of the embodiments of FIGS. 12D-12F, the replacement fluid is not used and only the synchronization operation of FIG. 12E takes place. In that case, the flow of replacement fluid in the operation of FIG. 12G is zero.

Note that to establish the waste treatment fluid pump 574 speed, the controller may simply calculate the shaft speed of a peristaltic pump equal to the sum of the shaft speeds corresponding to the command speeds used to establish the dialysate and replacement fluid flow rates at the time of the respective synchronizations. Note that in all of the embodiments, the effluent pump may be increased above the synchronized rate to provide a prescribed ultrafiltration rate as described herein and particularly as described with reference to FIGS. 13A to 13C.

Note in a further variation of FIG. 12E, instead of synchronizing by tracking a pressure of the inlet waste pressure sensor 575.

Note that in this or any of the embodiments, including those defined by the claims, the ratio of commanded pump speed to estimated flow may be given by a pump curve that is based on inlet pressure, outlet-inlet pressure difference, or a combination thereof, depending on suitability for the type of pump used. Other factors may also be used for pump flow compensation such as temperature and duration of use.

Figure 13A:
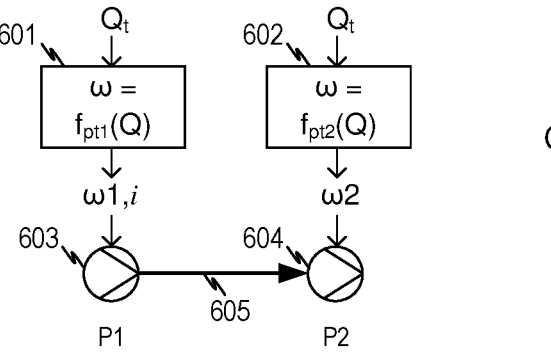
FIGS. 13A-13C show the abstract elements and processes for pump balancing according to various embodiments of the disclosed subject matter.
Figure 13B:
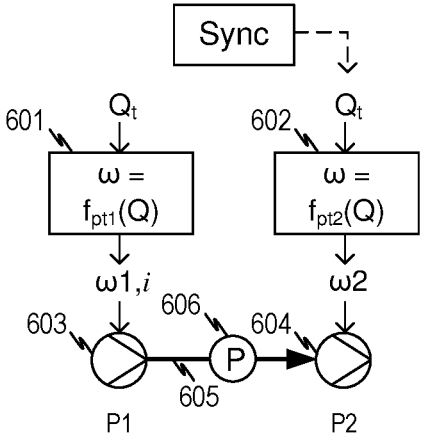

Referring to FIGS. 13A-13B, a summary of how synchronization is combined with pump inlet pressure compensation is described. Referring now to FIG. 13A Illustrated are two pumps 603 and 604 connected in series by a flow channel 605. The flow channel 605 may be a constant volume channel such as a bypass connection or a blood treatment device where one of the compartments is sealed or it may be a "leaky" membrane channel such as in a blood treatment device where a pressure that establishes zero transmembrane pressure condition will be established during synchronization. First, a controller generates a desired flow rate $Q_t$ and converts that using a standard conversion 601 (e.g., formula, lookup table) to a rotational frequency for each pump ($\omega1,i$ and $\omega2$, respectively) where the first pump rotational frequency is an initial speed for the desired flow rate $Q_t$ which is updated during synchronization. Note that Qt and $\omega1,i$ and $\omega2$ are ultimately commanded speeds and a controller may bypass the conversion 601 and simply command pump speed directly but typically inputs originate as desired flow rates so the conversion between a physician's prescription in fluid volume flow rate units would generally be converted into the same units in an application level control scheme until ultimately converted to a rotational frequency (otherwise identified herein as pump speed). This is all merely to note that it will be understood in the discussion that discussion of a commanded pump flow rate or pump speed relate to the same thing. However it is recognized that the conversion 601 and 602 is not exact which is why a synchronization is performed. The conversions 601 and 602 may depend on the type of pump so different functions $f_{pt1}$ and $f_{pt2}$ are shown but it should be understood that the pumps could be of the same type in which case the functions would then be the same.

Referring now to FIG. 13B, once flow is initially established between the pumps 603 and 604, a synchronization procedure is performed according to any of the embodiments described above. As the synchronization procedure progresses, the commanded flow rate (or equivalently, the pump speed or rotational frequency) of the pump 603 is varied until sufficient data are obtained to estimate the commanded flow rate that matches the actual flow rate of the pump 604. As will be understood from the disclosure herein, the data the error variable and the commanded pump speed of pump P correlated with the error variable where the error variable may be weight, volume (e.g., FIGS. 6A, 6B) or pressure (e.g., FIGS. 1A-1C including the treatment fluid-balancing alternative), pressure (e.g., FIGS. 3A-3E), or pressure drop (e.g., FIG. 5). The commanded rate of the pump 603 is adjusted by a controller to find a synchronized speed which is then recorded along with the inlet pressure of the pump 604 that corresponds to it. Note that the pressure 606 at the inlet of the second pump 604 may be known in advance if the zero-transmembrane flow condition is provided through pressure management as in the example of FIGS. 3A-3E. Once the synchronized speed of the first pump 603 is established the pump 604 can be operated thereafter at the commanded rate Qt and the upstream pump 603 at the synchronized speed to achieve a flow balance as long as conditions remain the same, for example, the pressure upstream of the pump 604 remains the same.

Figure 13C:
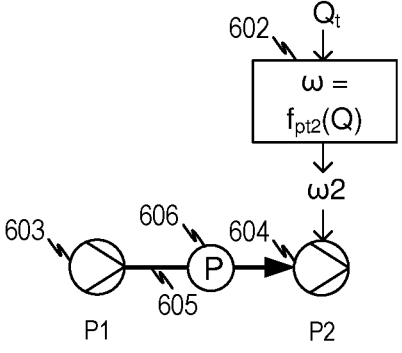

Referring to FIG. 13C, after the synchronized speed of the pump 603 is established, the speed of pump 604 may thereafter be varied in response to the inlet pressure 606 which has been identified above as "pressure compensation." Pressure compensation specifies a change of volume flow rate to the change inlet pressure of the pump 604. This ratio may vary over different pump speeds so multiple compensation curves may be provided and used. Generally the compensation ratio or ratios are obtained by doing experiments with a specific pump and tubing configuration where peristaltic pumps are used.

Pressure compensation-based speed adjustment may be performed continuously or at predefined intervals during a treatment, for example. As noted above, the pressure 606 may change is if the treatment calls for the pump 604 to be operated at a higher flow rate than pump 603 in order to achieve a net flow out of the channel 605 (e.g., when the channel 605 is a treatment device that can draw fluid from a patient's blood through a membrane thereof), i.e., there is a net ultrafiltration. The speed of pump 604 can be lowered relative to the synchronized speed of pump 603 if a negative ultrafiltration rate is indicated by the controller or user.

To implement such predefined difference in the flows of the pumps, the speed of pump 604 may be adjusted proportionately to the higher volume rate sought. For example, if the target flow rate Qt is 200 ml./min and the ultrafiltration rate desired is 5 ml./min, then the pump 604 speed can be commanded to 2.5% higher than Qt. The higher speed of the pump 604 will result in a drop in pressure 606 which will produce a slightly lower rate of flow than the rate sought (2.5% higher than Qt). So the pump 604 speed must then be adjusted so that the rate of flow of pump 604 according to the compensation ratio matches the incrementally higher rate sought. This may need to be done iteratively until the flow rate of the pump 604 converges to the estimated target value. This may be done using feedback control based on an optimization algorithm that minimizes the error between the calculated Qt by varying the pump 604 rate. Alternatively, a function relating the rate of pressure drop to the flow difference (the flow difference being equal to the ultrafiltration rate) may allow for the adjusted flow rate of the pump 604 to be predicted in a feedforward fashion.

The compensation ratio relates actual flow rate with a reference flow rate (in the example, Qt) by the following formula.

$$Q\mathrm{act}(t)=(1+\alpha*(P\mathrm{inlet}(t)-P\mathrm{ref}))*Q(t)$$

where Qact(t) is the actual flow rate through the compensated pump, $\alpha$ is a pump efficiency correction factor (i.e., the pump pressure compensation coefficient), Pinlet(t) is the inlet pressure, and Pref is the pressure where the pump was calibrated or synchronized (the reference point where the pump efficiency was measured). The pump pressure compensation coefficient $\alpha$ is dependent on the characteristics of the pump and the pump tubing segment. In embodiments, the inlet pressure correction may be 1.8%/25 mmHg deviation from the previous sync pressure. This value was obtained for a particular pump type and a particular type of pumping tube segment after certain predefined operating conditions which include a break-in operating period and using a certain fluid type. Thus the value is by no means limiting.

It should be clear from the foregoing how the correct value of a pump pressure compensation correction formula or lookup table may be obtained for other operating conditions. Note also that the above formula is a particular relationship that can be expressed analytically quite simply. However, other types of pumps may have performance characteristics that depend on additional variables and on inlet pressure in other ways that make a different compensation function or lookup table desirable. For example, the flow may depend on other measurable variables such as interval of time that the pumping tube segment has been in use (e.g., number of roller strikes or shaft rotations of a peristaltic pump actuator) and fluid temperature in addition to inlet pressure. Pump outlet pressure may also be included as a factor. In general correction may be handled by means of an offset proportional correction as in $$Q\text{act}=[(1+\alpha_{Pin}(P\text{in}-P\text{ref}))(1+\alpha_{life}(t))(1+\alpha_{temp}(T-T\text{ref}))]Q\text{ref}$$

where Qact is the compensated flow rate, Qref is the commanded flow rate as synchronized. Pref and Tref are the reference conditions of pressure and temperature and t is the amount of time or number of pump cycles for pump tube segment usage. Pin and Tare the current measure inlet pressure and fluid temperature, respectively.

It should be clear from the above, that the compensated flow rate may still contain a systematic error relative to the actual flow rate and that compensation merely adjusts for a departure from synchronized flow rates. Effectively this provides ratiometric proportioning with ratios (compensation factors) governing the offsets required to achieve a desired ultrafiltration from a patient.

During synchronization, the pressure of the channel between the pumps undergoing synchronization may be unsteady and gradually, based on feedback control using a PID control function implemented by a controller, progress toward a synchronized state. There may be several parameters for example, two time intervals defined for purposes of controlling the synchronization procedure. A first time interval is defined between the start of the synchronization procedure, when the two pumps are commanded to an initial speed, and the point at which the feedback signal rate of change falls below a threshold. The latter may be obtained by a moving average of the signal. The moving average may be defined by an averaging window of a predefined shape and time width. The second time interval may be an averaging period over which, after the moving average has fallen below the threshold, the pressure signal is averaged. There is value in minimizing the lengths of these time intervals. There may also be defined a threshold standard deviation for high frequency variations in the error signal that indicate "bad" synchronization. Together these criteria may establish when the synchronization is completed and whether the data obtained from the synchronization is valid.

Positive displacement pumps such as peristaltic pumps generate pressure pulses at their inlet and at their outlets. This causes the error signal used to synchronize pumps to be pulsatile. It has been discovered that combinations of certain speeds of the first and second pumps arranged for synchronization, particularly at low flow rates, generate pressure variations that fail to converge in a short period of time producing "bad" or incomplete synchronizations according to reasonable time periods for the intervals discussed above. These undesirable speed combinations can be discovered in the laboratory and used by the controller to allow the identification of allowed and non-allowed conditions of the pumps undergoing synchronization. To avoid non-allowed conditions while still providing a full range of flow rate combinations, the controller can use flow restrictions to generate artificially low inlet pressures to one pump or the other in order to alter the pulse frequency of that pump for a given flow rate. Thus, the controller may contain a matrix correlating the first pump flow rate and the second flow rate and for each, establish allowed ranges of inlet pressures for the first pump that avoid the speed combinations that produce slow or bad synchronizations.

Figure 14A:
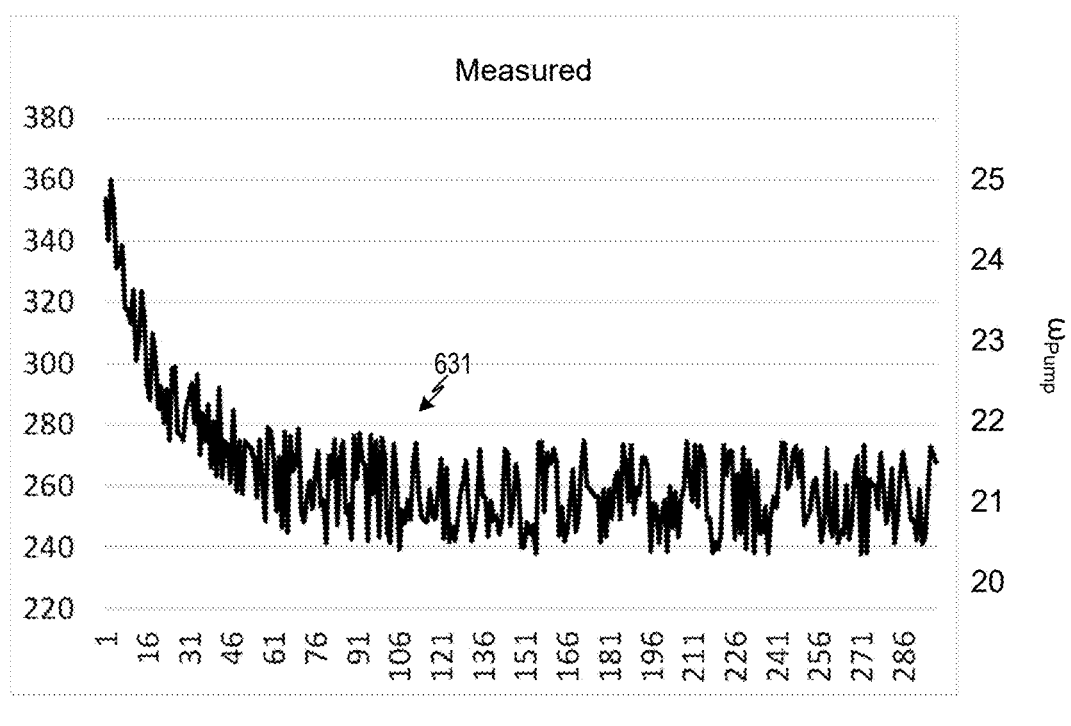
FIGS. 14A-14B illustrate synchronization dynamically by sampling and extrapolating from a synchronization signal in order to reduce the time of pump synchronization, according to various embodiments of the disclosed subject matter.
Figure 14B:
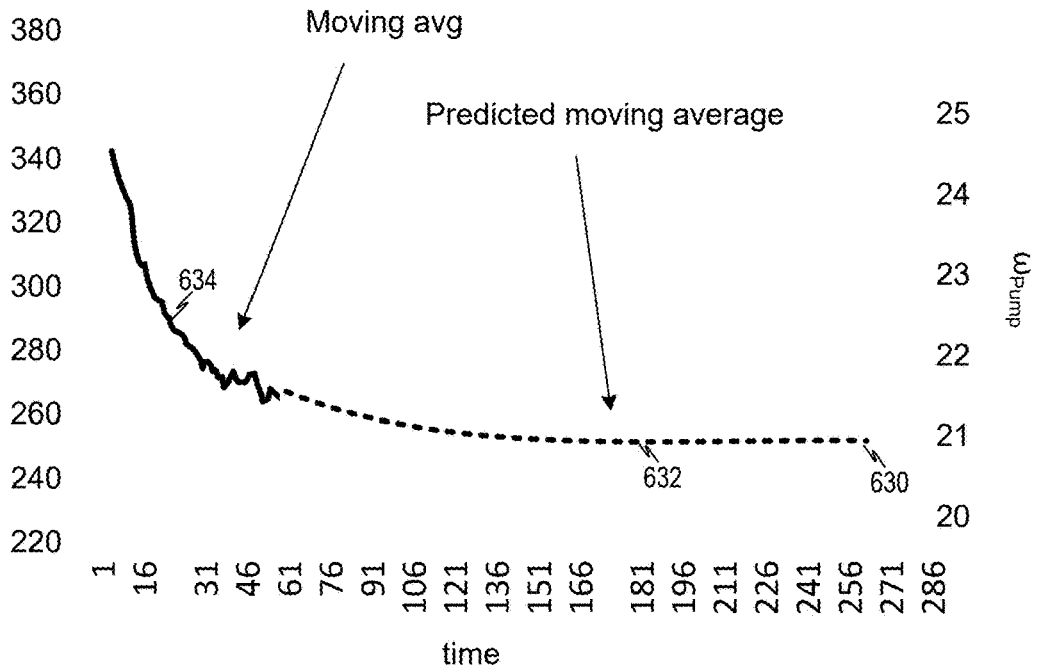

Referring now to FIG. 14A, a profile of instantaneous pressure signal from two synchronized pumps and a corresponding speed of the first pump are shown. The data are merely representative and not limiting of the disclosed embodiments. The variations 631 in the pressure signal are typical, but a general trend is visible. FIG. 14B shows the same data with a moving average calculated from the initial data indicated at 634. The remaining data are indicated at 632 and obtained from a model fitted to the moving average of data 634 to extrapolate a terminal average value indicated at 630 which closely approximates the terminal average obtained by averaging over a final period of the initial data 634. Thus, by fitting an exponential, gaussian, power series, or other function to the data it may be possible to estimate the terminal average after the acquisition of a smaller amount of data over a shorter period of time. The amount of data and the probability of error may vary depending on the conditions, for example, at low flow rates, a longer interval of data may be required. The best parameters to use will be best obtained through laboratory experiments with the specific pump types, materials, and operating conditions for the treatment being performed.

It will be observed that the foregoing shows an example of a way to dynamically determine a synchronized speed of the upstream pump without coming to a full synchronization equilibrium. Thus the embodiment illustrates one example of a method for controlling flow in a fluid circuit, the method being applicable to any blood treatment system that regulates the net ultrafiltration of a patient by balancing fluid withdrawn from a blood treatment device against fluid pumped into the blood treatment device by controlling the relative volume displaced during a treatment by independently-regulated inflow and outflow volumetric pumps. In the method, during a testing mode, the controller connects the inflow and outflow pumps directly while measuring a change in a flow property. The flow property may be flow rate, pressure, or mass. Next, the controller stores synchronized flow data representing the change measured by said measuring and then calculates, from the synchronized flow data, control parameters for regulating the inflow and outflow volumetric pumps. The method continues with performing a treatment including controlling a net flow of fluid to or from a patient by controlling said inflow and outflow volumetric pumps responsively to said control parameters. During the testing mode, the inflow and outflow pumps are not adjusted to be synchronized fully. In particular embodiments the operation of connecting the inflow and outflow pumps directly includes connecting the inflow and outflow pumps through a blood treatment device. In additional embodiments, the operation of connecting the inflow and outflow pumps directly includes defining a fixed-volume flow channel between the inflow and outflow pumps. The flow property may include pressure. The method may further include, during the testing mode, calculating a moving average of the flow property and fitting the same to a curve, wherein the calculating includes fitting the curve to a resulting fitted curve. The method may further include calculating, during the testing mode, a moving average of the flow property and fitting the same to a curve, wherein the calculating includes extrapolating the fitted curve to a corresponding point in pump-speed-to-time curve where the curve is calculated to be flat.

The above methods may be implemented by a controller of a treatment machine. For example, a system for controlling flow in a fluid circuit may have a blood treatment system with a reconfigurable fluid circuit and blood treatment device (for example a disposable fluid circuit and actuators controlled by the machine to define multiple flow paths through the fluid circuit). The system may have inflow and outflow volumetric pumps that are controlled by the controller to regulate the net ultrafiltration of a patient by balancing fluid withdrawn from a blood treatment device against fluid pumped into the blood treatment device by controlling the relative volume displaced during a treatment by independently regulating the speeds of the inflow and outflow volumetric pumps. The controller may receive signals from the flow a sensor indicating the flow property.

Figures 15A, 15B, 15C:
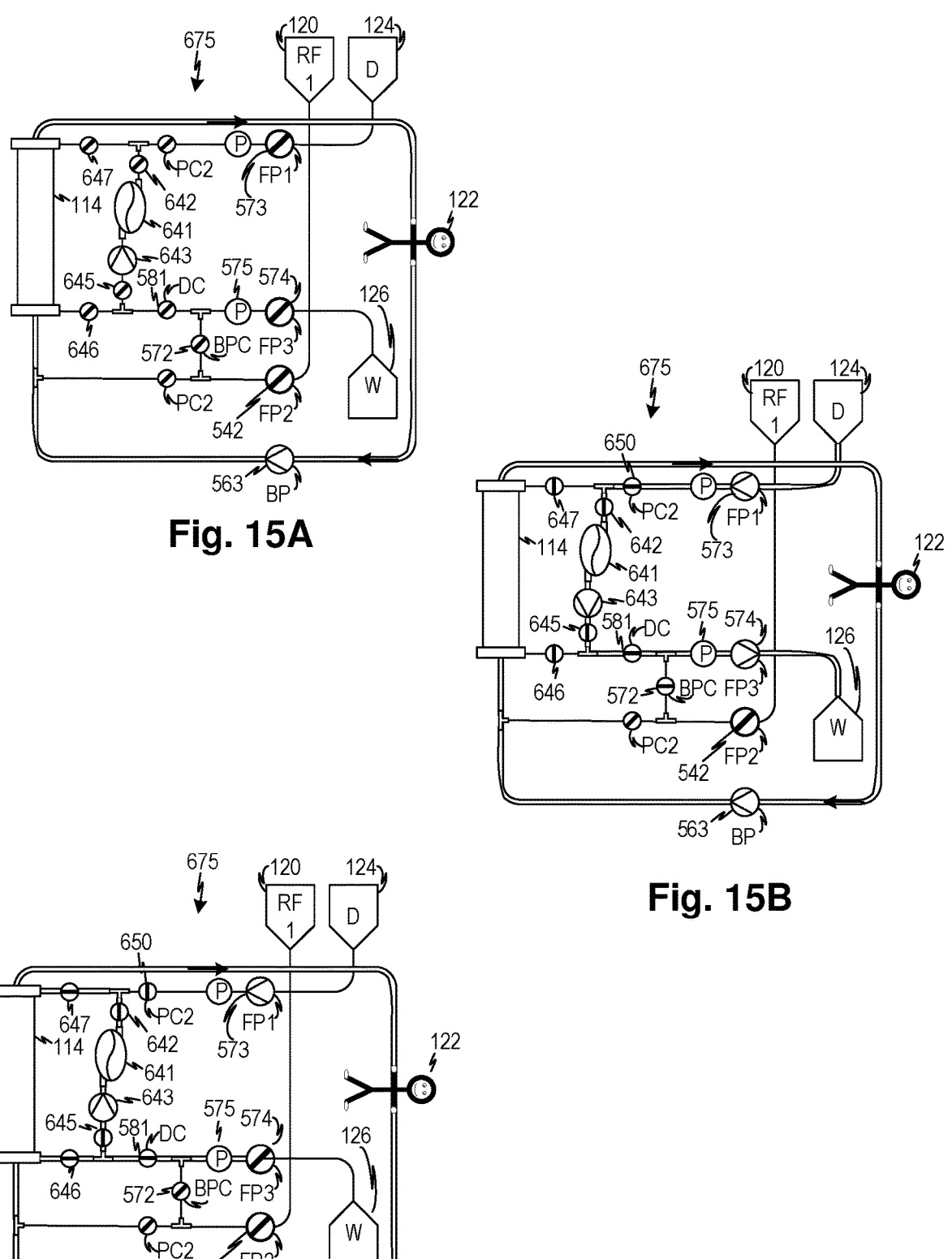
FIGS. 15A-15C show a system and method in which a zero transmembrane flow is established without halting the flow of treatment fluid according to various embodiments of the disclosed subject matter.

Referring now to FIG. 15A, an additional mechanism is described for providing a zero transmembrane flow condition to allow the measurement of treatment device pressure at this condition. The circuit 675 of FIG. 15A may correspond to that of FIG. 11 or a subset thereof with an additional set of components. The added components include the following. A multi-chamber element 641 has a rigid housing and a flexible diaphragm dividing the internal volume of the multi-chamber element 641 such that as one side of the diaphragm receives a fluid at one end of the multi-chamber element 641, the other side's volume is diminished by precisely the same amount forcing an equal volume of fluid out the other end. Thus, as a pump 643 forces fluid into the multi-chamber element 641, fluid from the other end is pushed out at the same rate as pumped in. Pinch clamps 647 and 646 as well as pinch clamps 645 and 642 serve to allow the controller to selectively isolate the multi-chamber element 641 and the treatment device 114 as will be observed from the following description.

FIG. 15B shows the circuit 675 in a configuration for filling a fresh treatment fluid side of the multi-chamber element 641. Blood is pumped by the blood pump 563 as indicated. The fresh treatment fluid pump 573 and pump 643 are operated with clamps 650, 642, 645, and 581 in open positions to flow treatment fluid into one side of the multi-chamber element 641 while emptying the other side into the waste line. The pump 643 is operated in a reverse direction as indicated by the direction of arrowhead in the pump symbol. The waste treatment fluid pump 574 may be operated to convey waste fluid to the drain 126. This operation charges the multi-chamber element 641 with fresh treatment fluid from the treatment fluid 124. FIG. 15C shows a closed loop being formed by operation of the indicated clamps with the pump 643 operated in the forward direction. The volume of the closed loop flow path is completely fixed as can be confirmed by inspection and the description of multi-chamber element 641. Thus, even as there is a flow in the non-blood compartment through the treatment device 114, the transmembrane flow is zero. The pinch clamp 581 is opened to allow the pressure in the closed loop to communicate with the inlet waste pressure sensor 575. Thus, the pressure of the non-blood compartment of the treatment device 114 may be measured under zero transmembrane flow conditions while fresh treatment fluid is circulated through the treatment device, thereby continuing dialytic cleansing of the blood during this initial step of pump synchronization. The remaining steps may completed as indicated and discussed relative to FIGS. 12D to 12F and other embodiments.

Note that in FIGS. 15A-15C, the double lines indicate flow paths in a flow is established and the single lines indicate a flow path in which no flow is present. Clamps are illustrated as in FIGS. 12A to 12F.

It should be evident from the discussion of FIGS. 12A through 12F and elsewhere that the disclosed subject matter provides a method and a system for controlling fluid flow in a fluid circuit, in embodiments, a fluid circuit that includes treatment fluid and blood portions. The method may include connecting first inflow and outflow lines to one of blood and non-blood compartments of a blood treatment device and connecting second inflow and outflow lines to the other of blood and non-blood compartments of the blood treatment device. Then using a controller, regulating a speed of a first inflow pump connected to the first inflow line to establish a flow into said one of blood and non-blood compartments of a blood treatment device. The method includes regulating a speed of a first outflow pump connected to the first outflow line to establish a flow out of said one of blood and non-blood compartments of a blood treatment device and detecting a pressure of at least one of the blood and non-blood compartments, said pressure indicating a magnitude of a difference between the rates of the flows into and out of said one of blood and non-blood compartments. The method includes calculating a flow control parameter responsively to said pressure and thereafter regulating a net transfer of fluid between the blood and non-blood compartments responsively to the control parameter. In variations, the method includes during the detecting, flowing fluid through the second inflow and outflow lines. In further variations, the method may include, during said detecting, blocking the flow of fluid through the second inflow and outflow lines such that the first inflow and outflow lines and said one of blood and non-blood compartments of a blood treatment device constitute a fixed volume fluid channel. The pressure may indicate a magnitude of a transmembrane transport between the blood and non-blood compartments. This can be due to the fluid channel being a fixed volume channel or due to the regulation of a pump speed such that a zero-transmembrane flow is established. The pressure at which zero-transmembrane flow is established may be determined automatically by the controller using the methods and mechanisms described herein. The pressure may indicate a magnitude of a transmembrane transport between the blood and non-blood compartments and the calculating includes comparing the pressure to a predefined threshold pressure indicative of zero magnitude of a transmembrane transport between the blood and non-blood compartments.

Thus, it will be observed, that the synchronization method allows the pumps to be synchronized during a treatment mode (albeit, in embodiments, a briefly-interrupted treatment mode) or during a priming stage. It may also be done at other times such as a factory calibration. Advantageously, the synchronization may be done without removing blood from the blood compartment of the treatment device. Further, advantageously, the method may be applied to synchronize inflow and outflow pumps on the blood side or the treatment fluid side of the treatment device. That is, in the embodiment delineated immediately above, the first inflow and outflow lines may be blood lines or treatment fluid lines. Instead of pressure, one may substitute volume flow measurement technique described in connection with FIGS. 6A and 6B or the flow measurement device described with reference to FIG. 5. It should be clear that the pressure signal from which the flow control parameter is calculated may arise due to the blockage of any shift of fluid between the blood and non-blood compartments (e.g., flow through a membrane separating the compartments) or simply the resistance of the membrane. The pressure or the rate of change of pressure may indicate synchronization. In either case, the inflow and outflow pumps may be regulated such that the outflow pump's inlet pressure is at a desired operating pressure determined to be present during a treatment.

The pressure may indicate a magnitude of a transmembrane transport between the blood and non-blood compartments and the calculating may include comparing the pressure to a predefined threshold pressure indicative of zero magnitude of a transmembrane transport between the blood and non-blood compartments. In this case, the method may include determining the predefined threshold pressure by detecting a pressure of the at least one of the blood and non-blood compartments while blocking transport between the blood and non-blood compartments.

The pressure may indicate a magnitude of a transmembrane transport between the blood and non-blood compartments, the calculating may include comparing the pressure to a predefined threshold pressure indicative of zero magnitude of a transmembrane transport between the blood and non-blood compartments and the method may further include determining the predefined threshold pressure by detecting a pressure of the at least one of the blood and non-blood compartments while blocking transport between the blood and non-blood compartments and while establishing flow through the second inflow and outflow lines at a predefined flow rate.

Figure 16:
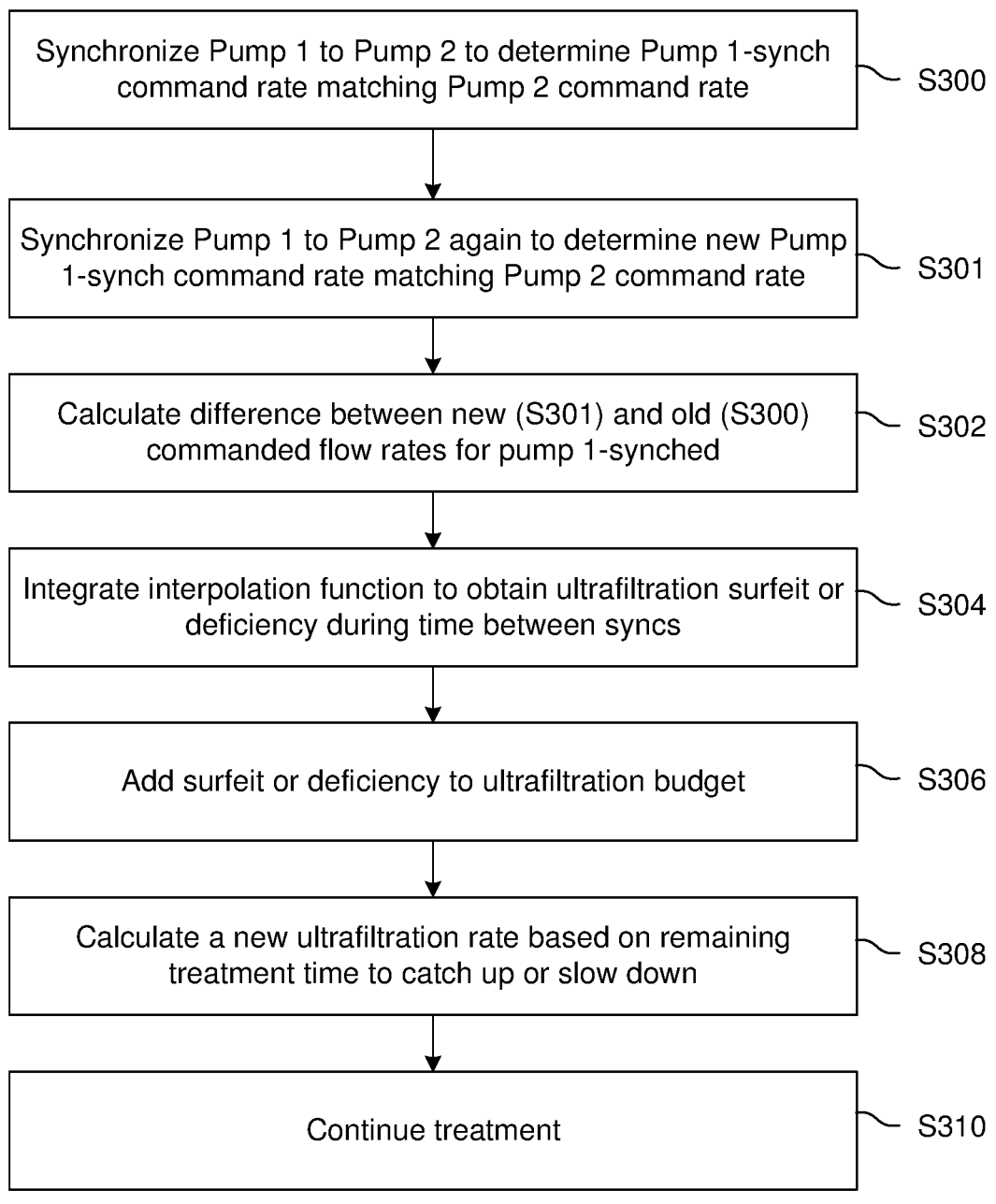
FIG. 16 shows a method of calculating to maintain an ultrafiltration budget over the course of multiple pump synchronization, according to various embodiments of the disclosed subject matter.
Figure 17A:
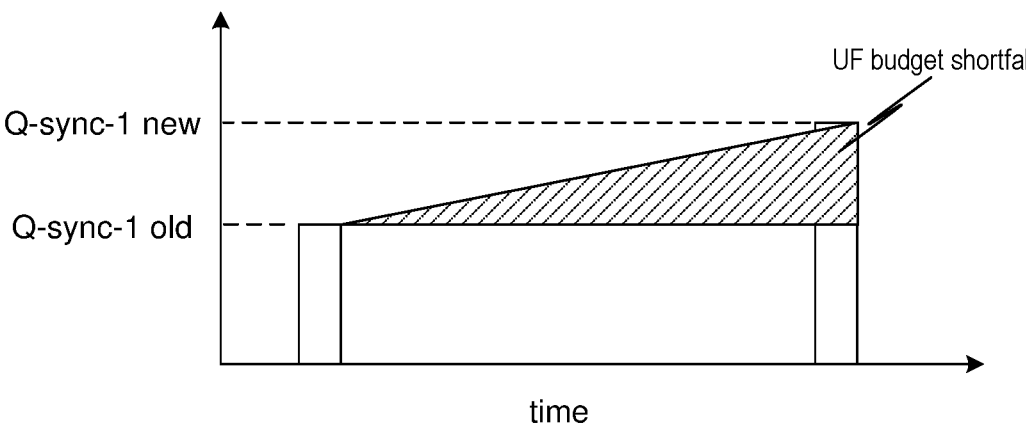
FIGS. 17A-17B illustrate command rate vs. time graphs for purposes of discussing a method of calculating to maintain an ultrafiltration budget over the course of multiple pump synchronization, according to various embodiments of the disclosed subject matter including the embodiments of FIG. 16.

Referring to FIG. 16, in any of the embodiments involving synchronization of two pumps, an error may be generated by a gradual change in the ratio of actual flowrate to commanded flowrate. Thus, at time t0, during or before a treatment, a synchronization may be performed S300 in which the commanded rate of an upstream pump, Pump 1, that generates a flow equal to the commanded flow rate for the downstream pump, Pump 2. At a later time, during treatment, the synchronized rate may be updated S301 resulting a new commanded flow rate for Pump 1. At S302, the difference between the new and old commanded flow rates yields a flow rate difference, calculated at S302, which may arise progressively during the time from the first synchronization to the later one. The flow rate difference may be interpolated between synchronizations and integrated over the assumed distribution of the change in the synchronized commanded rate over time. Assuming the difference accrued linearly over the time between the first synch and the second, a surfeit or deficiency may be calculated from the triangle function, i.e., multiplying the time between synchronizations by ½ the difference between the old and new Pump 1-synched commanded flow rates. If the later synchronized speed is higher, then this amount may be added to the ultrafiltration budget so that the required volume to be ultrafiltered during a remainder of the treatment will be increased. If the later synchronized speed is lower, then this amount may be subtracted from the ultrafiltration budget. S306. At S308, a new ultrafiltration rate may be calculated so that by the time the treatment is completed, the entire budget has been spent. Thereafter the budget may be applied to perform a remainder of the treatment S310 or the process may be repeated if additional synchronizations are to be performed. The parameters are illustrated graphically in FIG. 17A which shows two bar graphs for the two command rates for the first pump after synchronization with an exaggerated change. The shaded triangle superimposed on the bars indicates the cumulative UF shortfall when the new command rate of the first pump shows that a higher rate is required to keep up with the second pump. The symbol Q represents the commanded pump rate.

Figure 17B:
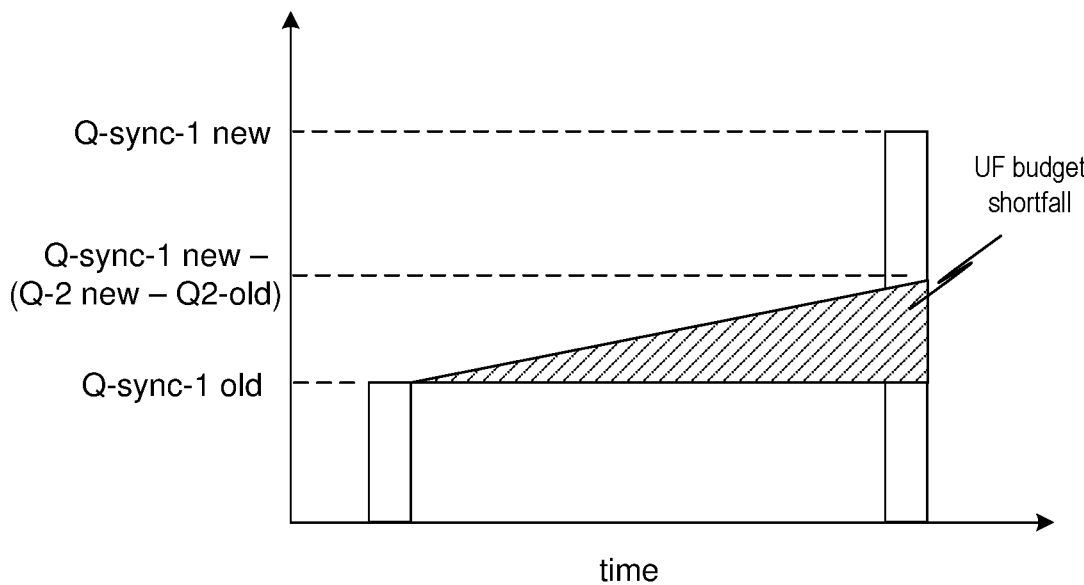

Note that if, in a procedure similar to FIG. 16, is performed, in which a subsequent synchronization is performed at a different Pump 2 commanded flow rate than the first synchronization, a budget surfeit or deficiency can still be calculated if the difference between the old Pump 2 commanded flow rate is removed from the calculation. Thus, subtracting Pump 2-commanded new from Pump 2-commanded old and then subtracting this difference from the old and new Pump 1-commanded-synched rates gives a Pump 1-commanded-synched that can be used to be used for the interpolation calculation. The parameters are illustrated in FIG. 17B. The new synchronized command rate for the first pump is reduced by the difference between the new and old second pump command rates and the ultrafiltration shortfall calculated from the reduced rate as before.

FIGS. 18A-18B illustrate the generation and use of a map of commanded flow and pressure conditions for determining the synchronized command speed of a slave pump 702 responsively to a command speed of a master pump 704 according to various embodiments of the disclosed subject matter. For example, the method may be used to obtain a formula or lookup table to calculated the rates of a replacement fluid pumped by replacement fluid pump 542 (FIG. 11) for a given pressure indicated by the inlet waste pressure sensor 575 and target effluent pump speed indicated by replacement fluid pump 542. FIG. 18A shows a generic synchronization scheme with symbols used in FIG. 18B with a first pump 702 (e.g., replacement fluid pump 542) and a second pump 704 (e.g., waste treatment fluid pump 574). The two pumps 702 and 704 are linked by a flow channel 714 which may be any of any type including those of the variety of embodiments disclosed herein. The flow balance sensor 706 indicates a flow mismatch between the two pumps 702 and 704. The flow balance sensor 706 may be indicated, for example, by the inlet waste pressure sensor 575.

Referring to FIG. 18B at S400, master pump (e.g. waste fluid pump 574) is run at a commanded rate of F2 and slave pump (e.g., replacement fluid pump 542) is synchronized with it at a predefined pressure of the effluent pump from the inlet waste pressure sensor 575, for example, 100 mmHg. The synchronized speed of master pump and the measured value of the pressure from inlet waste pressure sensor 575 are recorded. At S402, the master pump is run at a commanded rate of F2 and slave pump is synchronized with it at a predefined pressure from inlet waste pressure sensor 575, for example, 300 mmHg. The synchronized speed of the slave pump and the measured value of the pressure from the inlet waste pressure sensor 575 are recorded. At S404, master pump is run at a commanded rate of F3 and slave pump is synchronized with it at a predefined pressure of the inlet waste pressure sensor 575, for example, 100 mmHg. The synchronized speed of the slave pump and the measured value of pressure from the inlet waste pressure sensor 575 are recorded. At S406, the master pump is run at a commanded rate of F3 and the slave pump is synchronized with it at a predefined pressure of the inlet waste pressure sensor 575, for example, 300 mmHg. The synchronized speed of the slave pump and the measured value of the inlet waste pressure sensor 575 are recorded. At S410, the recorded speeds and pressure values are fitted to a function to allow the calculation of the synchronized command slave pump rate responsively to the commanded master pump rate and pressure. At S414, the master pump is adjusted according to the pressure compensation coefficient and the difference between the desired pressure of the inlet waste pressure sensor 575 and the measured magnitude.

At S412, the function is used to calculate a synchronized rate for the slave pump responsively to a commanded master pump rate and a current effluent pressure of the inlet waste pressure sensor 575. The inlet waste pressure sensor 575 pressure used for obtaining the synchronized rates at steps S400-S406 are predefined values. The target independent variable used in S412 is the measured value of the effluent pressure when the blood is flowing through the hemofilter and there is no flow from the effluent pump. At S414, during a hemofiltration treatment, the replacement fluid pump that pumps the first replacement fluid, may be set using the formula or lookup table and a current measured pressure from the inlet waste pressure sensor 575. With pressure compensation running, as the effluent pressure departs from the pressure of the inlet waste pressure sensor 575 originally entered in the formula, the speed of the effluent pump is adjusted accordingly.

Figure 19A:
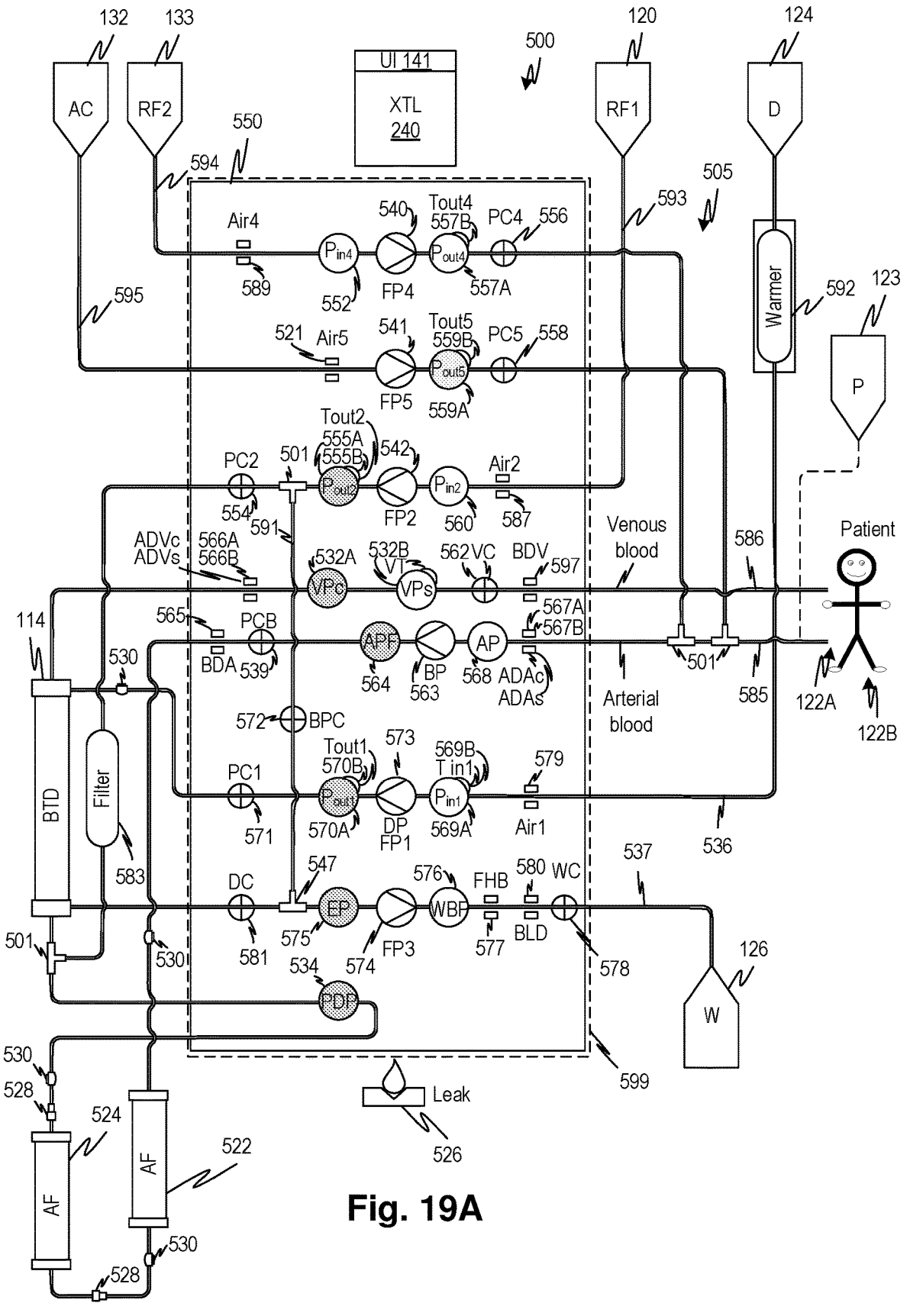
FIG. 19A illustrates a dialysis-like treatment device according to embodiments of the disclosed subject matter.

FIG. 19A shows a blood treatment machine figuratively with various actuators and sensors and an attached fluid circuit according to embodiments of the disclosed subject matter that is largely the same as that shown and described with reference to FIG. 11. In the present embodiment, ancillary filters 522 and 524 such as sepsis filters may be used in embodiments. The ancillary filters 522 and 524 are located upstream of the treatment device 114 with regard to the path of the arterial blood line 585 and downstream of the blood pump 563. A pressure sensor 534 is located between the treatment device 114 and the ancillary filters 522 and 524. The leak sensor 526 is provided to detect fluids dripping from the fluid circuit. Indicated in dashed outline is a cartridge 599 that may be configured to carry the enclosed elements for engagement with sensors and actuators of the blood treatment machine 550 to facilitate engagement of the fluid circuit 505 with the blood treatment machine. Note that any number or type ancillary filter(s) can be substituted including 1 or more and zero as illustrated in the FIG. 11, for example. Combinations of different types of filters may be used, such as additional sterile filters, adsorbent filters, ultrafilters, dialyzers, etc. Also, one or more connectors 528 or sampling ports 530 may be present or excluded.

FIG. 19D shows a table that correlates drawing element identifiers and reference numerals with abbreviations that are used in the figures. The identifiers and reference numerals are from FIG. 19A, elements of which form a superset of the elements in FIG. 11.

Figure 19B:
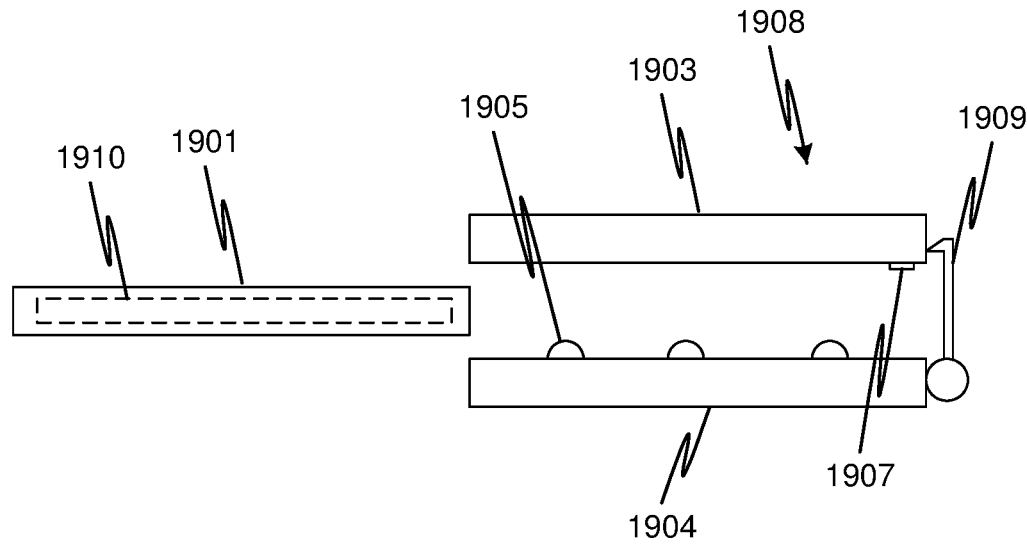
FIGS. 19B and 19C illustrate a fluid circuit cartridge with a loading mechanism and lock sensor, according to embodiments of the disclosed subject matter.
Figure 19C:
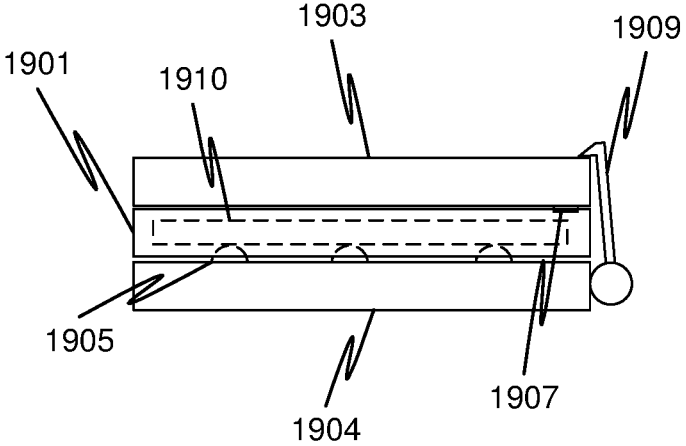

FIG. 19B shows a cartridge 1901 (e.g., the cartridge 599 shown more abstractly) having a fluid circuit 1910 that is supported by the cartridge 1901. The cartridge 1901 engages with a loading mechanism and locking sensor. The fluid circuit may contain tubing, chambers, sensors, accumulators, portions for engaging with sensors and actuators and other elements. A cartridge 1901 is loaded by positioning it between backplanes 1903 and 1904 of a loading mechanism 1908 supporting multiple actuators 1905. The backplanes 1903 and 1904 define a loading mechanism 1911. FIG. 19B shows the cartridge and loading mechanism 1908 prior to loading a locking. A locking mechanism 1909 is poised prior to engagement with the backplane 1903. A locking sensor 1907 detects when the locking mechanism 1909 is moved to the locking position shown in FIG. 19C. The cartridge may contain or support a fluid circuit which is not explicitly shown. When the cartridge 1901 is loaded and locked, the locking sensor 1907 detects a properly loaded cartridge 1901. If the cartridge is improperly loaded the cartridge lock sensor 1907 will detect a non-loaded state and a controller 240 may generate an error signal. The locking mechanism 1909 may be a spring loaded latch and the cartridge lock sensor 1907 may be a magnetic switch, microswitch or other such device. The multiple actuators 1905 may include peristaltic pump actuators, sensors, or valve actuators that engage respective portions of the fluid circuit. Although one type of latch is shown it will be understood that any type of latch and lock sensor may be provided. Note also that the backplane 1903 and backplane 1904 converge around the cartridge 1901 to thereby engage the fluid circuit and lock the locking mechanism 1909.

In any of the disclosed embodiments, the pressure used for synchronization, which corresponds to a condition of zero flow through the membrane of the treatment device, may be an average of the treatment fluid inlet and outlet pressures, the treatment fluid outlet pressure alone, the pressure of the non-blood compartment of a specially constructed blood treatment device that permits the pressure inside the treatment device to be measured with a single pressure transducer, an average of the blood inlet and outlet pressures, the blood outlet pressure alone, or the pressure of the blood compartment of a specially constructed blood treatment device that permits the pressure inside the treatment device to be measured with a single pressure transducer.

In all of the embodiments, valve actuators may include pinch clamps which can be replaced with other types of valves and circuit elements, for example, stopcocks, flow switchers, etc.

In any of the disclosed embodiments, the oncotic pressure of blood may be measured by halting a flow of treatment fluid and measuring the pressure difference between the blood and treatment fluid sides of the treatment device. This may be done each time the pumps are synchronized or it may be done independently for the purpose of sampling the blood oncotic pressure. The samples of oncotic pressure may be used to calculate a trend that may be compared to a predefined trend in oncotic pressure. The comparison may indicate that the pace of fluid withdrawal is drawing down the fluid in the blood compartment too fast relative to the patient's ability to replenish it from the upstream fluid compartments such as the interstitial and cellular compartments. The restoration of fluid to the blood compartment is known in the art as fluid rebound. Too high rate of ultrafiltration can cause a temporary hypovolemia which can be detrimental.

The controller may store a predefined rate of change in oncotic pressure that is permitted and slow the rate of ultrafiltration to fall under, or at that rate. The controller may compare the oncotic pressure to a predefined value and control a duration of the treatment so that the oncotic pressure is permitted to reach that value. Note that instead of storing actual values of oncotic pressure, data responsive to it may be stored, such as a derivative of oncotic pressure and or combinations with other variables. For example, oncotic pressure may be combined with a hematocrit sensor signal to produce a combined parameter indicating the patient's fluid load. In further embodiments, the controller may halt, or otherwise vary, the rate of ultrafiltration and combine data indicative of the varying rate of ultrafiltration with the oncotic pressure trend data in order to determine the fluid load or the rate of fluid rebound. A combined parameter such as a ratio of rate of oncotic pressure change to rate of ultrafiltration may be calculated and used to control the rate of ultrafiltration or the duration of ultrafiltration (or duration of treatment). The rate of ultrafiltration may be varied continuously during a treatment cycle responsively to the trend. The rate may be varied so as to decline progressively during a treatment according to predefined constraints on the oncotic pressure or rates of change thereof. As indicated, the oncotic pressure may indicate when the patient has reached a dry weight by measuring the magnitude of oncotic pressure relative to a predefined value (which may be custom for the patient) or the rate of fluid rebound, or the magnitude of the change in oncotic pressure over a test interval during which a predefined rate of ultrafiltration (for example zero rate of ultrafiltration) is maintained.

In all of the embodiments, pinch clamps can be replaced with other types of valves and circuit elements, for example, stopcocks, flow switches, etc.

In any of the embodiments, a newly connected fluid circuit, connected to a treatment machine having sensors and actuators to engage it, may be subjected to a break-in interval during priming to condition the pumping tube segments before synchronization is performed, or at least relied upon for fluid balance. In an embodiment, in a treatment machine that controls the total volume of fluid flowing into or from a patient against the total volume of fluid drawn from the patient by regulating the relative speeds of peristaltic pumps that flow fluid in a fluid circuit connected to the patient, a special priming mode is implemented. In the priming mode, fluid is pumped through the fluid circuit to prime at least the treatment fluid portion of the attached fluid circuit. A predefined break-in period sufficient to subject the inflow and outflow treatment fluid pumps—the pumps relied upon for fluid balance and ultra-filtration—are subjected to a predefined number of roller strikes prior to performing a synchronization. The break-in interval, in embodiments, may last for greater than five minutes, before establishing a synchronization mode or a treatment in which the peristaltic pumps are relied upon to control a net flow of fluid into or from the patient. In embodiments, the treatment machine is a hemodialysis machine or a hemofiltration machine where the pumps regulate the flow of dialysate into and out of a dialyzer or hemofilter.

Note that as used herein, embodiments refer to the embodiments described in the specification as well as any independent claim and any combination of an independent claim with any combination or sub-combination of the claims depending from an independent claim.

In the foregoing embodiments, the fresh treatment fluid pump pumping rate was determined by the controller, during treatment, from a function, or equivalent, that depended on the rate of the waste treatment fluid pump and the blood compartment pressure (Ave Pb). In alternative embodiments, the fresh treatment fluid pump may be feedback controlled on a balanced pressure signal calculated as the difference between the non-blood compartment pressure, Ave Ptf, and Ave Pb offset by the error and oncotic pressure which are both stored by the controller. Then the determined fresh treatment fluid pumping rate can be changed to obtain the prescribed ultrafiltration rate. In the modified method, S72 is replaced by an operation in which the fresh treatment fluid pump is negative feedback controlled by the calculated error signal. This may be employed, for example instead of the feedforward technique of S72.

In the foregoing embodiments, the TMP is provided as a function of Ave Pb and Qtfw, however, the TMP error may not be a function of these independent variables in which case it may be stored as a fixed value in the controller.

Note that as the term is used herein, "balanced" flow may refer to equal flows or flows that differ by a predefined amount, for example to account for ultrafiltration. During synchronizations, balanced flows may have a zero differential, however, an arbitrary predefined offset from equal flows may still be accommodated using the techniques of synchronization, as should be clear to the skilled practitioner. As a term used herein, "balanced" may refer to flows that are balanced but offset by a predefined ultrafiltration rate.

In any of the embodiments, the fluid in the treatment fluid circuit and treatment device non-blood compartment may be a priming fluid as is used commonly during priming stage in preparation for a treatment.

In any of the embodiments, the ultrafiltrate or net transfer of fluid from a patient can be positive or negative. A negative ultrafiltrate refers to a net transfer of fluid to a patient while a positive ultrafiltrate refers to a net transfer from a patient. The term balanced in reference to flow may refer to zero net ultrafiltrate volume or rate or a target net ultrafiltrate volume or rate. It does not necessarily mean equal flows in and out of a priming fluid source/sink or patient.

In other embodiments, the oncotic pressure of blood may be measured as described above and used for real-time feedback control of the difference in the average pressure in the blood compartment minus the pressure in the treatment fluid compartment (the compartments being compartments of the blood treatment device) minus the oncotic pressure. The real time feedback control on the pressure difference may continue during a treatment to control the relative speeds of the treatment fluid pumps in a configuration such as that of FIG. 3A and FIG. 7. The oncotic pressure may be measured again at certain points during treatment and used to provide the other functions discussed above.

Figure 20A:
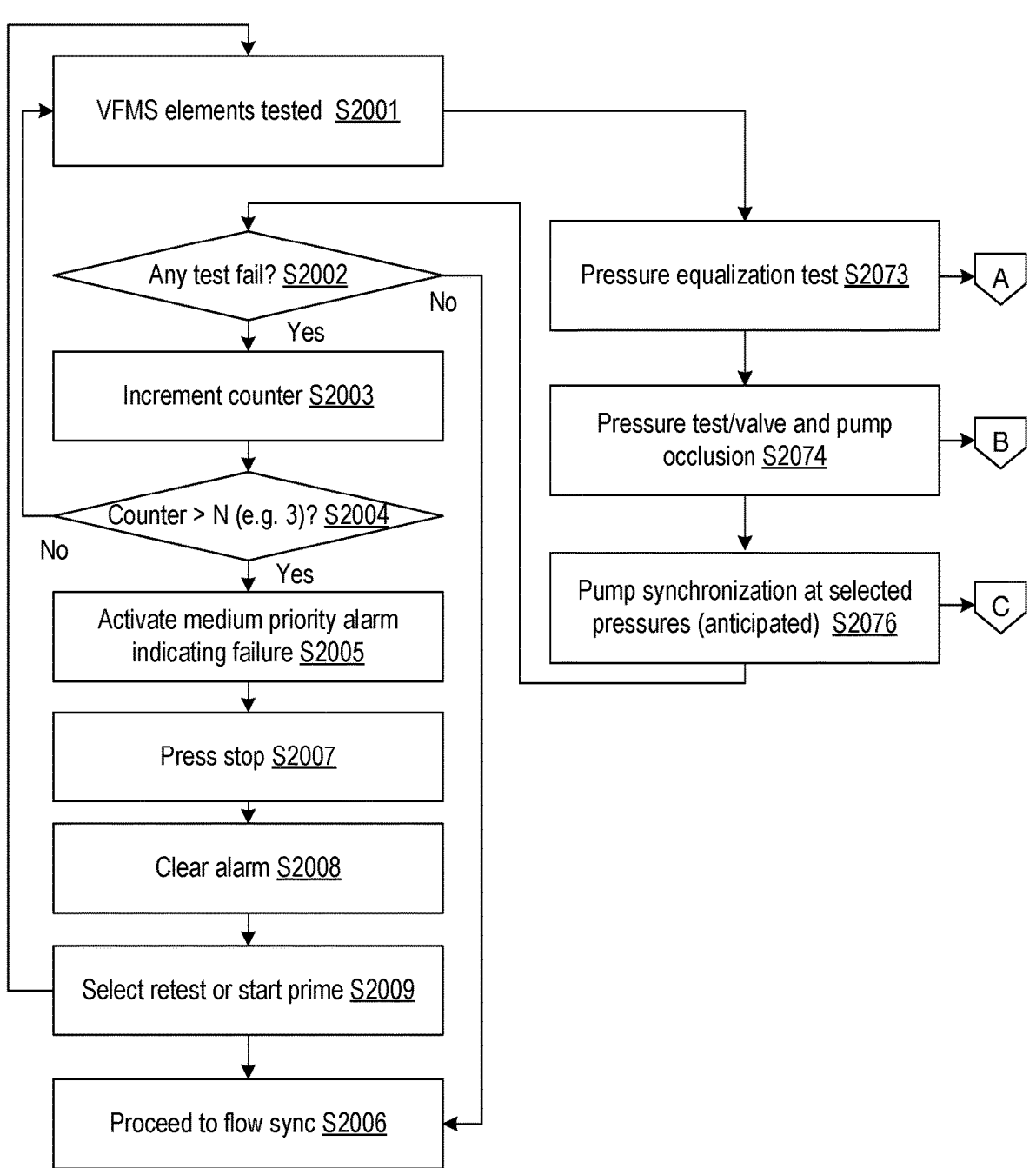
Figure 20B:
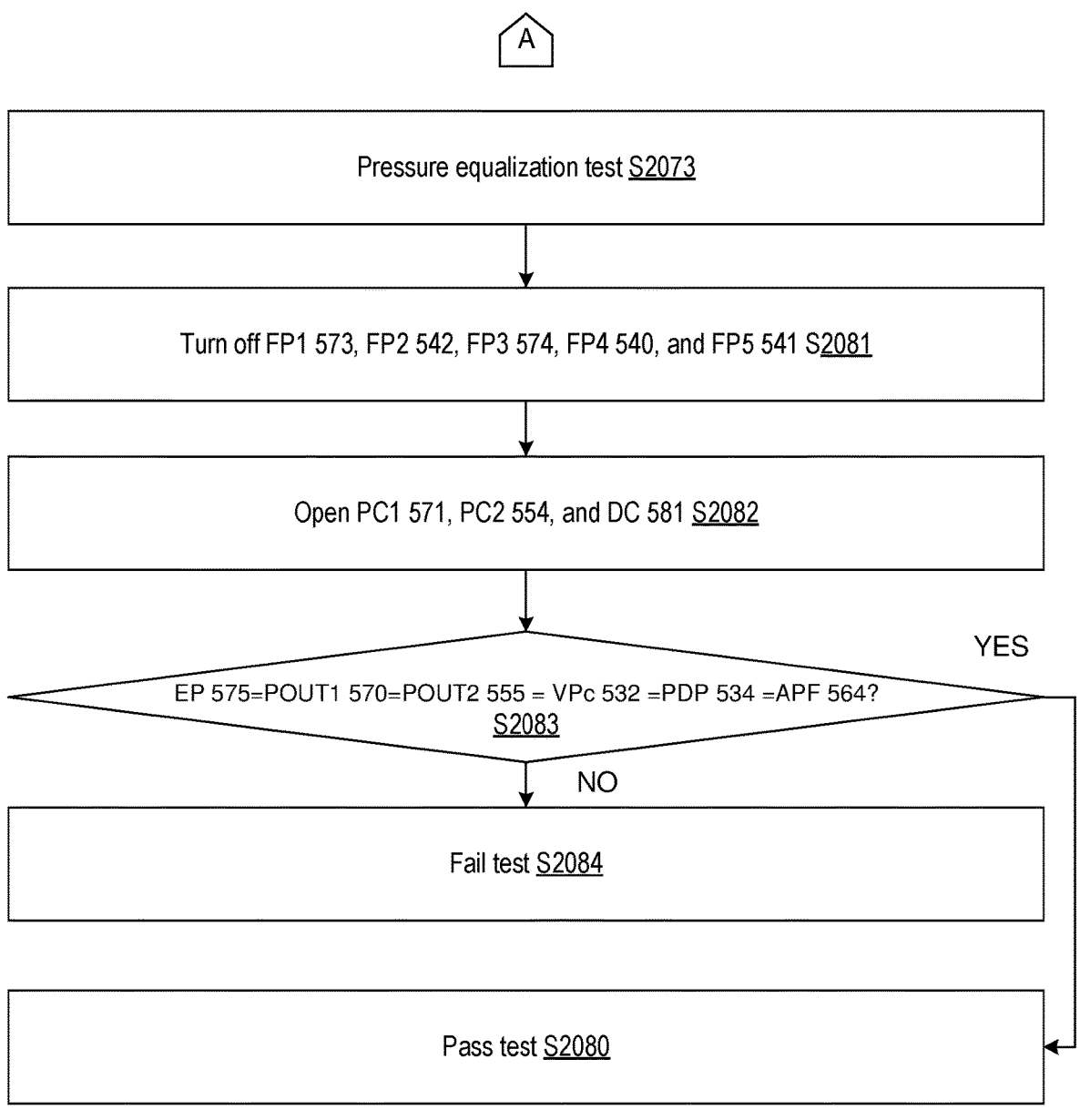

FIGS. 20A through 20D show a process for testing sensors and actuators prior to performing a flow synchronization. The control flow may halt or permit a flow synchronization depending on the results of the testing before treatment according to embodiments of the foregoing disclosed subject matter. Referring now to FIG. 20A, at S2001 the volumetric synchronization test is performed before treatment. If at S2002 any of the tests are determined to have failed, then a counter is incremented at S2003. At S2004, the counter is incremented and if less than a number N (e.g., 3) the volumetric flow management system (VFMS) sync test is repeated at S2001. Otherwise, if the counter has run out, then at S2005, a medium priority alarm is activated indicating the nature of the failure. At S2007, the user can press a control to stop the system, clear the alarm S2009 and retest or start prime at S2009. Then control reverts to S2001. If at S2002 the VFMS passes (not tests fail) then the system proceeds to flow synchronization at S2006.

Between S2001 and S2002 a series of tests are identified. The first test S2073 is described in FIG. 20B. This is a pressure equalization test that ensures that the pressure signals provided by a plurality of pressure sensors are within range of each other when the sensors are located at a similar height and the fluid path between them is open. From S2073, at S2081, the following pumps are turned off: fresh treatment fluid pump 573, replacement fluid pump 542, the waste treatment fluid pump 574, second replacement fluid pump, and supplemental fluid pump 541 (See FIG. 19). At S2082, the clamps pinch clamp 571, pinch clamp 554, and pinch clamp 581 are opened. At S2083, it is determined whether the following pressure sensors give readings that are within a predetermined range of each other. The pressure sensors are the inlet waste pressure sensor 575, fresh treatment fluid outlet pressure 570A, pressure sensor 555A, venous primary control pressure sensor 532A and venous secondary pressure sensor 532B, pressure sensor 534, blood pump outlet pressure sensor 564. The pressure sensors' mutual elevations may be used adjust the readings so that the readings can be compared more accurately. In other words, the pressure readings may be compensated for relative height before determined if they are in the range of each other.

At S2083 the controller determines if the pressure sensors are within a predefined range (e.g. 10 mmHg) with adjustment for relative height. If the pressures are not in range, at S2084, the test is indicated as failed. If the pressure signals are in range, then at S2080, the test is deemed to have passed and indication to that effect is generated by the controller 240.

FIG. 20C shows a procedure for pressure testing valve and pump occlusion. Here, a valve to be tested at S2086 is selected by its proximity to a pump with an intervening pressure sensor between them so that the valve can be tested for its ability to occlude the line. At S2086, a valve is closed to be tested. The pump upstream of the valve is used to pressurize the line between the pump and valve so that a pressure sensor between them can read the pressure in the line at S2087. The pump is then halted at S2088 and the pressure decay profile is sampled to determine if the decay rate and pressure plateau that is reach is in a predefined range at S2089. If the pressure does not plateau in range then the test is deemed to have failed and an output to that effect is indicated at S2090. Otherwise, the clamp is opened, the pump rotated to pressurize and the pump stopped at a next roller whose ability to occlude is to be tested. S2091. The process repeats until all rollers have been tested at S2092. A roller counter may be incremented. Once occlusion of all rollers have been tested, a next valve and pump combination is also tested until all are completed at which point, if the test hasn't failed yet, it is indicated as having passed at S2093.

Figure 20D:
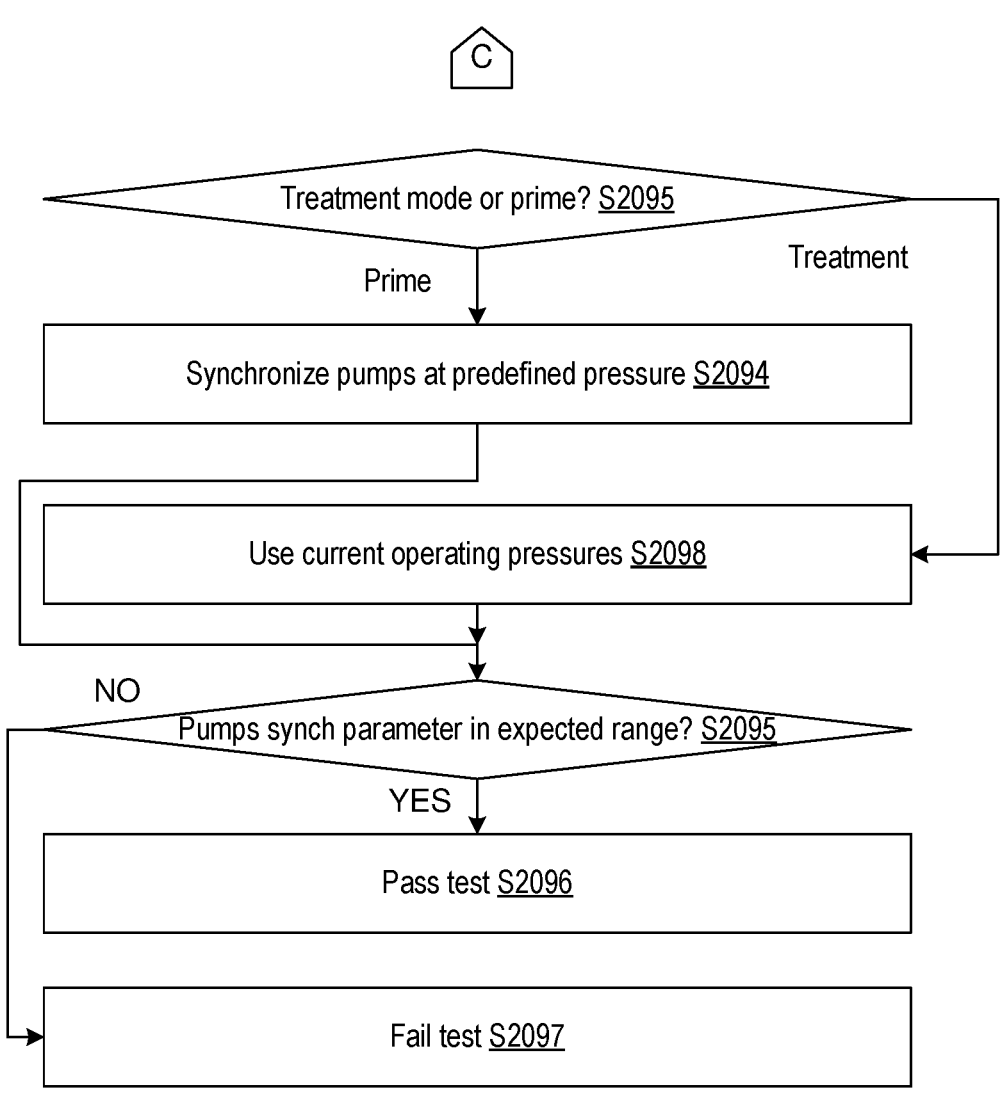

FIG. 20D shows a procedure where pumps are synchronized using either predefined pressure (S2094) or current operating pressure (S2098) depending on whether the system is in prime mode or treatment mode at S2095. The system uses synchronization to determine a relationship between the commanded pump rate and the synchronized rate of pumping. If the relationship is in an expected range at S2095, then the test passes at S2096. If not, the test fails at S2097.

Figure 21:
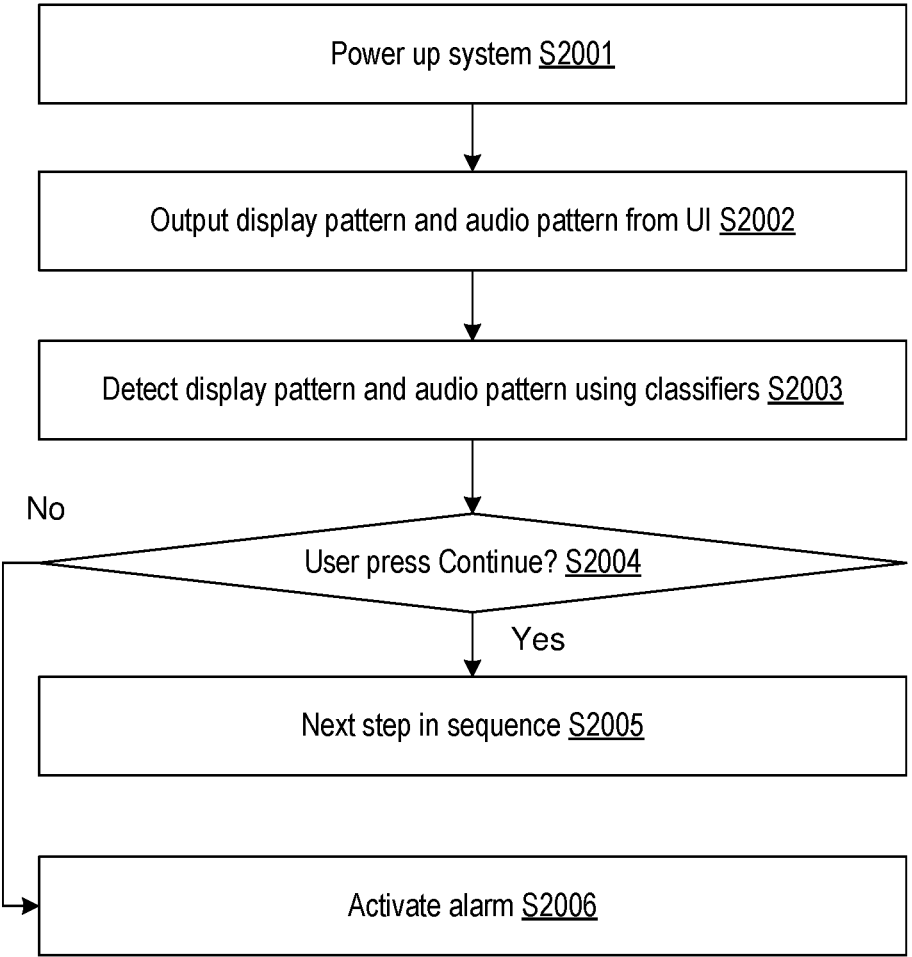
FIG. 21 illustrates a method for a power-on self-test according to embodiments of the disclosed subject matter.

Referring now to FIG. 21, when the system is initially powered up at S2001, a display and/or audio pattern are output at S2002. At S2003, one or both of the audio and test patterns is/are received through an input device—microphone for audio and camera or light sensor for video. At S2004 if the test pattern is received with no anomalies, the controller receives an acknowledgement from user input, e.g., the user activates a control to continue at S2005 and proceed to a next step otherwise an alarm is generated at S2006.

Figure 22:
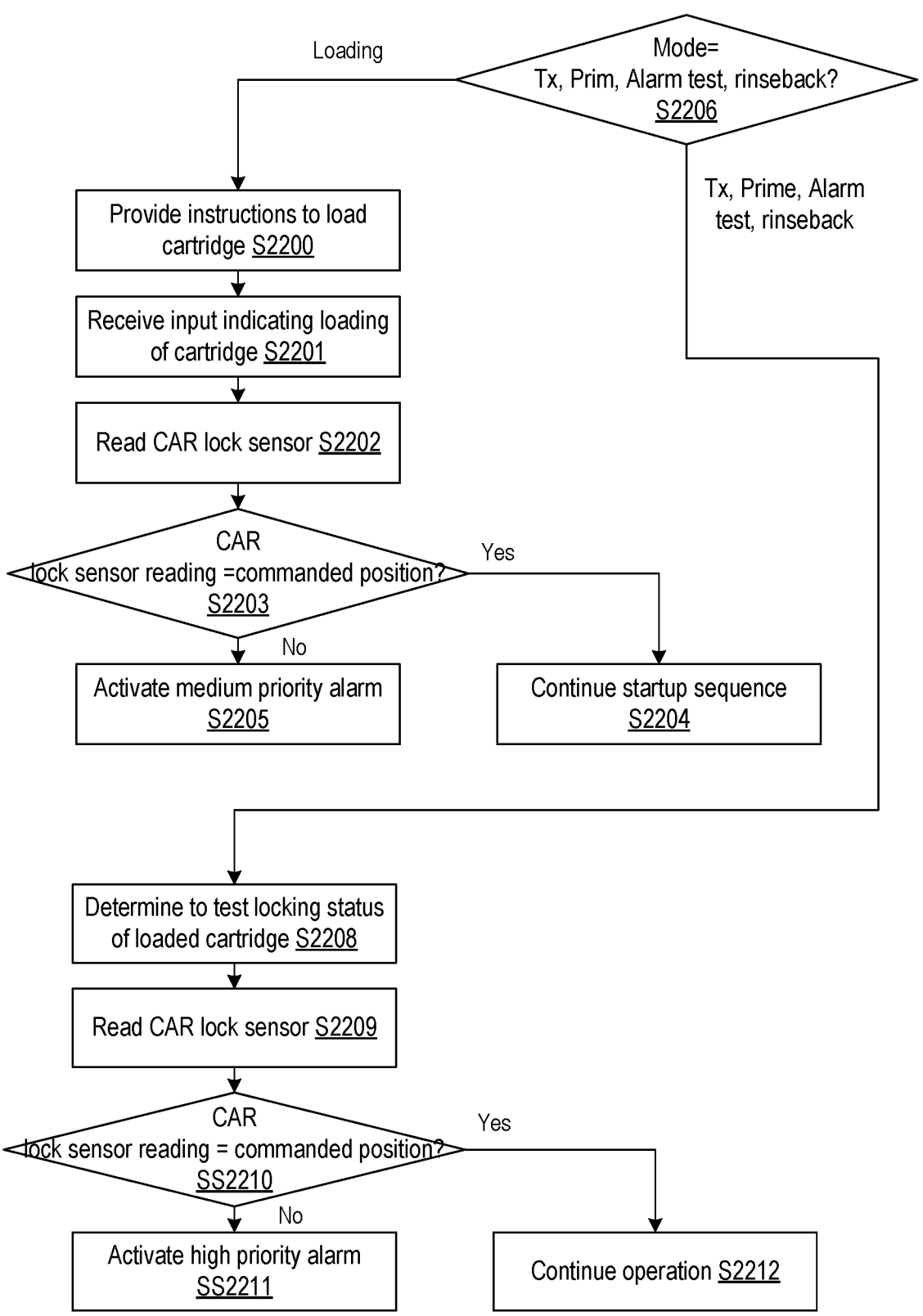
FIG. 22 illustrates a method for detecting improperly engaged fluid circuit and cartridge components according to embodiments of the disclosed subject matter.

FIG. 22 is a flowchart of test processes for cartridge loading or for continuous monitoring of the cartridge sensor during loading (first branch) and during treatment, prime, alarm test, and rinseback modes (second branch). In loading mode, tests detect whether the mechanical position of an actuator that engages the cartridge is consistent with a commanded state. The control flow run through command states and verifies the actuator configuration. The test process in FIG. 22 loading branch (decided at S2206) is performed during the cartridge load step of the startup sequence. If the cartridge lock sensor does not indicate the commanded position, a cartridge loading failure is determined and a high priority alarm is activated. For recovery, a user may open cartridge loading and reload the cartridge.

The test process in FIG. 22 treatment, prime, alarm test, rinseback branch is performed during startup steps following the load step (i.e., after successful loading), for example, during prime, alarm test, treatment, and rinseback. If the cartridge lock sensor does not indicate the commanded position and the prime has started or it is later in the process, a high priority alarm is activated. For recovery, a user may stop the current mode, disconnect the patient if connected, return to cartridge loading, and call service personnel.

As shown in FIG. 22, the process of the loading branch first outputs instruction to the user to load the cartridge S2200. Then, an input is received indicating that the cartridge is loaded at S2201. Then, the cartridge lock sensor is read S2202 and it is determined whether the reading corresponds to the commanded position S2203. If yes, the process continues the startup sequence S2204. If no, a medium priority alarm is activated at S2205.

As shown in FIG. 22, treatment, prime, alarm test, rinseback branch, the process first determines (e.g., periodically) to test the locking status of the loaded cartridge at S2208. Then, at S2209, the cartridge lock sensor is read, and it is determined at S2210 whether the reading relates to the commanded position. If yes, then normal operation is continued S2212. If no, a high priority alarm is activated S2211.

Figure 23A:
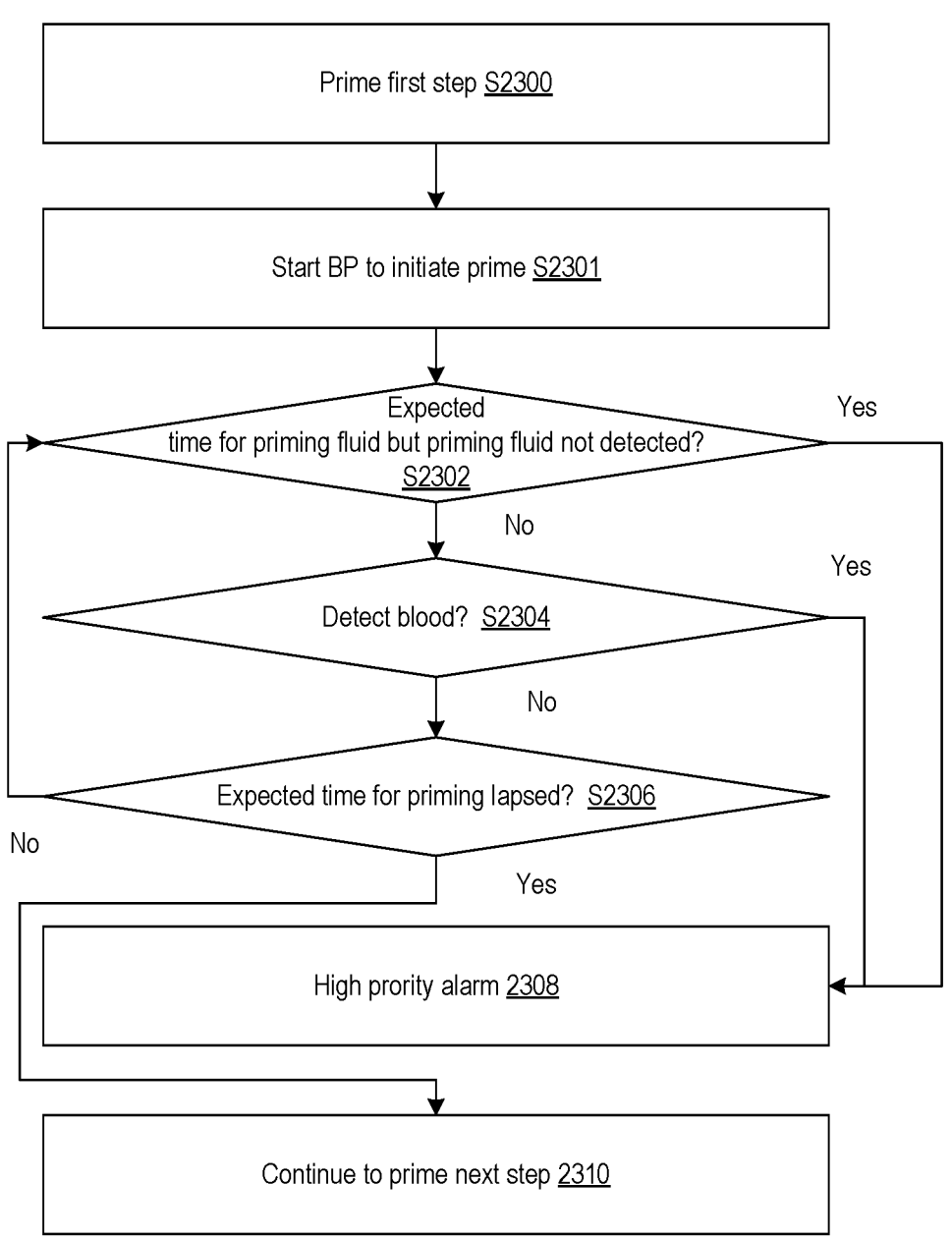
FIG. 23A illustrate a method for confirming an initiation of priming and checking for presence of blood according to embodiments of the disclosed subject matter.

FIG. 23A shows a method for responding to conditions during the priming first step. At S2300 the controller 240 confirms that the first step of priming is to be initiated after the user has loaded the cartridge and connected the priming fluid to the blood circuit. At S2301, the blood pump is activated to initiate prime. At S2302, the controller 240 determines whether two conditions are met, the first being that the time expected for priming fluid to be detected by the arterial control air sensor 567A and arterial secondary air sensor (and venous control primary air sensor 566A and venous secondary air sensor 566B) has lapsed since the initiation of the priming first step and the second being that priming fluid has failed to be detected. If the condition of S2302 has not been met, then at S2304 it is determined if blood has been detected by the arterial blood detector 565 and/or venous blood detector 597. If not, then at S2306 it is determined if the expected time for priming fluid to be detected by the arterial control air sensor 567A and arterial secondary air sensor and venous control primary air sensor 566A and venous secondary air sensor 566B has lapsed since the initiation of the priming first step. If it has, then at S2310, the present procedure terminates and priming further steps may proceed. If at S2302 or S2304 a respective one of the conditions is met, at 2308, a high priority alarm is activated. The alarm output may indicate the one or more particular events that caused it to be activated, in particular a user interface may output an indication that the time for priming fluid to reach the detectors has lapsed or it may indicate that blood was detected in the fluid line at a time during which the patient should not be connected and therefore there should be no blood in the blood line. If at S2306 the expected time has not lapsed, then control reverts to S2302.

Figure 23B:
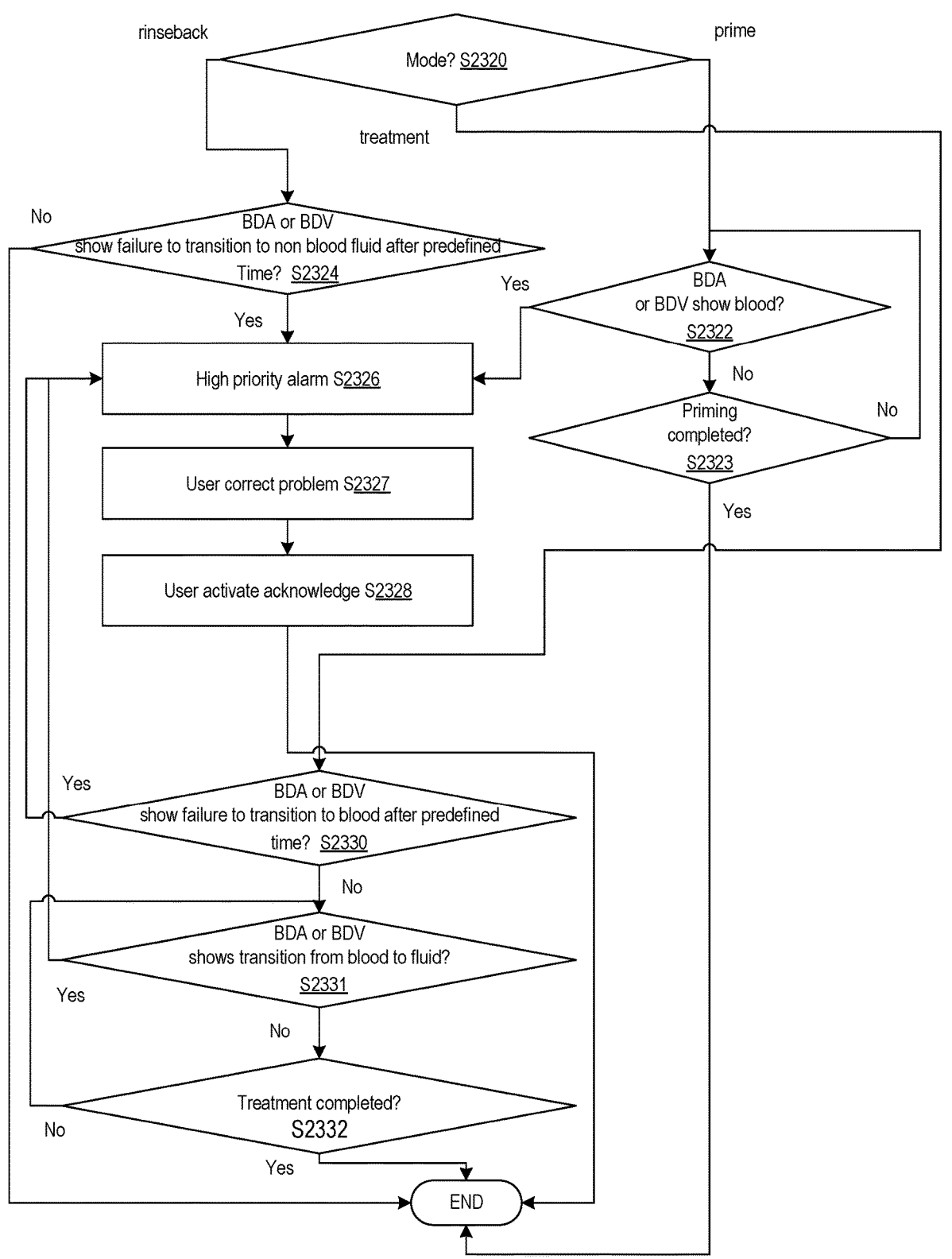
FIG. 23B illustrates a method for confirming an initiation of a treatment mode and incorrect presence of fluid according to embodiments of the disclosed subject matter.

Referring now to FIG. 23B, a process for confirming that a patient is connected correctly is described. At S2320 the system is determined to be in rinseback, priming, or treatment mode.

If the system is in rinseback mode, at 2324, the controller 240 determines if the arterial blood detector 565 or venous blood detector 597 has failed to detect a non-blood fluid after a period of time. This marks the transition from an unprimed fluid circuit to one that is primed. If failure is indicated, at S2326, a high priority alarm is activated, directions are output giving the nature of the problem and the user given an opportunity to identify the cause and correct the problem S2327. At S2383, an acknowledge command is then received by the controller and the user may be directed by the system to unload the cartridge.

If the system is treatment mode then at S2330 the controller 240 determines if the arterial blood detector 565 or venous blood detector 597 indicates a failure to detect a transition from a non-blood fluid (e.g., priming fluid) to blood after a period of time. The respective periods of time are selected responsively to the operating mode and flow rate. If at S2324 a failure is detected then control proceeds to S2326. If at 2331 the arterial blood detector 565 or venous blood detector 597 show a transition from blood to non-blood fluid then control proceeds to S2326. If S2330 shows no transition from blood to non-blood fluid then control proceeds to termination after treatment has been complete at S2332.

If the system is in prime mode, then if the arterial blood detector 565 or venous blood detector 597 show blood the control proceeds to S2326. S2322 is repeated until priming is completed as indicated by the loop between S2323 and S2322.

Figure 24:
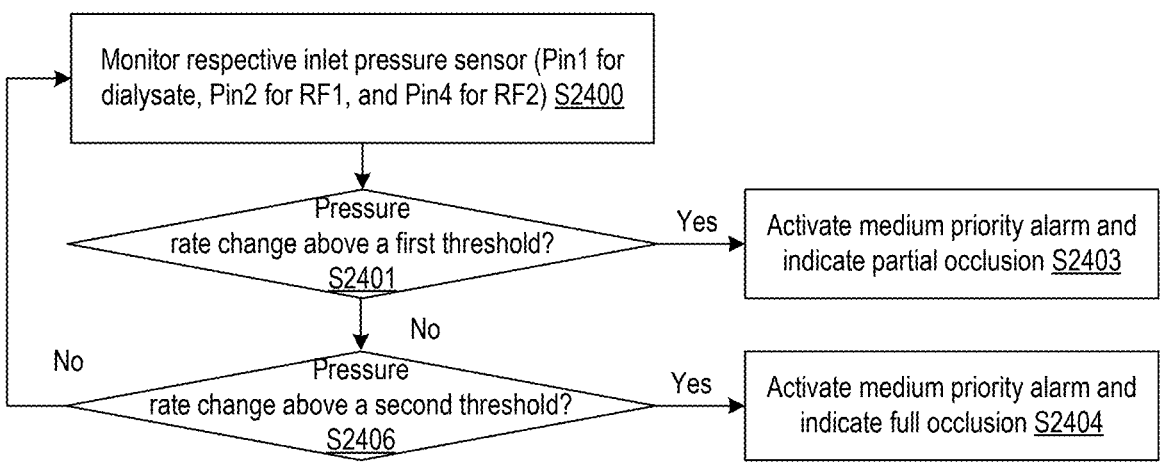
FIG. 24 illustrates an occlusion test on an inlet line for receiving therapy fluid, according to embodiments of the disclosed subject matter.

FIG. 24 provides a flowchart of a test process for identifying inlet line restrictions, for example, dialysate (or therapy fluid in HF mode) inlet line restrictions, replacement fluid inlet line restrictions, or flex pump inlet line restrictions, during patient connect, treatment, or rinseback modes. A pressure sensor in a respective inlet line may be used to detect low pressure (against a respective threshold) indicative of occlusion. For each one of dialysate, first replacement fluid 120, and second replacement fluid 540, the process uses respective inlet pressure sensors on the respective prescription fluid inlet lines to monitor for occluded or partially occluded inlet prescription fluid lines due to bag restrictions, clamped lines, or partially kinked tubing. The process also monitors for continuous pressure monitor function. The process uses the respective inlet pressure sensors to monitor for predicted rate change in bag head height that exceeds a predefined threshold for partial occlusion and another predefined threshold for full occlusion. If occlusion is indicated in the inlet line of replacement fluid pump 542 (first replacement fluid line 593), both fresh treatment fluid pump 573 and replacement fluid pump 542 pumps are stopped.

As shown in FIG. 24, the process monitors a respective inlet pressure sensor (fresh treatment fluid inlet pressure sensor 569A for dialysate, pressure sensor 552 for first replacement fluid RF1, and pressure sensor 560 for second replacement fluid 540) at S2400. The process determines if there is a pressure rate change above a first threshold S2401. If yes, a medium priority alarm is activated at S2403 to indicate partial occlusion. In no, the process determines if there is a pressure rate change above a second threshold at S2406. If yes, then at S2404 a medium priority alarm is activated to indicate full occlusion. If no, the process continues the monitoring at S2400.

Figure 25:
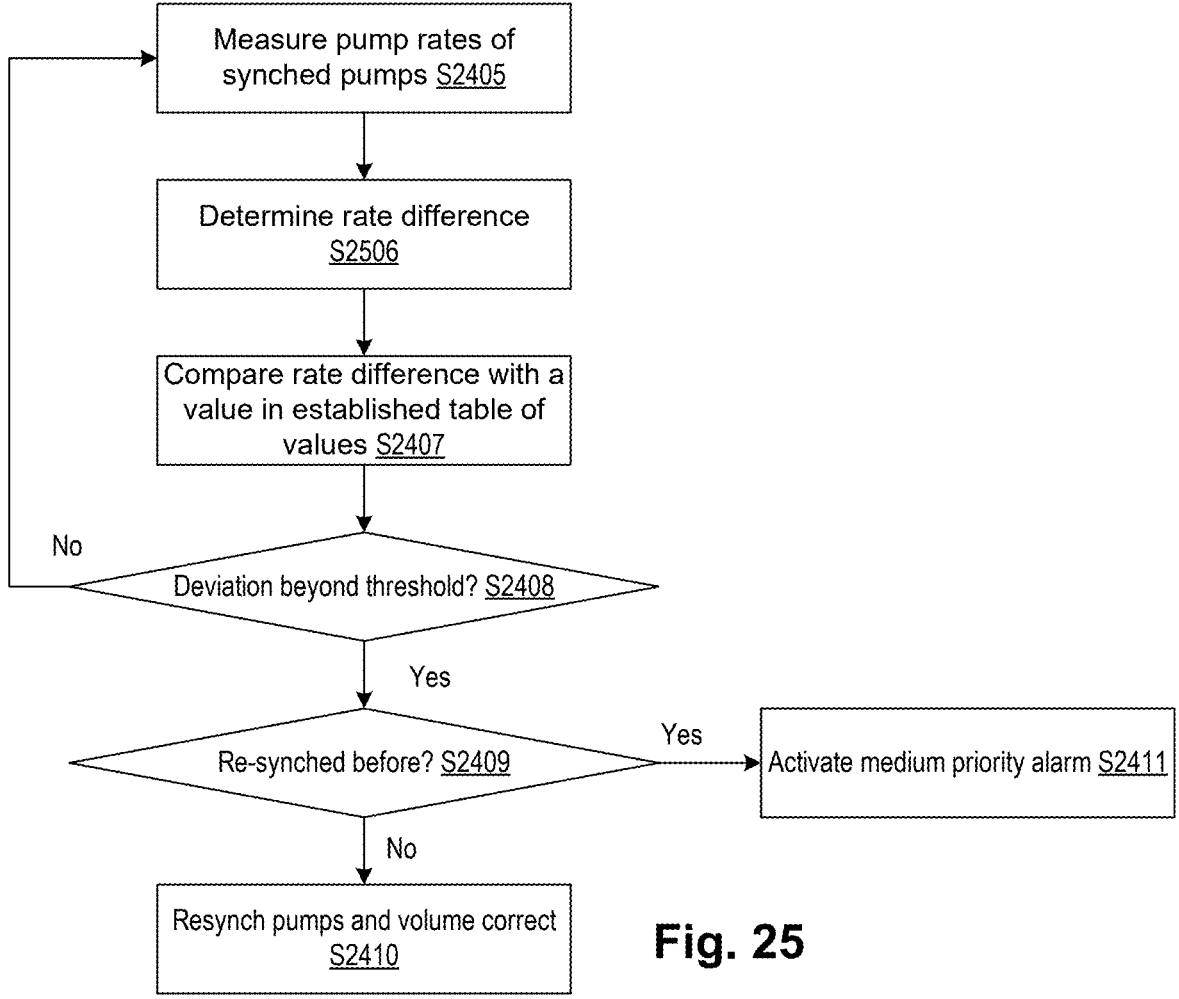
FIG. 25 illustrates a method of validating pump synchronization parameters according to embodiments of the disclosed subject matter.

FIG. 25 provides a flowchart of a test process for identifying pump synchronization error by comparing a standard table of values to a priming synchronization test, where the fit of a current synch is compared to a standard fit. In case of detecting incorrect synch values for VFMS pump rates, correction may be made by executing rinseback and unloading the cartridge. More specifically, in order to recover, a user may press "Mute" for 2 minute audio override, press "Help" for additional info and press "Done" when finished, identify the alarm cause, press "Acknowledge", and press "Rinseback" followed by "Unload Cartridge".

As shown in FIG. 25, during priming or treatment, the process measures pump rates of two synched pumps fresh treatment fluid pump 573 and replacement fluid pump 542 at S2405. At S2506, the process determines the pump rate difference between the two pumps and compares the rate difference with a value in a previously established table of values at S2407. If there is deviation beyond an acceptable threshold at S2408, the process determines if the pumps have been resynchronized before S2409. If yes, the process activates a medium priority alarm S2411. If no, the process resynchronizes the pumps, volume corrects, and repeats by measuring pump rates at S2410.

The previously established table of values may take the form of a rate difference between two pumps versus an inlet pressure of a downstream one of the pumps. The rate is the commanded rate of the pumps, i.e., a nominal flow rate which is related to an actual flow rate. The commanded rate difference is determined by synchronization of the pumps with regard to the flow rate. This yields a list of corresponding values. A second dimension, hence a table, is provided by a second parameter, namely the upstream pump's inlet pressure to which the actual flow rate is sensitive, as explained above. Of course the table may take the form of rate ratios or other parameters that yield equivalent determinations. The pumps used to construct the table may be the same pumps to be compared after synchronization to the values in the table or different pumps of the same construction. Manufacturing variability or variability in usage history may affect how close the table values are to the pumps that are actually synchronized and whose synchronization parameters are to be compared to the table values.

Note that instead of a table of values, a formula could be used which relates the actual flow rate to the inlet pressure of the downstream pump, a reference pressure and a commanded flow rate.

Figure 26:
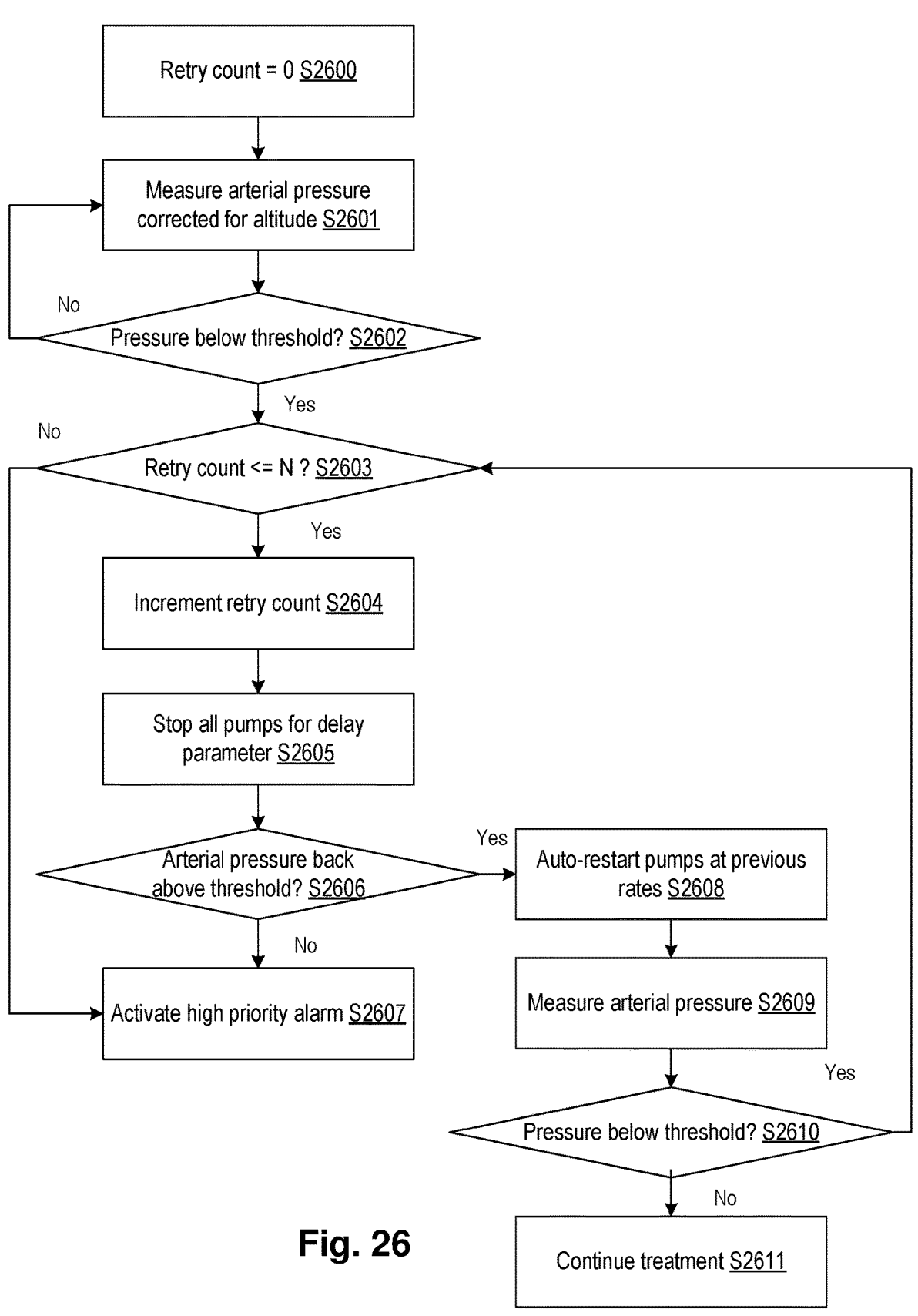
FIG. 26 illustrates a method for checking arterial pressure for evidence of an access restriction according to embodiments of the disclosed subject matter.

FIG. 26 provides a flowchart of a test process for monitoring the pump inlet pressure sensor 568 and identifying patient arterial access restriction during patient connection, treatment, or rinseback. If arterial pressure goes lower than a threshold under certain time constraints, access restriction is identified. The time constraint may define that the arterial pressure stays below the threshold for a delay parameter. The threshold may be defined as an established limit at an adjustable amount more negative than the stable average arterial pressure plus an offset parameter, but not more than −400 mmHg. Alternatively, the threshold may be defined as −400 mmHg.

Arterial access line restriction correction may be performed by inspecting for pinched/kinked lines. Access position correction may be performed by inspecting patient access for needle/catheter position and patient position. Access clotting correction may be performed by following the unit's procedures and performing rinseback if appropriate. In order to recover, a user may press "Mute" for 2 minute audio override, press "Help" for additional info and press "Done" when finished, identify the alarm cause, correct the alarm cause, press "Acknowledge", press "Continue Treatment", open appropriate pinch clamps, and restart pumps at previous rates with blood pump 563 Start Test.

As shown in FIG. 26, the arterial pressure test starts by setting the retry count equal to zero at S2600 and monitoring the arterial pressure the pump inlet pressure sensor 568 at S2601. If the arterial pressure drops below a threshold S2602, the process determines if the retry count is less than 3 (the count may be any number and 3 is just a basis for illustration) at S2603. If it is greater than or equal to 3, a high priority alarm is activated at S2607. If the retry count is less than 3, the retry count is incremented at S2604 and all pumps are stopped for a time period equal to a delay parameter at S2605. If the arterial pressure is not back above the threshold S2606, a high priority alarm is activated at S2607. If the arterial pressure at S2606 is back above the threshold, the pumps are re-started at their respective previous rates S2608 and the arterial pressure is measured at S2609. If it is below the threshold at S2610, the process proceeds by looping back to S2603 determining whether the retry count is less than 3. If the arterial pressure is not below the threshold, the treatment is continued at S2611.

Figure 27:
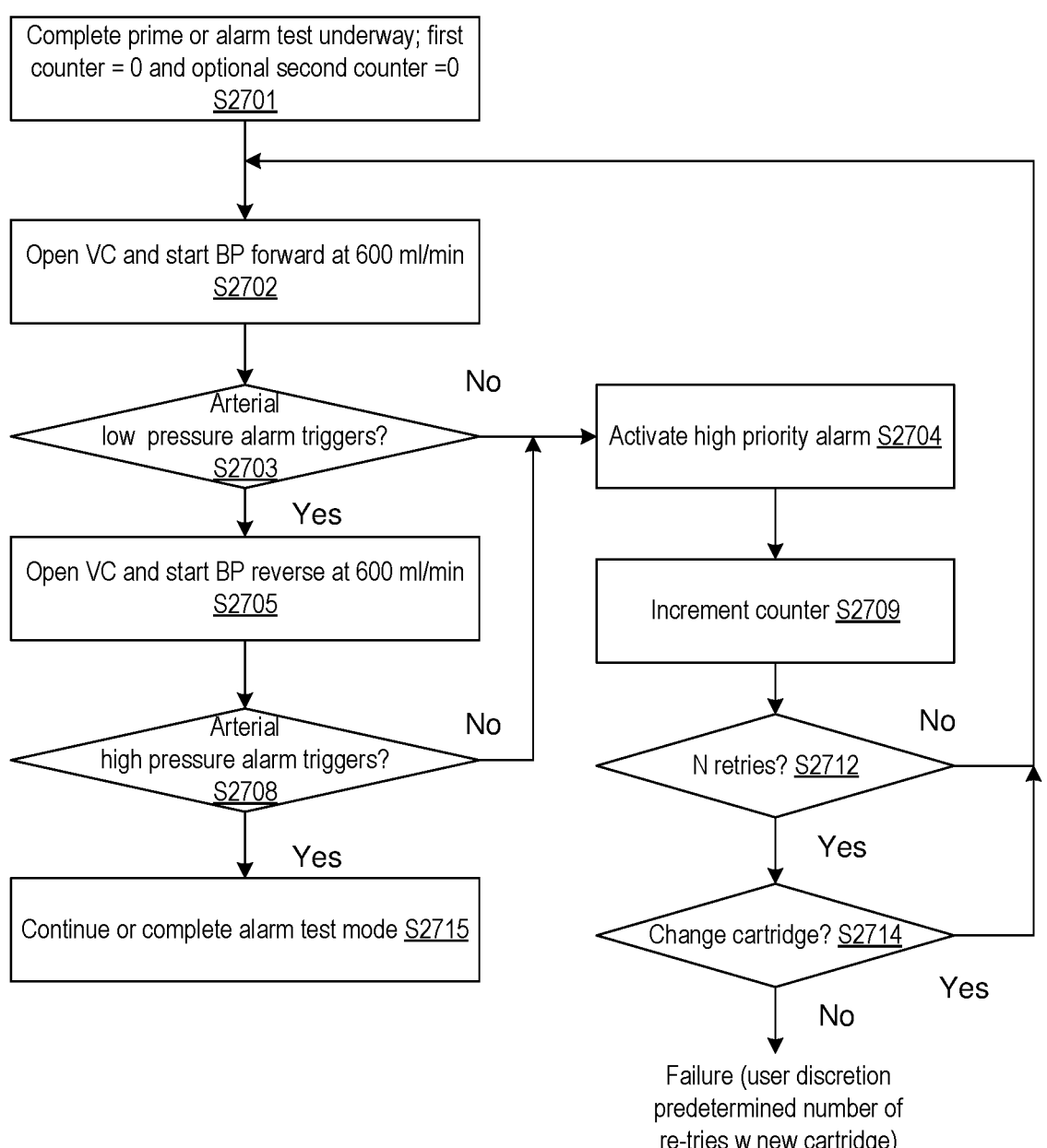
FIG. 27 illustrates a method for verifying the triggering of pressure alarms for pre-pump testing in forward and backward pumping according to embodiments of the disclosed subject matter.

FIG. 27 provides a flowchart of an alarm test process for alarms on pump inlet pressure sensor 568. The test is performed for a high pressure alarm and a low pressure alarm. The system cannot continue through the alarm test sequence until the test passes. Another test is used to test to test the triggering of the alarm for blood pump outlet pressure sensor 564. See FIG. 28.

As shown in FIG. 27, and indicated at S2701, the alarm test starts when the prime step is completed. Also at S2701, a first counter is zeroed. A second counter for counting cartridge changes and retries beginning with priming may also be zeroed in case one of the alarm tests fails to trigger after a first retry. The procedure of FIG. 27 may also be performed at any time during the alarm test mode rather than immediately after. For example, it can follow the procedure of FIG. 28.

At S2702 the process opens the venous line clamp 562 and starts the blood pump 563 in forward mode at a predefined rate (e.g., 600 ml/min, but the disclosed subject matter is not limited to this value; it could be some other value or range of values selected to trigger the tested low and high pressure arterial pressure alarms). At S2703, the process verifies that the arterial low pressure alarm triggers. If not, a high priority alarm is generated at S2704. If the arterial low pressure alarm triggers then at S2705, the process again opens the venous line clamp 562 if not still open and starts the blood pump 563 in reverse mode at a predefined rate (e.g., 600 ml/min, and again, the disclosed subject matter is not limited to this value; it could be some other value or range of values selected to trigger the tested low and high pressure arterial pressure alarms). Then at S2708, the process verifies that the arterial high pressure alarm triggers. If not the high priority alarm is activated at S2704.

If either the low or high arterial pressure alarm triggers and the high priority alarm is activated then at S2709 the first counter is incremented and at S2712 it is determined if the counter has reach a predetermined value, N. The predefined number of times (=N), for example 3 times; again the disclosed subject matter is not limited to a particular value of N. If the counter is less N, then the test is retried and control reverts to S2702. When the counter reaches N, the controller 240 may output instructions on a user interface to change the cartridge for a new one.

The number of tests with a new cartridge may be at the user's discretion. Each retry, using the second counter, begins by reverting to S2702. The cartridge may be replaced and the entire test repeated some number of times or optionally not at all. A new cartridge must be primed again. The cartridge change and retry may be required some number of retries so the controller may keep count using the second counter. Again the alarm test mode cannot be completed until both the arterial high pressure and low pressure alarms trigger.

Figure 28:
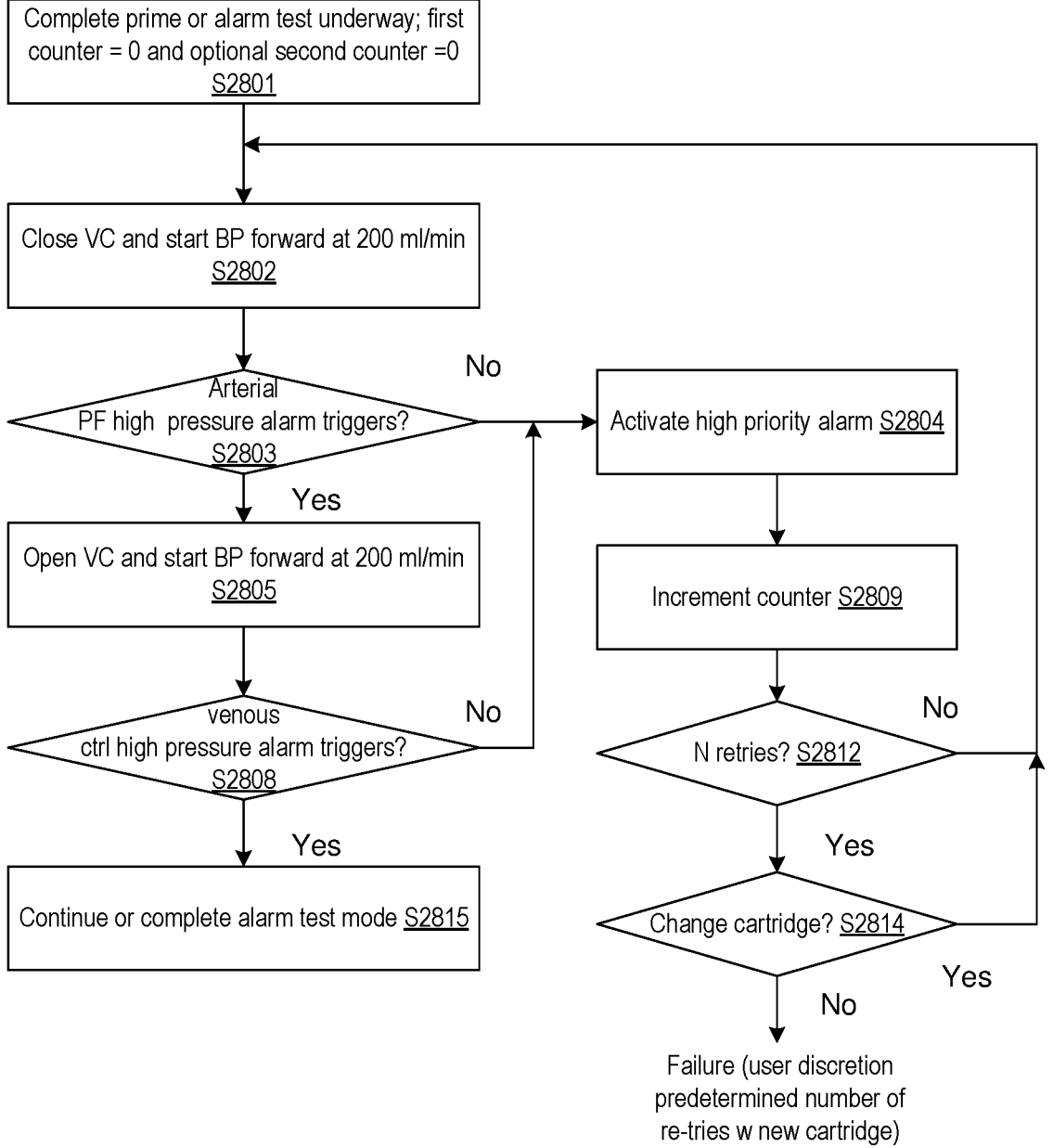
FIG. 28 illustrates a method for pre-filter testing of alarms according to embodiments of the disclosed subject matter.

FIG. 28 provides a flowchart of an alarm test process for verifying the triggering of an alarm on high pressure from blood pump outlet pressure sensor 564. As in the procedure described with reference to FIG. 27, the system cannot continue through the alarm test sequence until the test passes. The procedures of FIGS. 27 and 28 can be done sequentially or at different times during the alarm test mode in any order.

As shown in FIG. 28, and indicated at S2801, the alarm test starts when the prime step is completed. Also at S2801, a first counter is zeroed. A second counter for counting cartridge changes and retries beginning with priming may also be zeroed in case one of the alarm tests fails to trigger after a first retry. The procedure of FIG. 28 may also be performed at any time during the alarm test mode rather than immediately after.

At S2802 the process closes the venous line clamp 562 and starts the blood pump 563 in forward mode at a predefined rate (e.g., 200 ml/min, but the disclosed subject matter is not limited to this value; it could be some other value or range of values). At S2803, the process verifies that the pre-filter/dialyzer arterial high pressure alarm triggers. The arterial high pressure is detected by blood pump outlet pressure sensor 564. If not triggered, a high priority alarm is generated at S2804. If the arterial high pressure alarm triggers then at S2805, the process again opens the venous line clamp 562, if not still closed, and starts the blood pump 563 in forward mode at a predefined rate (e.g., 200 ml/min, and again, the disclosed subject matter is not limited to this value; it could be some other value or range of values). Then at S2808, the process verifies that the control venous (VPc) high pressure alarm triggers. If not the high priority alarm is activated at S2804.

If either of the high or low pressure alarms triggers and the high priority alarm is activated then at S2809 the first counter is incremented and at S2812 it is determined if the counter has reach a predetermined value, N. The predefined number of times (=N), for example 1 time, 2 times, or 3 times; again the disclosed subject matter is not limited to a particular value of N. If the counter is less than N, then the test is retried and control reverts to S2802. When the counter reaches N, the controller 240 may output instructions on a user interface to change the cartridge for a new one.

The number of tests with a new cartridge may be at the user's discretion. Each retry, using the second counter, begins by reverting to S2802. The cartridge may be replaced and the entire test repeated some number of times or optionally not at all. A new cartridge must be primed again. The cartridge change and retry may be required some number of retries so the controller may keep count using the second counter. Again the alarm test mode cannot be completed until both the arterial high pressure and low pressure alarms trigger.

Figure 29:
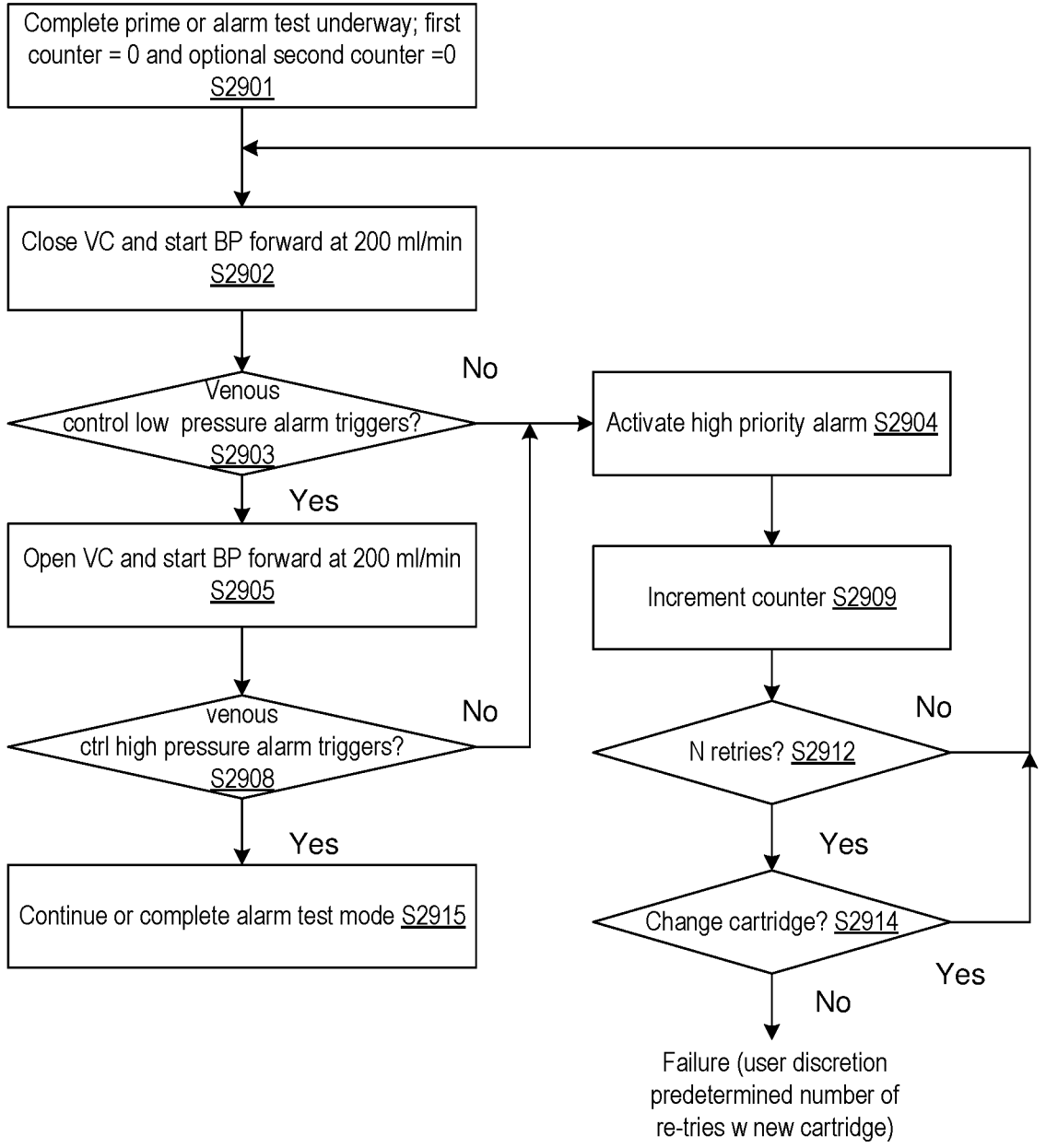
FIG. 29 illustrates a method for testing venous control pressure alarm according to embodiments of the disclosed subject matter.

FIG. 29 provides a flowchart of an alarm test process for verifying the triggering of an alarm on high pressure from blood pump outlet pressure sensor 564. As in the procedure described with reference to FIG. 27, the system cannot continue through the alarm test sequence until the test passes. The procedures of FIGS. 27 and 28 can be done sequentially or at different times during the alarm test mode in any order.

As shown in FIG. 29, and indicated at S2901, the alarm test starts when the prime step is completed. Also at S2901, a first counter is zeroed. A second counter for counting cartridge changes and retries beginning with priming may also be zeroed in case one of the alarm tests fails to trigger after a first retry. The procedure of FIG. 29 may also be performed at any time during the alarm test mode rather than immediately after.

At S2902 the process closes the venous line clamp 562 and starts the blood pump 563 in forward mode at a predefined rate (e.g., 200 ml/min, but the disclosed subject matter is not limited to this value; it could be some other value or range of values). At S2903, the process verifies that the pre-filter/dialyzer arterial high pressure alarm triggers. The arterial high pressure is detected by blood pump outlet pressure sensor 564. If not triggered, a high priority alarm is generated at S2904. If the arterial high pressure alarm triggers then at S2905, the process again opens the venous line clamp 562, if not still closed, and starts the blood pump 563 in forward mode at a predefined rate (e.g., 200 ml/min, and again, the disclosed subject matter is not limited to this value; it could be some other value or range of values). Then at S2908, the process verifies that the control venous 532A (VPc) high pressure alarm triggers. If not the high priority alarm is activated at S2904.

If either of the high or low pressure alarms triggers and the high priority alarm is activated then at S2909 the first counter is incremented and at S2912 it is determined if the counter has reach a predetermined value, N. The predefined number of times (=N), for example 1 time, 2 times, or 3 times; again the disclosed subject matter is not limited to a particular value of N. If the counter is less N, then the test is retried and control reverts to S2902. When the counter reaches N, the controller 240 may output instructions on a user interface to change the cartridge for a new one.

The number of tests with a new cartridge may be at the user's discretion. Each retry, using the second counter, begins by reverting to S2902. The cartridge may be replaced and the entire test repeated some number of times or optionally not at all. A new cartridge must be primed again. The cartridge change and retry may be required some number of retries so the controller may keep count using the second counter. Again the alarm test mode cannot be completed until both the arterial high pressure and low pressure alarms trigger.

Figure 30:
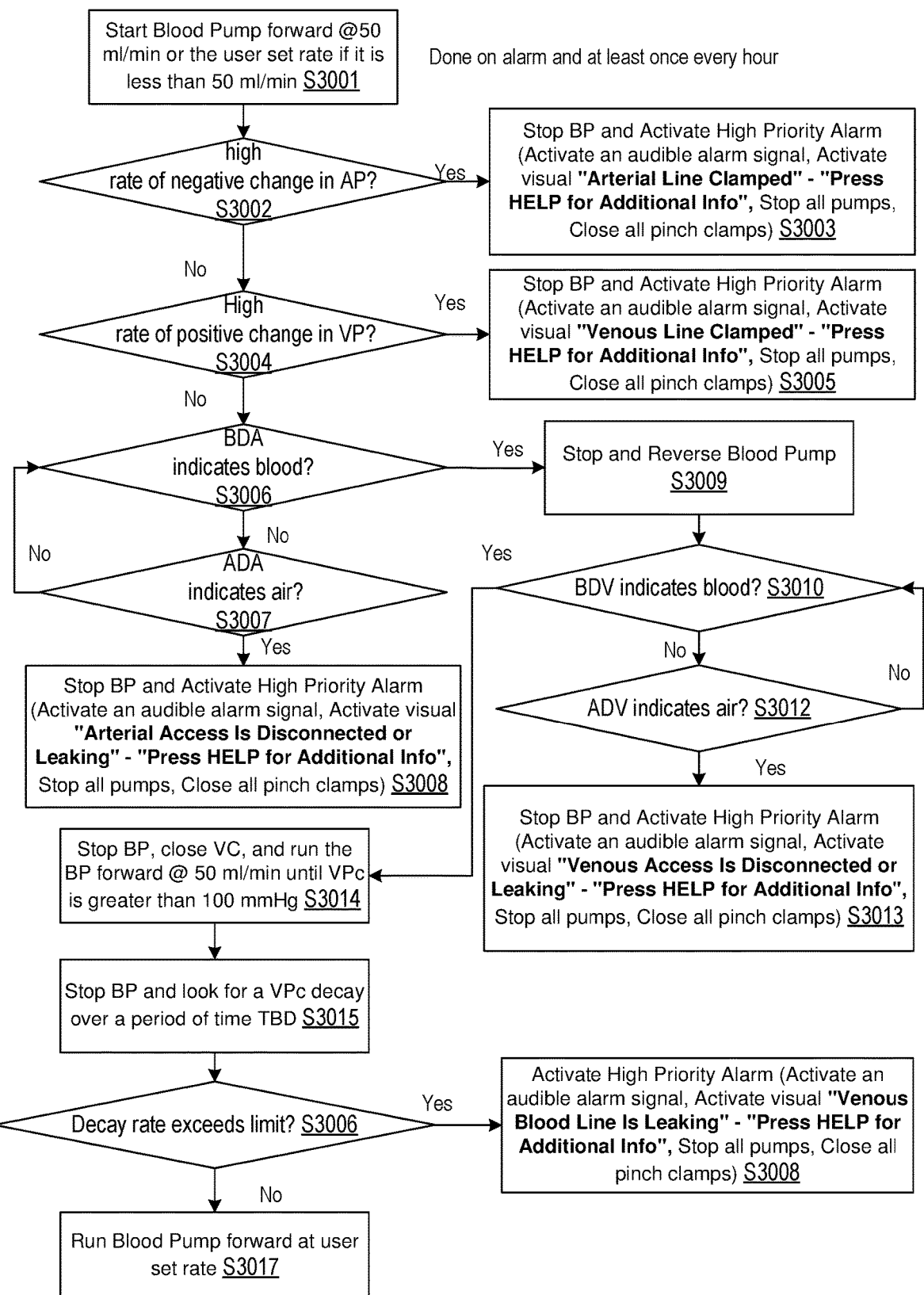
FIG. 30 illustrates a method for testing a blood pump each time it is started according to embodiments of the disclosed subject matter.

FIG. 30 provides a flowchart of a test process for blood pump start up. This test occurs each time the blood pump is started to detect unopened clamps, patient connection, and leaks to the environment. A pressure test of the venous line employs a pressure decay test procedure. A pressure rate threshold distinguishes a clamped line from a blood line occlusion. If air is detected at startup, the user is prompted to disconnect. If the test fails due to clamped lines during connection, correction may be performed by undoing clamps when prompted. If the test fails due to leaking access connections, correction may be performed by correcting connections when prompted. If the test fails due to leaking caps/connectors on blood line, correction may be performed by correcting connection when prompted.

In order to recover in case of failure, the user can press "Mute" for 2 minute audio override, press "Help" for additional info and press "Done" when finished, identify the alarm cause, correct the alarm cause, press "Acknowledge", press "Continue Treatment", open appropriate pinch clamps, and restart at pumps rates prior to the Blood Pump Start-Up Test.

As shown in FIG. 30, the test starts by starting the blood pump in forward mode at 50 ml/min or at the user-set rate if it is less than 50 ml/min S3001. Then, the process determines at S3002 if the pump inlet pressure sensor 568 indicates high rate of negative change. If yes, the control proceeds to S3003 and the controller 240 stops the blood pump 563 and activates a high priority alarm which activates an audible alarm signal, activates visual "Arterial Line Clamped"-"Press HELP for Additional Info", stops all pumps, and closes all pinch clamps. Otherwise, at S3004 the process determines if venous primary control and secondary pressure sensor 532A and 532B (VPc, VPs) indicate a high rate of change. If yes, at S3005 the process stops blood pump 563 and activates a high priority alarm which activates an audible alarm signal, activates visual "Venous Line Clamped"-"Press HELP for Additional Info", stops all pumps, and closes all pinch clamps. Otherwise, at S3006 the process determines if arterial blood detector 565 indicates blood. If no, at S3007, the process determines if arterial control air sensor and arterial secondary air sensor 567A, 567B (ADAc and ACAs) indicate air, and if so, at S3008 the process stops the blood pump 563 and activates a high priority alarm which activates an audible alarm signal, activates visual "Arterial Access Is Disconnected or Leaking"-"Press HELP for Additional Info", stops all pumps, and closes all pinch clamps. If arterial control air sensor and arterial secondary air sensor 567A, 567B (ADAc and ACAs) do not indicate air, the process loops back to S3002. If at S3006 arterial blood detector 565 indicates blood, at S3009 the process stops and reverses the blood pump 563, and then at S3010 determines if venous blood detector 597 indicates blood. If no, at S3012 the process determines if venous control air sensor and venous secondary air sensor 556A, 556B (ADVc and ADVs) indicate air, and if so, at S3013 the process stops the blood pump 563 and activates a high priority alarm which activates an audible alarm signal, activates visual "Venous Access Is Disconnected or Leaking"-"Press HELP for Additional Info", stops all pumps, and closes all pinch clamps. If at S3012 venous control air sensor and venous secondary air sensor 556A, 556B (ADVc and ADVs) does not indicate air, the process loops back to S3010 and determines if venous blood detector 597 indicates blood. If it does, at S3014 the process stops the blood pump 563, closes the venous line clamp 562, and runs the blood pump 563 forward at 50 ml/min until venous primary control and secondary pressure sensor 532A and 532B (VPc, VPs) is greater than 100 mmHg. The process then stops the blood pump 563 and looks for a venous primary control and secondary pressure sensor 532A and 532B (VPc, VPs) decay over a predefined period of time at S2015. If at S3016 the decay rate exceeds the limit, then the process, at S3018, activates a high priority alarm which activates an audible alarm signal, activates visual "Venous Blood Line Is Leaking"-"Press HELP for Additional Info", stops all pumps, and closes all pinch clamps. If the decay rate is acceptable, then, at S3017, the process runs the blood pump 563 in forward mode at the user set rate.

Figure 31:
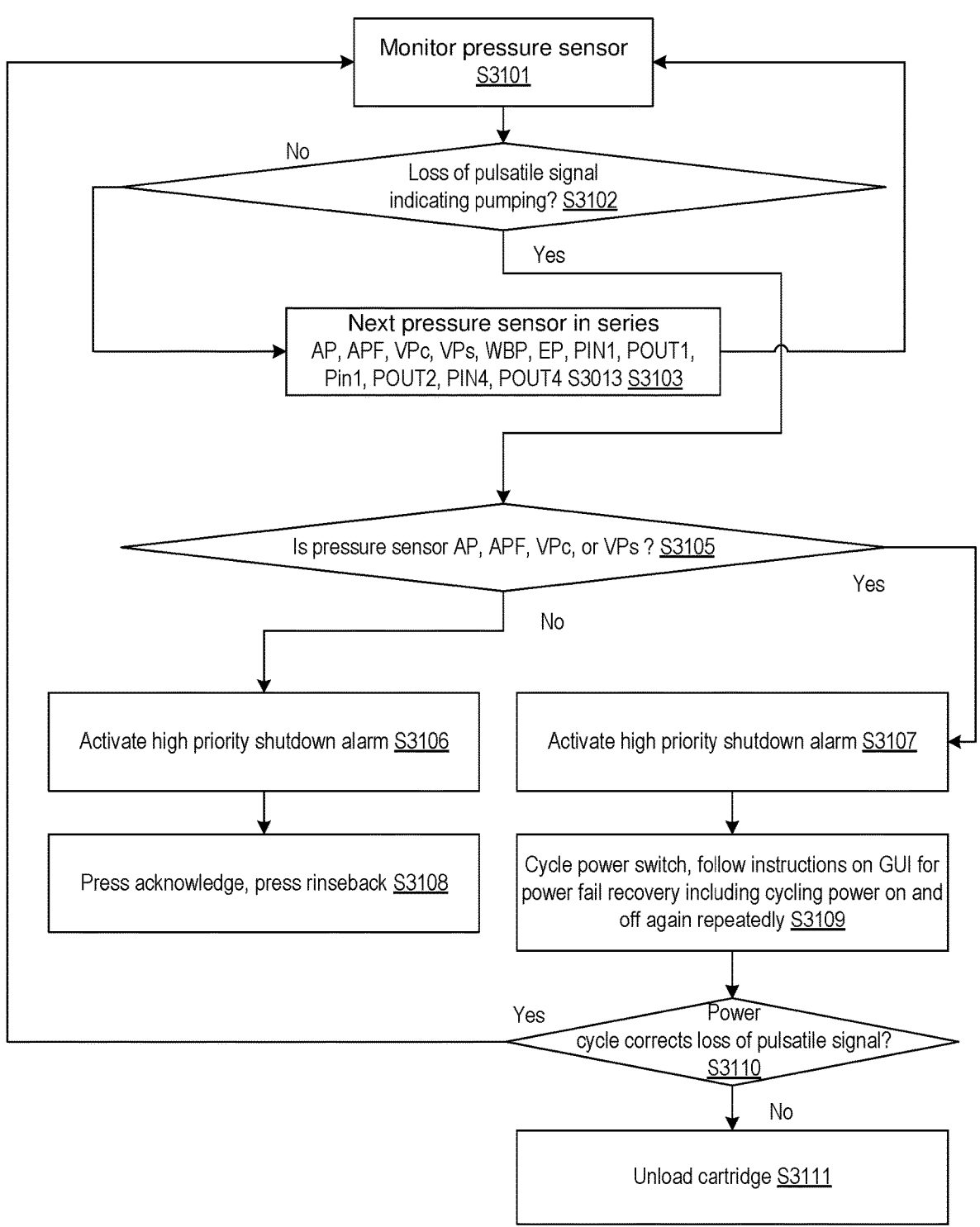
FIG. 31 illustrates a method for testing pressure sensors and pumps according to embodiments of the disclosed subject matter.

FIG. 31 provides a flowchart of a test process for continuous pressure sensor monitoring S3101 of pressure sensors during treatment. If a pressure sensor shows pressure pulses from a pump at S3102, a next pressure in an indicated series is tested as indicated at S3103. If the pressure pulses are lost by a sensor, it is determined at S3105 whether the pressure sensor is one of the pump inlet pressure sensor 568, blood pump outlet pressure sensor 564, venous primary control and secondary pressure sensor 532A and 532B (VPc or VPs). If not, a high priority shutdown is activated at S3107 and the user is instructed at S3109 to cycle the power switch and follow instructions on the user interface to do a power fail recovery. The power of the system may be turned on and off (power cycle) to determine if the pulsatile signal is recovered. This may be done more than once as indicated at S3109. The user may then repeat the power cycle or unload the cartridge. If the power cycle restores the pulsatile signal then control reverts back to S3101 and if not, the user interface outputs instructions to unload the cartridge. If at S3105 the pressure sensor is one of the pump inlet pressure sensor 568, blood pump outlet pressure sensor 564, venous primary control and secondary pressure sensor 532A and 532B (VPc or VPs) then a high priority shutdown is activated at S3106 and the user is instructed to acknowledge and activate a rinseback control.

As shown in FIG. 31, the test continually monitors the pressure sensor and determines if there is loss of the pulsatile signal that indicates the pressure sensors are functioning improperly.

Figure 32:
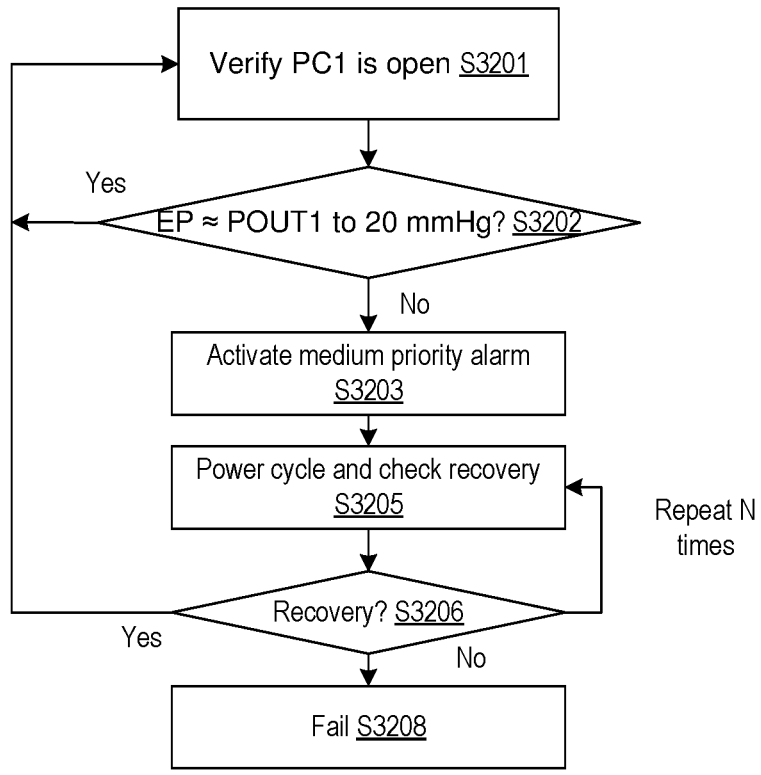
FIG. 32 illustrates a method for checking pressure sensors according to embodiments of the disclosed subject matter.

FIG. 32 provides a flowchart of a test process for effluent pressure control monitoring. The test is performed whenever VFMS the volumetric flow management system is active and verifies if a standing fluid column with no flow causes fresh treatment fluid outlet pressure sensor 570A and inlet waste pressure sensor 575 to output the same value of pressure. The test fails in case of system failure of the pressure sensors, and correction may be performed by cycler power ON/OFF or by executing rinseback. In order to recover in case of test failure, the user may turn off the power switch located on rear of the unit, turn the power switch back on, and follow instruction on GUI for "Power Fail Recovery." If the alarm reoccurs, the user may either turn off the power switch, turn the power switch back on, and unload the cartridge, or press "Acknowledge" and then press "Rinseback".

As shown in FIG. 32, the test starts by verifying that pinch clamp 571 is open at S3201. The process then determines if the pressure from the inlet waste pressure sensor 575 is within a predefined pressure (e.g., 20 mmHg) of the pressure of pressure sensor 552. If no, the process activates a medium priority alarm at S3203. Following the activation of the alarm, at S3205, the user is instructed by the controller to cycle the system on and off and check if there was a recovery at S3206. This may be repeated some number of times as indicated. If there is no recovery at S3206, then the test fails at S3208.

Figure 33A:
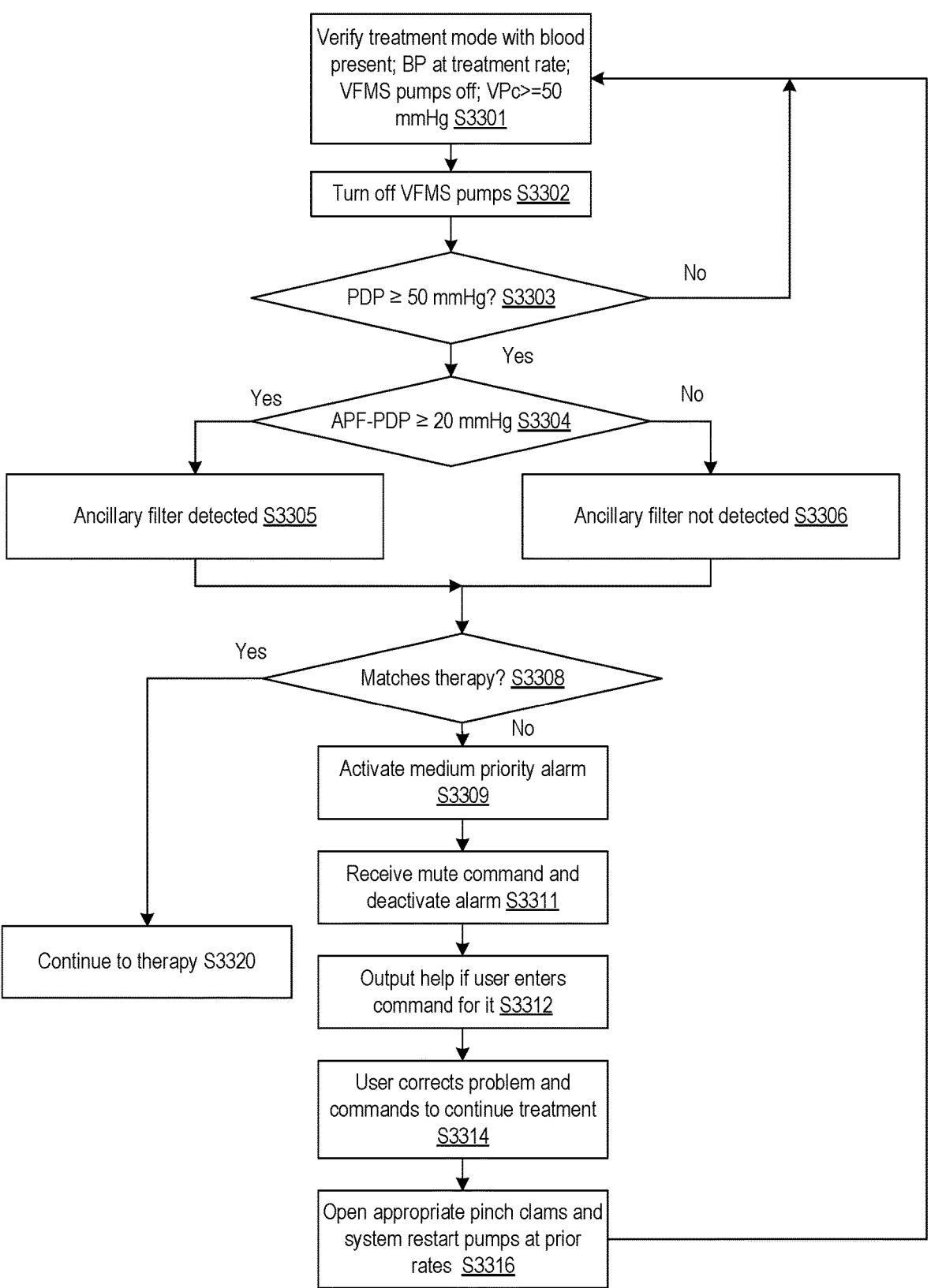
FIGS. 33A and 33B illustrate methods of detecting high venous blood temperature during treatment and rinseback according to embodiments of the disclosed subject matter.

FIG. 33A provides a flowchart of a test process for detecting an incorrect correspondence between a detected therapy configuration and a current therapy selection as entered by command to the treatment machine. For example, the illustrated process detects pressure drop to verify presence of an ancillary filter (e.g. sepsis filter). This test occurs each time the blood pump is started following the blood pump 563 Start Up Test. If the detection of an ancillary filter does not match the selected therapy than a medium priority alarm is generated. Instructions to correct the issue may be automatically output by the controller. The user can add the filter to make the configuration match the selected therapy or change the therapy to match the configuration and then continue the therapy. When the alarm is triggered, the user may press "Mute" for 2 minute audio override, press "Help" for additional info. The user may command the system to continue treatment, open appropriate pinch clamps, and restart pumps at previous rates.

As shown in FIG. 33A, the test starts by verifying that the device is in treatment mode with blood present, that the blood pump is running at the treatment rate, that the venous control primary pressure sensor 532A and venous secondary pressure sensor 532B at least 50 mmHg at S3301. I.e., the process runs the blood pump 563 in forward mode at treatment rate until Venous primary control pressure sensor 532A (VPc) is greater than or equal to a predefined pressure (e.g., 50 mmHg). The process then turns VFMS pumps off S3302, and determines at S3303 whether pressure sensor 534 which follows the ancillary filters 522 and 524 but upstream of the blood treatment device 114 is greater than or equal to a predefined pressure (e.g., 50 mmHg). If yes the controller determines at S3304 if the difference between the blood pump outlet pressure sensor 564 and pressure sensor 534 is greater than another predefined value (e.g., 20 mmHg). If so indicates that an ancillary filter is detected S3305. If not, then it indicates an ancillary filter was not detected S3306.

The system at S3308 then determines whether the presence of absence of the filter is correct for a selected therapy at S3308. If yes, control proceeds to S3320 and the system continues to therapy. If not, then a medium priority alarm is activated at S3309 whereupon a user activated recovery process is followed beginning with the receipt of a mute command S3312 from the user, a selective output of help instructions identifying the mismatch between the detection and selection. Then the user corrects the problem and the system accepts a command to continue S3314. Next the appropriate pinch clamps are opened and the pumps restarted at S3316. Control reverts to S3301 to confirm and pass the test to arrive at S3320, the test having finally been completed.

An example of an ancillary filter is a sepsis filter.

Figure 33B:
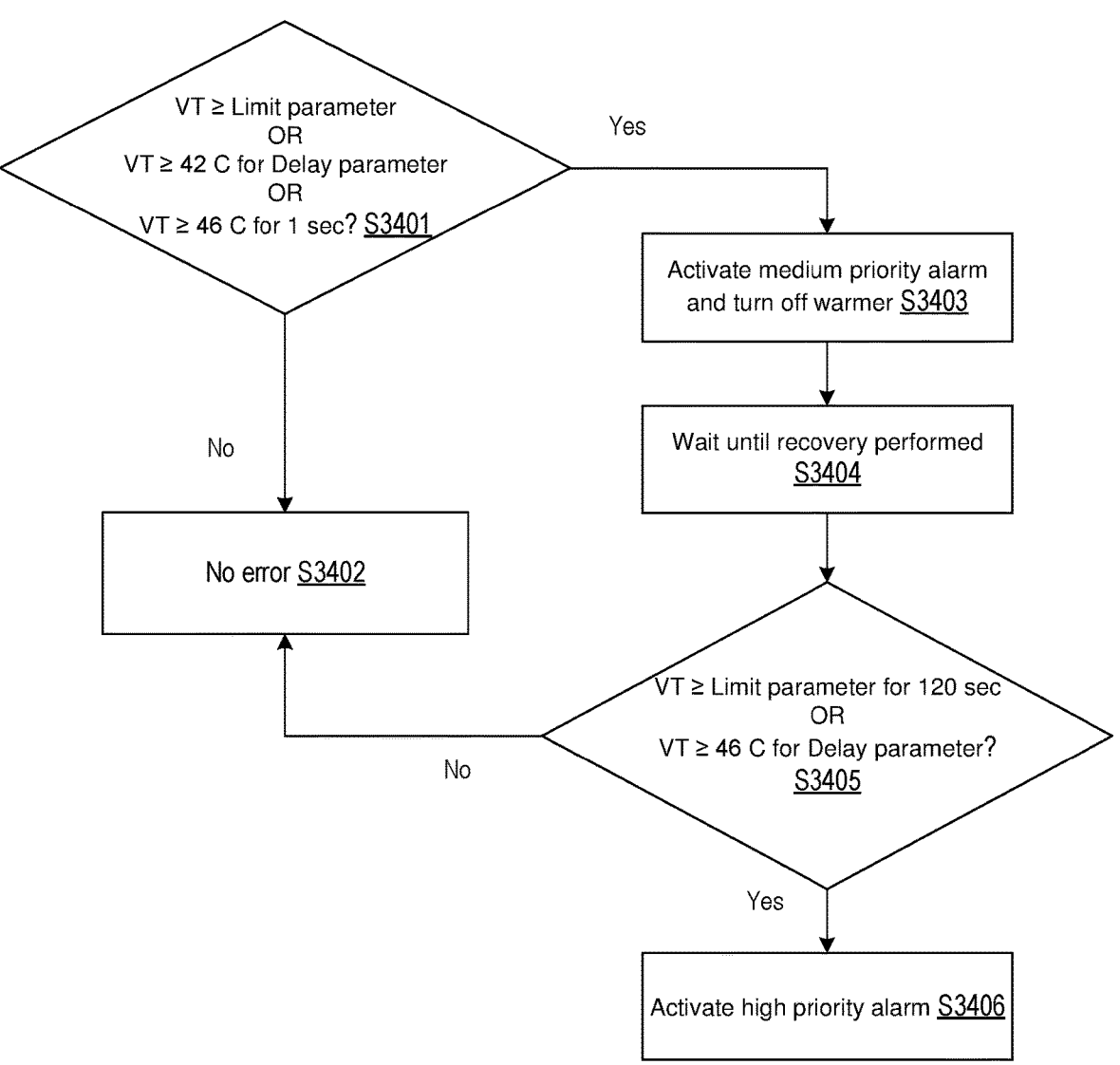

FIG. 33B provides a flowchart of a test process for identifying high venous blood temperature during treatment and rinseback. The test applies temperature and duration bounds on venous blood temperature. High venous blood temperature may result from over temperature prescription fluids, in which case correction may be performed by verifying bag temperature and using bags within temperature limits. High venous blood temperature may also result from warmer over temp failure, in which case correction may be performed by not using the warmer and repairing it.

As shown in FIG. 33B, the test starts by determining whether venous blood temperature is above a limit parameter, or above 42 C for a time above a delay parameter, OR above 46 C for a predetermined interval, e.g., 1 second S3401. If yes, then a medium priority alarm is activated at S3403 and the warmer is turned off. If no, then at S3402 no error is detected. After the medium priority alarm is activated and the warmer is turned off, the process waits to receive acknowledgment of recovery action S3404. Then, the process determines whether venous blood temperature is greater than or equal the limit parameter for 120 seconds, OR greater than or equal to 46 C for the duration of the delay parameter at S3405. If yes, then the process activates a high priority alarm which activates an audible alarm signal at S3405, and activates a visual "Blood High Temperature" at S3406, stops all pumps, and closes all pinch clamps.

In order to recover after a medium priority alarm is activated, the user may press "Mute" for 2 minute audio override, press "Help" for additional info and press "Done" when finished, identify the alarm cause, correct the alarm cause, press "Acknowledge", clear the alarm, and press "Continue Treatment". The user may then verify that venous blood temperature is below the limit parameter, and then open appropriate pinch clamps and restart pumps at previous rates. In order to recover after a high priority alarm is activated, the user may press "Mute" for 2 minute audio override, identify the alarm cause, correct the alarm cause, press "Acknowledge", clear the alarm, press "Continue Treatment", open appropriate pinch clamps, and restart pumps at previous rates.

Figure 34:
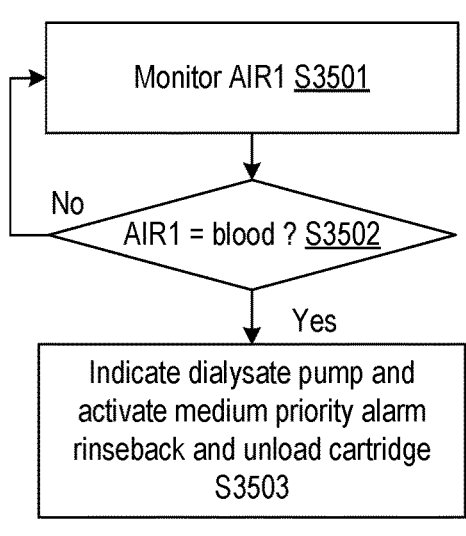
FIGS. 34 and 35 illustrate methods of detecting blood in a fluid line according to embodiments of the disclosed subject matter.
Figure 35:
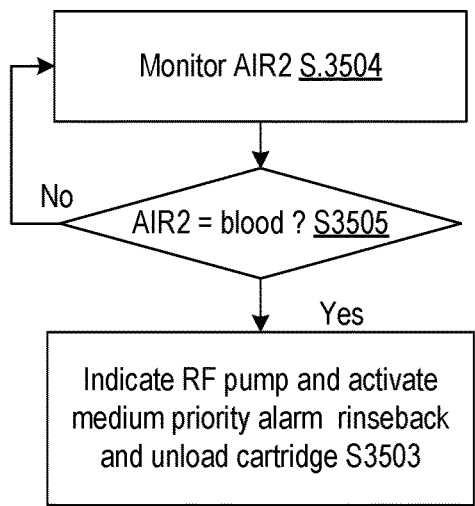

FIGS. 34 and 35 provide flowcharts of test processes for identifying pump occlusion failure for dialysate or therapy fluid, fresh treatment fluid pump 573 and for replacement fluid pump 542, during patient connect mode, treatment mode, rinseback mode, and patient disconnect mode. Pump failure is identified when blood is detected up-stream of the pump (via fresh treatment fluid air sensor 579 in the dialysate line or via the air sensor 587 in the replacement fluid line), and correction may be performed by executing rinseback and unloading the cartridge. In order to recover, the user may stop the current mode, return to cartridge loading, clean the system, and prime the new cartridge.

As shown in FIG. 34, the process monitors blood and Fresh treatment fluid inlet pressure sensor to determine if there is blood in the waste treatment fluid line 536 at S3501 and S3502. indicates blood, and if it does, the process goes to S3503 and the controller indicates dialysate pump failure and activates a medium priority alarm. As shown in FIG. 35, the process monitors blood and air sensor 587 determines whether air sensor 587 indicates blood at S3504 and S3505, and if it does, the process indicates replacement fluid pump failure and activates a medium priority alarm at S5306.

Figure 36:
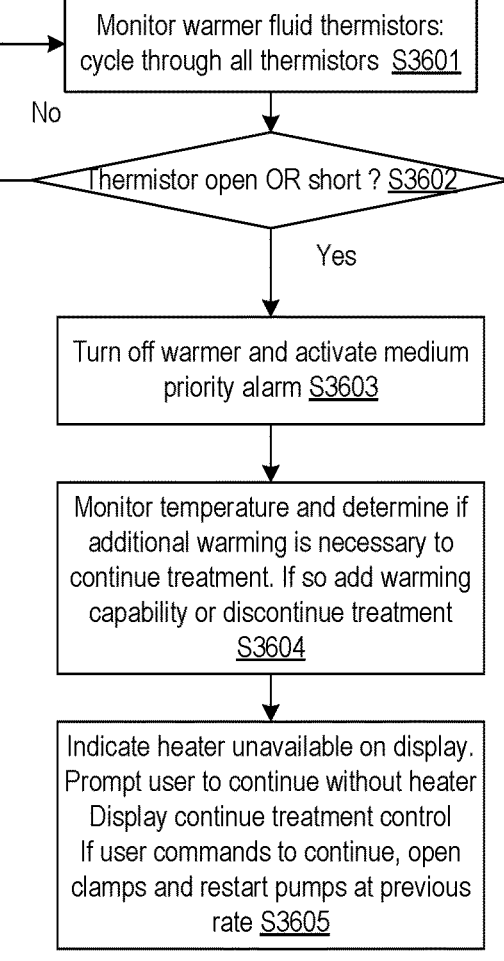
FIG. 36 illustrates a method for detecting a fluid warming thermistor failure according to embodiments of the disclosed subject matter.

FIG. 36 provides a flowchart of a test process for identifying warmer fluid thermistor failure during patient connect mode, treatment mode, rinseback mode, and patient disconnect mode. Warmer is determined to have failed based on the status of its thermistor, in which case correction may be performed by executing rinseback and unloading. In order to recover, the user may stop the current mode and return to cartridge loading.

As shown in FIG. 36, at S3601 the controller monitors warmer fluid thermistors, cycling through all the monitored thermistors. At S3602 the process determines whether a thermistor is open or short, and if so, the process activates a medium priority alarm S3603 and turns off the warmer. If not control reverts to S3601. The system then monitors temperature and determines if additional warming is necessary to continue treatment. If so warming capability is added or user discontinues treatment S3604. The system then, at S3605, indicates the heater is unavailable on the display and prompts the user to continue without the heater. The system displays the continue treatment control. If the user commands to continue treatment, the clamps are opened and pumps restarted at previous rates.

Figure 37:
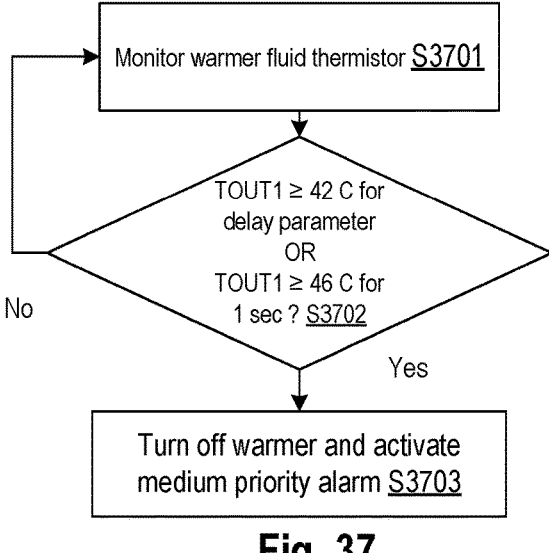
FIG. 37 illustrates a method for detecting a high warmer fluid temperature according to embodiments of the disclosed subject matter.

FIG. 37 provides a flowchart of a test process for identifying high warmer fluid temperature based on out of bounds warmer fluid thermistor signal, during patient connect mode, treatment mode, rinseback mode, and patient disconnect mode. If the warmer is determined to have failed, correction may be performed by executing rinseback and unloading. In order to recover, the user may press "Mute" for 2 minute audio override, press "Help" for additional info and press "Done" when finished, identify the alarm cause, correct the alarm cause, press "Acknowledge", clear the alarm, and open pinch clamp 571. If the temperature of fresh treatment fluid outlet temperature sensor 570B<46 C, the user may start fresh treatment fluid pump 573 forward at previous rate for predetermined volume. If the temperature of fresh treatment fluid outlet temperature sensor 570B≤42 C, the user may press "Continue Treatment", open appropriate pinch clamps, restart pumps at previous rates, and adjust delivered dialysate volume by a predetermined volume.

As shown in FIG. 37, the process monitors the fluid thermistor and at S3702 determines whether thermistor ≥42 C for delay parameter OR thermistor ≥46 C for 1 sec. If so, the process activates a medium priority alarm and turns off the warmer.

Figure 38:
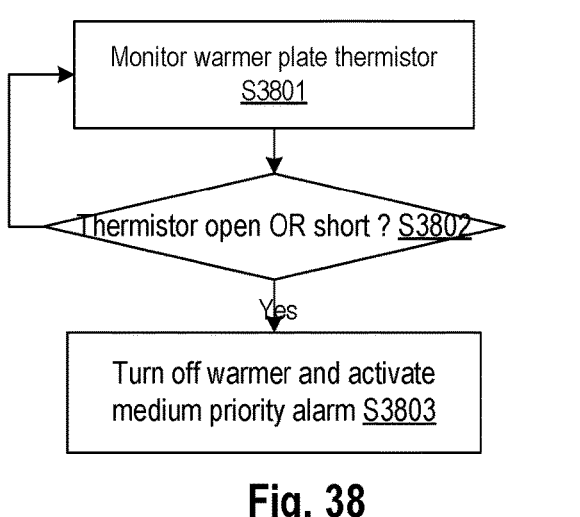
FIGS. 38 and 39 illustrate methods for detecting a warmer plate thermistor failure according to embodiments of the disclosed subject matter.

FIG. 38 provides a flowchart of a test process for identifying warmer plate thermistor failure based on out of bounds heater plate thermistor signal, during patient connect mode, treatment mode, rinseback mode, and patient disconnect mode. If the warmer is determined to have failed, correction may be performed by monitoring temperature to determine if additional warming is necessary to continue treatment, and if so, adding warming capability or discontinuing treatment. In order to recover, the user may press "Mute" for 2 minute audio override, press "Help" for additional info and press "Done" when finished, identify the alarm cause, correct the alarm cause, press "Acknowledge", clear the alarm, and press "Continue Treatment".

As shown in FIG. 38, in S3801, the process monitors the heater plate thermistor and determines if the thermistor is open or short at S3802. If yes, at S3803 the process turns the warmer off and activates a medium priority alarm.

Figure 39:
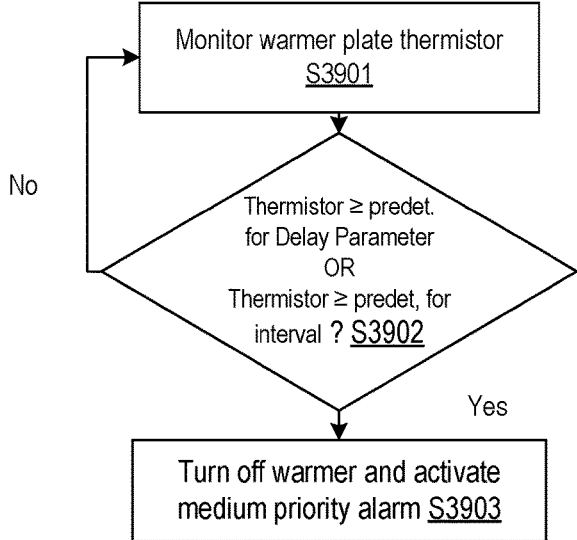

FIG. 39 provides a flowchart of another test process for identifying warmer plate thermistor failure based on out of bounds heater plate thermistor signal, during patient connect mode, treatment mode, rinseback mode, and patient disconnect mode. If the warmer is determined to have failed, correction may be performed by monitoring temperature to determine if additional warming is necessary to continue treatment, and if so, adding warming capability or discontinuing treatment. In order to recover, the user may press "Mute" for 2 minute audio override, press "Help" for additional info and press "Done" when finished, identify the alarm cause, correct the alarm cause, press "Acknowledge", clear the alarm, and press "Continue Treatment".

As shown in FIG. 39, the process monitors the heater plate thermistor at S3901 and, at S3902, determines if thermistor a first threshold temperature for a predefined delay parameter OR thermistor a second threshold temperature C for 1 sec. If yes, the process turns the warmer off and activates a medium priority alarm at S3903.

FIGS. 40A and 40B show an apparatus that detects the loss of pressure attending a level change and concomitant loss of pressure when a bag of fluid empties. The principle can be applied to a system with a kinked line where pressure generated not by gravity but by means of a pressure generating pump. In the example shown a fluid container 4010 contains a fluid whose level is indicated at 4016. In FIG. 40A, the level is high and a fluid column in line 4018 from the level 4016 to the heater accumulator held in a heater 4012. The heater accumulator in an embodiment is a flexible container 4002 which is pressurized by the fluid column maintaining pressure on a pressure (or temperature) sensor 4006 in FIG. 40A. When the flexible container 4002 pressure drops due a level change, shown in FIG. 40B, resulting from the emptying of the container 4010, the pressure in the flexible container 4002 is lost reducing the pressure (or temperature) on the pressure (or temperature) sensor 4006. The same problem will result if no fluid container 4010 present. As shown in the following procedure, both events will generate an alarm.

Figure 40C:
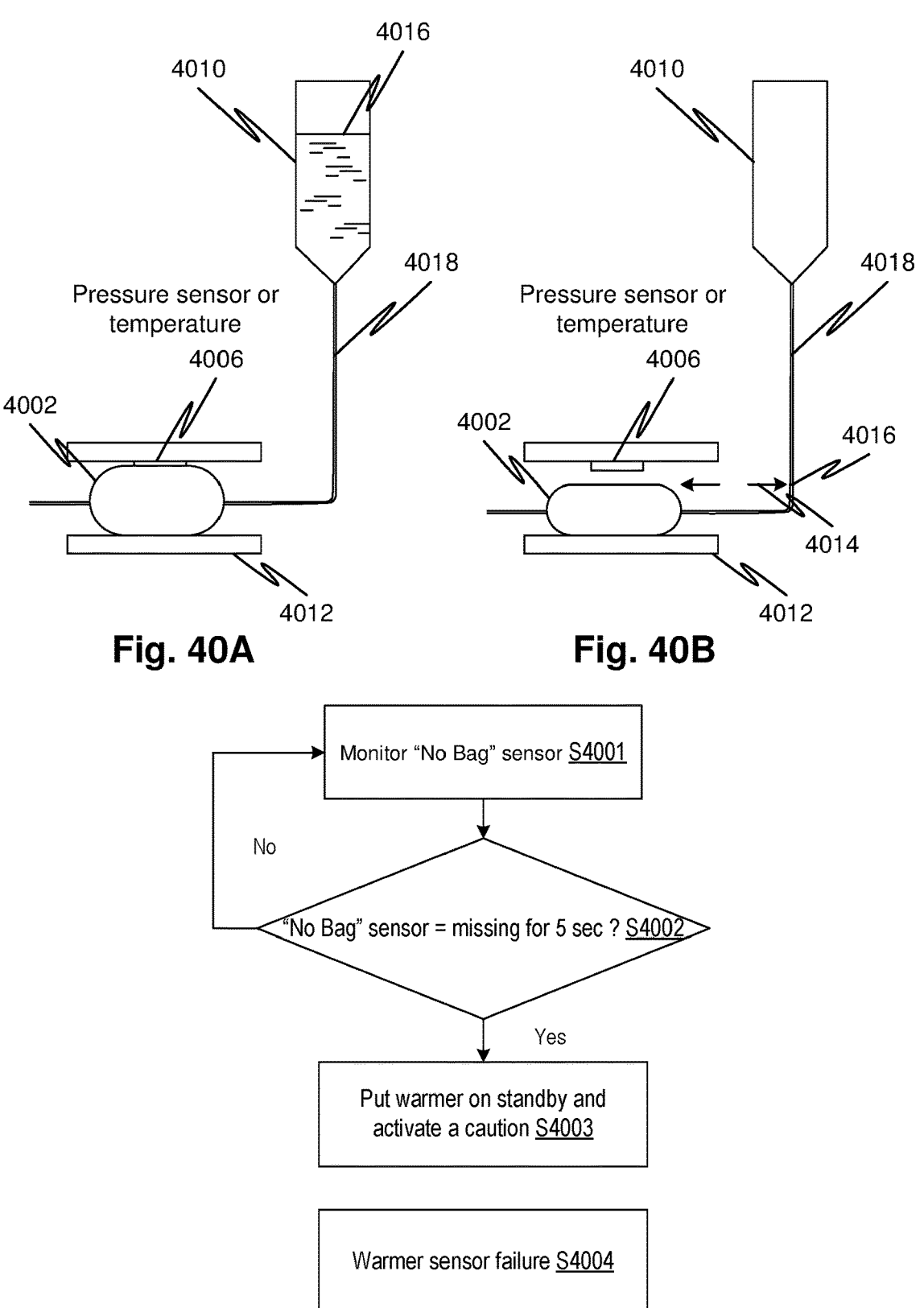

FIG. 40C provides a flowchart of a test process for identifying filled warmer bag presence (i.e., warmer not loaded when expected) based on the "No Bag" sensor, during patient connect mode, treatment mode, rinse back mode, and patient disconnect mode. The test is responsive to a sensor that detects pressure from a fluid bag on an upper heater surface of a heater on which it rests. If this test fails because the warmer disposable is running out of fluid, correction may be performed by adding a filled bag (or correcting kink if that is the problem) and continuing treatment. In order to recover, the user may press "Mute" for 2 minute audio override, press "Help" for additional info and press "Done" when finished, identify the alarm cause, correct the alarm cause, press "Acknowledge", and clear the alarm. Then, when "No Bag" sensor is re-pressurized, the user may press "Continue Treatment", and set the warmer to heating mode.

As shown in FIG. 40C, the process monitors the "No Bag or empty bag" sensor at S4001, and if it indicates that "bag missing" at S4002 for 5 seconds, the process puts the warmer on standby and activates a low priority caution at S4003.

Figure 41:
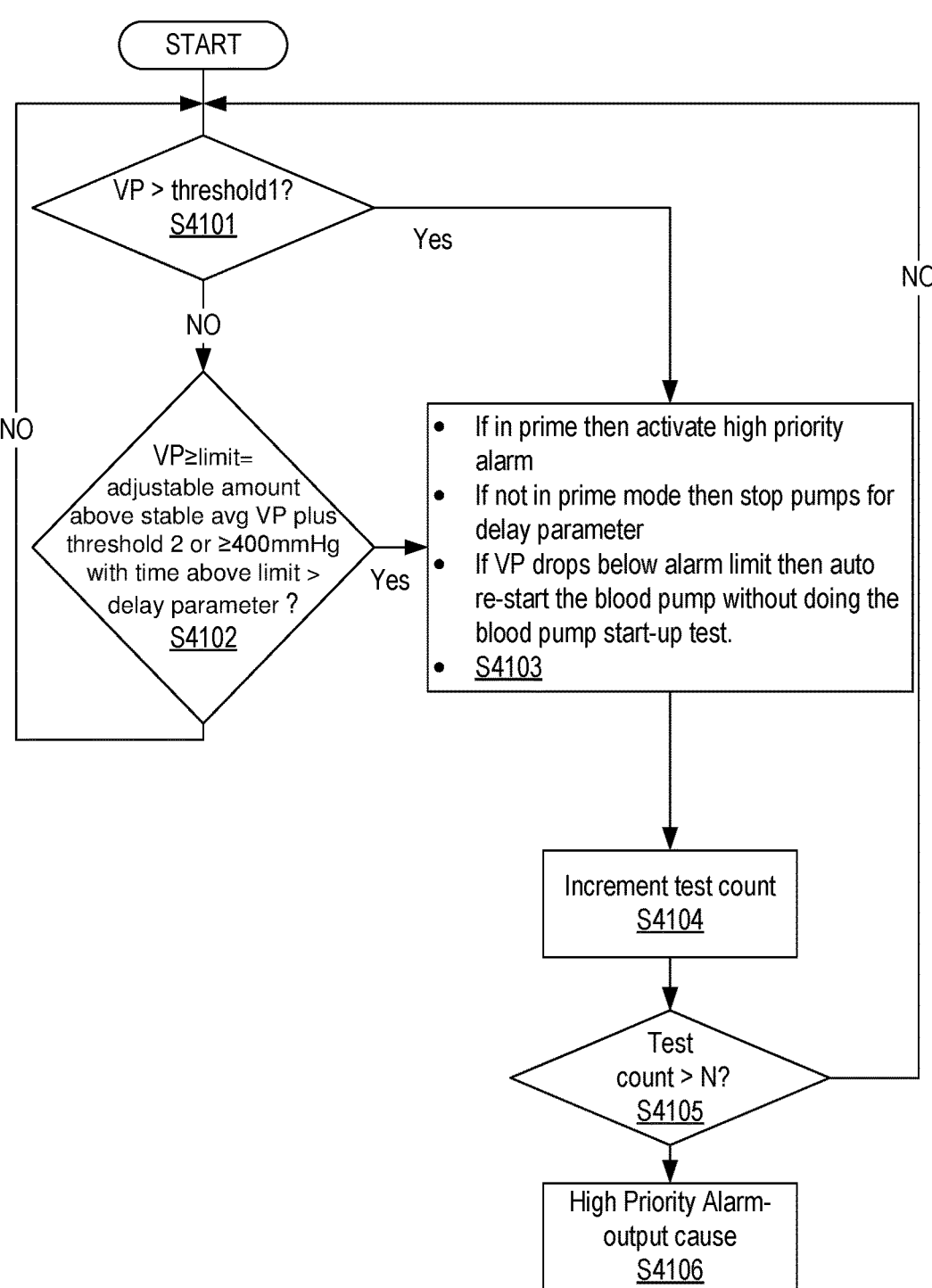
FIG. 41 illustrates a method for monitoring a venous high pressure, according to embodiments of the disclosed subject matter.

FIG. 41 illustrates a process flow of an embodiment of a test process that monitors or checks the pressure in the venous line. In embodiments, this test may detect a fixed venous access restriction or an adjustable venous access restriction by monitoring and responding to conditions in the venous line based on one or more pressure measurements. A restriction in the venous access may be caused by a kinked, a pinched, or a clamped patient line. The venous access may also be blocked due to other causes such as a clotting. The test may be continuous, such that a pressure sensor in the venous line outputs a signal that is monitored continuously, or the test may be periodic, with the value of the pressure signal output being checked on a predetermined schedule or in response to events. This test may be conducted when the patient is first connected to the treatment system 500. The test may also, or instead, be performed during the medical treatment provided by system 500. The test may also or instead be performed during the rinse-back operation, when the patient's blood is returned to the patient via the venous line at the conclusion of the treatment.

At the beginning of this test, the venous blood pressure is measured by a blood pressure sensor, such as venous control primary pressure sensor 532A and venous secondary pressure sensor 532B. In an embodiment, the value of the pressure signal is integrated over a period of time, or the value of the pressure signal is summed over a time period, and if the integrated value exceeds a second threshold, the test process continues as if the first threshold was exceeded. In embodiments, the pressure value may be multiplied by the duration over which the pressure value is measured. While FIG. 42 illustrates both checking the instantaneous pressure value and the integrated pressure value, it should be understood that the test can use either condition without the other.

If the venous pressure is above a first threshold at S4101, or at S4102, the venous pressure is greater than or equal to a second threshold equal to an adjustable amount above a stable average venous pressure plus a second threshold or greater than or equal to 400 mmHg with a time above a limit equal to a delay parameter then the system process goes to S4103 where, if the system is not in prime mode then the pumps are stopped for a delay parameter. If the venous pressure drops below the alarm limit then the blood pump is re-started without performing the blood pump start-up test of FIG. 30. If the system is not in prime mode then the system stops pumps for delay parameter. If the venous pressure drops below alarm limit then the system auto re-starts the blood pump without doing the blood pump start-up test. The test is retried N times, where N may be equal to 3, as indicated at S4104, S4105, and S4106. If the count exceeds N then a high priority alarm is activated.

Figure 42A:
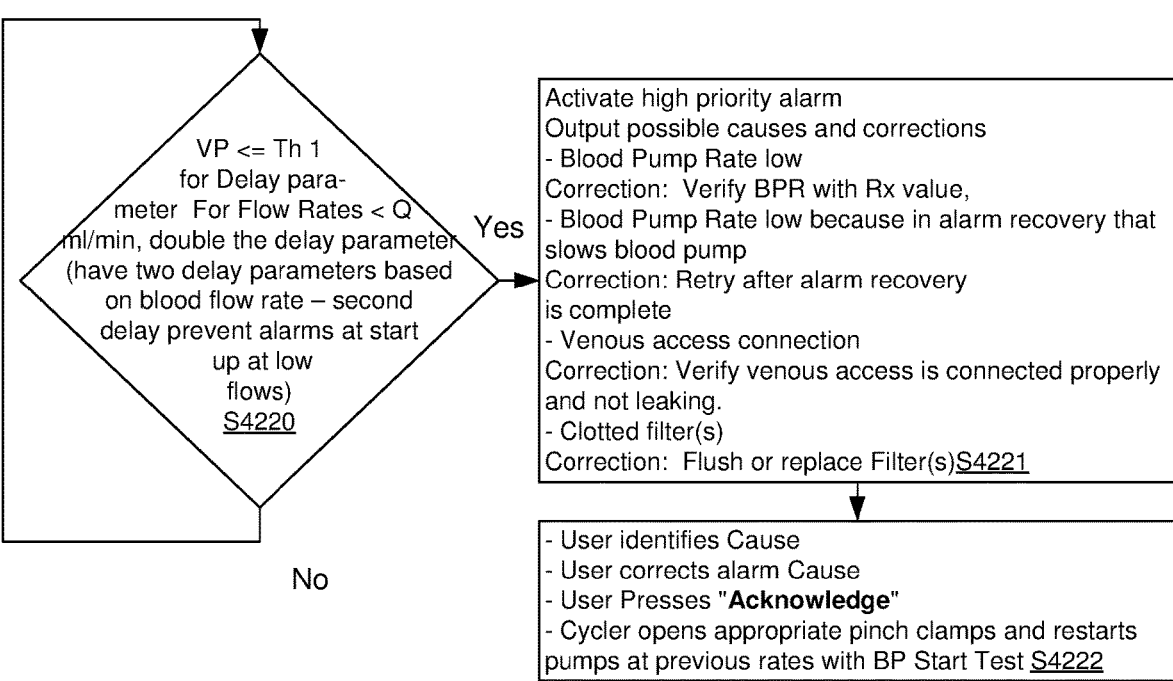
FIGS. 42A and 42B illustrate parallel or sequential methods for monitoring a venous low pressure indicated by an excursion from a limit or from a stable average, according to embodiments of the disclosed subject matter.

FIG. 42A shows a venous pressure monitoring algorithm in which the venous pressure is monitored continuously at S4220. If the venous pressure falls to a threshold (e.g., 20 mmHg) or below for a first predefined interval for a first flow rate range then a high priority alarm is activated. The alarm is also activated for a second flow rate below the first flow rate range when the venous pressure falls to or below the threshold for at least a second predefined interval that is longer than the first. If so, a high priority alarm is output as indicated at S4221. The response to the alarm may be output along with possible causes including blood flow rate that is too low. The recommended correction may be output as well, for example directing the operator to check the prescription against the blood flow rate. Also, too great a flow fraction which may corrected by increasing the blood flow rate or reducing the ultrafiltration rate. Another cause may be clotting or plugging of the filter which may be corrected by replacing the filter. Another cause may be a venous line restriction which may be corrected by opening a clamp or fixing a kinked line. At S4222, the user inputs an acknowledge signal after correcting the problem. The controller receives the acknowledge signal and opens predefined pinch clamps and starts the pumps at the previous rates.

Figure 42B:
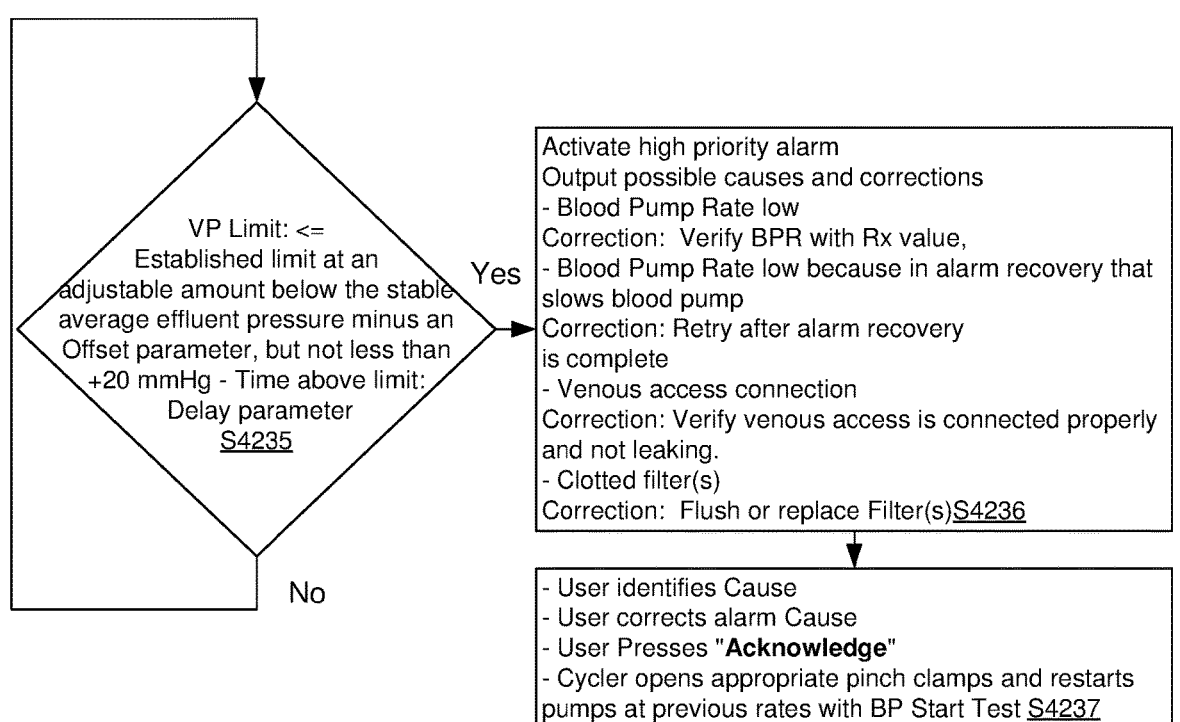

FIG. 42B shows an effluent pressure monitoring algorithm in which the effluent pressure is monitored continuously at S4235. If the effluent pressure falls below an established limit at an adjustable amount below the stable average effluent pressure minus an offset parameter but not less than 20 mmHg with a delay indicating a minimum time during which the pressure deficit exists, then at S4236, a medium priority alarm is activated. The alarm is also activated for a second flow rate below the first flow rate range when the effluent pressure falls to or below the threshold for at least a second predefined interval that is longer than the first. The alarm is indicated as activated at S4221. The response to the alarm may be output along with possible causes including too great a flow fraction which may corrected by increasing the blood flow rate or reducing the ultrafiltration rate. Another cause may be clotting or plugging of the filter which may be corrected by replacing the filter. Another cause may be an effluent line restriction which may be corrected by opening a clamp or fixing a kinked line. At S4237, the user inputs an acknowledge signal after correcting the problem. The controller receives the acknowledge signal and opens predefined pinch clamps and starts the pumps at the previous rates.

Figure 43A:
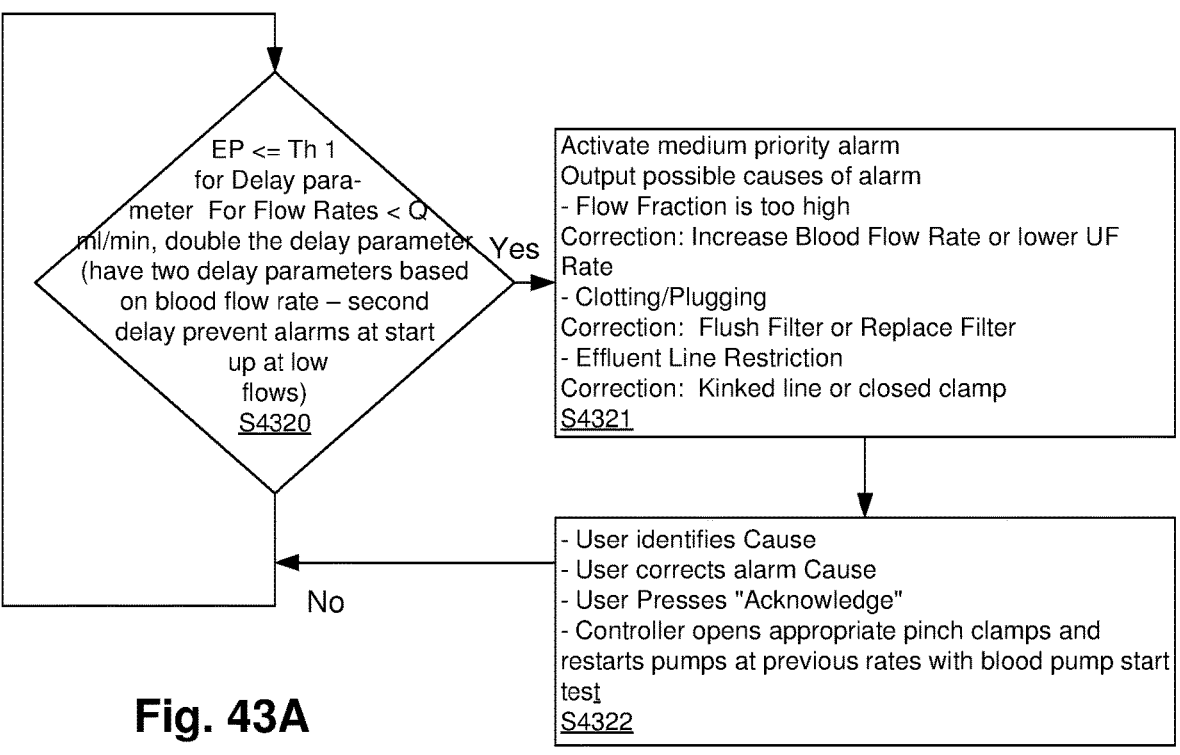
FIGS. 43A and 43B illustrate parallel or sequential methods for monitoring an effluent pressure indicated by an excursion from a limit or from a stable average, according to embodiments of the disclosed subject matter.

Referring now to FIG. 43A, the effluent pressure is continuously monitored (S4340) for a pressure until a pressure in the effluent line waste pressure sensor 575. The pressure must fall below the threshold for a minimum delay. The delay may be longer when the flow rate of blood is below a threshold. So there may be two delay parameters, one for flow rates above a certain flow rate threshold and one for flow rates above for a second threshold. If the effluent pressure drops below the threshold for the given flow rate, then a medium priority alarm is output by the controller. The controller may output several possible causes for the alarm and suggestions for correcting the alarm. The causes may include a flow fraction that is too high, which can be corrected by increasing the blood flow rate or lowering the ultrafiltration rate. The causes may include clotting or plugging and a correction may include flushing or replacing the treatment device or filter. The causes may include a restriction in the effluent line or a closed clamp on the line whose correction is to remove the condition. Thus the user identifies the cause, corrects it, and inputs an acknowledge command to the controller. When the controller receives the acknowledge command the controller opens the appropriate pinch valves and restarts the pump at the prior rate. S4322. Once corrected, control reverts to the testing loop.

Figure 43B:
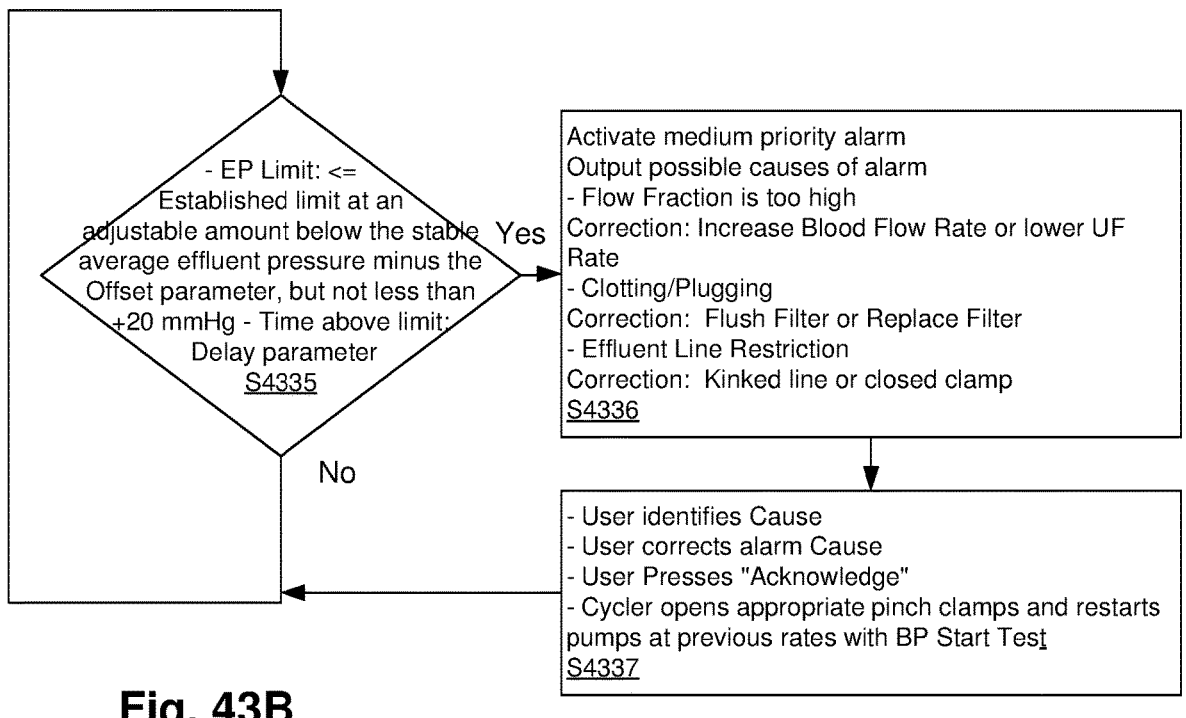

Referring to FIG. 43B, the controller loops through S4335 until effluent pressure falls below a threshold under certain time constraints. The time constraint may define that the effluent pressure stays below the threshold for a delay parameter. The threshold may be defined as an established limit at an adjustable amount more negative than the stable average effluent pressure plus an offset parameter, but not more than a predetermined value, e.g., 20 mmHg. If the condition is met, at S4336 a medium priority alarm is activated. The controller may output several possible causes for the alarm and suggestions for how address them. The causes may include that the flow fraction is too high which can be corrected by increasing the blood flow rate or lowering the ultrafiltration rate. The causes may include clotting or plugging of the filter and the associated correction being to flush or replace the filter. The causes may also include a restriction in the effluent line. Thus the user identifies the cause, corrects it, and inputs an acknowledge command to the controller. When the controller receives the acknowledge command the controller opens the appropriate pinch valves and restarts the pump at the prior rate. S4337. Once corrected, control reverts to the testing loop.

FIG. 43B illustrates a process flow of an embodiment of a test process that monitors or checks the pressure in the waste treatment fluid line 537 to detect a possible flow restriction or excess flow through the drain line. A flow restriction may be caused by a clog or fouling of the drain line. Excess flow may be caused if the system 500 removes more fluid from the patient than is desirable.

This test may be performed when the patient is connected, during treatment, and/or during the rinse-back process. It is desirable for the pressure in the effluent line to remain below a first threshold, as pressure above the threshold could be indicative of a pinched effluent line, the flow fraction being too high, and/or clogging of the effluent line.

During the test, the pressure of the effluent line is measured by the outlet waste pressure sensor 576 in FIG. 19A. The sensor may output a pressure signal directly, which is compared against the first threshold. In embodiments, the first threshold is 20 mmHG. The pressure value may also be integrated over a period of time, and the integrated value compared against a second threshold. The pressure value may also be multiplied by a time duration, or sampled over multiple time periods and summed, and the result compared to a threshold.

In embodiments, the threshold may be adjustable, but may be kept above some predefined value, e.g., 20 mmHG. The adjustments may be made to account for gradual buildup of fouling in the effluent line that is still considered to be within normal operating parameters, such that no alarm is needed.

If the pressure value or the integrated value exceeds the respective threshold, the system may stop the dialysate pump fresh treatment fluid pump 573, the replacement fluid pump 542, and waste treatment fluid pump 574 for a duration of a delay parameter. After the delay parameter has passed, the effluent drain pressure is checked again. If the effluent drain pressure is below the first threshold, then the treatment resumes, including the restarting of the pumps which were turned off above.

If, however, the effluent drain pressure exceeds the first threshold again, the stopping, delay, and restarting of the pumps is repeated for a predetermined number of times. In embodiments, the number of times is 3. After the test is repeated the predetermined number of times, and the effluent drain pressure keeps exceeding the first threshold, the medium priority alarm is activated. The system may also output visible and/or audible information for the patient or the caretaker about a possible drain line clog or kink, and steps to take. These may include checking the drain line for kinks or closed clamps.

The system may also output information for the caretaker to increase the blood flow rate and/or to lower the UF [ultrafiltration] rate, which is intended to reduce the effluent drain line pressure. The system may also output information indicating that the sterilizing filter 583 needs to be flushed or replaced.

In embodiments, the first threshold can be updated to account for gradual accumulation of material in the drain line, which does not negatively affect the operation of the blood treatment system, but which does increase the pressure in the effluent drain line. In embodiments, the pressure in the effluent drain line is averaged over time, and the threshold is set to the value of the stable average pressure. In embodiments, the value can be adjusted by an offset parameter to allow for some fluctuation in the pressure.

FIG. 44 illustrates a process flow of an embodiment of a test process that continuously monitors the venous blood line for possible air in the line. Air detectors, such as venous control primary air sensor 566A and venous secondary air sensor 566B detect a reduction of a predetermined percentage for a predetermined duration. In an embodiment, the percentage and the duration are selected to provide an air detection sensitivity approximately of a 60 micro liter bubble at 400 mmHG venous pressure and 600 ml/min blood flow. This test may be performed during the treatment and/or during the rinseback operation. S4401

Air in the venous line is a serious situation, so any detection as noted above will cause the system 500 to activate a high priority alarm at S4402. The condition may be caused by air in the treatment device 114 header and/or air in the venous air trap which may be present in the blood circuit. The system may output a visual and/or audio message and information to the patient or the caregiver with the possible causes, and steps for correcting the problem. At S4401, the system continuously monitors the venous air detectors Venous control primary air sensor 566A and Venous secondary air sensor 566B for bubbles matching the above-identified sensitivity. If air is detected, in an embodiment, a high priority alarm is activated at S4402. Then the system outputs information on causes and corrections, for example on a display of graphical user interface, at S4403. The venous air removal process may include attaching a 20 ml luer lock syringe to the treatment device 114 header vent port or venous air trap vent. Further, the process may include opening the venous line clamp 562. The process may include pulling back on the syringe plunger to extract air from the filter header or the air trap. The process may include returning blood from the syringe back to the chamber without air; closing a clamp on the vent line; and removing the syringe.

Next, the system may request a user input indicating that the process above has been completed, such as pressing an acknowledgement button or field on a touch sensitive display screen. Alternatively, or additionally, the system may request the user to input a command to start the blood pump, which may be accomplished by pressing a button or a field on a touch sensitive display screen. Subsequently, the system starts the blood pump at a predetermined pumping rate and may display a message on the GUI indicating that the system is in a venous air recovery state. The system may display a message stating "Venous Air Recovery." In an embodiment, the pumping rate during venous air recovery is 50 ml/min.

It is expected that the patient or caregiver will monitor the venous line for any air bubbles during the air recovery process. Once this process is complete, the user inputs a command to continue treatment. The command may be a button on the system, or pressing a message, such as "continue treatment" on a touch sensitive graphical display of the system. In response to the user command, the system opens all appropriate pinch clamps (which were closed during the venous air recovery) and restarts all pumps at their previous rates (before the venous air recovery). The system may also perform the blood pump startup test, as illustrated in FIG. 30 and discussed above.

Figure 45A:
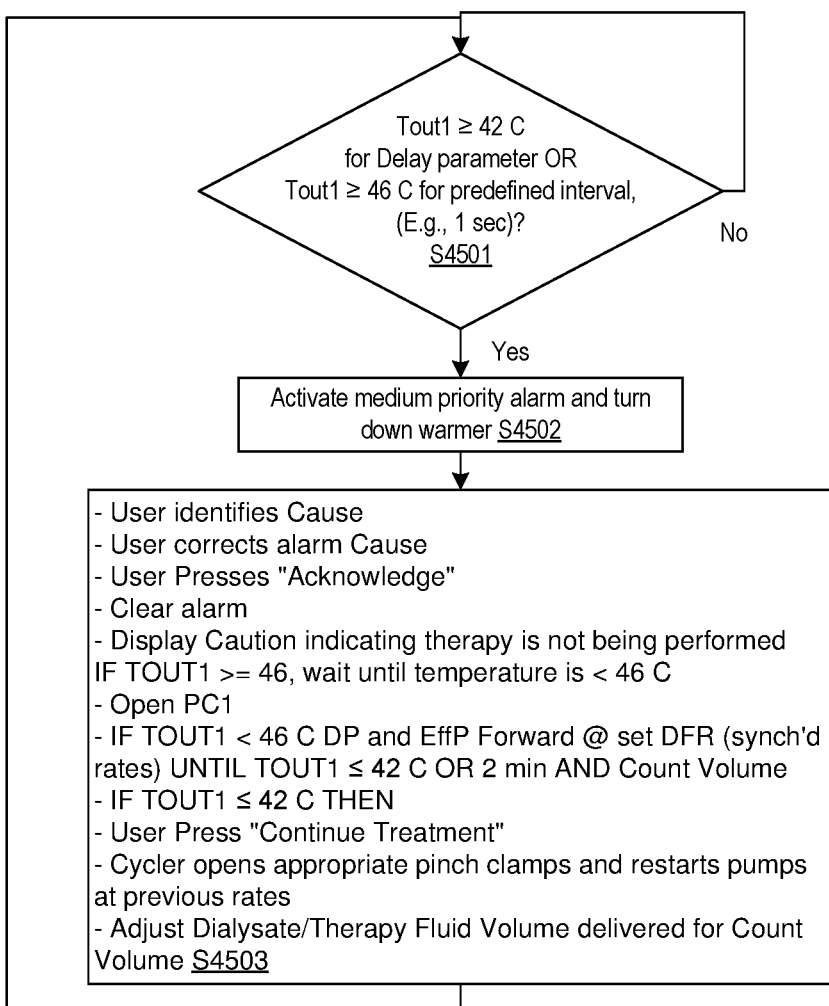
FIGS. 45A-45C show flows of a test process for identifying high temperatures of fluids used by a dialysis-like treatment device according to embodiments of the disclosed subject matter.

FIG. 45A provides a flowchart of a test process for identifying high temperature of fluids used by the dialysis-like treatment device 500 for various treatments during treatment and rinseback. In embodiments, device 500 may use treatment fluid 124 (e.g., dialysis fluid), replacement fluid 120, replacement fluid 133, and supplemental fluid 132, referred to collectively as therapeutic fluids or treatment fluids. It will be understood that not all of the therapeutic fluids may be present in various embodiments. One or more of these therapeutic fluids may be prescription fluids that are specifically prescribed for a patient treated by device 500.

The test applies temperature and duration bounds on the temperature of the therapeutic fluids. High therapeutic fluid temperature may result from overheating of the fluids by the warmer 592 of device 500, or by passive heating due to the environment. The warmer 592 has a setting controlling its temperature and its heating effect on therapeutic fluid, and the setting may be set too high. The warmer can be turned down to address this condition. Normally, only the dialysate bag is heated by the warmer 592. Thus, if any of the other therapeutic fluids are too warm, they are simply allowed to cool down passively without changing the warmer 592 setting.

As shown in FIG. 45A, at S4501 the test starts by determining the fresh treatment fluid outlet temperature sensor 570B and whether it is above a first predetermined temperature, for example 42 C for a time above a predetermined time delay parameter. Alternatively it determines whether the temperature is above a higher temperature, for example 46 C, for a predetermined time interval that is shorter than the first. For example the delay may be one second.

If at S4501 the condition is met, then, at S4502, a medium priority alarm is activated and information is presented as an audible and/or visible message from device 500. The message may provide the cause of the condition and the steps for the user to take. If the cause is the warmer 592 being too warm, the device 500 may adjust the warmer setting to reduce its temperature; See S4503. The user is then requested to indicate acknowledgement by the device 500, such as pressing an "acknowledge" button at S4503.

Then, the device 500 checks whether the recovery was successful. In the case of the treatment fluid 124 being over temperature, the pinch clamp 571 is initially closed when the over temperature condition is detected. After the user's acknowledgment and/or the heater has been turned down, the pinch clamp 571 is opened to allow flow of the dialysate fluid from the source container toward the treatment device 114. The temperature of the dialysate fluid is measured, and if the warmer is turned off. If no, then no error is detected.

After the medium priority alarm is activated and the warmer is turned off, the process waits to receive acknowledgment of recovery action. Then, the process determines whether venous blood temperature is greater than or equal the limit parameter for 120 seconds, OR greater than or equal to 46 C for the duration of the delay parameter. If yes, then the process activates a high priority alarm which activates an audible alarm signal, activates a visual "Blood High Temperature", stops all pumps, and closes all pinch clamps.

In order to recover after a medium priority alarm is activated, the user may press "Mute" for 2 minute audio override, press "Help" for additional info and press "Done" when finished, identify the alarm cause, correct the alarm cause, press "Acknowledge", clear the alarm, and press "Continue Treatment". The user may then verify that venous blood temperature is below the limit parameter, and then open appropriate pinch clamps and restart pumps at previous rates. In order to recover after a high priority alarm is activated, the user may press "Mute" for 2 minute audio override, identify the alarm cause, correct the alarm cause, press "Acknowledge", clear the alarm, press "Continue Treatment", open appropriate pinch clamps, and restart pumps at previous rates.

As shown in FIG. 45A, at S4501 the test starts by determining whether a therapeutic fluid temperature is above a first predetermined temperature, for example 42 C for a time above a first predetermined time delay parameter, OR above a predetermined temperature, for example 46 C for a second predetermined time delay parameter that is shorter than the first, for example, one second. The temperatures of the various therapeutic fluids used by device 500 are measured by respective temperature sensors, and output at Tout2 as shown in FIG. 19A.

If at S4501 the condition is met, then, at S4502, a medium priority alarm is activated and information is presented as an audible and/or visible message from device 500. The message may provide the cause of the condition and the steps for the user to take. If the cause is the warmer 592 being too warm, the device 500 may adjust the warmer setting to reduce its temperature; See S4503. The user is then requested to indicate acknowledgement by the device 500, such as pressing an "acknowledge" button at S4503.

Then, the device 500 checks whether the recovery was successful. In the case of the treatment fluid 124 being over temperature, the pinch clamp 571 is initially closed when the over temperature condition is detected. After the user's acknowledgment and/or the heater has been turned down, the pinch clamp 571 is opened to allow flow of the dialysate fluid from the source container toward the treatment device 114. The temperature of the dialysate fluid is measured, and if the warmer is turned off. If no, then no error is detected. After the medium priority alarm is activated and the warmer is turned off, the process waits to receive acknowledgment of recovery action. Then, the process determines whether venous blood temperature is greater than or equal the limit parameter for 120 seconds, OR greater than or equal to 46 C for the duration of the delay parameter. If yes, then the process activates a high priority alarm which activates an audible alarm signal, activates a visual "Blood High Temperature" message, stops all pumps, and closes all pinch clamps.

In order to recover after a medium priority alarm is activated, the user may press "Mute" for 2 minute audio override, press "Help" for additional info and press "Done" when finished, identify the alarm cause, correct the alarm cause, press "Acknowledge", clear the alarm, and press "Continue Treatment". The controller may receive the command to continue treatment. The user may then verify that venous blood temperature is below the limit parameter, and then open appropriate pinch clamps and restart pumps at previous rates. In order to recover after a high priority alarm is activated, the user may press "Mute" for 2 minute audio override, identify the alarm cause, correct the alarm cause, press "Acknowledge", clear the alarm, press "Continue Treatment", open appropriate pinch clamps, and restart pumps at previous rates.

Figure 45B:
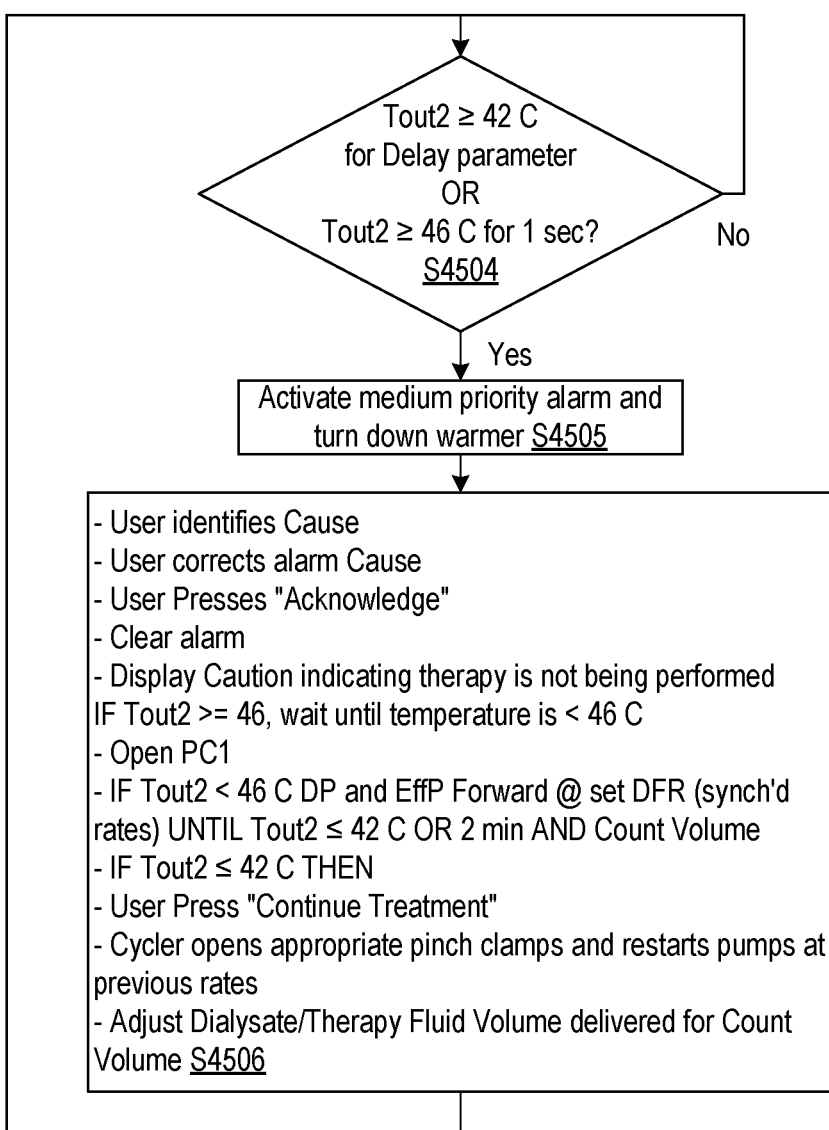

As shown in FIG. 45B, at S4504 the test starts by determining whether a therapeutic fluid temperature is above a first predetermined temperature, for example 42 C for a time above a predetermined time delay parameter, OR above a predetermined temperature, for example 46 C for a second shorter predetermined time interval, for example, one second. The temperatures of the various therapeutic fluids used by device 500 are measured by respective temperature sensors, and output at Tout4 as shown in FIG. 19.

If at S4504 the condition is met, then, at S4505, a medium priority alarm is activated and information is presented as an audible and/or visible message from device 500. The message may provide the cause of the condition and the steps for the user to take. If the cause is the warmer 592 being too warm, the device 500 may adjust the warmer setting to reduce its temperature; See S4506. The user is then requested to indicate acknowledgement by the device 500, such as pressing an "acknowledge" button at S4506.

Then, the device 500 checks whether the recovery was successful. In the case of the treatment fluid 124 being over temperature, the pinch clamp 571 is initially closed when the over temperature condition is detected. After the user's acknowledgment and/or the heater has been turned down, the pinch clamp 571 is opened to allow flow of the dialysate fluid from the source container toward the treatment device 114. The temperature of the dialysate fluid is measured, and if the warmer is turned off. If no, then no error is detected. After the medium priority alarm is activated and the warmer is turned off, the process waits to receive acknowledgment of recovery action. Then, the process determines whether venous blood temperature is greater than or equal the limit parameter for 120 seconds, OR greater than or equal to 46 C for the duration of the delay parameter. If yes, then the process activates a high priority alarm which activates an audible alarm signal, activates a visual "Blood High Temperature", stops all pumps, and closes all pinch clamps.

In order to recover after a medium priority alarm is activated, the user may press "Mute" for 2 minute audio override, press "Help" for additional info and press "Done" when finished, identify the alarm cause, correct the alarm cause, press "Acknowledge", clear the alarm, and press "Continue Treatment". The user may then verify that venous blood temperature is below the limit parameter, and then open appropriate pinch clamps and restart pumps at previous rates. In order to recover after a high priority alarm is activated, the user may press "Mute" for 2 minute audio override, identify the alarm cause, correct the alarm cause, press "Acknowledge", clear the alarm, press "Continue Treatment", open appropriate pinch clamps, and restart pumps at previous rates.

Figure 45C:
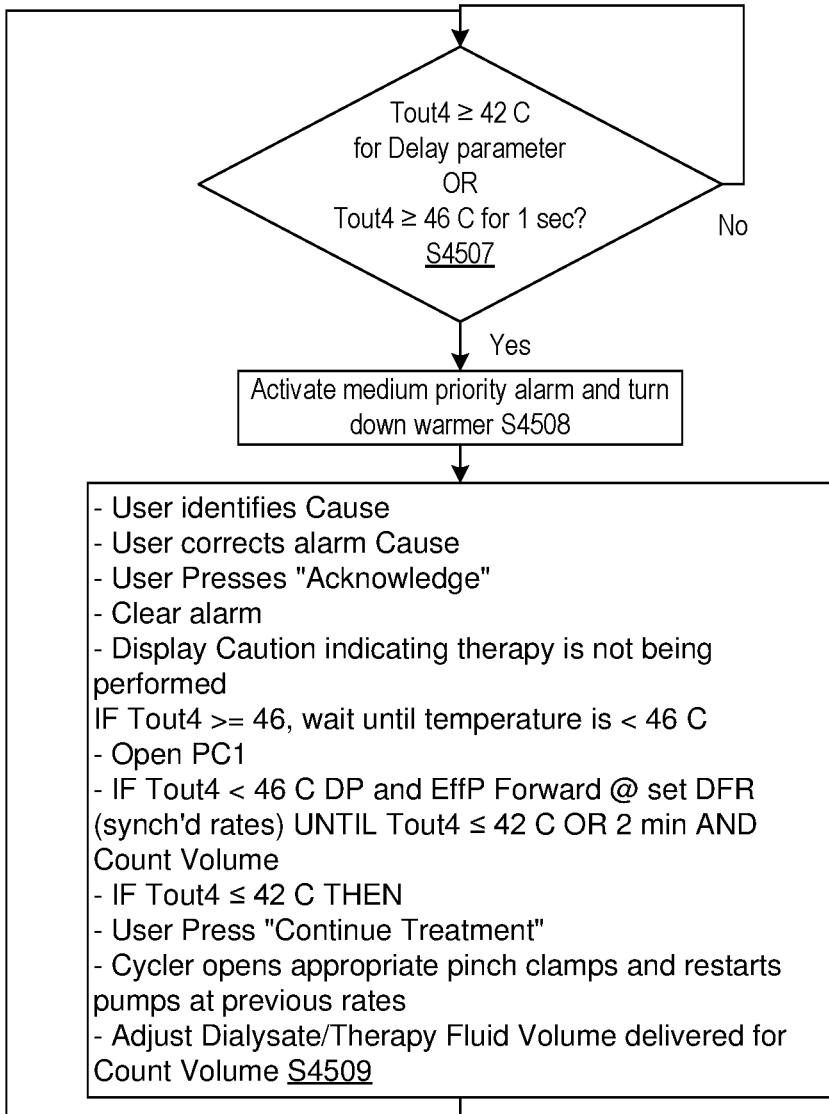

As shown in FIG. 45 C, at S4507 the test starts by determining whether a therapeutic fluid temperature is above a first predetermined temperature, for example 42 C for a time above a predetermined time delay parameter, or above a predetermined temperature, for example 46 C for a predetermined time interval, for example, one second at S4501. The temperatures of the various therapeutic fluids used by device 500 are measured by respective temperature sensors, and output at Tout4 as shown in FIG. 19.

If at S4508 the condition is met, then, at S4508, a medium priority alarm is activated and information is presented as an audible and/or visible message from device 500. The message may provide the cause of the condition and the steps for the user to take. If the cause is the warmer 592 being too warm, the device 500 may adjust the warmer setting to reduce its temperature; See S4509. The user is then requested to indicate acknowledgement by the device 500, such as pressing an "acknowledge" button at S4509.

Then, the device 500 checks whether the recovery was successful. In the case of the treatment fluid 124 being over temperature, the pinch clamp 571 is initially closed when the over temperature condition is detected. After the user's acknowledgment and/or the heater has been turned down, the pinch clamp 571 is opened to allow flow of the dialysate fluid from the source container toward the treatment device 114. The temperature of the dialysate fluid is measured, and if the warmer is turned off. If no, then no error is detected. After the medium priority alarm is activated and the warmer is turned off, the process waits to receive acknowledgment of recovery action. Then, the process determines whether venous blood temperature is greater than or equal to the limit parameter for 120 seconds, OR greater than or equal to 46 C for the duration of the delay parameter. If yes, then the process activates a high priority alarm which activates an audible alarm signal, activates a visual "Blood High Temperature", stops all pumps, and closes all pinch clamps.

In order to recover after a medium priority alarm is activated, the user may press "Mute" for 2 minute audio override, press "Help" for additional info and press "Done" when finished, identify the alarm cause, correct the alarm cause, press "Acknowledge", clear the alarm, and press "Continue Treatment". The user may then verify that venous blood temperature is below the limit parameter, and then open appropriate pinch clamps and restart pumps at previous rates. In order to recover after a high priority alarm is activated, the user may press "Mute" for 2 minute audio override, identify the alarm cause, correct the alarm cause, press "Acknowledge", clear the alarm, press "Continue Treatment", open appropriate pinch clamps, and restart pumps at previous rates.

Figure 46:
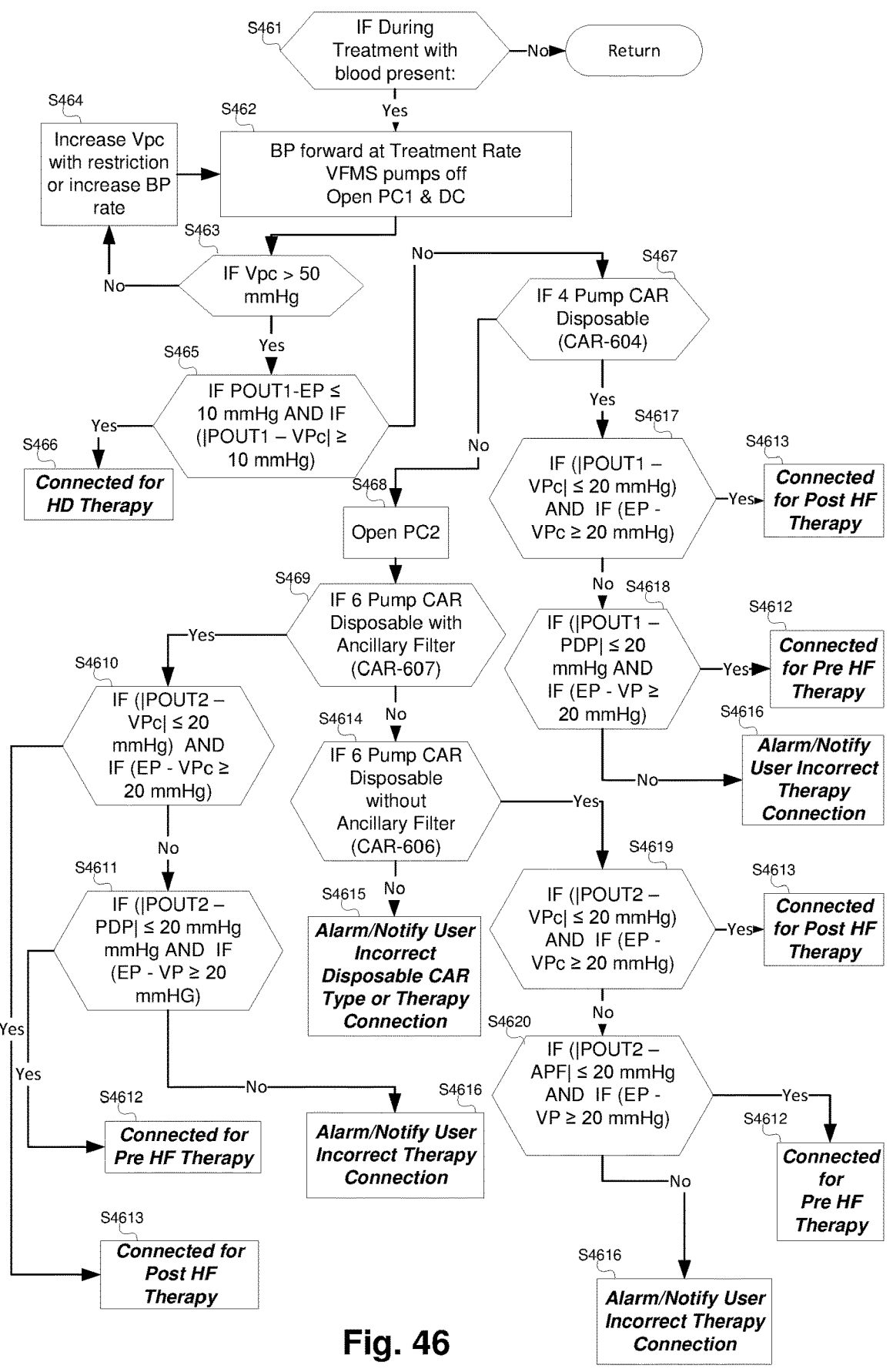
FIG. 46 illustrates a process flow that determines the configuration of the connections, type of fluid circuit, and errors in therapy type selection according to various embodiments of the disclosed subject matter.

Referring to FIG. 46, a test is performed to determine whether the therapy fluid connections are correct. It may be desirable to perform this test whenever the treatment system is activated, whenever a patient treatment is activated, and/or whenever the system is notified that a therapy fluid connection has been changed.

The test begins by confirming that a patient treatment is ongoing, and that blood is present in the lines of the system at S461. If it is determined that the treatment is not ongoing or that there is no blood in the system lines, the test is terminated. Otherwise, the process continues to S462. At S462, the blood pump 563 operates at the treatment rate. Fresh treatment fluid pump 573 and waste treatment fluid pumps are turned off, which effectively stops the flow of a treatment fluid 124 through the system. As part of this step, pinch clamp 571 and pinch clamp 581 are opened. The waste treatment fluid line 536 at this stage may assure a fluid connection is maintained between fresh treatment fluid outlet pressure 570A and a top port of treatment device 114 and between the inlet waste pressure sensor 575 and the bottom port of treatment device 114. In this manner, it is possible to use the pressure sensors to measure a pressure differential across the two ports of the treatment device 114.

The test continues at S463, where the venous blood pressure Vpc, (pressure indicated by venous primary control pressure sensor 532A) the pressure indicated by venous primary control pressure sensor 532A, is measured by the venous control primary pressure sensor 532A and venous secondary pressure sensor 532B. If the value of Vpc is below a threshold value (for example, 50 mmHg), it is desirable to increase the pressure Vpc by increasing the flow rate and/or by creating a restriction in the venous line that will result in an increased pressure, as shown at S464. More specifically, the pumping rate of the blood pump 563 can be increased by a predetermined amount, and the process continues again at S462. Alternatively, the venous line can be restricted, for example by venous line clamp 562. In embodiments, the venous line clamp 562 can introduce a partial restriction, such that the effective cross sectional area of the fluid line is reduced by a controlled amount. In other embodiments, a separate restriction, such as a line clamp, can be added to the venous blood line downstream of the venous control primary pressure sensor 532A and venous secondary pressure sensor 532B.

When pressure Vpc is above the threshold value at S463, the process continues at S465. A measurement of pressure Pout1 (the pressure indicated by fresh treatment fluid outlet pressure sensor 570A). is made on the waste treatment fluid line 536, and a measurement of Ep (the pressure indicated by the inlet waste pressure sensor 575). The measurement of VPc can be made again, or the pressure reading from S463 may be reused in some embodiments. A determination is made whether the difference between Pout1 and Ep is less than or equal to a second threshold (e.g., 10 mmHg), and whether the absolute value of the difference between Pout1 and Vpc is greater than or equal to a third threshold (e.g., 10 mm Hg). This can be written as the mathematical expression (Pout1−Ep≤10 mmHg) AND (|Pout1−Vpc|≥10 mmHg). In embodiments, the value of the second and third threshold may be the same. In other embodiments, the values may be different and may be other values.

If the determination in S465 is YES, then the system determines that it is connected for hemodialysis therapy, as shown in S466. On the other hand, if the determination in S465 is No, the process continues to S467.

At S467, the system determines whether a 4 pump cartridge 599 has been inserted. This can be determined in various ways, including an RFID identifier on the cartridge that is read by the system. In other embodiments the cartridge may have an optical code, such as a bar code or QR code that is read by the system before or while the cartridge is inserted. In other embodiments, the type of the cartridge can be input by a user of the system through a user interface, such as a keyboard, buttons, and/or a display. The system may include sensors, such as mechanical pins that are pressed by parts of the cartridge that uniquely identify the cartridge type.

If at S467 it is determined that a 4 pump cartridge is inserted, the process continues to S4617. At S4617, a measurement of pressure Pout1 is made by fresh treatment fluid outlet pressure sensor 570A. Alternatively, the pressure measurement of Pout1 may be retained from earlier steps and used herein. Similarly, a pressure of the venous line Vpc is made by the venous control primary pressure sensor 532A, or a value that has been previously measured above may be used. A value of Ep is also measured by pressure sensor 575, or may be obtained from earlier steps. A determination is made whether the absolute value of Pout1−Vpc is less than or equal to a threshold value. In embodiments, the threshold value is 20 mmHg. Further, a determination is made whether Ep−Vpc is greater than or equal to a threshold value. In embodiments, this threshold value is also 20 mmHg. In other embodiments, the two threshold values may be different. If both of these determinations are true (i.e., |Pout1−Vpc|≤20 mmHg AND Ep−Vpc≥20 mmHg), the system determines that the connections are connected for hemofiltration with post-dilution therapy at S4613.

If the determination in S4617 is No, the process continues at S4618 where a determination is made whether the absolute value of Pout1−pressure Pdp, (the pressure measured by the pressure sensor 534), is less than or equal to a threshold value. In embodiments, this threshold value is 20 mmHg, and may be the same as the threshold values in steps above. Additionally, a determination is made whether the Ep, from the inlet waste pressure sensor 575, minus venous pressure Vpc, measured by the venous control primary pressure sensor 532A, is greater than or equal to a threshold value. In embodiments, this threshold value is 20 mmHg, and may be the same as the threshold values described above. If both of the conditions are true (i.e., |Pout1−Pdp|≤20 mmHg AND E−Vpc≥20 mmHg), then the system determines that it is connected for hemofiltration with pre-dilution therapy at S4612. Otherwise, the system generates an alarm condition that notifies a user that an incorrect therapy connection has been made at S4616.

Returning again to S467, if it is determined that a 4 pump cartridge is not inserted, the process continues to S468 where the pinch clamp 554) which is interposed in the fluid line between replacement fluid container 120 and the sterilizing filter 583 is opened.

At S469, the system determines whether a 6 pump cartridge 599 with an ancillary filter has been inserted. This can be determined in various ways, including an RFID identifier on the cartridge that is read by the system. In other embodiments the cartridge may have an optical code, such as a bar code e.g., a QR code that is read by the system before or while the cartridge is inserted. In other embodiments, the type of the cartridge can be input by a user of the system through a user interface, such as a keyboard, buttons, and/or a display. The system may include sensors, such as mechanical pins that are pressed by parts of the cartridge that uniquely identify the cartridge type.

If the determination at S469 is No, the process continues to S4614, where it is determined whether a 6 pump cartridge 599 without an ancillary filter has been inserted. This determination can be made similarly to those above in S469 and S467. If the determination here is No, the system generates an alarm condition at S4615 and outputs a notification that an incorrect cartridge type has been inserted or an incorrect therapy connection has been made.

If the determination at S469 is Yes (i.e., a 6 pump cartridge with ancillary filter has been inserted), the process continues at S4610. At S4610, it is determined whether the difference in pressure Pout2 (the pressure indicated by pressure sensor 555A) and Vpc, is below a threshold value. In embodiments, the threshold value is 20 mmHg, and may be the same value as other threshold values above. Further, a determination is made whether effluent pressure Ep minus venous pressure Vpc is greater than or equal to a threshold value. In embodiments, the threshold value is 20 mmHg and may be the same value as other threshold values above. The expression can be written as (|Pout2−Vpc|≤20 mmHg AND (Ep−Vpc 20 mmHg)). If the determination is Yes, the process continues at S4613, where it is determined that the system is connected for hemofiltration with post dilution therapy.

If the determination at S4610 is No, the process continues to S4611, where it is determined whether the system is connected for hemofiltration with pre dilution therapy. More specifically, the values of Pout2, Pdp, Ep, Vpc are compared. If ($|$Pout2–Pdp$|\leq$20 mmHg AND (Ep–Vpc)$\geq$20 mmHg), the system determines that it is connected for hemofiltration with pre dilution therapy at S4612. While 20 mmHg is used as the threshold value above, it is understood that different values can be used, and can be the same as other threshold values above.

If the determination at S4611 is No, the system generates an alarm condition and outputs a notification that an incorrect therapy connection exists at S4616.

Returning to S4614, if the determination is Yes (i.e., 6 pump cartridge without an ancillary filter is detected), the process continues to S4619, where it is determined whether the system is connected for hemofiltration with post dilution therapy. More specifically, if ($|$Pout2–VPc$|\leq$20 mmHg AND (Ep–Vpc)$\leq$20 mmHg), the system determines that it is connected for hemofiltration with post dilution therapy at S4613. While 20 mmHg is used as the threshold value above, it is understood that different values can be used, and can be the same as other threshold values above.

If the determination at S4619 is No, the process continues to S4620, where a determination is made whether the system is connected for hemofiltration with pre dilution therapy. More specifically, the values of Pout2, Pdp, Ep and pressure Vpc are compared. If ($|$Pout2–Pdp$|\leq$20 mmHg AND (Ep–Vpc)$\geq$20 mmHg), the system determines that it is connected for hemofiltration with pre dilution therapy at S4612. While 20 mmHg is used as the threshold value above, it is understood that different values can be used, and can be the same as other threshold values above.

If the determination at S4620 is No, the system generates an alarm condition and outputs a notification that an incorrect therapy connection exists at S4616.

Figure 47A:
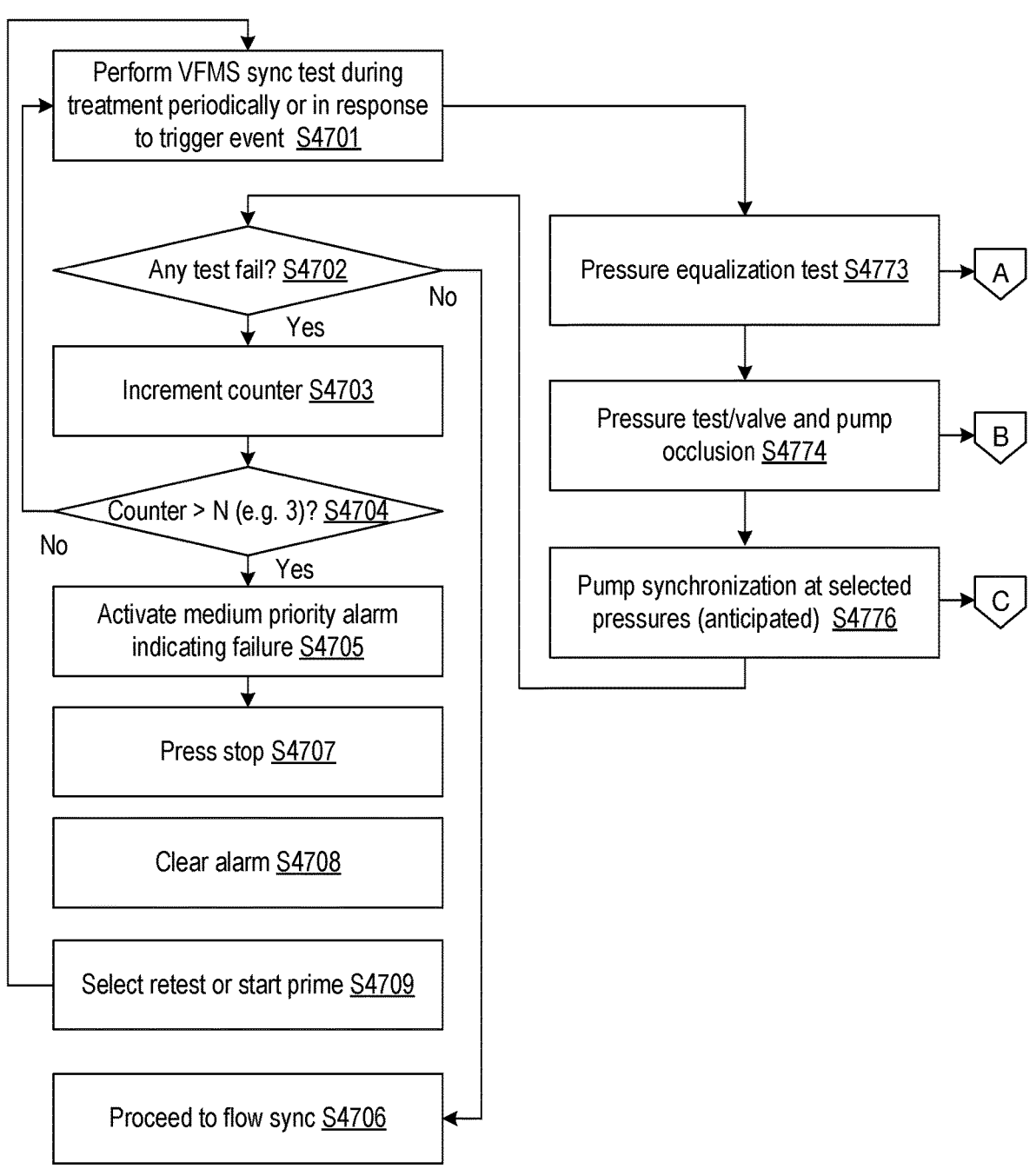
Figure 47B:
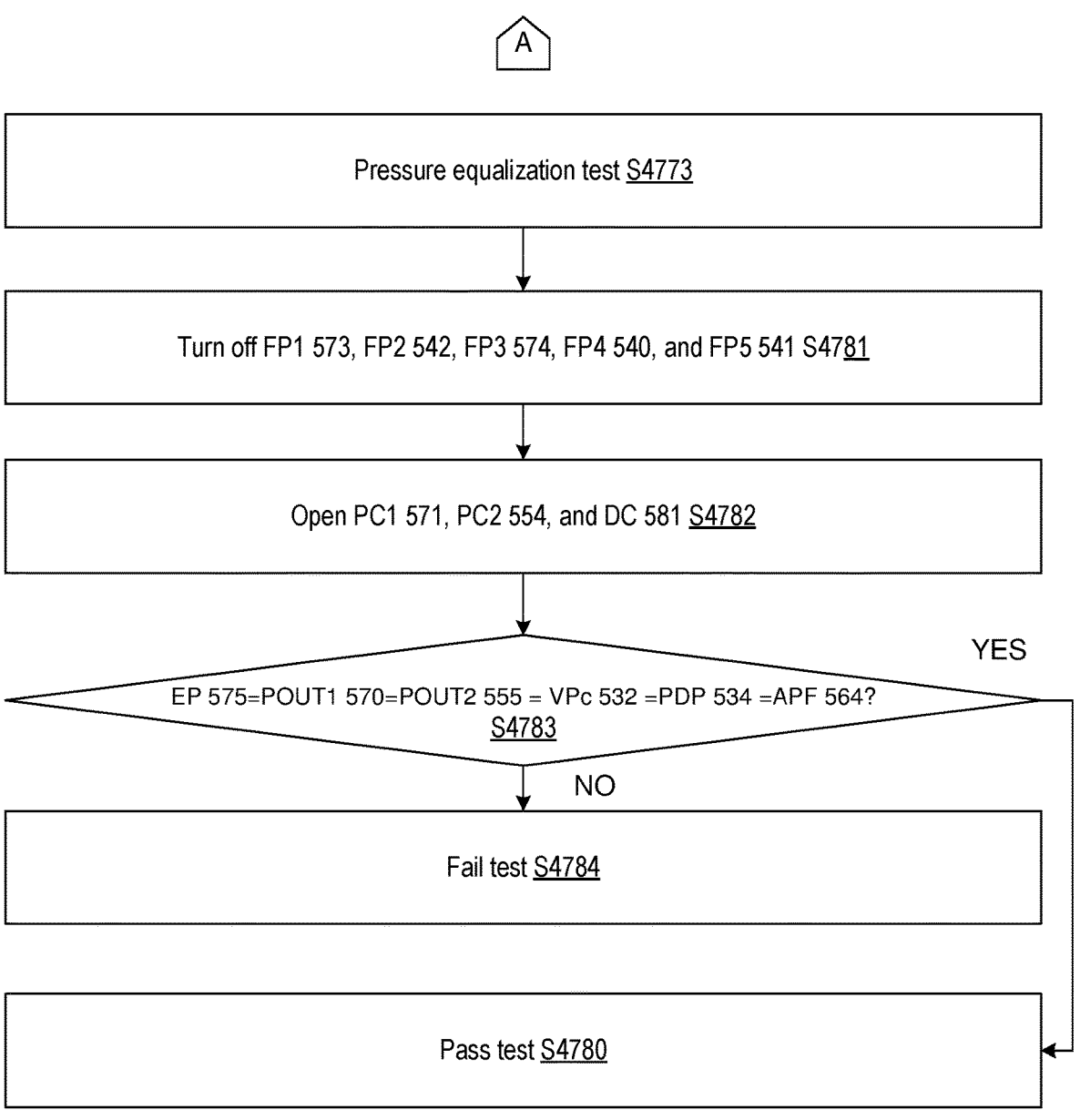

FIGS. 47A through 47D show a process for halting or permitting a flow synchronization during treatment according to embodiments of the foregoing disclosed subject matter. Referring now to FIG. 47A, at S4701 the volumetric synchronization test is performed during treatment at predefined intervals or after a change in the system settings is made, for example, a change in the fluid circuit, a change in flow rate of blood or treatment fluids or a change in any of the pump inlet pressures. If at S4702 any of the tests are determined to have failed, then a counter is incremented at S4703. At S4704, the counter is incremented and if less than a number N (e.g., 3) the VFMS sync test is repeated at S4701. Otherwise, if the counter has run out, then at S4705, a medium priority alarm is activated indicating the nature of the failure. At S4707, the user can press a control to stop the system, clear the alarm S4709 and retest or start prime at S4709. Then control reverts to S4701. If at S4702 the VFMS passes (not tests fail) then the system proceeds to flow synchronization at S4706.

Between S4701 and S4702 a series of tests are identified. The first test S4773 is described in FIG. 47B. This is a pressure equalization test that is arranged to ensure that the pressure signals provided by a plurality of pressure sensors are within range of each other when the sensors are located at a similar height and the fluid path between them is open. From S4773, at S4781, the following pumps are turned off: fresh treatment fluid pump 573, replacement fluid pump 542, the waste treatment fluid pump 574, second replacement fluid pump, and supplemental fluid pump 541 (See FIG. 19). At S4782, pinch clamp 571, pinch clamp 554, and pinch clamp 581 are opened. At S4783, it is determined whether the following pressure sensors give readings that are within a predetermined of each other. The pressure sensors are the inlet waste pressure sensor 575, fresh treatment fluid outlet pressure 570A, pressure sensor 555A, the venous control primary pressure sensor 532A and venous secondary pressure sensor 532B, pressure sensor 534, blood pump outlet pressure sensor 564. The pressure sensors mutual elevations may be used adjust the readings so that the readings can be compared more accurately. At S4783 the controller determines if the pressure sensors are with a predefined range (e.g. 10 mmHg) with adjustment for relative height. If the pressures are not in range, at S4784, the test is indicated as failed. If the pressure signals are in range, then at S4780, the test is deemed to have passed and indication to that effect is transmitted by the controller 240.

FIG. 47C shows a procedure for pressure testing valve and pump occlusion. Here, a valve to be tested at S1086 is selected by its proximity to a pump with an intervening pressure sensor between them so that the valve can be tested for its ability to occlude the line. At S4786, a valve is closed to be tested. The pump upstream of the valve is used to pressurize the line between the pump and valve so that a pressure sensor between them can read the pressure in the line at S4787. The pump is then halted at S1088 and the pressure decay profile is sampled to determine if the decay rate and pressure plateau that is reach is in a predefined range at S4789. If the pressure does not plateau in range then the test is deemed to have failed and an output to that effect is indicated at S4790. Otherwise, the clamp is opened, the pump rotated to pressurize and the pump stopped at a next roller whose ability to occlude is to be tested. S4791. The process repeats until all rollers have been tested at 54792A roller counter is also incremented. The process repeats until all rollers are tested at S4792. Once occlusion of all rollers have been tested, a next valve and pump combination is also tested until all are completed at which point, if the test hasn't failed yet, it is indicated as having passed at S4793.

Figure 47D:
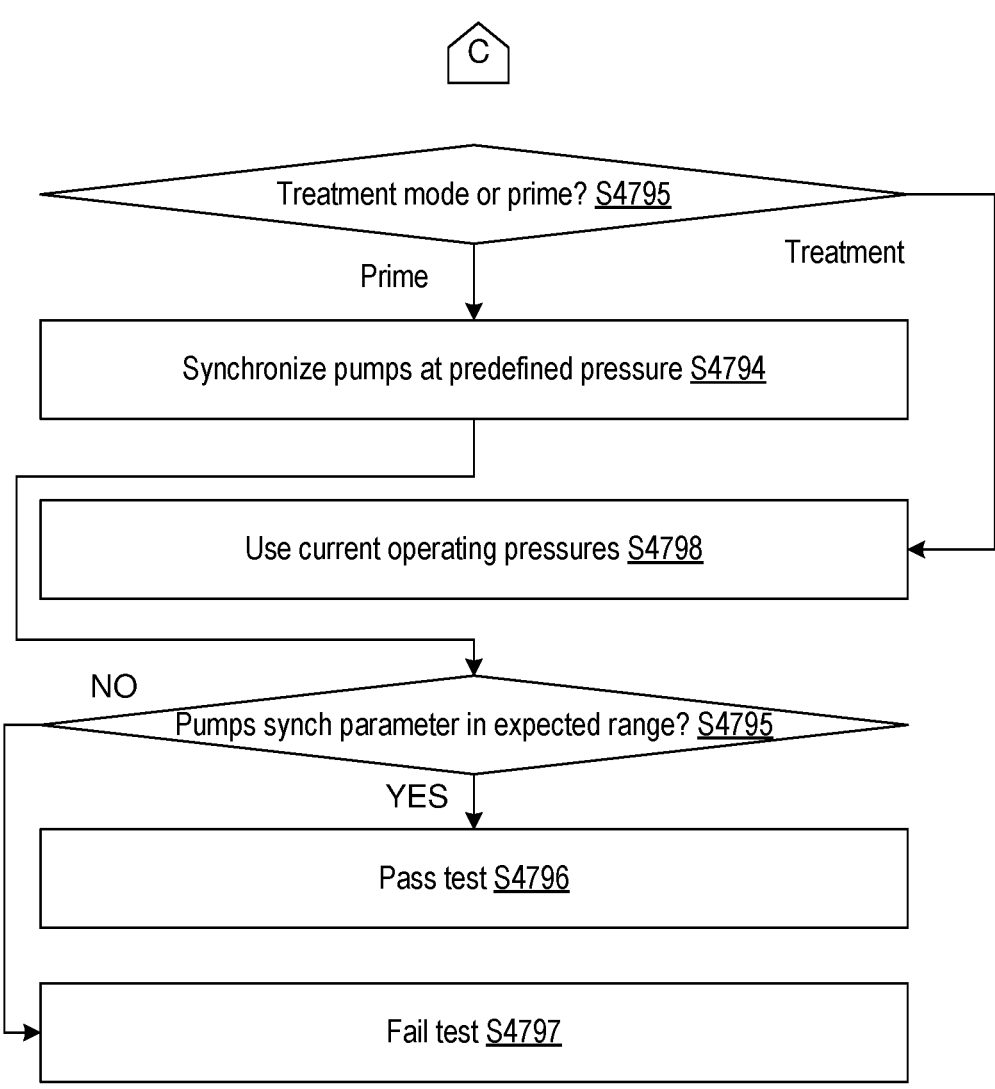

FIG. 47D shows a procedure where pumps are synchronized using either predefined pressure (S4794) or current operating pressure (S4798) depending on whether the system is in prime mode or treatment mode. The system uses synchronization to determine a relationship between the commanded pump speed and the synchronized rate of pumping. If the relationship is in an expected range at S4795, then the test passes at S4796. If not, the test fails at S4797.

The foregoing procedure differs from that of FIGS. 20A-20D in that the procedure is performed at times during treatment.

Figure 48A:
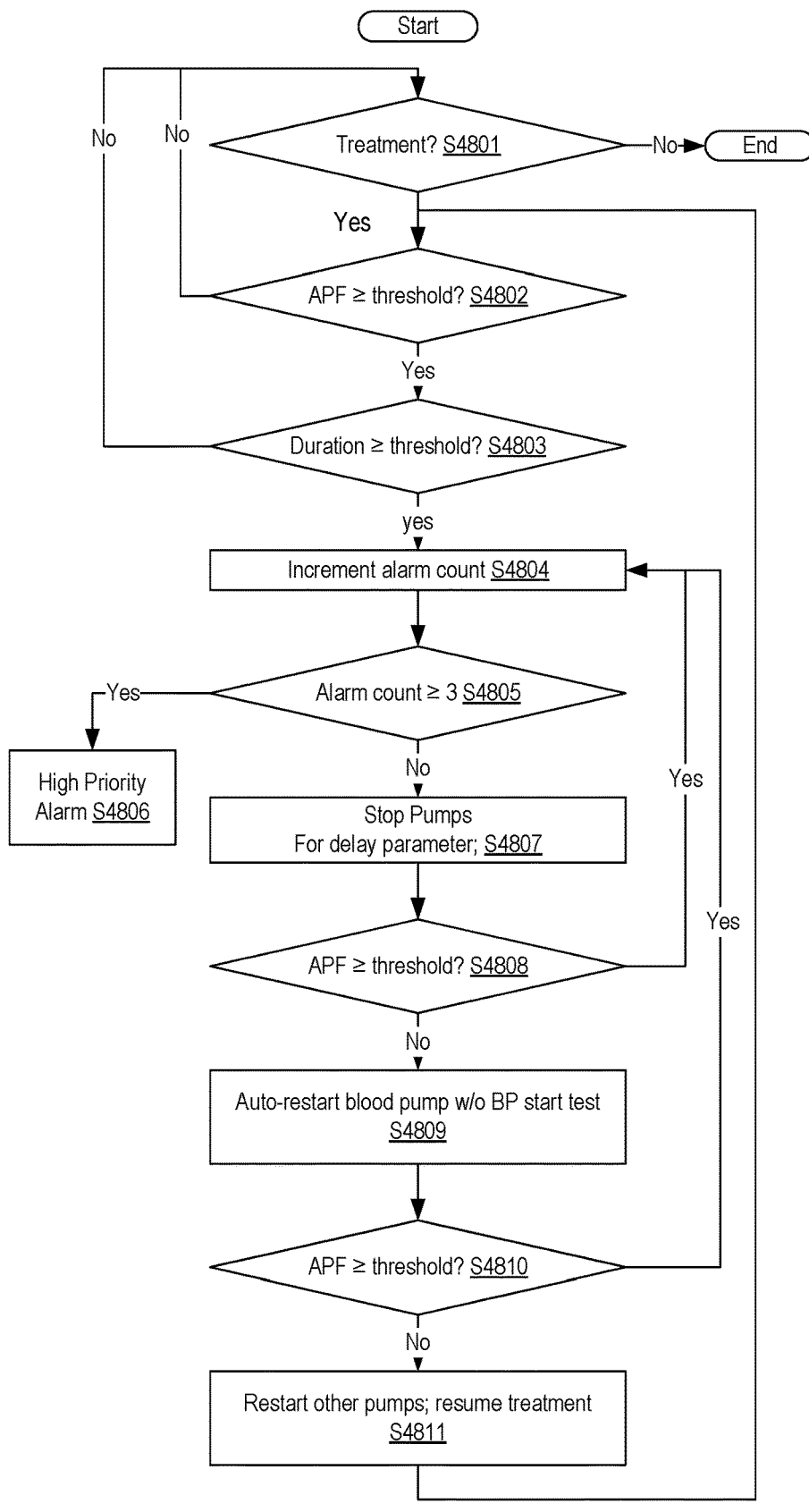
FIGS. 48A and 48B illustrate processes for detecting possible clotting in filters, according to embodiments of the disclosed subject matter.

FIG. 48A illustrates a process for detecting possible clotting in filters. This process may be carried out during the medical treatment and/or during the rinseback operation. Briefly, this process takes into account that clotting building up in a filter (e.g., a blood filter) will obstruct blood flow, and thus increase resistance of flow thorough the filter, which will be observable as an increase in the pressure at the inlet to the filter when the blood flow rate has not changed.

First, it is determined whether the system is in active treatment at S4801. If yes, the process continues to a check of the arterial pressure blood pump outlet pressure sensor 564 measured by blood pump outlet pressure sensor 564. The blood pump outlet pressure sensor 564 can be continuously monitored or may be sampled at a predetermined frequency. If the blood pump outlet pressure sensor 564 exceeds a predetermined threshold value, the system checks the duration during which the threshold is exceeded S4802. If the blood pump outlet pressure sensor 564 exceeds a threshold for a duration, checked at S4803, that exceeds a duration threshold, an alarm condition is detected and an alarm counter can be incremented to keep track of the number of times the threshold has been exceeded S4804. By checking both the level of the blood pump outlet pressure sensor 564 and the duration, the operation can be thought of as integrating the pressure above the threshold over the time duration of the time threshold. If this integrated pressure exceeds a threshold value, an alarm is detected.

If three such alarms are detected, at S4805, a high priority alarm is generated at S4806 by the system. In response, the user of the system may acknowledge the alarm and take remedial measures, such as flushing and/or replacing filters.

If the alarm count is below 2, the system stops all pumps S4807 for a period of time, and then checks the blood pump outlet pressure sensor 564 pressure after the period of time has passed. It is expected that if the filter(s) are not clogged, the pressure reading will be at a normal level. If blood pump outlet pressure sensor 564 still exceeds the threshold S4808, the alarm counter may be incremented; or the process may return to the beginning step above, such that an integral of the pressure reading is considered rather than just the reading of the blood pump outlet pressure sensor 564 after expiration of the period of time.

If blood pump outlet pressure sensor 564 is below the threshold after the pumps have been stopped for a period of time, the system may restart the blood pump S4809 and again check the value of blood pump outlet pressure sensor 564 and compare it against a threshold. If the threshold is exceeded again, the alarm parameter can be incremented, or the process may return instead to the initial step such that the integral of the pressure measurement blood pump outlet pressure sensor 564 is compared against a threshold S4810.

If blood pump outlet pressure sensor 564 remains below the threshold, the process continues and other pumps are restarted. The process then returns to the initial step above and the pressure blood pump outlet pressure sensor 564 is monitored S4811.

Figure 48B:
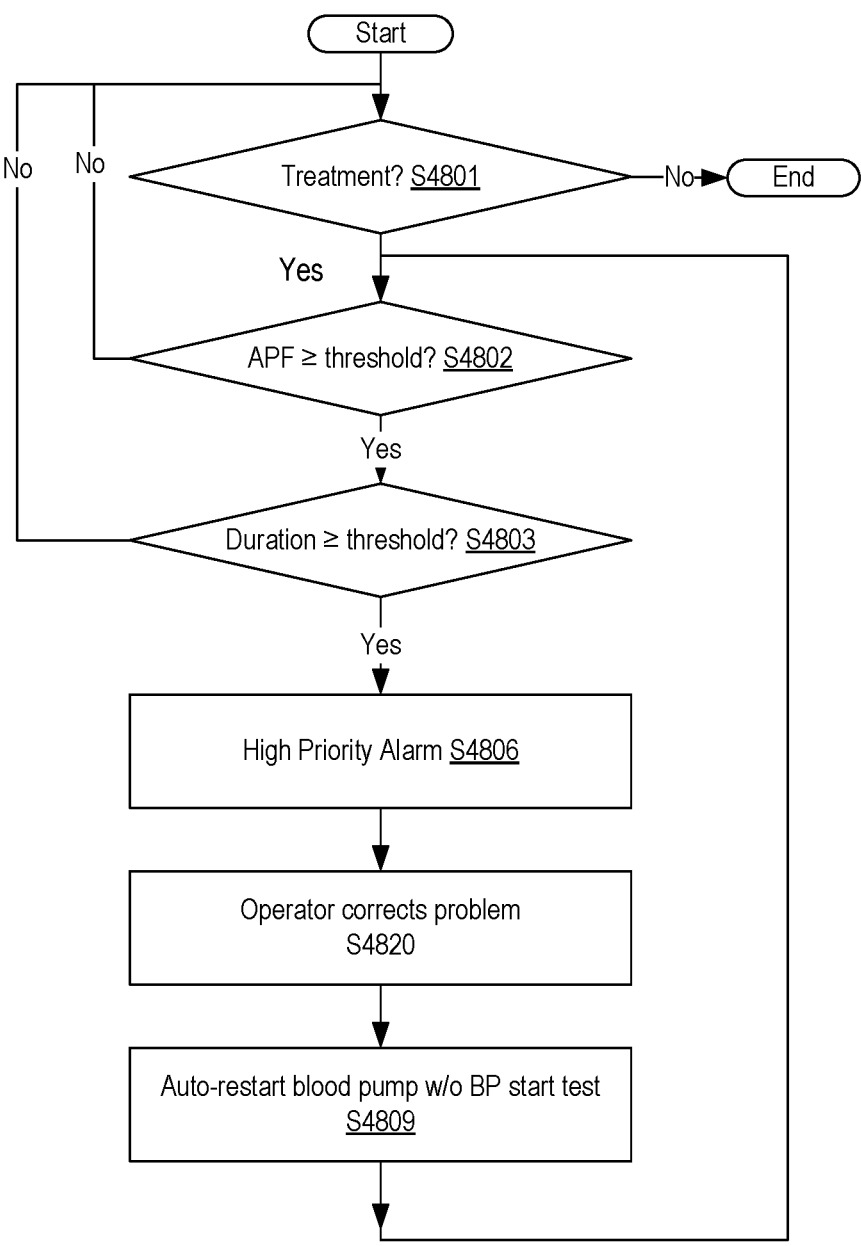

FIG. 48B illustrates a process for detecting possible clotting in filters. This process may be carried out during the medical treatment and/or during the rinseback operation. Briefly, this process takes into account that clotting building up in a filter (e.g., a blood filter) will obstruct blood flow, and thus increase resistance of flow thorough the filter, which will be observable as an increase in the pressure at the inlet to the filter when the blood flow rate has not changed.

First, it is determined whether the system is in active treatment at S4801. If yes, the process continues to a check of the arterial pressure blood pump outlet pressure sensor 564 measured by blood pump outlet pressure sensor 564. The blood pump outlet pressure sensor 564 can be continuously monitored, or may be sampled at a predetermined frequency. If the blood pump outlet pressure sensor 564 exceeds a predetermined threshold value, the system checks the duration during which the threshold is exceeded S4802. If the blood pump outlet pressure sensor 564 exceeds a threshold for a duration, checked at S4803, that exceeds a duration threshold, an alarm condition is detected and an alarm counter can be incremented to keep track of the number of times the threshold has been exceeded S4804. By checking both the level of the blood pump outlet pressure sensor 564 and the duration, the operation can be thought of as integrating the pressure above the threshold over the time duration of the time threshold. If this integrated pressure exceeds a threshold value, an alarm is detected.

If the duration and threshold are exceeded control advances to S4806 where a high priority alarm is output. The user then corrects the problem at S4820 by replacing the filter or flushing it after a cause is output by the controller 240, for example a clogged filter.

At S4809, the blood pump 563 is automatically restarted and the blood pump start up test performed as described with reference to FIG. 29.

Figure 49A:
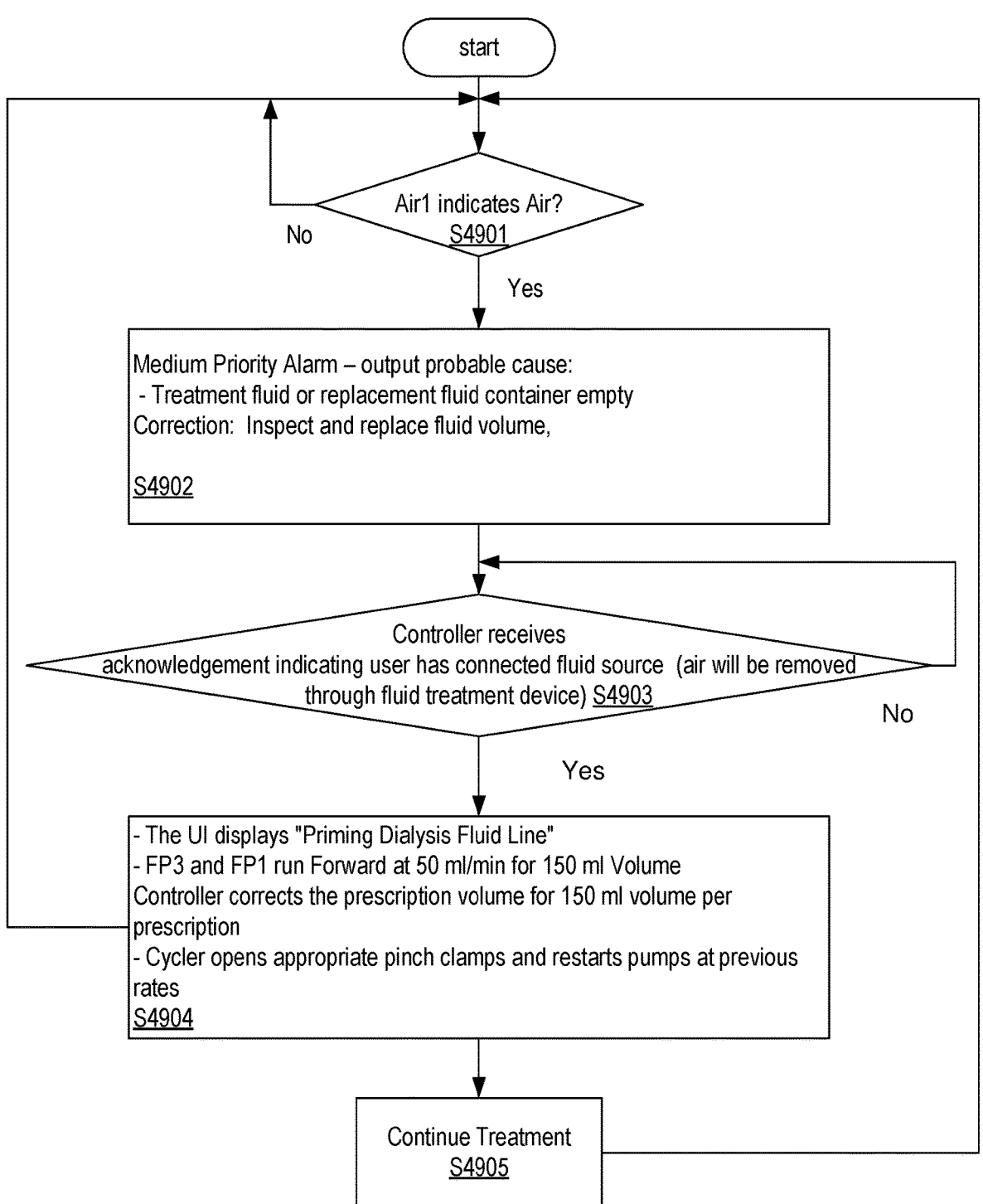
FIG. 49A illustrates a process for detecting when a dialysis fluid container is empty, according to embodiments of the disclosed subject matter.

Referring now to FIG. 49A, a process for detecting when the container holding treatment fluid 124 is empty is now described. Air in a fluid line from the container holding treatment fluid 124 is detected by the fresh treatment fluid air sensor 579 which may indicate the fluid container therein has been exhausted while the fresh treatment fluid pump 573 is still running. Control flow loops through S4901 until air is detected by the fresh treatment fluid air sensor 579. If air is detected a medium priority alarm is generated at S4902. The user interface outputs an indication of the affected air sensor and probable cause or causes. The user replaces the empty container and the controller generates a prompt to the user to acknowledge the problem is resolved by generating an acknowledgement command through the user interface at S4903. This may be done by generating an output defining the affected sensor and outputting a soft key control labeled "acknowledge," for example. The control loops through 4903 until an acknowledgment is received by the controller. By inputting an acknowledgment the user is indicating that the cause of the problem has been corrected. For example, the container for treatment fluid 124 may be replaced by the user. Once the acknowledgment is received at S4903, control goes to S4904 where the controller outputs a display indicating "priming the dialysis fluid line." The controller then runs the waste treatment fluid pump 574 and fresh treatment fluid pump 573 at a predefined rate, for example, 50 ml/min, for a predefined interval of time or displaced total volume, for example 150 ml. The controller then corrects the cumulative quantity of treatment fluid so that the total quantity does not contribute to the prescribed amount. Once the fluid source is reconnected, the priming operation can push the air and fluid to waste fluid outlet or it may be drained manually by the user. After this, the controller 140 may generate a soft key indicating "continue treatment," opening previously closed clamps and restarting the treatment at the previous flow rates S4904 and S4905.

Figure 49B:
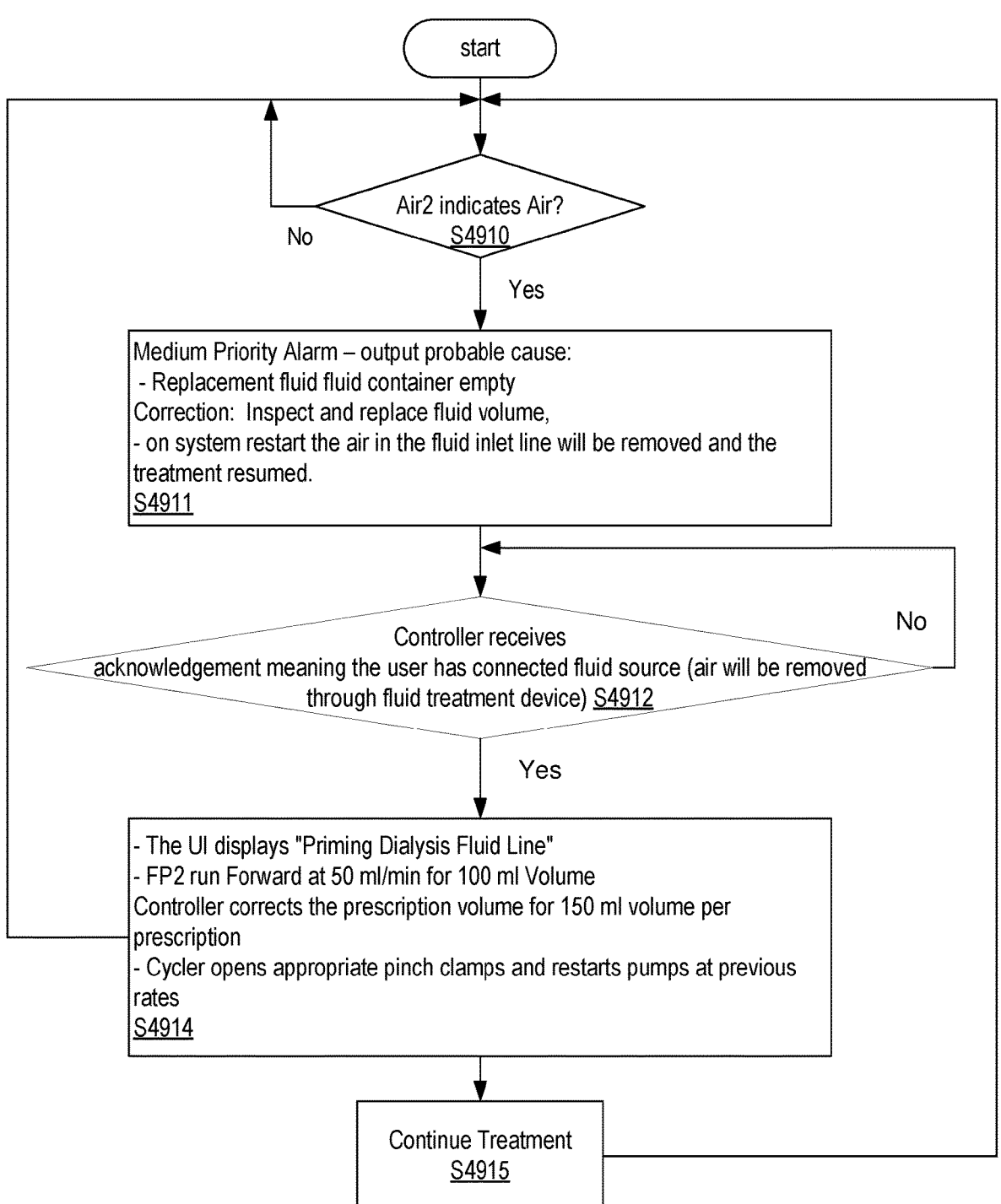
FIG. 49B illustrates a process for detecting when a replacement fluid container is empty, according to embodiments of the disclosed subject matter.

Referring now to FIG. 49B, a process for detecting when replacement fluid container 120 is empty is now described. Air in a fluid line from replacement fluid container 120 is detected by the air sensor 587 which may indicate the fluid container therein has been exhausted while the replacement fluid pump 542 is still running. In response to the detection of air the replacement fluid pump 542 is halted by the controller. Control flow loops through S4910 until air is detected by the air sensor 587. If air is detected a medium priority alarm is generated at S4911. The controller, via the user interface outputs an indication of the affected air sensor and waits for a prompt from the user acknowledging the problem by generating an acknowledgement command through the user interface at S4912. By entering the acknowledgment command the user indicates that a fresh source of the fluid has been connected. This may be done by generating an output defining the affected sensor and outputting a soft key control labeled "acknowledge," for example. The user interface then generates an output indicating the system is priming the first replacement fluid line 593. This operation is summarized at S4914. The priming operation is executed by the controller 240 by running the replacement fluid pump 542 in the forward direction at a predefined rate, for example, 50 ml/min, for a predefined interval of time. Once the fluid source is reconnected, the priming operation can push the air and fluid to waste fluid outlet or it may be drained manually by the user. After this, the controller 140 may generate a soft key indicating "continue treatment," opening previously closed clamps and restarting the treatment at the previous flow rates S4915.

Figure 49C:
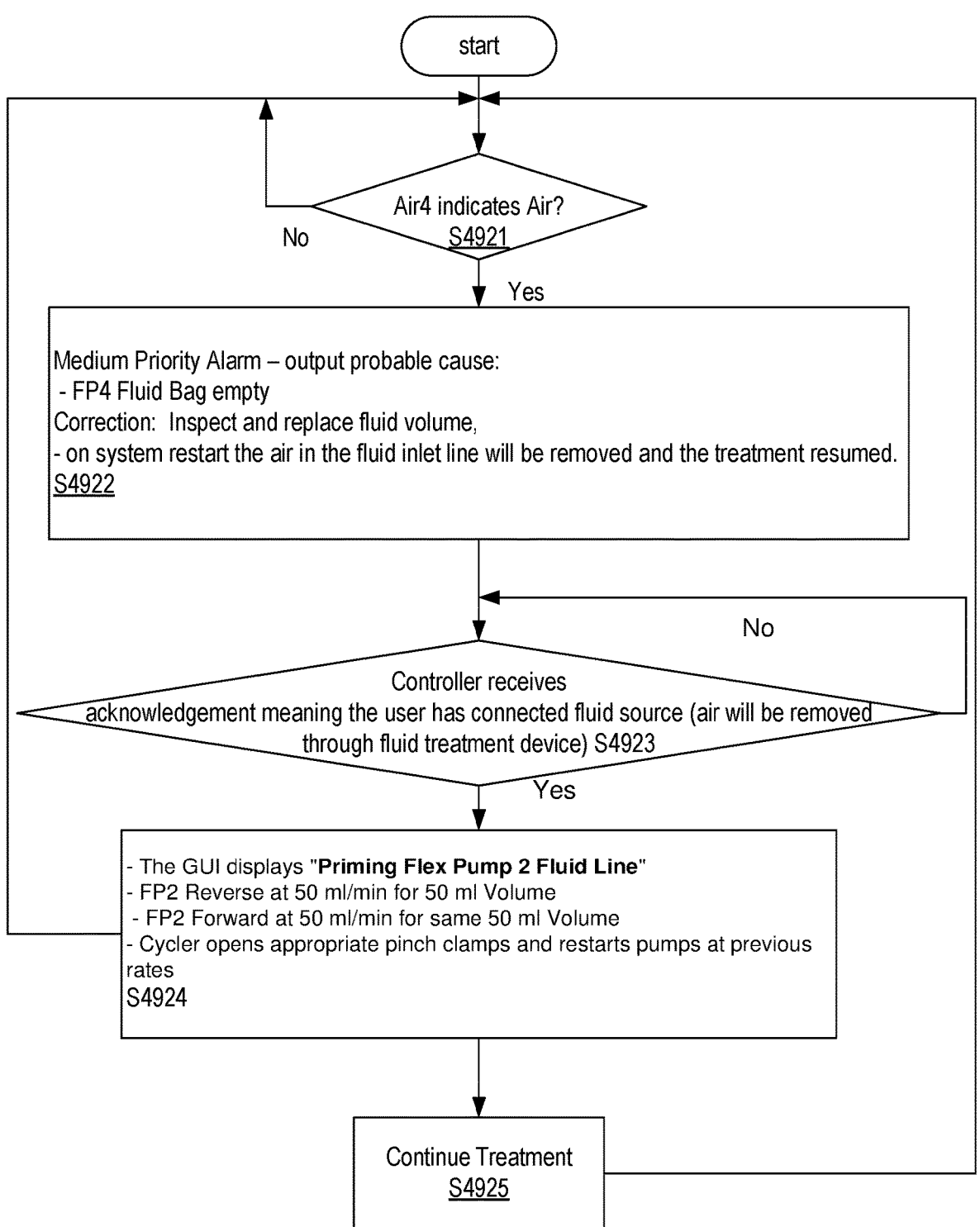
FIG. 49C illustrates a process for detecting when a fluid container is empty, according to embodiments of the disclosed subject matter.

Referring now to FIG. 49C, a process for detecting when flexible fluid container 133 is empty is now described. Air in a fluid line from flexible fluid container 133 is detected by the air sensor 589 which may indicate the fluid container 133 therein has been exhausted while the supplemental fluid pump 540 is still running. Control flow loops through S4921 until air is detected by the air sensor 589. If air is detected a medium priority alarm is generated at S4922. The user interface outputs an indication of the affected air sensor and waits for a prompt from the user acknowledging the problem by generating an acknowledgement command through the user interface at S4923. This may be done by generating an output defining the affected sensor and outputting a soft key control labeled "acknowledge," for example. By pressing this key, the user is indicating that the fluid supply (second replacement fluid 133) has been replaced. The user interface then generates an output indicating the system is priming the second replacement fluid line 594. This operation is summarized at S4923. The priming operation is executed by the controller 240 by running the second replacement fluid pump 540 in the forward direction at a predefined rate, for example, 50 ml/min, for a predefined interval of time. After this, the controller 140 may generate a soft key indicating "continue treatment." The user enters the command to "continue treatment" and the controller opens previously closed clamps and restarts the treatment at the previous flow rates S4925.

Figure 50:
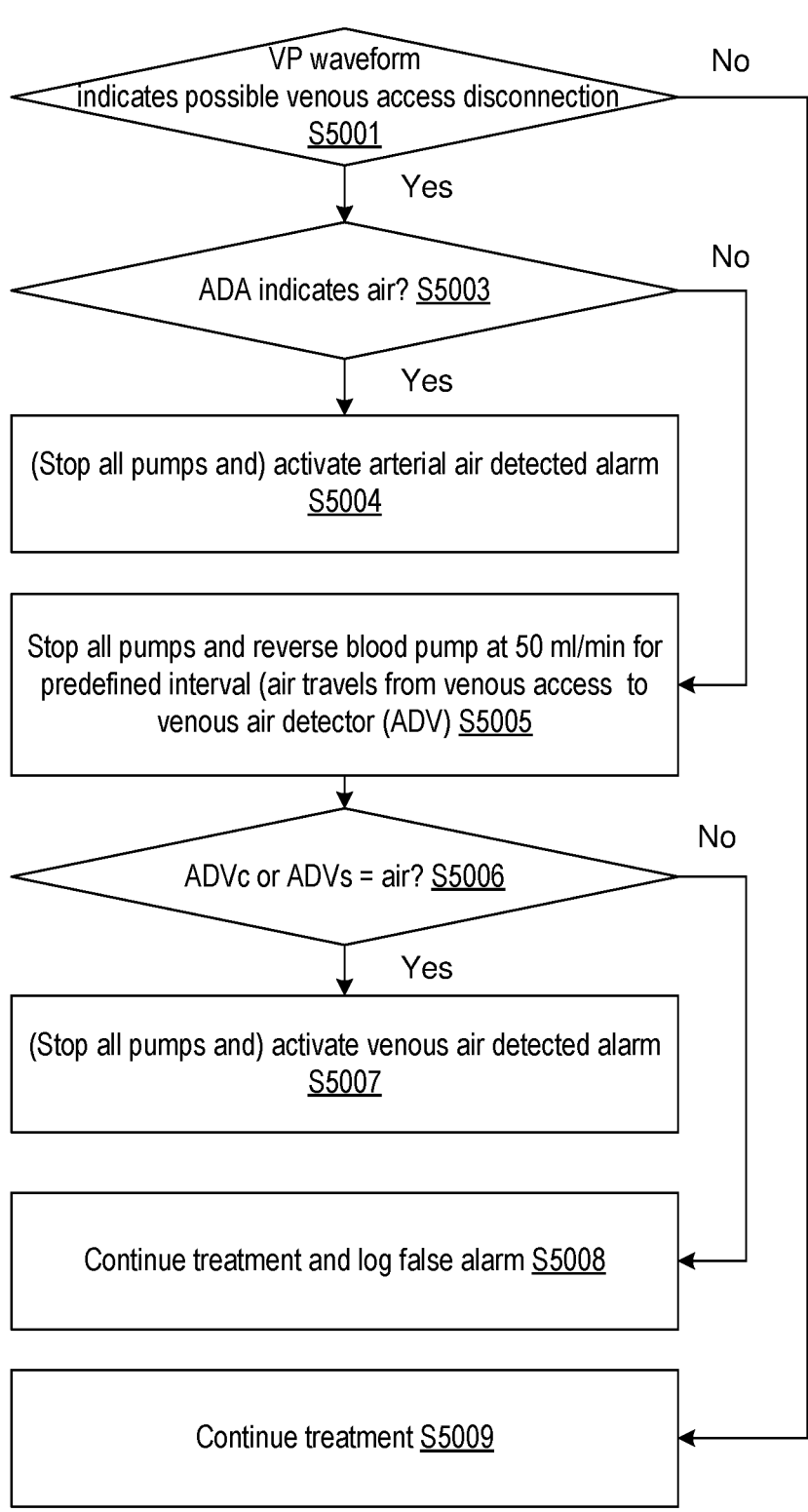
FIG. 50 illustrates a procedure for detecting a patient access disconnection is shown during treatment or rinseback according to embodiments of the disclosed subject matter.

Referring now to FIG. 50, a procedure for detecting a patient access disconnection is shown during treatment or rinseback. At S5001, a predefined waveform is indicated by the venous control primary pressure sensor 532A and venous secondary pressure sensor 532B, for example, a precipitous drop in the pressure indicated by the venous control primary pressure sensor 532A and venous secondary pressure sensor 532B, a drop in the same below a predefined threshold for a predefined interval of time, or a combination of the two. If the signal fails the disconnection criteria the treatment or rinseback continues at S5009. If the criteria are satisfied, then at S5003, it is determined whether arterial control air sensor 567A and arterial secondary air sensor indicate the presence of air in the blood line and if so, at S5004, the system stops all pumps and outputs an "arterial air detection" alarm. Note there may be a delay before the ADA can be presumed to indicate the presence of air to allow time for air to reach the sensor after an access disconnect is detected by the aforementioned criteria. This alarm may take a variety of forms such as a display output coupled with an output from an annunciator such as a beep or specific beep pattern to alert the operator. If the arterial control air sensor 567A and arterial secondary air sensor do not indicate the presence of air in the arterial line, then at S5005 all pumps are stopped and the blood pump is run in reverse at a predefined rate. In embodiments, the predefined rate may be 50 ml/min. In further embodiments it may be in the range of 40-60 ml/min. At S5006, it is determined whether air is detected by one or both of the venous control primary air sensor 566A and venous secondary air sensor 566B. If no air is detected then the treatment is continued at S5008. The detection is determined after the lapse of a predefined interval selected to ensure air drawn from the patient access through the arterial line to the venous control primary air sensor 566A and venous secondary air sensor 566B at the selected flow rate. If no air is detected at S506 then treatment is continued, after the blood pump is run in the normal direction and the other fluid pumps are restarted. A log entry in a machine or treatment log may be made at this point to account for issues with false alarms. If, at S5006, air is detected, then all pumps are stopped S5007 and a venous air detected alarm is output. Again, this alarm may take a variety of forms such as a display output coupled with an output from an annunciator such as a beep or specific beep pattern to alert the operator.

Figure 51:
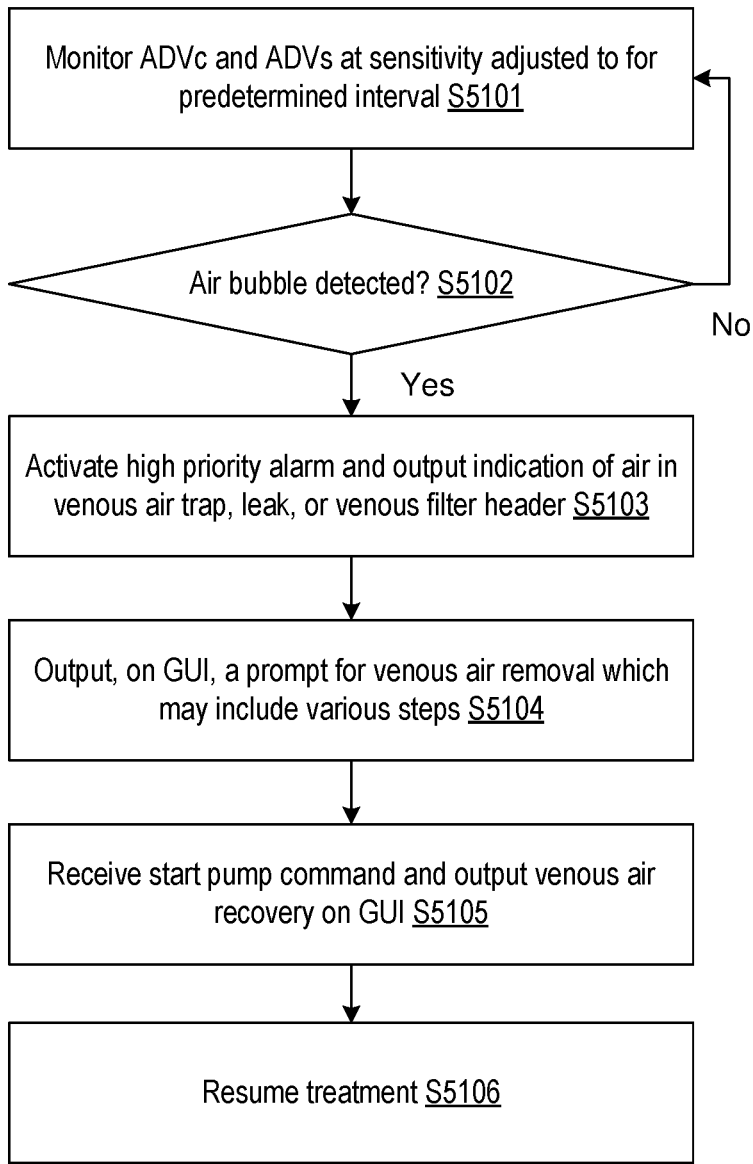
FIG. 51 illustrates a procedure whereby both venous air sensors are monitored for an indication of an air bubble according to embodiments of the disclosed subject matter.

Referring now to FIG. 51, during treatment or rinseback, at both of the venous control primary air sensor 566A and venous secondary air sensor 566B are monitored for an indication of an air bubble. The target threshold is a bubble of about 60 microliters at a pressure of 400 mmHg at 600 ml/min blood flow. This is a sensitivity threshold for detection and not conditions that are required for monitoring. If air is indicated at the identified sensitivity threshold at S5102, a high priority alarm is output at S5103. At S5104, the graphical user interface may output a prompt for air removal which may include various steps for the operator. The system may wait for a command to restart the blood pump at S5105 and at S5106 the treatment is resumed.

Figure 52:
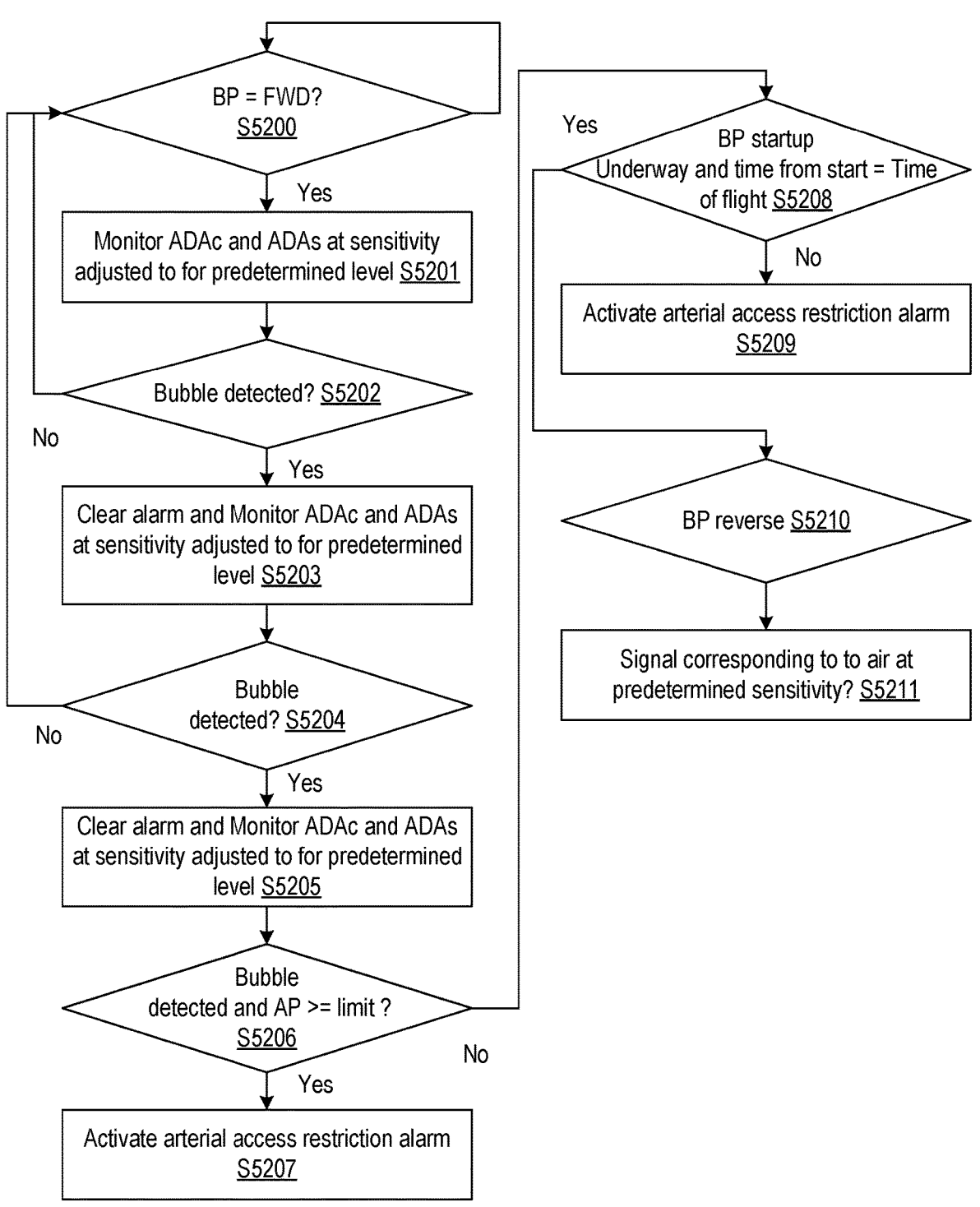
FIG. 52 illustrates a procedure for detecting bubbles in blood lines according to embodiments of the disclosed subject matter.

Referring now to FIG. 52, during treatment or rinseback, the currently described control flow is executed. At S5200, it is determined if the blood pump 563 is running in the forward direction and if the time it takes an air bubble to reach the ADA since the pump was activated in the forward direction reaches a threshold value. If yes is determined at S5200, then at S5201, at the arterial control air sensor 567A and arterial secondary air sensor 567A are monitored for the detection at a sensitivity corresponding to a 60 microliter bubble at 400 mmHg venous pressure and 600 ml/min blood flow rate. If a bubble is detected at the indicated sensitivity level at S5202 then at S5203, the alarm is cleared and the arterial control air sensor 567A and arterial secondary air sensor 567A continue to be monitored at the same sensitivity. The procedure of clearing the alarm and monitoring is repeated at S5206 if another bubble is detected at S5204 and if a third bubble is detected at S526 and the arterial pressure exceeds a predefined limit at S526, then at 527, an arterial access restriction alarm is activated.

Figure 53:
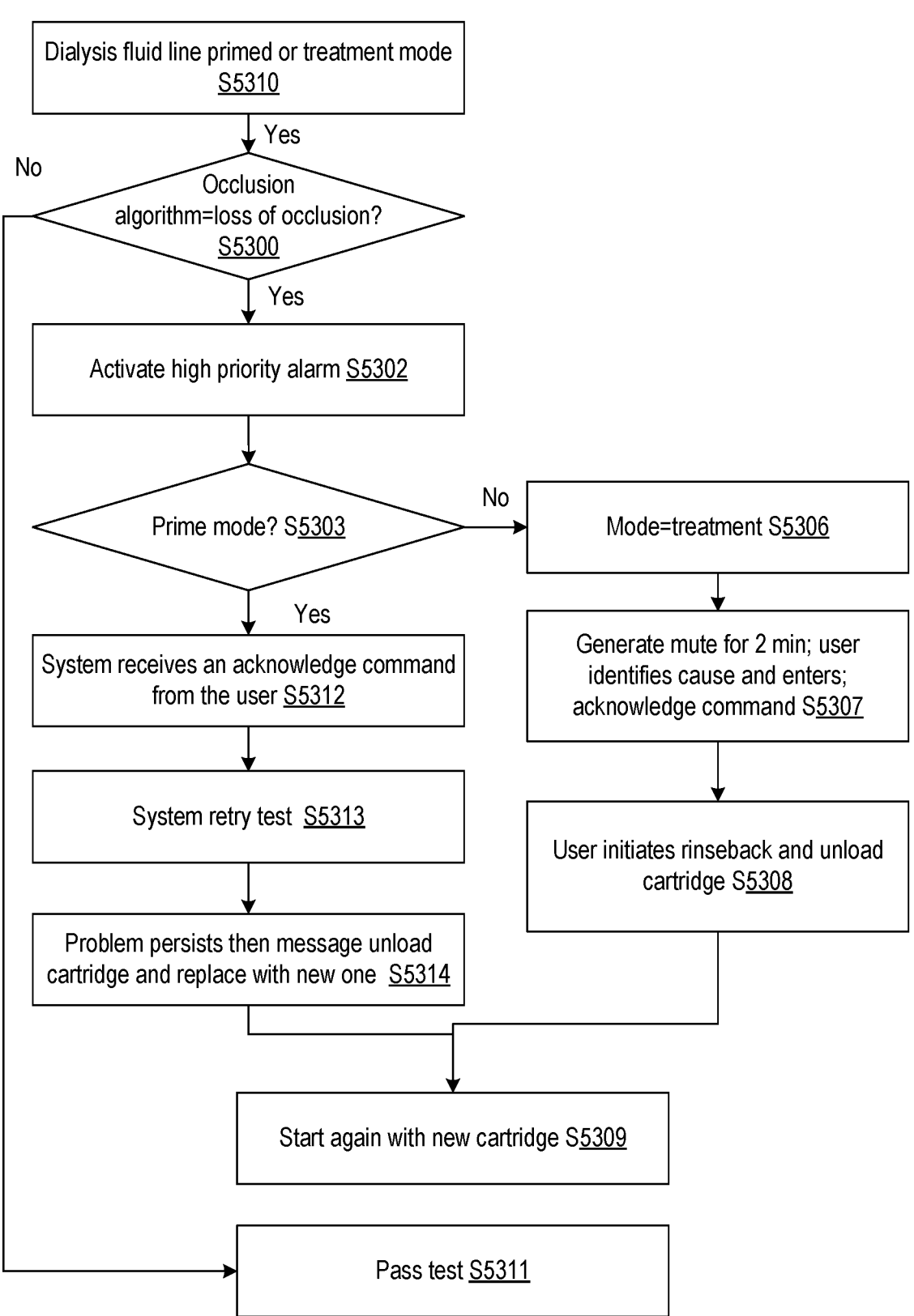
FIG. 53 illustrates a procedure during priming or treatment to perform an occlusion test of each of several pumps according to embodiments of the disclosed subject matter.

Referring now to FIG. 53, at S5310, the procedure is performed when dialysis fluid is primed during priming mode or during treatment. This procedure corresponds to S2074 in FIGS. 20A and 20C. At S5300 the controller 240 performs an occlusion test on each of several fluid pumps including the fresh treatment fluid pump 573, the waste treatment fluid pump 574, and the second replacement fluid pump 540. The occlusion test includes closing a pinch clamp downstream of the pump and a corresponding downstream pressure sensor. Pinch clamp 571 is closed for the fresh treatment fluid pump 573. Waste clamp 578 is closed for the waste treatment fluid pump 574. A pinch clamp 556 is closed for the second replacement fluid pump 540. Pressure is detected using fresh treatment fluid outlet pressure 570A for the fresh treatment fluid pump 573. Pressure is detected using the outlet waste pressure sensor 576 for the waste treatment fluid pump 574. Pressure is detected using pressure sensor 557A for the second replacement fluid pump 540. Each respective pump is run for a predefined interval while the respective clamp is closed and the respective pressure sensor is monitored to determine if the pump is fully occluding the respective line. If the pressure declines faster than a predetermined rate, it indicates the pump is not sufficiently occluding the corresponding line and the pump fails the occlusion test. If at S5300 any of the pumps shows a loss of occlusion, then at S5302 a high priority alarm is generated. At S5303 it is determined if the system is in prime mode or treatment mode. If in prime at S5312 the system receives an acknowledge command from the user, if entered, and at S5313, the system retries the test. If the problem persists at S5314 then the user is instructed to unload the cartridge and replace it with a new one. Then the system begins with set up, loading of a new cartridge and proceeding again to priming at S5309. If at S5303, the mode is determined to be the treatment mode S5306, then at S5307, the user can generate a mute command that quiets the high priority alarm for a predefined interval whereupon the user identifies the cause of the problem, enters an acknowledge command, which initiates rinseback and instructions to unload the cartridge.

Figure 54:
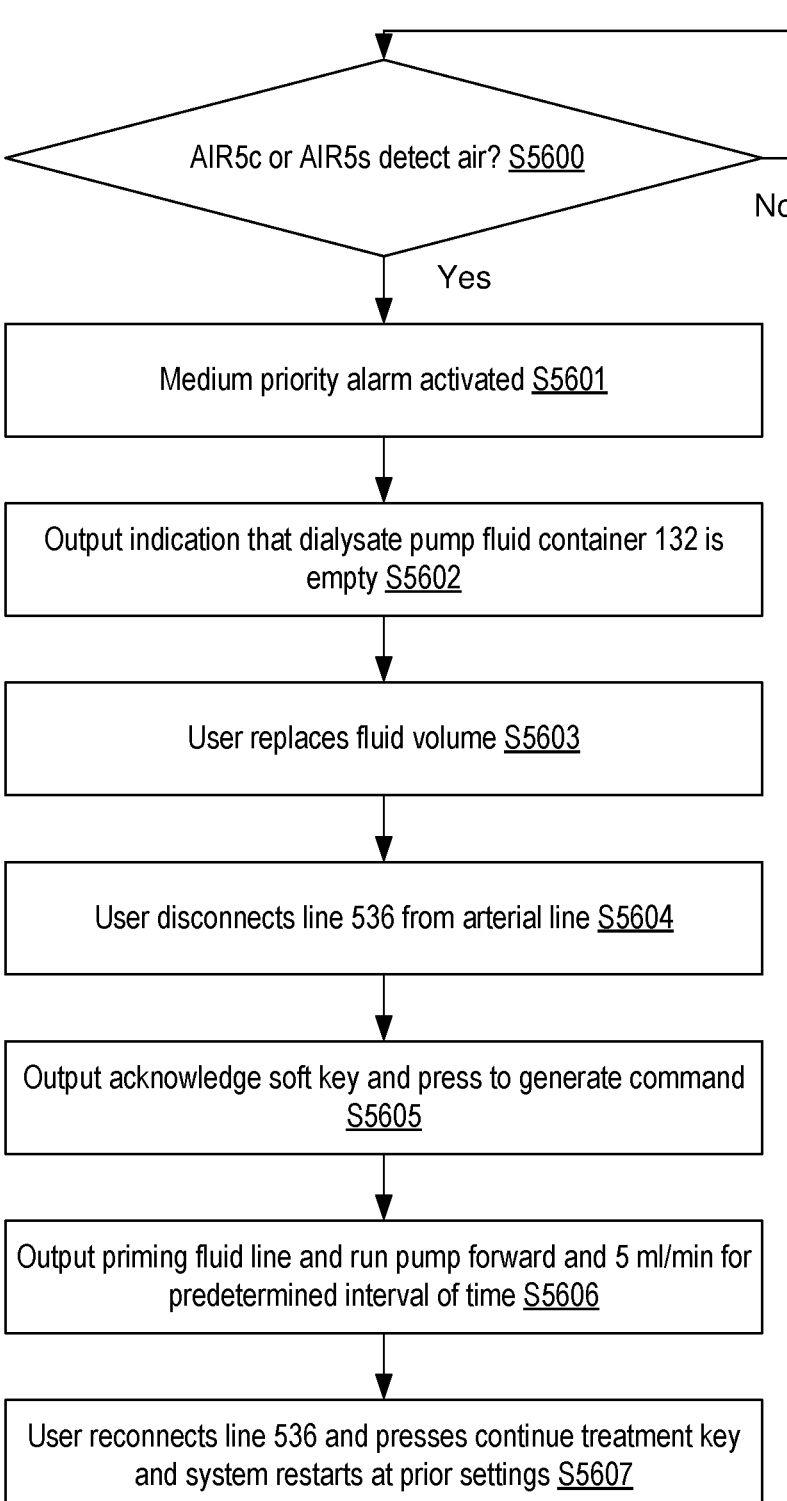
FIG. 54 illustrates a response to air detection in a fluid line according to embodiments of the disclosed subject matter.

Referring now to FIG. 54, control loops through S5600 until air is detected by air sensor 521. If air is detected then at S5601, a medium priority alarm is generated. At S5602, an indication of an empty fluid container is output. The fluid container may be that indicated at 132 in FIG. 19. At S5603 the user replaces the fluid volume, for example by exchanging the empty container for a replacement. At S5604 the user is instructed to disconnect the line e.g., supplemental fluid line 595 from the arterial line. At S5605 an acknowledgment key is activated and pressed to generate an acknowledgement command whereupon at S5606 the system outputs an indication that it is priming the fluid line and the supplemental fluid line 595 is then primed at 5 ml/min for a predetermined interval of time. At S5607, the user reconnects the supplemental fluid line 595 to the arterial line and enters a command to restart treatment at the prior settings.

Figure 55A:
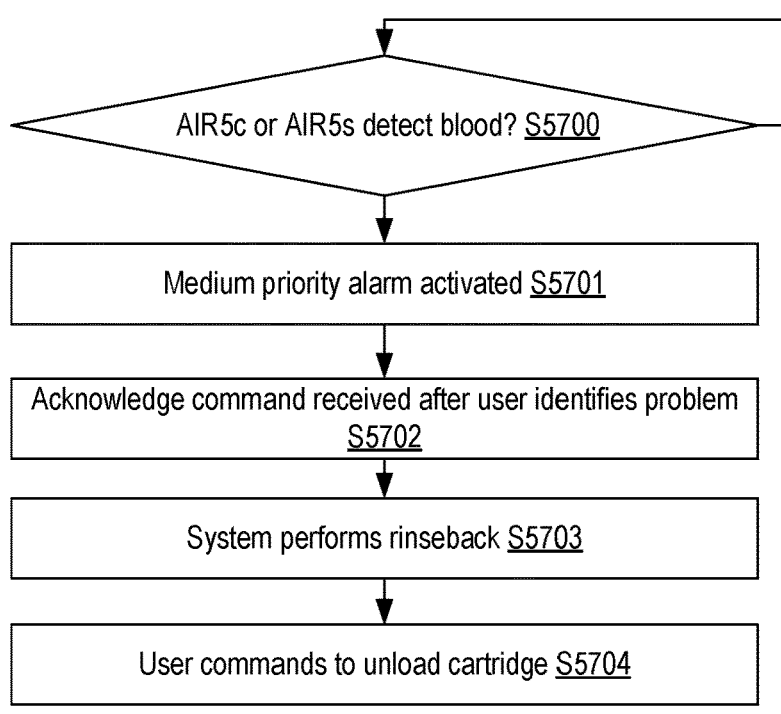
FIGS. 55A and 55B illustrate responses to blood detection in a fluid line according to embodiments of the disclosed subject matter.

Referring now to FIG. 55A, showing a method for detecting blood in a non-blood fluid line, control loops through S5700 until blood is detected at air sensor 521. If blood is detected then at S5701, a medium priority alarm is generated. At S5702, an acknowledgement key is activated and entered by the user. In response, the system performs a rinseback procedure at S5703 and then the user is instructed to unload the cartridge at S5704.

Figure 55B:
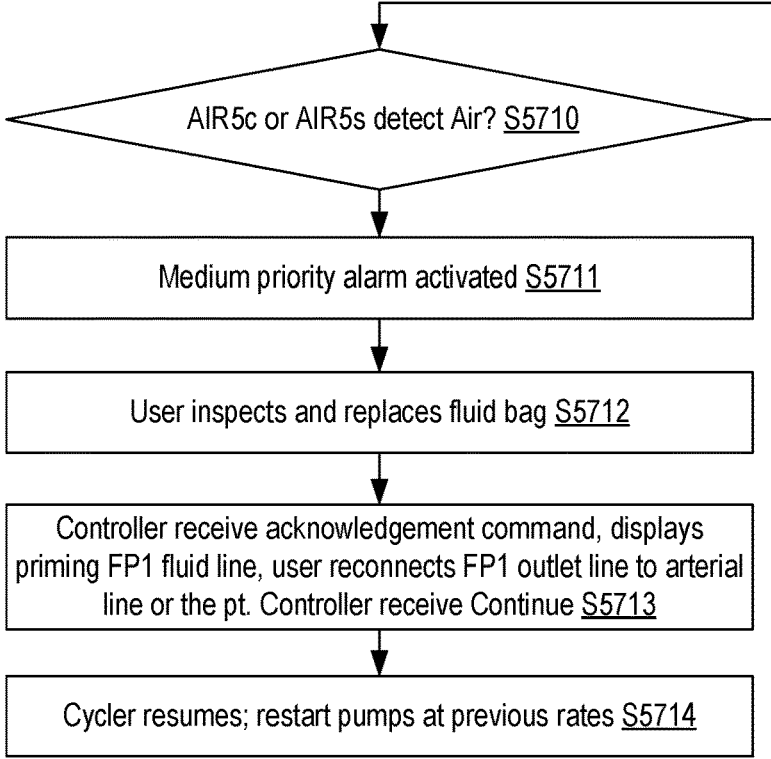

Referring now to FIG. 55B, showing a method for detecting air in flex line 1. Control loops through S5710 until blood is detected at air sensor 521. If blood is detected then at S5711, a medium priority alarm is generated. At S5712, the user inspects and replaces the fluid volume. At S5713 the controller receives an acknowledgement command, displays a message that it is priming the dry fluid line (flex line 1). The user reconnects the flex line 1 to the arterial line or the patient and the controller receives a command to resume. At S5714, the cycler restarts the pumps at the previous rates.

Figure 56:
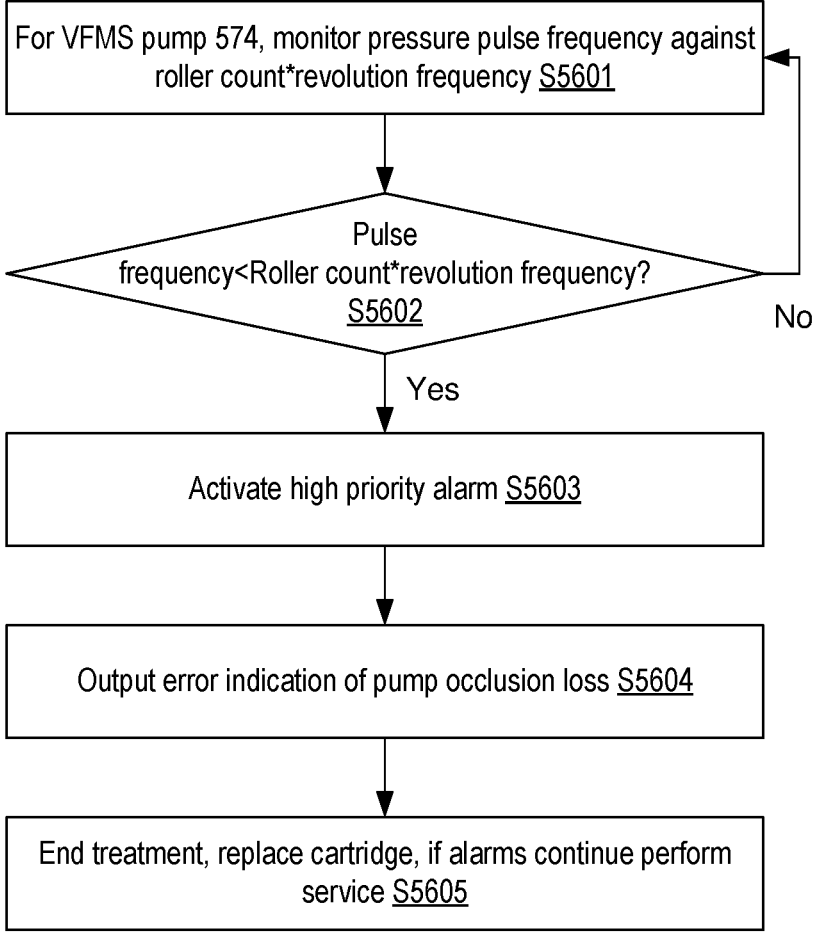
FIG. 56 illustrates a method for detecting failure of pump occlusion according to embodiments of the disclosed subject matter.

Referring now to FIG. 56, the controller 240 monitors the pressure pulse frequency for the VFMS pump during prime, alarm test, treatment, rinseback, and temporary disconnect modes at S581. At S582, if the Pulse frequency is not less than the roller count multiplied by the revolution frequency then control reverts to S81. Otherwise a medium priority alarm is activated at S583 and an error indication of pump occlusion loss is output at S584.

Figure 57:
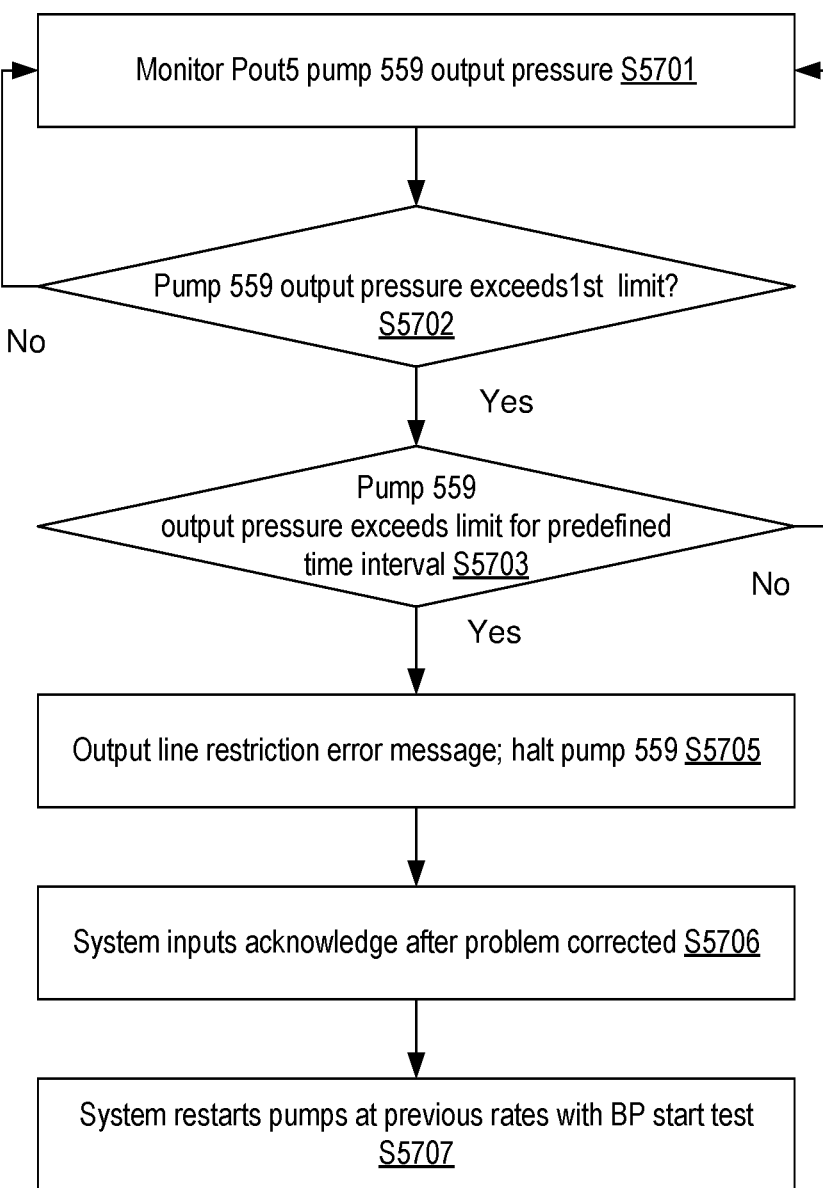
FIG. 57 illustrates a method for detecting a pump exceeding pressure limits according to embodiments of the disclosed subject matter.

Referring now to FIG. 57, during patient treatment or rinseback, the supplemental fluid pump 541 output pressure is continuously monitored at S5701. If the output pressure exceeds a first limit (e.g. 400 mmHg) at any time at S592 then control proceeds to S5703. If so then at S5703, the controller 240 determines if the supplemental fluid pump 541 output pressure has exceeded a second limit for a period greater than a predefined time interval. If so, then control proceeds to S5705. If not then control reverts to S5701. At S5705, supplemental fluid pump 541 is halted and pinch clamp 558 is closed. At S5705, an output line restriction error message may be output by the controller 240 on the user interface 141. At S5706, the system inputs an acknowledge indication from the user after the user has corrected the problem and at S5707 a rinseback procedure is run if appropriate.

Figure 58:
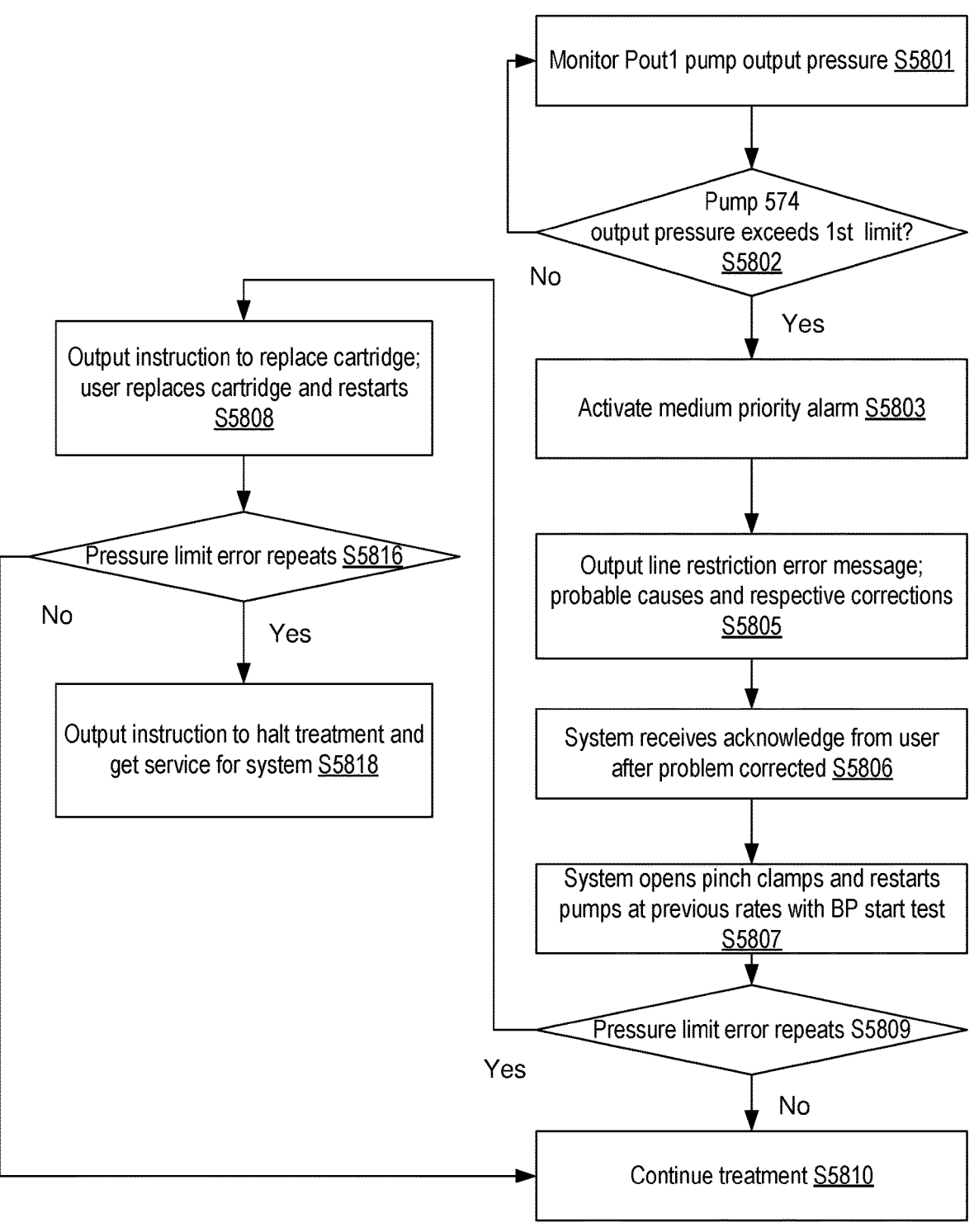
FIG. 58 illustrates a method for detecting a restriction in a respective fluid line according to embodiments of the disclosed subject matter.

Referring now to FIG. 58, during prime, alarm test, treatment, or rinseback, at S5801, the output pressure of fresh treatment fluid pump 573 is detected by fresh treatment fluid outlet pressure sensor 570A and monitored. If the output pressure exceeds a predefined threshold (e.g., 1000 mmHg) at any time, for a predefined delay interval at S5802, then control proceeds to S5803 where the controller 240 activates a medium priority alarm. If not then control reverts to S5801. At S5805, the controller outputs line restriction error message as well as probable causes and respective corrections. At S5806, the controller receives an input indicating the alarm is acknowledged. At S5807, the controller 240 opens pinch clamps and restarts the pumps at the previous rates. If the pressure limit error recurs at S5809, then the controller outputs an instruction to replace the fluid circuit S5808. At S5816 the controller determines whether the pressure limit was exceeded again and if so, the controller outputs an instruction to halt the treatment and obtain service for the system.

Figure 59:
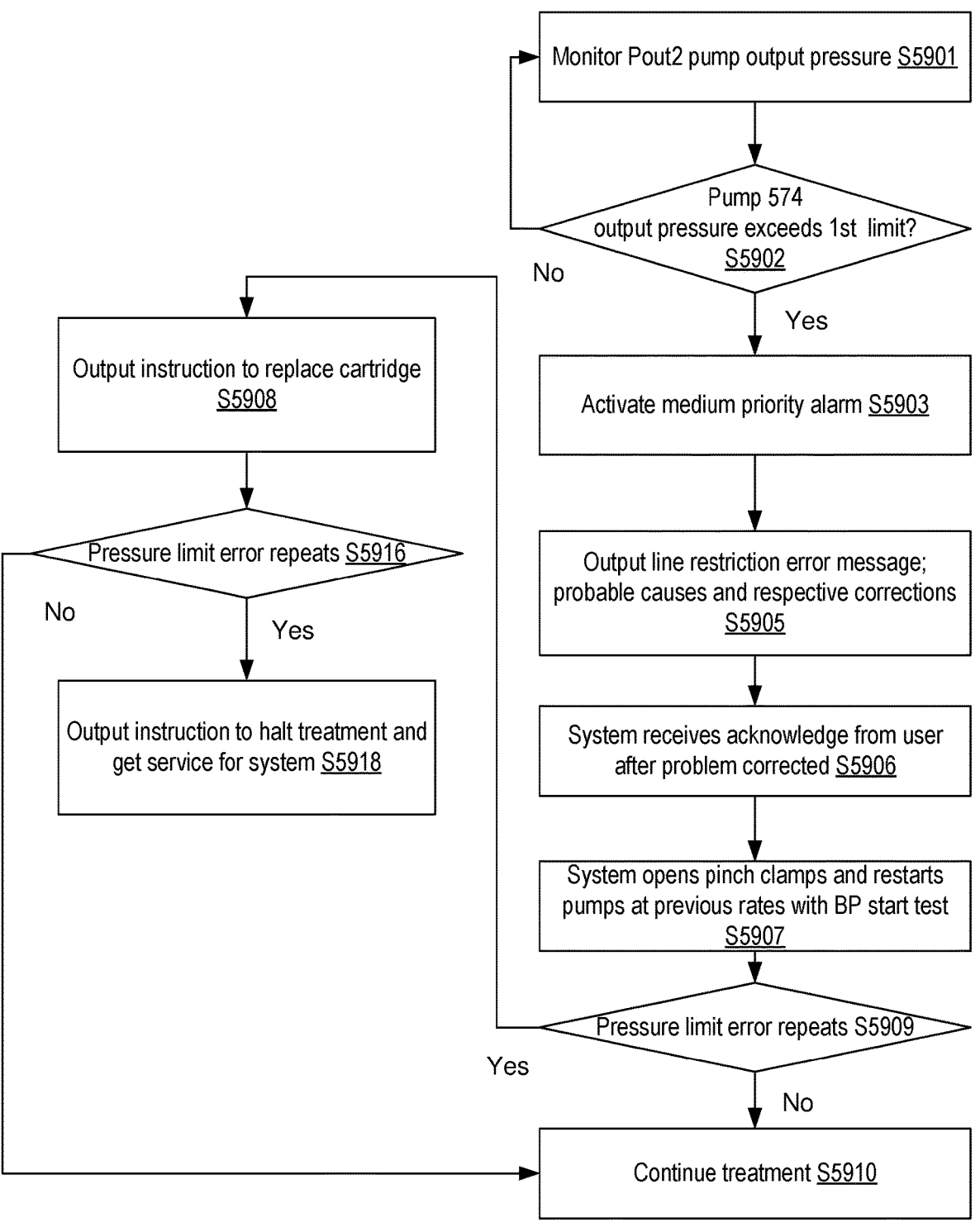
FIG. 59-60 illustrate methods for detecting a restriction in a respective fluid line according to embodiments of the disclosed subject matter.

Referring now to FIG. 59, during prime, alarm test, treatment, or rinseback, at S5901, the output pressure of replacement fluid pump 542 is detected by pressure sensor 555A and monitored. If the output pressure exceeds a predefined threshold (e.g., 1000 mmHg) at any time, for a predefined delay interval at S5902, then control proceeds to S5903 where the controller 240 activates a medium priority alarm. If not then control reverts to S5901. At S5905, the controller outputs line restriction error message as well as probable causes and respective corrections. At S5906, the controller receives an input indicating the alarm is acknowledged. At S5907, the controller 240 opens pinch clamps and restarts the pumps at the previous rates. If the pressure limit error recurs at S5909, then the controller outputs an instruction to replace the fluid circuit S5908. At S5916 the controller determines whether the pressure limit was exceeded again and if so, the controller outputs an instruction to halt the treatment and obtain service for the system.

Figure 60:
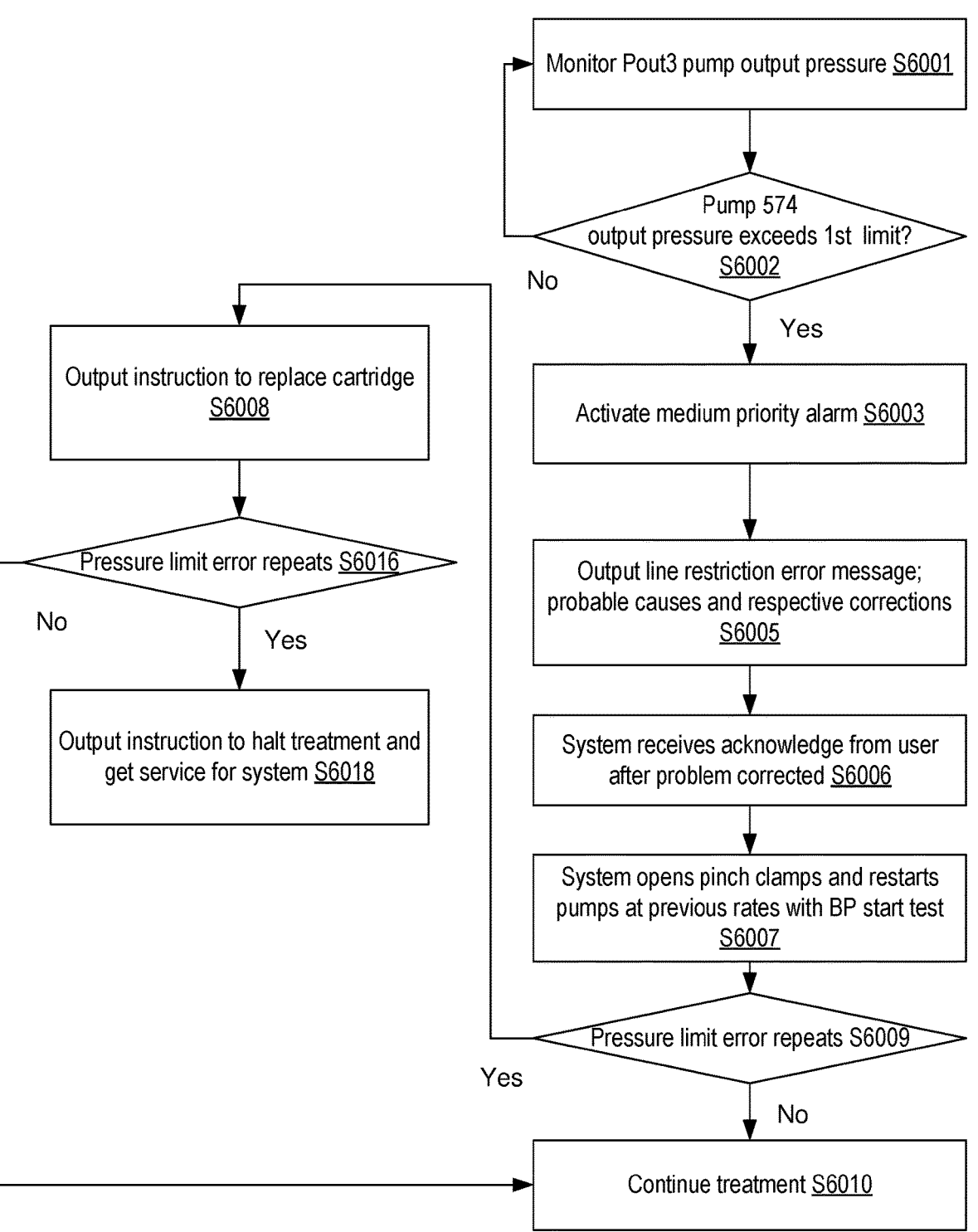

Referring now to FIG. 60, during prime, alarm test, treatment, or rinseback, at S6001, the output pressure of second replacement fluid pump 540 is detected by fresh treatment fluid outlet pressure sensor 557A and monitored. If the output pressure exceeds a predefined threshold (e.g., 400 mmHg) at any time, for a predefined delay interval at S6002, then control proceeds to S6003 where the controller 240 activates a medium priority alarm. If not then control reverts to S6001. At S6005, the controller outputs line restriction error message as well as probable causes and respective corrections. At S6006, the controller receives an input indicating the alarm is acknowledged. At S6007, the controller 240 opens pinch clamps and restarts the pumps at the previous rates. If the pressure limit error recurs at S6009, then the controller outputs an instruction to replace the fluid circuit S6008. At S6016 the controller determines whether the pressure limit was exceeded again and if so, the controller outputs an instruction to halt the treatment and obtain service for the system.

Figure 61:
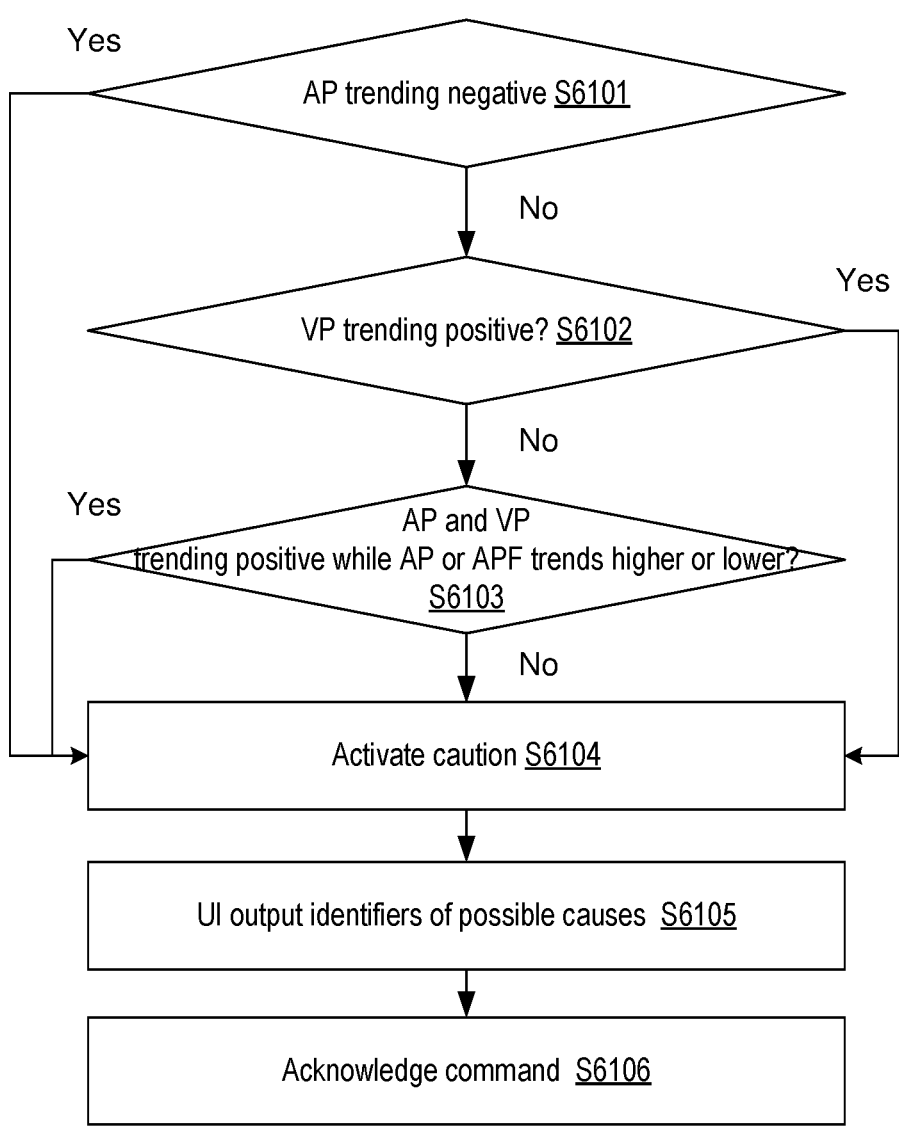
FIG. 61 illustrates a method that identifies pressure trends and actions taken in response to them, according to embodiments of the disclosed subject matter.

FIG. 61 illustrates a method that identifies pressure trends and actions taken in response to the trends. At S6101, the pump inlet pressure sensor 568 is continuously monitored by looping back to S6101 after cycling through S6102 and S6103 without triggering any of the respective events. If at S6101, the arterial pressure is indicated as trending negatively then control branches to S6104 where a caution is activated otherwise control reverts to S6101 where the loop is repeated. At S6105, the user interface outputs identifiers of possible causes such as clotting of the filter or patient access and waits at S6106 for an acknowledgement command entered by the user indicating the user has identified and corrected the cause of the caution. At S6102, if venous pressure is trending positive as indicated by venous control primary pressure sensor 532A and venous secondary pressure sensor 532B, venous line clamp 562 then control branches to S6104 where the previous process is followed. At S6103, if arterial and venous pressure trend positively while arterial pressure or blood pump outlet pressure sensor 564 trend higher or lower then control branches to S6104 otherwise control reverts to S6101 where the loop is repeated.

Figure 62:
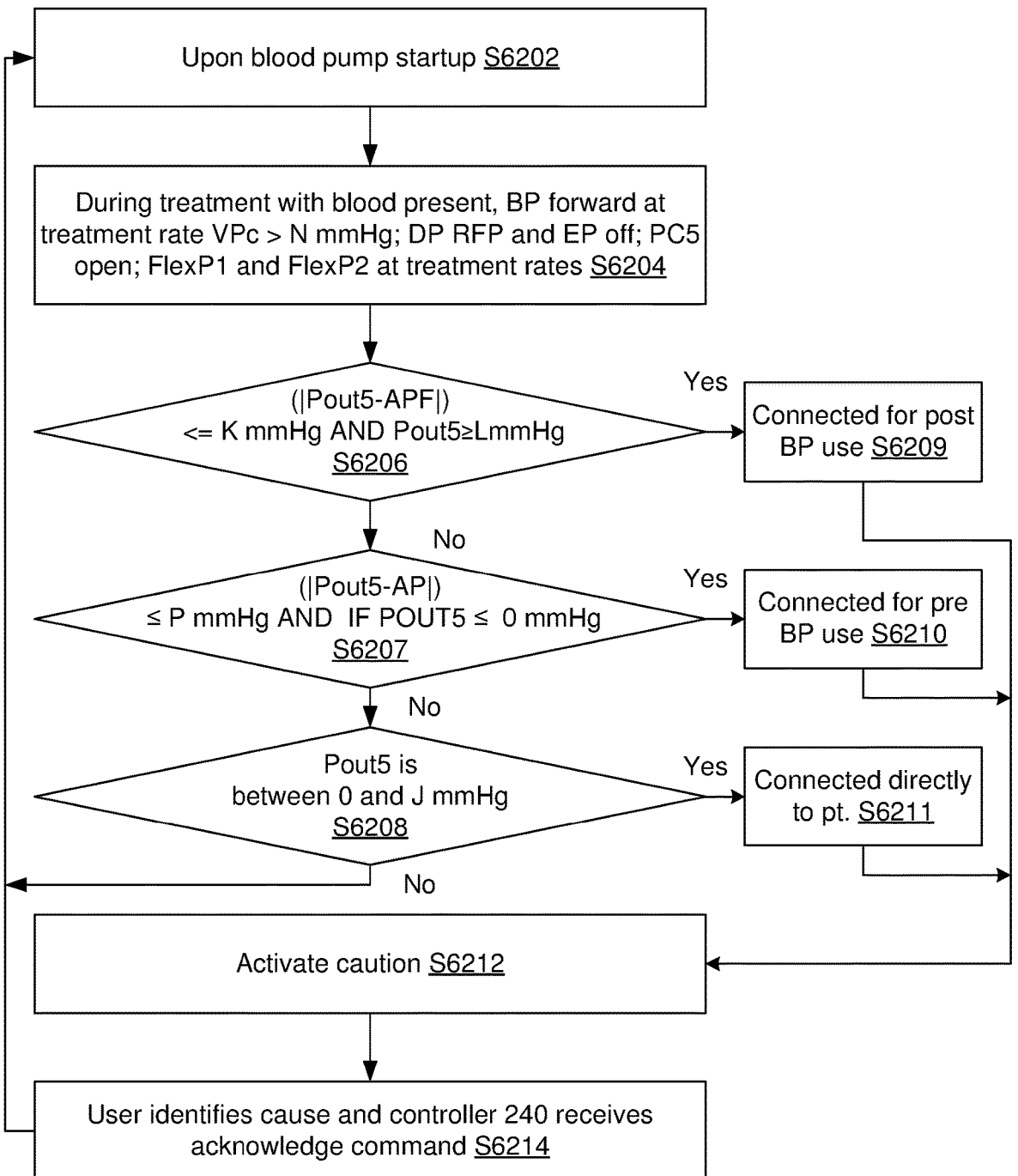
FIG. 62 illustrates a method of detecting a change of location of a fluid line, according to embodiments of the disclosed subject matter.

Referring now to FIG. 62, a system and method for determining a change in a blood processing machine's configuration is described. After the blood pump is started, S6202 and during treatment with blood present, the blood pump 563 runs in a forward direction at a treatment rate. The venous primary control pressure sensor 532A is greater than a predefined threshold (e.g., 50 mmHg). The venous primary control pressure sensor 532A indicates a pressure greater than another predefined pressure (e.g., 50 mmHg). The fresh treatment fluid pump 573, replacement fluid pump 542, and waste treatment fluid pump 574 are all off. Pinch clamp 558 is open and second replacement fluid pump 540 and supplemental fluid pump 541 are operated at the treatment rates. See S6204. At S6206, If the absolute value of the difference between the pressures given by pressure sensor 559A and blood pump outlet pressure sensor 564 is less or equal to a predefined threshold pressure (e.g., 10 mmHg) then the controller 240 determines that the system is connected for post blood pump use S6209. If the absolute value of the difference between the pressures given by pressure sensor 559A and blood pump outlet pressure sensor 564 is less than or equal to a predefined threshold pressure (e.g., 10 mmHg) and blood pump outlet pressure sensor 564 indicates zero, then at 6207 control proceeds to S6210 where the controller 240 determines that the system determines that the system is connected for the blood pump 563 use. If pressure sensor 559A is between 0 and another predefined threshold (e.g., 100 mmHg then the controller 240 determines, at S6211, the fluid is connected directly to the patient. If any of the connection options in S6209, S6210, or S6211 then true, then It will be appreciated that the modules, controllers, processes, systems, and sections described above can be implemented in hardware, hardware programmed by software, software instruction stored on a non-transitory computer readable medium or a combination of the above. For example, a method for balancing fluid flow can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C #.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Referring to FIG. 62, a procedure for detecting a change in the Flex fluid line connection to the blood circuit is now described. When the blood pump 538 starts this procedure is followed S6202. At S6202. The controller 240 verifies that the blood pump 538 that blood is present in the blood circuit, runs the blood pump 538 forward at the treatment rate. The controller 240 further verifies that venous primary control pressure sensor 532A greater than a predetermined pressure, in embodiments 50 mmHg. At S6204, the controller 240 further verifies that replacement fluid pump 542 and waste treatment fluid pump 574 are off. The controller 240 further verifies that pinch clamp 558 is open and second replacement fluid pump 540 and supplemental fluid pump 541 are running at treatment rates.

At S6206, the controller 240 determines if the absolute value of the difference between pressure sensor 559A and blood pump outlet pressure sensor 568 is greater than a predefined pressure, for example 100 mmHg. If so control proceeds to S6209 where the connection is determined and if it doesn't correspond to a currently commanded configuration, then a caution is activated at S6212. If no, control proceeds to S6207 where the controller 240 determines if the absolute value of the difference between pressure sensor 559A and pump inlet pressure sensor 568 is greater than a predefined pressure, for example 10 mmHg. If so control proceeds to S6210 where the connection is determined and if it doesn't correspond to a currently commanded configuration, then a caution is activated at S6212. If no, control proceeds to S6208 where it is determined if pressure sensor 559A indication lies between 0 and a predefined pressure, for example 100 mmHg. If so control proceeds to S6210 where the connection is determined at S6211 and if it doesn't correspond to a currently commanded configuration, then a caution is activated at S6212.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of controllers and especially digital controllers and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, flow balancing devices, methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A method for controlling flow in a fluid circuit, comprising:

using an extracorporeal fluid treatment system that includes a controller, controlling a balancing component that balances flows to and from a patient to maintain, or restore, a patient's normal fluid balance by regulating speeds of multiple pumps;

attaching a replaceable disposable fluid circuit through which flows of fluid are balanced to the extracorporeal fluid treatment system;

attaching bags containing fluids to the replaceable disposable fluid circuit;

pumping a priming fluid through the replaceable disposable fluid circuit including pumping fluid through pumping tube segments thereof;

after completion of the pumping of the priming fluid, detecting pressures in portions of the replaceable disposable fluid circuit, with pressure sensors, caused by a hydrostatic head of the fluids in the bags attached to the replaceable disposable fluid circuit;

determining, over a time interval, a rate of change of said hydrostatic-head pressures; and based on the determined rate of change of said hydrostatic-head pressures, generating a retry command or a fail command.

2. The method of claim 1, wherein the pressure sensors are located at respective inlets of said multiple pumps.

3. The method of claim 1, further comprising, during a blood treatment regulating speeds of the multiple pumps responsively to the pressures indicated by sa pressure sensors.

4. The method of claim 1, wherein the generating a retry or fail command is responsive to a difference in magnitudes of the pressures detected by the pressure sensors.

5. The method of claim 1, further comprising:

using each of the multiple pumps, generating a pressure between one of the pressure sensors and a control valve and detecting a pressure property indicating a closed state of the control valve or of at least one of the multiple pumps.

6. The method of claim 5, wherein the generating the pressure includes cycling at least one of the multiple pumps.

7. The method of claim 6, wherein the at least one of the multiple pumps is a blood pump.

8. The method of claim 7, wherein the generating the pressure includes running one of the multiple pumps at a rate of 10-20 ml/min.

9. The method of claim 1, further comprising:

comparing the determined rate of change to first and second thresholds corresponding respectively to partial occlusion and full occlusion, and wherein a retry command is generated when the first threshold is exceeded and a fail command is generated when the second threshold is exceeded.

10. The method of claim 9, further comprising compensating the detected pressures for pressure sensor elevation differences prior to the comparing.

11. The method of claim 9, wherein, during the determining, pumps contributing to the detected pressures are halted so that the detected pressures are attributable exclusively to the hydrostatic head.

12. The method of claim 9, wherein the comparing includes comparing respective rates of change determined at plural inlet pressure sensors to detect an asymmetry indicative of a partially occluded bag line.

13. The method of claim 1, wherein when the fail command indicates an occlusion in a replacement-fluid inlet line, the controller stops both a fresh treatment fluid pump and a replacement fluid pump.

14. The method of claim 1, further comprising maintaining a retry count and escalating from a retry command to a fail command after a predefined number of retries.

15. A system for controlling flow in a fluid circuit, comprising:

an extracorporeal fluid treatment system having a controller configured to command a balancing component that is configured to balance flows to and from a patient to maintain, or restore, a normal fluid balance of the patient by regulating speeds of two pumps of the balancing component;

a replaceable disposable fluid circuit attached to the extracorporeal fluid treatment system and connected to said two pumps and configured to convey fluids to be balanced;

a source of a priming fluid connected to the replaceable disposable fluid circuit and connected to a third pump that engages a pumping tube segment of the replaceable disposable fluid circuit; and bags containing fluids attached to the fluid circuit, wherein the controller is configured to pump the priming fluid through the replaceable disposable fluid circuit during a priming operation, the controller is further configured to, after completion of the priming operation, detect pressures, with pressure sensors, in portions of the replaceable disposable fluid circuit caused by a hydrostatic head of the fluids in the bags, the controller is further configured to determine, over a time interval, a rate of change of said hydrostatic-head pressures, and the controller is further configured to generate a retry or fail command based on the determined rate of change of said hydrostatic-head pressures.

16. The system of claim 15, wherein the pressure sensors are located at respective inlets of said two pumps.

17. The system of claim 15, wherein the controller is configured to, during a blood treatment, regulate speeds of the two pumps responsively to pressures indicated by said pressure sensors.

18. The system of claim 15, wherein the controller is configured such that the retry or fail command is generated responsively to a difference in magnitudes of the pressures detected by the pressure sensors.

19. The system of claim 18, wherein generating a pressure between one of the pressure sensors and a control valve includes cycling a blood pump.

20. The system of claim 15, wherein the controller is further configured to detect a pressure between at least one of the pumps and a control valve to identify an occlusion failure of the control valve or of the at least one of the pumps.

* * * * *